United States Patent
Kett et al.

(10) Patent No.: US 9,346,845 B2
(45) Date of Patent: May 24, 2016

(54) ANIONIC CONJUGATES OF GLYCOSYLATED BACTERIAL METABOLITE

(71) Applicant: GLYCAN BIOSCIENCES LLC, Corporate Centre, PA (US)

(72) Inventors: Warren Charles Kett, West Lebanon, NH (US); Yugang Chen, Hanover, NH (US)

(73) Assignee: GLYCAN BIOSCIENCES LLC, Corporate Centre, PA (US)

( * ) Notice: Subject to any disclaimer, the term of this patent is extended or adjusted under 35 U.S.C. 154(b) by 109 days.

(21) Appl. No.: 14/328,155

(22) Filed: Jul. 10, 2014

(65) Prior Publication Data

US 2014/0323422 A1   Oct. 30, 2014

Related U.S. Application Data

(63) Continuation of application No. 13/122,428, filed as application No. PCT/AU2009/001313 on Oct. 2, 2009, now Pat. No. 8,791,245.

(60) Provisional application No. 61/102,656, filed on Oct. 3, 2008.

(51) Int. Cl.

| | | |
|---|---|---|
| A61K 31/7036 | (2006.01) |
| C07H 15/23 | (2006.01) |
| C07H 15/232 | (2006.01) |
| C07H 15/224 | (2006.01) |
| C07H 15/234 | (2006.01) |
| C07H 15/238 | (2006.01) |
| A61K 31/702 | (2006.01) |
| A61K 31/7028 | (2006.01) |
| A61K 31/7034 | (2006.01) |
| A61K 31/7056 | (2006.01) |
| C07H 3/06 | (2006.01) |
| C07H 5/06 | (2006.01) |
| C07H 5/10 | (2006.01) |
| C07H 13/12 | (2006.01) |
| C07H 15/14 | (2006.01) |
| C07H 15/203 | (2006.01) |
| C07H 15/26 | (2006.01) |
| C07H 19/056 | (2006.01) |
| C07H 15/236 | (2006.01) |

(52) U.S. Cl.
CPC ............ *C07H 15/238* (2013.01); *A61K 31/702* (2013.01); *A61K 31/7028* (2013.01); *A61K 31/7034* (2013.01); *A61K 31/7036* (2013.01); *A61K 31/7056* (2013.01); *C07H 3/06* (2013.01); *C07H 5/06* (2013.01); *C07H 5/10* (2013.01); *C07H 13/12* (2013.01); *C07H 15/14* (2013.01); *C07H 15/203* (2013.01); *C07H 15/224* (2013.01); *C07H 15/23* (2013.01); *C07H 15/232* (2013.01); *C07H 15/234* (2013.01); *C07H 15/236* (2013.01); *C07H 15/26* (2013.01); *C07H 19/056* (2013.01)

(58) Field of Classification Search
None
See application file for complete search history.

(56) References Cited

U.S. PATENT DOCUMENTS

| | | | |
|---|---|---|---|
| 3,397,197 A | 8/1968 | Makepeace |
| 4,029,833 A | 6/1977 | Kosta |
| 4,136,254 A | 1/1979 | Nagabhushan et al. |
| 4,214,077 A | 7/1980 | Carney et al. |
| 4,230,847 A | 10/1980 | Nagabhushan et al. |
| 4,297,485 A | 10/1981 | Umezawa et al. |
| 4,337,335 A | 6/1982 | Nagabhushan et al. |
| 4,831,123 A | 5/1989 | Tann et al. |
| 4,902,790 A | 2/1990 | Mangia et al. |
| 5,442,047 A | 8/1995 | Tann et al. |
| 5,618,795 A | 4/1997 | Kondo et al. |
| 5,656,735 A | 8/1997 | Dall'Asta et al. |
| 5,763,587 A | 6/1998 | Mangia |
| 6,180,612 B1 * | 1/2001 | Hockensmith ..... A61K 31/7036 514/25 |
| 6,921,810 B2 * | 7/2005 | Wong ..................... A61K 31/70 536/17.2 |
| 6,967,242 B2 | 11/2005 | Swayze et al. |
| 7,022,684 B2 | 4/2006 | Banks et al. |
| 7,893,039 B2 | 2/2011 | Swayze et al. |
| 2004/0058880 A1 | 3/2004 | Liang et al. |
| 2005/0233983 A1 | 10/2005 | Banks et al. |
| 2008/0227213 A1 | 9/2008 | Disney |
| 2010/0261639 A1 | 10/2010 | Schweizer et al. |
| 2011/0195025 A1 | 8/2011 | Kett et al. |

FOREIGN PATENT DOCUMENTS

| | | |
|---|---|---|
| WO | 0139726 | 6/2001 |
| WO | 2005061523 | 7/2005 |

(Continued)

OTHER PUBLICATIONS

International Search Report for PCT/AU2009/001313, Completed by the Australian Patent Office on Nov. 9, 2009, 3 Pages.

(Continued)

*Primary Examiner* — Eric Olson

(74) *Attorney, Agent, or Firm* — Brooks Kushman P.C.

(57) ABSTRACT

The invention relates to anionic conjugates of glycosylated bacterial metabolites that may be used to mimic the structure and/or activity of the anionic bioactive molecules known as glycosaminoglycans (GAGs). The invention also relates to processes for the preparation of the conjugates. Such conjugates are useful in the prophylaxis and/or treatment of disease conditions and in particular chronic disease conditions such as inflammatory (including allergic) diseases, metastatic cancers and infection by pathogenic agents including bacteria, viruses or parasites.

7 Claims, No Drawings

(56) References Cited

FOREIGN PATENT DOCUMENTS

| WO | 2007064954 | 6/2007 |
|---|---|---|
| WO | 2007095688 | 8/2007 |

OTHER PUBLICATIONS

Bock et al. "Controlled reduction of acarbose: conformational analysis of acarbose and the resulting saturated products", Carbohydrate Research 1991, vol. 221, p. 1-16.
Coppola et al. "Acetylenic Amides 1. Synthesis of N-Substituted-2-Propynamides", Synthetic Communications 1993, vol. 23, No. 14, p. 2003-2010.
Celie et al. "Cardiovascular, Pulmonary and Renal Pathology: Subendothelial Heparan Sulfate Proteoglycans Become Major L-Section and Monocyte Chemoattractant Protein-1 Ligands upon Renal Ischemia/Reperfusion", The American Journal of Pathology Jun. 2007, vol. 170, No. 6, p. 1865-1878.
Truscheit et al. "Chemistry and Biochemistry of Microbial a-Glucosidase Inhibitors", Angew. Chem. Int. Ed. Engl. 1981, vol. 20, p. 744-761.
Tok et al. "Enhanced Binding of Aminoglycoside Dimers to a "Dimerized" A-Site 16S rRNA Construct", Bioorganic and Medicinal Chemistry Letters 2000, vol. 10, p. 1593-1595.
Taggi et al. "The Development of the First Catalyzed Reaction of Ketenes and Imines: Catalytic, Amymmetric Synthesis of B-Lactams", J Am Chem Soc 2002, vol. 124, p. 6626-6635.
Kolb et al. "Click Chemistry: Diverse Chemical Function from a Few Good Reactions", Angew. Chem. Int. Ed. 2001, vol. 40, p. 2004-2021.
Andrus et al. "Synthesis and analysis of polyethylene glycol linked P-glycoprotein-specific homodimers based on (−)-stipiamide", Tetrahedron Letters 2001, vol. 42, p. 3819-3822.
Fernig. "Optical Biosensor Techniques to Analyze Protein-Polysaccharide Interactions", Method in Molecular Biology 2001, vol. 171, p. 505-518.
Michael et al. "Enhanced RNA Binding of Dimerized Aminoglysocides", Bioorganic & Medicinal Chemistry 1999, vol. 7, p. 1361-1371.
Kempin et al. "Moenomycin A: New Chemistry that Allows to Attach the Antibiotic to Reporter Groups, Solid Supports and Proteins", Tetrahedron 1997, vol. 53, No. 52, p. 17669-17690.
Metten et al. "The First Enzymatic Degradation Products of the Antibiotic Moenomycin A.", Tetrahedron 1992, vol. 48, No. 39, p. 8401-8418.
Chengxun et al. "Studies of Active Diacylamides of Benzotriazole I. Synthesis of Polyamides and Polyesters", Polymer Communications 1985, No. 1, p. 42-47.
Yan et al. "The use of aminoglycoside derivatives to study the mechanism of aminoglycoside 6'-N-acetyltransferase and the role of 6'-NH2 in antibacterial activity", Bioorganic & Medicinal Chemistry 2007, vol. 15, p. 2944-2951.
Quader et al. "Multisite Modification of Neomycin B: Combined Mitsunobu and Click Chemistry Approach", J. Org. Chem. 2007, vol. 72, p. 1962-1979.
Speziale. "Ethanedithiol", Organic Syntheses, Coll. vol. 4, p. 401; vol. 30, p. 35, 3 Pages.
Schaefer et al. "Cinnamyl Bromide", Organic Syntheses, Coll. vol. 5, p. 249; vol. 48, p. 51, 3 Pages.
Uchimura et al. "Sulfated L-selectin ligands as a therapeutic target in chronic inflammation",TRENDS in Immunology 2006, vol. 27, No. 12, p. 559-565.
Ogawa et al. "Cleavage of Validoxylamine A Derivative with N-Bromosuccinimide: Preparation of Blocked Synthons Useful for the Construction of Carba-oligosaccharides Composed of Imino Linkages", J. Chem. Soc. Perkin Trans. 1991, vol. 1, p. 3287-3290.
Wang et al. "Dimeric Aminoglycosides: Design, Synthesis and RNA Binding", Bioorganic & Medicinal Chemistry Letters 1997, vol. 7, No. 4, p. 1951-1956.
Haddad et al. "Aminoglycoside Antibiotics: Structures and Mechanisms of Action", Ch.10, p. 307-351.
Gusrtafson et al. "Incorporation of Carbohydrates and Peptides into Large Triazine-Based Screening Libraries Using Automated Parallel Synthesis", Tetrahedron 1998, vol. 54, p. 4051-4065.
Ariza et al. "One-Pot Conversion of Azides to Boc-Protected Amines with Trimethylphosphine and Boc-ON", Tetrahedron Letters 1998, vol. 39, p. 9101-9102.
Polglase et al. Alkaline Degradation of Dihydrostreptomycin, J. Org. Chem. May 1962, p. 1923.
Tok et al. "Novel Synthesis and RNA-Binding Properties of Aminoglycoside Dimers Conjugated Via a Naphthalene Diimide-based Intercalator", Bioorganic & Medicinal Chemistry Letters 2001, vol. 11, p. 2987-2991.
Charles et al., Bioorganic & Medicinal Chemistry Letters 2002, vol. 12, p. 1259-1262, "Synthesis of Aminoglycoside—DNA Conjugates."
Kubata et al., Applied and Environmental Microbiology Apr. 1995, vol. 61, No. 4, p. 1666-1668, "Xylanase IV, an Exoxylanase of Aeromonas caviae ME-1 Which Produces Xylotetraose as the Only Low-Molecular-Weight Oligosaccharide from Xylan."

* cited by examiner

SEQUENCE LISTING

```
<160> NUMBER OF SEQ ID NOS: 2

<210> SEQ ID NO 1
<211> LENGTH: 33
<212> TYPE: DNA
<213> ORGANISM: Artificial Sequence
<220> FEATURE:
<223> OTHER INFORMATION: PCR primers for introducing restriction enzyme
      sites for cloning at the 5' end and at the transmernbrane domain
      of the L-selectin cDNA.
```

```
<400> SEQUENCE: 1
ccaagctttc aatgggctgc agaagaacta gag                                    33

<210> SEQ ID NO 2
<211> LENGTH: 43
<212> TYPE: DNA
<213> ORGANISM: Artificial Sequence
<220> FEATURE:
<223> OTHER INFORMATION: PCR primers for introducing restriction enzyme
      sites for cloning at the 5' end and at the transmernbrane domain
      of the L-selectin cDNA.

<400> SEQUENCE: 2
acggatccac ttacctgtat aatcaccctc cttaatcatt gag                         43
```

ANIONIC CONJUGATES OF GLYCOSYLATED BACTERIAL METABOLITE

CROSS-REFERENCE TO RELATED APPLICATION

This application is a continuation of U.S. application Ser. No. 13/122,428 filed Apr. 26, 2011, issued as U.S. Pat. No. 8,791,245 on Jul. 29, 2014, which is the U.S. national phase of PCT Application. No. PCT/AU2009/001313, filed Oct. 2, 2009 which claims the benefit of provisional application 61/102,656 filed Oct. 3, 2008, the disclosures of which are incorporated in their entirety by reference herein.

SEQUENCE LISTING

The text file dacc_ST25.txt of size 1 KB created Feb. 19, 2016, filed herewith, is hereby incorporated by reference.

FIELD OF THE INVENTION

The invention relates to anionic conjugates of glycosylated bacterial metabolites that may be used to mimic the structure and/or activity of the anionic bioactive molecules known as glycosaminoglycans (GAGs). The invention also relates to processes for the preparation of the conjugates. Such conjugates are useful in the prophylaxis and/or treatment of disease conditions and in particular chronic disease conditions such as inflammatory (including allergic) diseases, metastatic cancers and infection by pathogenic agents including bacteria, viruses or parasites.

BACKGROUND TO THE INVENTION

Natural and synthetic anionic saccharide-based compounds continue to be used, and developed for use, as therapeutics. A well known example of such a compound is the natural product heparin which has been used clinically for over 80 years as an anticoagulant. Heparin has undergone two generations of improvements resulting in products with greater selectivity and/or specificity for the target. The first was a semi-synthetic process which generated a low molecular weight heparin displaying a greater specificity of action. The second approach involved a synthetic pentasaccharide which was selective for the target protein. The synthetic approach, however, consisted of approximately 40 chemical steps, highlighting the technical difficulty associated with the synthesis of such compounds.

One approach to overcoming the challenges posed by the synthesis of heparin, and GAGs more broadly, has been to target GAG mimetics. One class of such mimetics is the semi-synthetic sulfated natural homo-oligosaccharides. There is, however, disparity between the small size of the oligosaccharides that are readily accessed from natural sources and the larger oligo- and polysaccharides which produce activity in many biological systems. In particular, access to oligosaccharides comprising 6 or more monosaccharides, whilst maintaining the goals of structural diversity and low cost, is especially difficult.

There remains a continuing need to produce GAG mimetics which display a high degree of selectivity and/or specificity, and which are able to be produced by simple, cost effective methods.

SUMMARY OF THE INVENTION

In one aspect the invention provides an anionic conjugate of 2 or more glycosylated bacterial metabolites, wherein prior to conjugation one or more of the metabolites is optionally modified.

In another aspect the invention provides a process for preparing an anionic conjugate of 2 or more glycosylated bacterial metabolites comprising the steps of:
  a) transforming at least one of the metabolites into an anionic derivative; and
  b) conjugating the metabolites via a linking group;
  wherein steps a) and b) may be performed in either order, and wherein one or more of the metabolites is optionally modified prior to step b).

The present invention utilises bacterial species as sources of large numbers of glycosylated metabolites for use as GAG mimetics. Conjugation of 2 or more such metabolites, and transformation into anionic derivatives, can produce very effective GAG mimetics. The judicious choice of process steps may have a dramatic impact on the nature of the product of such a process. Advantageously, the current industrial use of many of the bacterial species described herein makes the utilisation of the metabolites of the organisms commercially attractive.

Without wishing to be bound by theory it is believed that the use of glycosylated bacterial metabolites as "building-blocks" in the production of GAG mimetics is counter-intuitive for the following reasons:
1) Many glycosylated bacterial metabolites are positively charged and, accordingly, bind undesirably to negatively charged nucleic and ribonucleic acids as well as anionic GAGs such as heparin sulfate. The present invention, on the other hand, provides anionic conjugates which typically do not bind to negatively charged nucleic and ribonucleic acids or anionic GAGs;
2) The toxicity of certain glycosylated bacterial metabolites (in particular aminoglycoside antibiotics) makes this class of molecules an unlikely starting point for the development of new therapeutic agents not intended for specific use as antibiotics; and
3) Glycosylated bacterial metabolites typically do not share the same backbone structure and stereochemistry as the GAGs which they are intended to mimic. Such differences may adversely impact on the position of functional groups within the molecules which are otherwise important in intramolecular interactions. Furthermore, the glycosylated bacterial metabolites often contain unusual monosaccharides, including those with the L-gluco configuration, and hence are poor imitators of the structures of the GAGs.

DETAILED DESCRIPTION OF THE INVENTION

As used herein, the term "anionic" describes the net negative charge of a material. It will be understood that a given negatively charged material may have one or more positively charged counterions associated with it, or vice versa. In solution a negatively charged material may have dissociated from one or more positively charged counterions with which it is associated. As used herein, the term "anionic" is used to describe a property of that material and not the overall complex with one or more counterions which will typically render the complex neutral. It is understood that certain functional groups are negatively charged, neutral or positively charged at varying values of pH. Whether a material is anionic will be determined based on the sum of these charges. Accordingly, at a given pH, if a material has one positively charged functional group and two negatively charged functional groups, then the material has a net negative charge and is anionic as the term is used in the context of the present invention. In preferred embodiments the conjugates of the present invention have a net negative charge in aqueous solution at a pH of 5.

In preferred embodiments, the salts formed between the anionic conjugates of the present invention and the one or more counterions are pharmaceutically acceptable salts.

Glycosylated bacterial metabolites are structurally diverse and are particularly well-suited to the formation of larger conjugates. It will be understood that the skilled worker is familiar with techniques that allow for the isolation of bacterial metabolites or particular groups of bacterial metabolites. Furthermore many of the glycosylated bacterial metabolites are produced industrially and obtainable commercially.

The present invention also relates to metabolites produced by derivatives and variants of naturally occurring bacterial species. Preferred bacterial species which are used to obtain the metabolites of the present invention are obtained from members of the actinobacteria phylum (referred to herein as *actinobacter* species) and those obtained from members of the order of bacillales (referred to herein as *bacillus* species). Especially preferred species are actinobacter species. Members of the actinobacteria phylum are gram-positive bacteria that include, but are not limited to, the following families: Actinomyctes; Arthrobacter; Streptomycetes; Mycobacterium; Corynebacterium; Frankia; Micrococcus; Micromonospora; Mycobacterium; Nocardia; and Propionibacterium.

Many glycosylated bacterial metabolites are disclosed in U.S. Pat. No. 7,022,684 and US2005/233983, the entire contents of each document are incorporated herein by reference.

Examples of glycosylated bacterial metabolites are: Acarbose; 2-(N-Acetylcysteinyl)amido-2-deoxy-α-D-glucopyranosyl-D-myo-inositol disulfide; Adenomycin; Adenomycin, De-O-seryl; Adenosine 3'-(Butyl hydrogen phosphate); Adiposin 1; Adiposin 2; Amicetin; Amikacin; 3'-Amino-3'-deoxyadenosine, 6,6-Di-N-Me; 4-O-(6-Amino-6-deoxyglucopyranosyl)-2,5-dideoxystreptamine; 5"-Amino-4',5"-dideoxybutirosin A; 5"-Amino-3',4,5"-trideoxybutirosin A; Amylostatin; Angustmycin A; Annamycin; Antibiotic X 14766A; Antibiotic X 14931A; Antibiotic AC4437; Antibiotic BL 580, Antibiotic BL 580d; Antibiotic 66-40C; Antibiotic FU 10; Antibiotic I1; Antibiotic I-SKA$_1$; Antibiotic KA 70381V; Antibiotic KA 66061X; Antibiotic KA 6606IX, 1-Me; Antibiotic KA 6606IX, 1-Epimer; Antibiotic KA 6606IX, 1-Epimer, 1-Me; Antibiotic KA 6606IX, 1-Epimer, 1-Me, 4',5'-dehydro; Antibiotic KA 6606IX, 6-Epimer, 1-Me; Antibiotic KA 6606XV; Antibiotic LL-AC 541; Antibiotic NK 1012-2; Antibiotic SF 2052B; Antibiotic SS 56A; Antibiotic SS 56A, 4'-Epimer; Antibiotic SU1; Antibiotic SU2; Antibiotic SU3; Antibiotic SU4; Antibiotic XK 62-4; Antibiotic XK 62-4, 6',6'-Di-N-De-Me; Antibiotic XK 62-6; Antibiotic XK 62-6, N6'-Me; Antibiotic Y 02077Hγ; Antibiotic Y 02077Hg, N-De-Me; Antibiotic Y 03873J; Apramycin; Aristeromycin; Aristeromycin M; Aristeromycin M, 5'-Hydroxy; Ascamycin; Ashimycin A; Ashimycin B; 5-Azacytidine; Bluensomycin; Boholmycin; Butikacin; Butirosamine; Butirosamine, 5-Deoxy; Butirosin A; Butirosin A, 3"-Epimer; Butirosin A, 4'-Deoxy; Butirosin A, 3',4'-Dideoxy; Butirosin A, 3'-Deoxy, 3'-chloro; Butirosin A, 3',4'-Dideoxy, 3"-epimer; Butirosin A, 6'-Deamino, 6'-hydroxy; Butirosin A, 6'-Deamino, 6'-hydroxy, 3"-epimer; Butirosin A, 3',4'-Dideoxy, 6'-N-Me; Butirosin A, 3',4'-Dideoxy, 6'-N-methyl, 3"-epimer; Butirosin A, 2S-Hydroxy; Cadeguomycin; Cadeguomycin, 2'-Deoxy; Capuramycin; Combimicin A2; Combimicin B$_1$; Combimicin B$_2$; Curamycin A; Cytomycin; Cytosaminomycin A; Dactimicin; Dactimicin, 1-Epimer; Dapiramicin B; Dapiramicin B, 1'-Epimer, 6'-deoxy; Dapiramicin B, 6'-Deoxy; N-Deacyltunicamycin; N-Deacyltunicamycin, N4"-(11-Methyl-2-dodecenoyl); N-Deacyltunicamycin, N4"-(2-Tetradecenoyl); N-Deacyltunicamycin, N$^{4"}$-(12-Methyl-2-tridecenoyl); N-Deacyltunicamycin, N$^{4"}$-(2-Pentadecenoyl); N-Deacyltunicamycin, N$^{4"}$-(13-Methyltetradecanoyl); N-Deacyltunicamycin, N$^{4"}$-(13-Methyl-2-tetradec enoyl); N-Deacyltunicamycin, N$^{4"}$-(2-Hexadecenoyl); N-Deacyltunicamycin, N$^{4"}$-(14-Methyl-2-pentadecenoyl); N-Deacyltunicamycin, N$^{4"}$-(2-Heptadecenoyl); N-Deacyltunicamycin, N$^{4"}$-(15-Methyl-2-hexadecenoyl); Destomycin A; Destomycin A, N$^3$-Me; Destomycin A, N-De-Me, N$^3$-Me; Destomycin A, 2S-Hydroxy, N-de-Me, N1-amidino; Destomycin A, 4'-Epimer, N-de-Me, N3-Me; Destomycin A, 4',4"-Diepimer, N$^3$-Me; 3',4'-Dideoxykanamycin B; 3',4'-Dideoxykanamycin B, Sulfate salt (1:7); 3',4'-Dideoxykanamycin B, N1-(4-Amino-2-hydroxybutanoyl); 3',4'-Dideoxykanamycin B, 3"-N-Me; 3',4'-Dideoxykanamycin B, 3",6'-N,N-Di-Me; Dihydrostreptomycin; Dihydrostreptomycin, Sulfate (1:1.5); Erythromycin E; Ezomycin A$_1$; Ezomycin A$_2$; Ezomycin B$_1$; Ezomycin B1, 1-Epimer; Ezomycin B$_2$; Ezomycin B2, 1-Epimer; Ezomycin D$_1$; Ezomycin D$_1$; Formycin A; Formycin A, 3'-Epimer; Formycin B; Fortimicin A; Fortimicin A, Sulfate (2:1); Fortimicin A, Nw-Formyl; Fortimicin A, 3-O-De-Me; Fortimicin AH; Fortimicin AH, 3-Epimer; Fortimicin AK; Fortimicin AN; Fortimicin AO; Fortimicin AP; Fortimicin AP, 3-Epimer; Fortimicin AP, 4',5'-Didehydro; Fortimicin B; Fortimicin B, N1-Me; Fortimicin B, N1-(2-Hydroxyethyl); Fortimicin B, O-De-Me, 2'-N-glycyl; Fortimicin B, O-De-Me, 2'-N—(N-carbamoylglycyl); Fortimicin B, 4',5'-Didehydro; Fortimicin C; Fortimicin D; Fortimicin E; Fortimicin E, 6-Epimer; Fortimicin KE; Fortimicin KF; Fortimicin KG$_1$; Fortimicin KO$_1$; Fortimicin KO1, N2'-Aminoacetyl; Fortimicin KQ; Fortimicin KR$_1$; Garamine; Gentamicin A$_1$; Gentamicin A1, 6'-Me; Gentamicin A$_2$; Gentamicin A$_3$; Gentamicin A$_4$; Gentamicin A; Gentamicin A, 6'-Me; Gentamicin B$_1$; Gentamicin B1, 3',4'-Dideoxy; Gentamicin B; Gentamicin B, Sulfate (1:x); Gentamicin B, 1-N—[(S)-3-Amino-2-hydroxypropanoyl]; Gentamicin B, 3',4'-Dideoxy; Gentamicin C; Gentamicin C1; Gentamicin C1, 4"-Demethyl; Gentamicin C1a; Gentamicin C1a, 1-N-Et; Gentamicin C1a, 3"-N-De-Me; Gentamicin C1a, 4"-Demethyl; Gentamicin C2; Gentamicin C2,6'-Epimer; Gentamicin C2,4"-Demethyl; Gentamicin C2b; Gentamicin C2b, Hemipentasulfate; Gentamicin C2b, 3"-N-De-Me; Gentamicin C2b, 5-Deoxy; Gentamicin C2b, 5-Deoxy, 6'-N-Me; Gentamicin C2b, 2-Hydroxy; Gentamicin C2b, 2-Hydroxy, 6'-N-Me; Gentamicin G 418; Gentamicin X$_2$; Gentamine C$_{1a}$; Gentamine C$_2$; Gentamine C2, N6'-Me; Hikizimycin; Hybrimycin A1; Hybrimycin A1, 1-Deamino, 1-hydroxy; Hybrimycin A1, 6'''-Deamino, 6'''-hydroxy; Hybrimycin A1, 2-Epimer; Hybrimycin A1, 5"-Epimer; Hybrimycin A1, 5"-Epimer, 6'''-deamino, 6'''-hydroxy; Hybrimycin A1, 2,5"-Diepimer; Hybrimycin A1, 5-O-Deglycosyl; Hybrimycin A1, 5-O-Deglycosyl, 6'''-deamino, 6'''-hydroxy; Hybrimycin A1, 5-O-Deglycosyl, 2-epimer; Hydroxystreptomycin; Hydroxystreptomycin B; Hygromycin A; Hygromycin A, 4'-Epimer; Inosamycin A; Inosamycin B; Inosamycin C; Inosamycin D; Inosamycin E; Istamycin A; Istamycin A, N2"-Carbamoyl; Istamycin A, N2"-Formyl; Istamycin A, N-De(aminoacetyl); Istamycin A, 1-Epimer; Istamycin A, 1-Epimer, N2"-formyl; Istamycin A, 1-Epimer, N-de(aminoacetyl); Istamycin A3; Istamycin A3,6-Epimer; Istamycin C; Istamycin C, N-De (aminoacetyl); Istamycin C, N2"-Formyl; Istamycin X$_0$; Istamycin X0, 6-Epimer; Kanagawamicin; Kanamine; Kanamycin A; Kanamycin A, 3"-N-Me; Kanamycin A, 5-Deoxy; Kanamycin B; Kanamycin B, Sulfate; Kanamycin B, N-Ac; Kanamycin B, 4'-O-a-D-Glucopyranosyl; Kanamycin B, 3"-N-Me; Kanamycin B, 6"-O-Carbamoyl; Kanamycin C; Kanamycin C, 3'-Deoxy; Kanamycin C, 2-Hydroxy; Kasugamycin; Kasuganobiosamine; Lincomycin; Lincomycin, S-Oxide; Lincomycin, N-De-Me; Lincomycin, N-De-Me, N-Et; Lincomycin, S-De-Me, S-Et; Lincomycin, N,S-Di-de-Me, S-Et; Lincomycin, N,S-Di-de-Me, N,S-di-Et; Lincomycin, 1-De(methylthio), 1-hydroxy; Lincomycin B; Lividomycin A; Lividomycin A, 4'''-Deglycosyl; Lysinomycin; Mannimositose; Mannosylparomomycin; Methoxyhygromycin; Mildiomycin; Mildiomycin, 8'-Deoxy; Minosaminomycin; Moenomycin; Moenomycin A; Moenomycin A12; Moenomycin C1; Moenomycin C3; Moenomycin C4; Mutamicin $2_a$; Mutamicin 1; Mutamicin 2; Mutamicin 4; Mutamicin 5; Mutamicin 1A; Mutamicin 1B; Myomycin B; Myomycin A; Myomycin C; Narbomycin; Nebmycin T; Nebramycin factor 3; Nebramycin factor 3,3'-Deoxy; Nebramycin factor 7; Nebramycin factor 8; Nebramycin factor 9; Neomethymycin; Neomethymycin, 10-Hydroxy; Neomycin A; Neomycin B; Neomycin B, Mixt. with Neomycin A and C; Neomycin B, O5''-b-D-Glucopyranoside; Neomycin B, N-Diphosphate; Neomycin B, 6'''-Deamino, 6'''-hydroxy; Neomycin C; Neomycin C, N-Diphosphate; Neomycin C, 6'''-Deamino, 6'''-hydroxy; Netilmicin; Netilmicin, Sulfate (1:5); Oxazinomycin; Paldimycin; Paldimycin A; Paldimycin A2; Paldimycin B; Paldimycin B2; Paromamine; Paromamine, O5-β-D-Xylofuranosyl; Paromomycin; Paromomycin, Sulfate; Paromomycin, N1-Ac; Paromomycin, 3-N-Me; Paromomycin, 2'-N-Et; Paromomycin, 6-Deoxy; Paromomycin, 6'''-Deamino, 6'''-hydroxy; Paromomycin, 5'''-Epimer; Paromomycin, 5'''-Epimer, 6-deoxy; Paromomycin, 5'''-Epimer, 6''-deamino, 6'''-hydroxy; Pentostatin; Plicacetin, 3' b-Hydroxy; Plicacetin, 3' b-Hydroxy, 4''-N-Me; Polyoxin B; Polyoxin L; Propikacin; Prumycin; Psicofuranine; Puromycin; Puromycin Hydrochloride (1:2); Pyrazomycin; Pyrazomycin, a-D-form; Ribostamycin; Ribostamycin, Sulfate (2:1); Ribostamycin, N3-Ac; Ribostamycin, N1-Me; Ribostamycin, N3-Carboxymethyl; Ribostamycin, 3',4'-Dideoxy; Ribostamycin, 2a-Hydroxy; Ribostamycin, 2b-Hydroxy; Saccharocin; Saccharocin, 3'-Hydroxy; Salbostatin; Sangivamycic acid, Amide; Sangivamycic acid, Nitrile; Sangivamycic acid, Nitrile, 5'-O-a-D-glucopyranoside; Sangivamycic acid, 5'-Deoxy, nitrile; Sannamycin C; Sannamycin C, N2'-(N-Formylglycyl); Sannamycin C, 6'-N-De-Me; Sannamycin E; Sannamycin E, N-De-Me; Sannamycin K; Seldomycin 1; Seldomycin 2; Seldomycin 3; Seldomycin 5; Showdomycin; Sibiromycin; Sisomicin; Sisomicin, Sulfate (1:2.5); Sisomicin, 2'-N-Formyl; Sisomicin, N1-Me; Sisomicin, 6'-N-Me; Sisomicin, N-De-Me; Sisomicin, Stereoisomer; Sisomicin, N-De-Me, 3''-N-Et; Sisomicin B; Sisomicin D; Spenolimycin; Spicamycin; Sporaricin A; Sporaricin A, N*-Formimidoyl; Sporaricin B; Sporaricin B, O-De-Me; Sporaricin E; Streptomycin; Streptomycin, Sulfate (2:3); Streptomycin, N-De-Me; Streptomycin, 2-Deoxy; Streptomycin, Isonicotinoyl hydrazone; Streptomycin B; Streptothricin A; Streptothricin B; Streptothricin C; Streptothricin D; Streptothricin E; Streptothricin F; Tobramycin; Tobramycin, 6''-N-Carbamoyl; Tobramycin, 6''-O-Carbamoyl; Tobramycin, 2'-N-Carbamoyl; Tubercidin; Validamycin C; Validoxylamine B; Validoxylamine B, 4-O-b-D-Glucopyranoside; Validoxylamine B, 6-Deoxy; Validoxylamine B, 6-Deoxy, 4-O-b-D-glucopyranoside; Validoxylamine B, 6-Deoxy, 4-O-[b-D-glucopyranosyl-(1®4)-b-D-glucopyranoside]; Validoxylamine B, 6-Deoxy, 4-O-[b-D-glucopyranosyl-(1®6)-b-D-glucopyranoside]; Validoxylamine G, 4-O-b-D-Glucopyranoside; Verdamicin; Verdamicin, 6'-N-Me; Youlemycin; Antibiotic X 14847; Antibiotic D 53; Antibiotic JI 20A; Antibiotic JI 20B; Antibiotic K 52B; Antibiotic KA 6606IV; Antibiotic LL-AM 31α; Antibiotic LL-AM 31a, N2-Ac; Antibiotic LL-AM 31a, N4-Propanoyl; Antibiotic LL-BM $782\alpha_1$; Antibiotic LL-BM $782\alpha_{1a}$; Antibiotic LL-BM $782\alpha_2$; Antibiotic LL-BM 123α; Antibiotic LL-BM 408; Antibiotic Ro 09-0766; Antibiotic S-11-A; Glysperin A; Glysperin B; Glysperin C; Norplicacetin; Oligostatin C; Oligostatin D; Oligostatin E; Oxanosine; Oxazinomycin; Polyoxin I; Polyoxin A; Polyoxin C; Polyoxin D; Polyoxin E; Polyoxin F; Polyoxin G; Polyoxin H; Polyoxin J; Polyoxin K; Polyoxin L, 5-Fluoro; Polyoxin M; Polyoxin M, 5-Fluoro; Polyoxin N; Sinefungin; Sorbistin B; Sorbistin C; Sorbistin D; Thuringiensin; 3-Trehalosamine; Trestatin A; Trestatin B; Trestatin C; Tubercidin, 5'-O-a-D-Glucopyranosyl; and Xylostacin.

In particular, the expression "glycosylated bacterial metabolites" refers to bacterial metabolites comprising an aglycone and a glycone moiety. The aglycone and glycone moieties may be coupled through a glycosidic linkage. These bacterial metabolites are known as glycosides. Bacteria produce a large number of structurally distinct glycosylated metabolites, examples of aglycones portions being: cyclitol; anthraquinone moiety; 1,3-dideoxy-1,3-diguanido-scyllo-inositol; 1,3-dideoxy-1,3-diamino-scyllo-inositol; 1,3-dideoxy-1,3-bis(methylamino)-myo-inositol; 1,3-diamino-1,3-dideoxy-myo-inositol; 1-O-carbamoyl-3-deoxy-3-guanido-scyllo-inositol; 1,2,3-trideoxy-1,3-diamino-scyllo-inositol; 1,2,3-trideoxy-1-amino-3-methylamino-scyllo-inositol; 1,2,3-trideoxy-1-methylamino-3-amino-scyllo-inositol; 1,2,3-trideoxy-1,3-bis(methylamino)-scyllo-inositol; L-myo-inosamine-1; myo-inosamine-2; D-chyro-inositol; myo-Inositol; 1,4-dideoxy-1-methylamino-2-O-methyl-4-amino-chiroinositol; 3,5-dichloro-4-hydroxy-6-methylbenzoic acid; Allosamizoline; olivine; chromomycinone; peptides; phospholipids; purines; and nucleosides.

Where present, the cyclitol aglycone portion may comprise an amine group or derivative thereof. Furthermore such nitrogen-containing cyclitols may contain 7 carbon atoms. This particular type of cyclitol residue is referred to herein as a $C_7N$ cyclitol. Preferred examples of $C_7N$ cyclitols are valeinamine, validamine, hydroxyvalidamine and epoxyvalidamine:

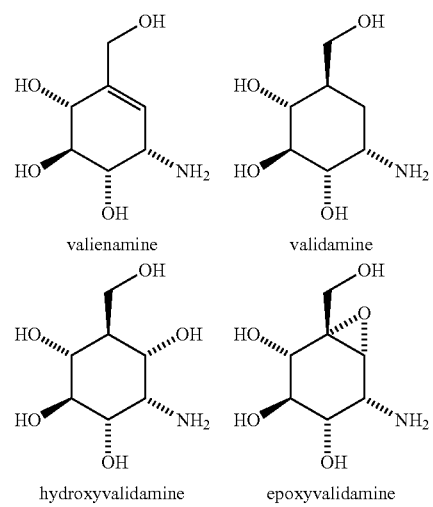

Glycosylated bacterial metabolites comprising a $C_7N$ cyclitol are referred to herein as $C_7N$ cyclitol metabolites. Examples of $C_7N$ cyclitol metabolites are: Validamycins; Acarbose and Amylostatins; Adiposins; Oligostatins; Trestatins; Oxirane; pseudo-oligosaccharides; Salbostatin and Suidatrestin; and Pyralomicins.

Examples of C$_7$N cyclitol metabolites are shown below:
Acarbose:
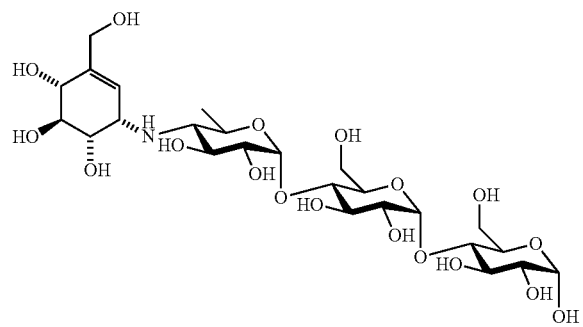
Adiposins:
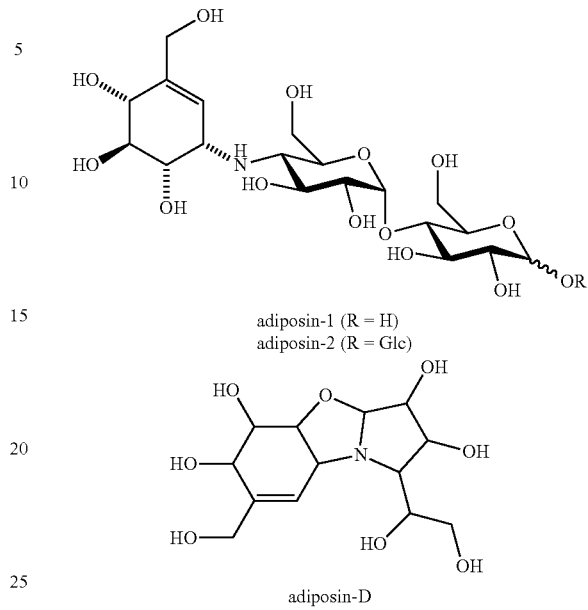
adiposin-1 (R = H)
adiposin-2 (R = Glc)
adiposin-D
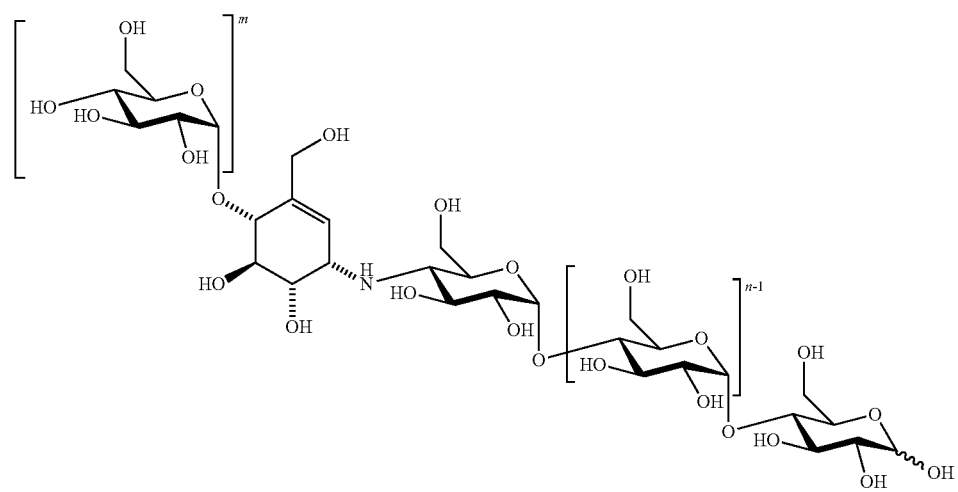
$m = 0$ to $8$
$n = 1$ to $8$
$m + n = 1$ to $8$ Oligostatins:
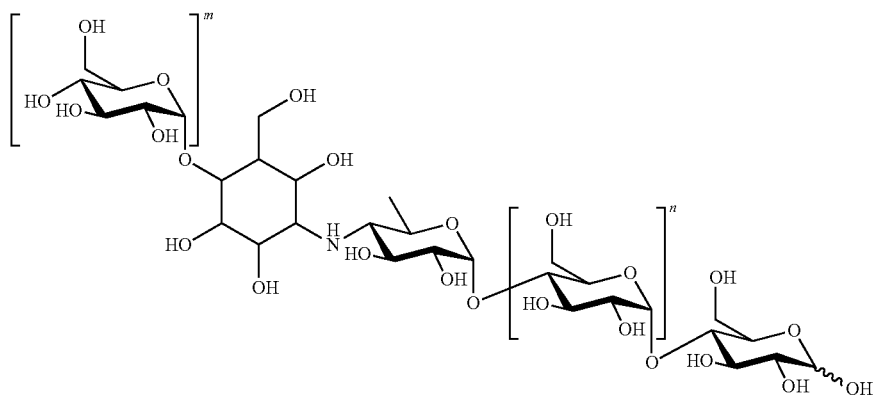
oligostatin C ($m = 0, n = 2$)
oligostatin D ($m = 0, n = 3$)
oligostatin E ($m = 1, n = 3$)
Trestatins and Related Metabolites:
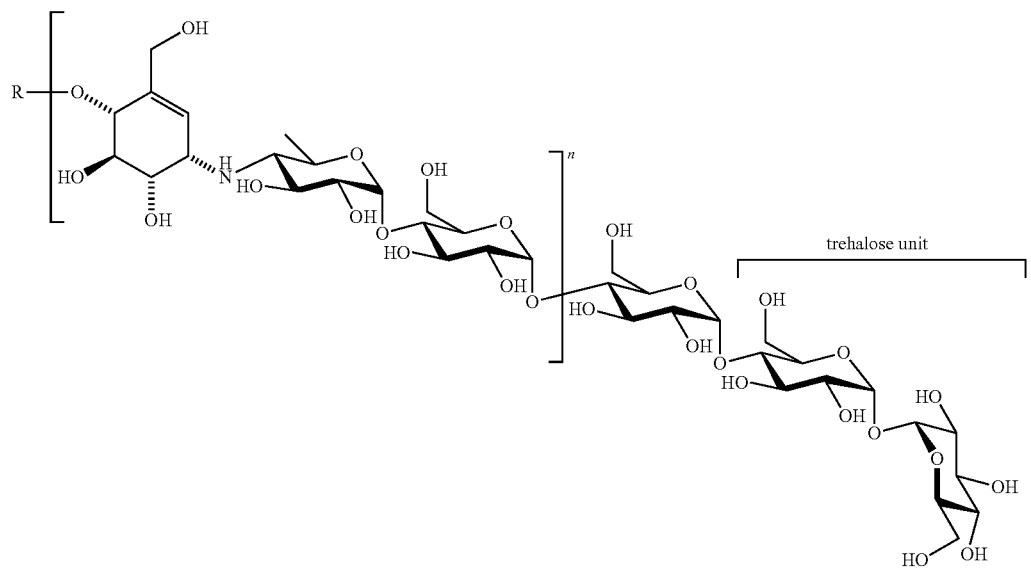
Trestatin A ($n = 2$); R = H
Trestatin B ($n = 1$); R = H
Trestatin C ($n = 3$); R = H
Ro 09-0766 ($n = 3$); R = glc(1-4)-glc(1-4)
Ro 09-0767 ($n = 2$); R = glc(1-4)-glc(1-4)
Ro 09-0768 ($n = 1$); R = glc(1-4)-glc(1-4)

Validamycins:

| | R₁ | R₂ | R₃ | R₄ | R₅ | R₆ |
|---|---|---|---|---|---|---|
| Validamycin A | H | H | β-D-Glc | H | H | H |
| Validamycin B | H | H | β-D-Glc | H | OH | H |
| Validamycin C | H | α-D-Glc | β-D-Glc | H | H | H |
| Validamycin D | H | H | H | H | H | α-D-Glc |
| Validamycin E | H | H | α-D-Glc (1,4)-β-D-Glc | H | H | H |
| Validamycin F | α-D-Glc | H | β-D-Glc | H | H | H |
| Validamycin G | H | H | β-D-Glc | OH | H | H |
| Validamycin H | H | H | α-D-Glc (1,4)-β-D-Glc | H | H | H |

Some glycosylated bacterial metabolites possess antibiotic properties. Bacterial metabolites with antibiotic properties, and comprising an aglycone and a glycone moiety coupled through a glycosidic linkage are referred to herein as glycoside antibiotics. Some glycoside antibiotics comprising an amine (or derivatised amine group) are referred to herein as aminoglycoside antibiotics. Examples of aminoglycoside antibiotic metabolites are: streptamines (e.g. streptomycin and spectinomycin); 2-deoxystreptamines (e.g. kanamycin, tobramycin, gentamycin); fortamine and 2-deoxyfortamines (e.g. fortamicin and istamycin); glycopeptides (e.g. vancomycin, avoparcin, ristocetin); Aureolic acids; Orthosomycins (e.g. Avilamycin and eveminomycins); Macrolides; Amicetins; Angucyclines; Lincomycins; Glycocinnamoylspermidines; and Nucleoside antibiotics (e.g. tunicamycins and muraymycins).

Structural examples of aminoglycoside antibiotics are given below. As can be seen a number of aminoglycoside antibiotics comprise a 6-membered cyclitol aglycone portion.

Streptomycins and Related Metabolites:

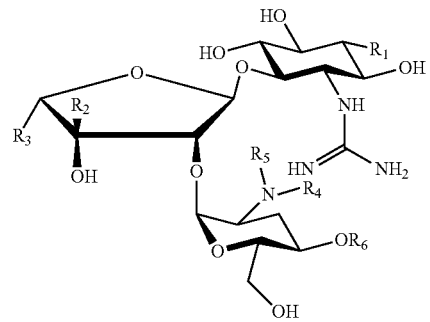

| | R₁ | R₂ | R₃ | R₄ | R₅ | R₆ |
|---|---|---|---|---|---|---|
| streptomycin | NHC(NH)NH₂ | CHO | Me | Me | H | H |
| dihydro-stretopmycin | NHC(NH)NH₂ | CH₂OH | Me | Me | H | H |
| 5'-Hydroxy-streptomycin | NHC(NH)NH₂ | CHO | CH₂OH | Me | H | H |
| N-Demethylstreptomycin | NHC(NH)NH₂ | CHO | Me | H | H | H |
| Bluensomycin | OC(O)NH₂ | CHO | Me | Me | H | H |
| Mannosido-Hydroxy-streptomycin | NHC(NH)NH₂ | CHO | CH₂OH | Me | H | α-D-Man |
| Dimannosido-streptomycin | NHC(NH)NH₂ | CHO | Me | Me | H | α-D-Man-1,6-α-D-Man |
| Ashimycin A | NHC(NH)NH₂ | CHO | Me | Me | H | 2'-carboxy-xylo-furanose |
| Ashimycin B | NHC(NH)NH₂ | CHO | Me | Me | C(O)CH₂OH | α-D-Man-1,6-α-D-Man |

Neomycins and Related Metabolites:

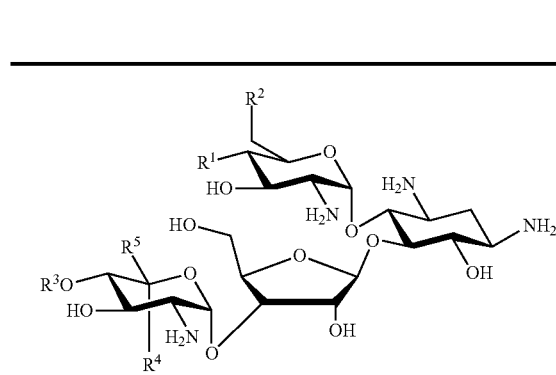

|  | $R^1$ | $R^2$ | $R^3$ | $R^4$ | $R^5$ |
|---|---|---|---|---|---|
| Neomycin B | OH | $NH_2$ | H | $CH_2NH_2$ | H |
| Neomycin C | OH | $NH_2$ | H | H | $CH_2NH_2$ |
| Paromomycin I | OH | OH | H | $CH_2NH_2$ | H |
| Paromomycin II | OH | OH | H | H | $CH_2NH_2$ |
| Mannosylparomomycin | OH | OH | α-D-Man | $CH_2NH_2$ | H |
| Lividomycin A | H | OH | α-D-Man | $CH_2NH_2$ | H |
| Lividomycin B | H | OH | H | $CH_2NH_2$ | H |

Butirosins and Related Metabolites:

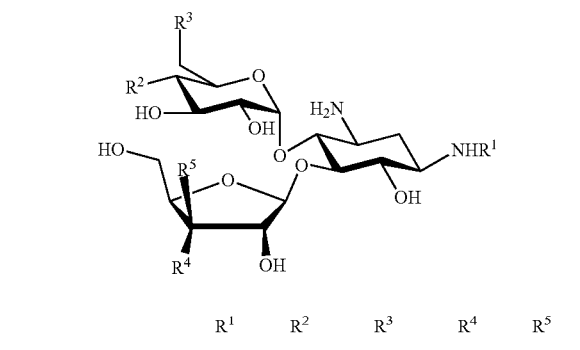

|  | $R^1$ | $R^2$ | $R^3$ | $R^4$ | $R^5$ |
|---|---|---|---|---|---|
| Butirosin A | ahb | OH | $NH_2$ | H | OH |
| Butirosin B | ahb | OH | $NH_2$ | OH | H |
| Butirosin E1 | ahb | OH | OH | H | OH |
| Butirosin E2 | ahb | OH | OH | OH | H |
| Butirosin C1 | ahb | H | H | H | OH |
| Butirosin C2 | ahb | H | H | OH | H |
| Ribostamycin | H | OH | H | OH | H |
| Xylostatin | H | H | H | H | OH |
| LL-Bm 408α | H | OH | H | OH | H | ahb = aminohydroxybutanoic acid $(C(O)CHOHCH_2CH_2NH_2)$

Kanamycins and Related Metabolites:

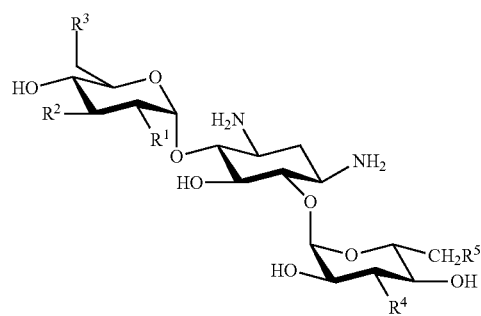

|  | $R^1$ | $R^2$ | $R^3$ | $R^4$ | $R^5$ |
|---|---|---|---|---|---|
| Kanamycin | OH | OH | $NH_2$ | $NH_2$ | OH |
| Kanamycin B | $NH_2$ | OH | $NH_2$ | $NH_2$ | OH |
| Kanamycin C | $NH_2$ | OH | OH | $NH_2$ | OH |
| NK-1001 | OH | OH | $NH_2$ | OH | OH |
| NK•1012•1 | $NH_2$ | OH | $NH_2$ | OH | OH |
| Tobramycin | $NH_2$ | H | $NH_2$ | $NH_2$ | OH |
| Nebramycin 4 | $NH_2$ | OH | $NH_2$ | $NH_2$ | $OC(O)NH_2$ |
| Nebramycin 5 | $NH_2$ | H | $NH_2$ | $NH_2$ | $OC(O)NH_2$ |

Gentamicins and Related Metabolites:

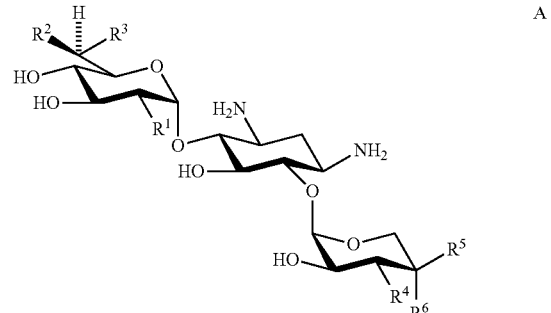

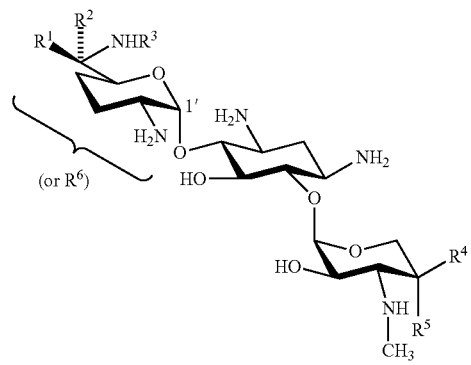

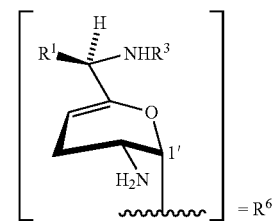

-continued

| A | R¹ | R² | R³ | R⁴ | R⁵ | R⁶ |
|---|---|---|---|---|---|---|
| Gentamicin A | NH₂ | H | OH | NHCH₃ | OH | H |
| Gentamicin A₁ | NH₂ | H | OH | NHCH₃ | H | OH |
| Gentamicin A2 | NH₂ | H | OH | OH | OH | H |
| Gentamicin A3 | OH | H | NH₂ | NHCH₃ | H | OH |
| Gentamicin A4 | NH₂ | H | OH | N(CHO)CH₃ | OH | H |
| Gentamicin B | OH | H | NH₂ | NHCH₃ | CH₃ | OH |
| Gentamicin B1 | NH₂ | H | OH | NHCH₃ | CH₃ | OH |
| Gentamicin X2 | NH₂ | H | OH | NHCH₃ | CH₃ | OH |
| G-418 | NH₂ | CH₃ | OH | NHCH₃ | CH₃ | OH |
| JI•20A | NH₂ | H | NH₂ | NHCH₃ | CH₃ | OH |
| JI•20B | NH₂ | CH₃ | NH₂ | NHCH₃ | CH₃ | OH |

| B | R¹ | R² | R³ | R⁴ | R⁵ | R⁶ |
|---|---|---|---|---|---|---|
| Gentamicin C₁ | CH₃ | H | CH₃ | CH₃ | OH | − |
| Gentamicin CIa | H | H | H | CH₃ | OH | − |
| Gentamicin C2 | CH₃ | H | H | CH₃ | OH | − |
| Gentamicin C2a | H | CH₃ | H | CH₃ | OH | − |
| Gentamicin C2-111a | H | H | H | CH₃ | OH | − |
| Sagamicin | H | H | CH₃ | CH₃ | OH | − |
| Sisomicin | H | H | H | CH₃ | OH | + |
| G•S2 | H | H | CH₃ | CH₃ | OH | + |
| 66-40B | H | H | H | OH | H | + |
| Verdamicin | CH₃ | H | H | CH₃ | OH | + |
| 66-40D | H | H | H | H | OH | + |

Seldomycins:

| | R¹ | R² | R³ | R⁴ |
|---|---|---|---|---|
| Seldomycin 1 | OH | OH | OH | OH |
| Seldomycin 3 | OH | NH₂ | OH | OH |
| Seldomycin 5 | H | NH₂ | NH₂ | OCH₃ |

Deoxystreptamines and Related Metabolites:

| | R¹ | R² | R³ |
|---|---|---|---|
| Paromamine | NH₂ | OH | OH |
| Neamine | NH₂ | OH | NH₂ |
| NK-1003 | OH | OH | NH₂ |
| Seldomycin 2 | NH₂ | H | NH₂ |

Apramycins:

| | R¹ | R² |
|---|---|---|
| Apramycin | H | NH₂ |
| Oxyapramycin | OH | NH₂ |
| Saccharocin (KA-5685) | H | OH |

Hygromycins and Related Metabolites:

| | R¹ | R² | R³ | R⁴ | R⁵ | R⁶ | R⁷ |
|---|---|---|---|---|---|---|---|
| Hygromycin B | H | CH₃ | H | OH | H | OH | H |
| Destomycin A | CH₃ | H | H | OH | H | OH | H |
| Destomycin B | CH₃ | CH₃ | H | H | OH | H | OH |
| Destomycin C | CH₃ | CH₃ | H | OH | H | OH | H |
| A•396-1 | H | H | H | OH | H | OH | H |
| A•16318-C | CH₃ | CH₃ | H | H | OH | H | H |
| SS•56-C | H | H | OH | OH | H | OH | H |
| 1•N-Amidino-1•N-demethyl-2•hydroxy•destomycin A | C(NH)NH₂ | H | OH | OH | H | OH | H |

Fortimicins and Related Metabolites:

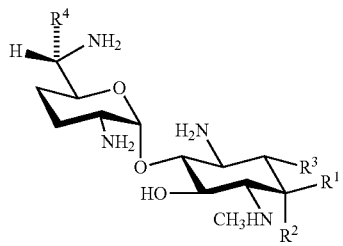

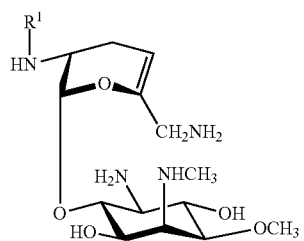

| A | R¹ | R² | R³ | R⁴ | R⁵ | R⁶ |
|---|---|---|---|---|---|---|
| Fortimicin A | NH₂ | H | OH | C(O)CH₂NH₂ | CH₃ | H |
| Fortimicin B | NH₂ | H | OH | H | CH₃ | H |
| 1-epi-Fortimicin B | H | NH₂ | OH | H | CH₃ | H |
| Fortimicin C | NH₂ | H | OH | C(O)CH₂NHC(O)NH₂ | CH₃ | H |
| Fortimicin D | NH₂ | H | OH | C(O)CH₂NH₂ | H | H |
| Dactimicin | NH₂ | H | OH | C(O)CH₂NHCH=NH | CH₃ | H |
| 1-epi-Dactimicin | H | NH₂ | OH | C(O)CH₂NHCH=NH | CH₃ | H |
| Sporaricin A | H | NH₂ | H | C(O)CH₂NH₂ | CH₃ | H |
| Sporaricin B | H | NH₂ | H | H | CH₃ | H |
| Istamicin A₀ | NH₂ | H | H | H | H | CH₃ |
| Istamicin A | NH₂ | H | H | C(O)CH₂NH₂ | H | CH₃ |
| Istamicin A₃ | NH₂ | H | H | C(O)CH₂NHCH=NH | H | CH₃ |
| Istamicin B₀ | H | NH₂ | H | H | H | CH₃ |
| Istamicin B | H | NH₂ | H | C(O)CH₂NH₂ | H | CH₃ |
| Istamicin B₃ | H | NH₂ | H | C(O)CH₂NHCH=NH | H | CH₃ |
| Istamicin C | NH₂ | H | H | C(O)CH₂NH₂ | H | CH₃ |
| Istamicin A₂ | NH₂ | H | H | C(O)CH₂NHC(O)NH₂ | H | CH₃ |

| B | R¹ | R² | R³ | R⁴ |
|---|---|---|---|---|
| Fortimicin KH | OCH₃ | H | OH | CH₃ |
| Fortimicin KR | H | OCH₃ | OH | CH₃ |
| Istamicin Y₀ | OCH₃ | H | H | H |
| Istamicin X₀ | H | OCH₃ | H | HH |

| C | R¹ |
|---|---|
| Fortimicin KG₃ | H |
| Lysinomicin | C(O)CH₂NHC(O)NH(CH₂)₃NH₂ |

Moenomycin is another preferred glycosylated bacterial metabolite that is typically not referred to as either a C₇N cyclitol metabolite or an aminoglycoside antibiotic. The structure of moenomycin is given below:

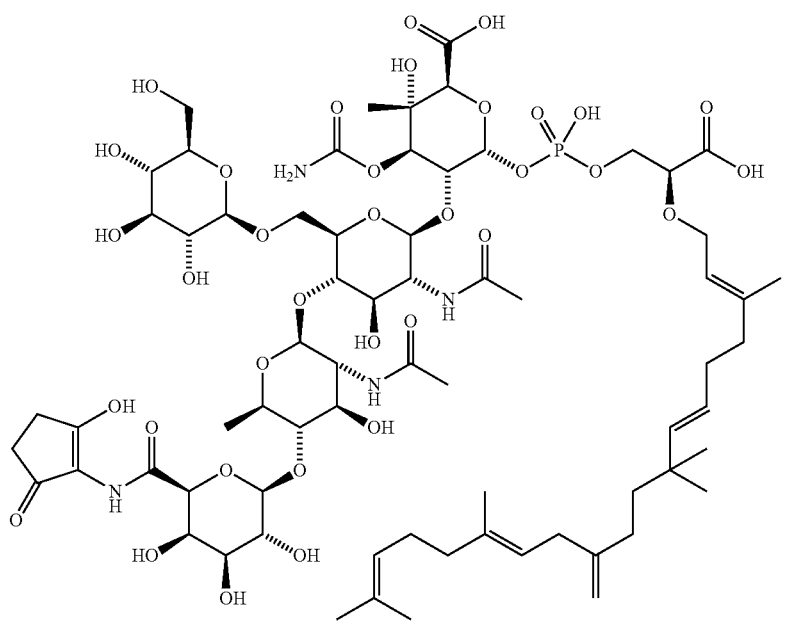

As used herein the term "conjugate" refers to the product of coupling 2 or more materials. The coupled materials may be the same or may be different. Such a coupling may be via 1 or more linking groups.

As used herein the term "linking group" refers to a multivalent group that covalently links 2 or more materials. Preferably the or each linking group is a multivalent form of a group selected from alkyl, alkenyl, alkynyl, aryl, acyl, carbocyclyl, heterocyclyl, heteroaryl, alkyloxy, alkenyloxy, alkynyloxy, aryloxy, acyloxy, carbocyclyloxy, heterocyclyloxy, heteroaryloxy, alkylthio, alkenylthio, alkynylthio, arylthio, acylthio, carbocyclylthio, heterocyclylthio, heteroarylthio, alkylalkenyl, alkylalkynyl, alkylaryl, alkylacyl, alkylcarbocyclyl, alkylheterocyclyl, alkylheteroaryl, alkyloxyalkyl, alkenyloxyalkyl, alkynyloxyalkyl, aryloxyalkyl, alkylacyloxy, alkylcarbocyclyloxy, alkylheterocyclyloxy, alkylheteroaryloxy, alkylthioalkyl, alkenylthioalkyl, alkynylthioalkyl, arylthioalkyl, alkylacylthio, alkylcarbocyclylthio, alkylheterocyclylthio, alkylheteroarylthio, alkylalkenylalkyl, alkylalkynylalkyl, alkylarylalkyl, alkylacylalkyl, arylalkylaryl, arylalkenylaryl, arylalkynylaryl, arylacylaryl, arylacyl, arylcarbocyclyl, arylheterocyclyl, arylheteroaryl, alkenyloxyaryl, alkynyloxyaryl, aryloxyaryl, arylacyloxy, arylcarbocyclyloxy, arylheterocyclyloxy, arylheteroaryloxy, alkylthioaryl, alkenylthioaryl, alkynylthioaryl, arylthioaryl, arylacylthio, arylcarbocyclylthio, arylheterocyclylthio, and arylheteroarylthio.

More preferably, the or each linking group is a multivalent form of any of the groups selected from $C_1$-$C_{18}$ alkyl, $C_2$-$C_{18}$ alkenyl, $C_2$-$C_{18}$ alkynyl, $C_6$-$C_{18}$ aryl, $C_1$-$C_{18}$ acyl, $C_3$-$C_{18}$ carbocyclyl, $C_2$-$C_{18}$ heterocyclyl, $C_3$-$C_{18}$ heteroaryl, $C_1$-$C_{18}$ alkyloxy, $C_2$-$C_{18}$ alkenyloxy, $C_2$-$C_{18}$ alkynyloxy, $C_6$-$C_{18}$ aryloxy, $C_1$-$C_{18}$ acyloxy, $C_3$-$C_{18}$ carbocyclyloxy, $C_2$-$C_{18}$ heterocyclyloxy, $C_3$-$C_{18}$ heteroaryloxy, $C_1$-$C_{18}$ alkylthio, $C_2$-$C_{18}$ alkenylthio, $C_2$-$C_{18}$ alkynylthio, $C_6$-$C_{18}$ arylthio, $C_1$-$C_{18}$ acylthio, $C_3$-$C_{18}$ carbocyclylthio, $C_2$-$C_{18}$ heterocyclylthio, $C_3$-$C_{18}$ heteroarylthio, $C_3$-$C_{18}$ alkylalkenyl, $C_3$-$C_{18}$ alkylalkynyl, $C_7$-$C_{24}$ alkylaryl, $C_2$-$C_{18}$ alkylacyl, $C_4$-$C_{18}$ alkylcarbocyclyl, $C_3$-$C_{18}$ alkylheterocyclyl, $C_4$-$C_{18}$ alkylheteroaryl, $C_2$-$C_{18}$ alkyloxyalkyl, $C_3$-$C_{18}$ alkenyloxyalkyl, $C_3$-$C_{18}$ alkynyloxyalkyl, $C_7$-$C_{24}$ aryloxyalkyl, $C_2$-$C_{18}$ alkylacyloxy, $C_4$-$C_{18}$ alkylcarbocyclyloxy, $C_3$-$C_{18}$ alkylheterocyclyloxy, $C_4$-$C_{18}$ alkylheteroaryloxy, $C_2$-$C_{18}$ alkylthio alkyl, $C_3$-$C_{18}$ alkenylthioalkyl, $C_3$-$C_{18}$ alkynylthioalkyl, $C_7$-$C_{24}$ arylthioalkyl, $C_2$-$C_{18}$ alkylacylthio, $C_4$-$C_{18}$ alkylcarbocyclylthio, $C_3$-$C_{18}$ alkylheterocyclylthio, $C_4$-$C_{18}$ alkylheteroarylthio, $C_4$-$C_{18}$ alkylalkenylalkyl, $C_4$-$C_{18}$ alkylalkynylalkyl, $C_8$-$C_{24}$ alkylarylalkyl, $C_3$-$C_{18}$ alkylacylalkyl, $C_{13}$-$C_{24}$ arylalkylaryl, $C_{14}$-$C_{24}$ arylalkenylaryl, $C_{14}$-$C_{24}$ arylalkynylaryl, $C_{13}$-$C_{24}$ arylacylaryl, $C_7$-$C_{18}$ arylacyl, $C_9$-$C_{18}$ arylcarbocyclyl, $C_8$-$C_{18}$ arylheterocyclyl, $C_9$-$C_{18}$ arylheteroaryl, $C_8$-$C_{18}$ alkenyloxyaryl, $C_8$-$C_{18}$ alkynyloxyaryl, $C_{12}$-$C_{24}$ aryloxyaryl, $C_7$-$C_{18}$ arylacyloxy, $C_9$-$C_{18}$ arylcarbocyclyloxy, $C_8$-$C_{18}$ arylheterocyclyloxy, $C_9$-$C_{18}$ arylheteroaryloxy, $C_7$-$C_{18}$ alkylthioaryl, $C_8$-$C_{18}$ alkenylthioaryl, $C_8$-$C_{18}$ alkynylthioaryl, $C_{12}$-$C_{24}$ arylthioaryl, $C_7$-$C_{18}$ arylacylthio, $C_9$-$C_{18}$ arylcarbocyclylthio, $C_8$-$C_{18}$ arylheterocyclylthio, and $C_9$-$C_{18}$ arylheteroarylthio.

Still more preferably, the or each linking group is a multivalent form of a group selected from alkyl (e.g. $C_1$-$C_{18}$, $C_1$-$C_5$, $C_8$-$C_{18}$, or $C_9$-$C_{18}$), aryl (e.g. $C_6$-$C_{18}$), heteroaryl (e.g. $C_3$-$C_{18}$), carbocyclyl (e.g. $C_3$-$C_{18}$), heterocyclyl (e.g. $C_2$-$C_{18}$), alkylaryl (e.g. $C_7$-$C_{24}$), alkylheteroaryl (e.g. $C_4$-$C_{18}$), alkylcarbocyclyl (e.g. $C_4$-$C_{18}$), and alkylheterocyclyl (e.g. $C_3$-$C_{18}$). The linking group or groups may comprise branched- or straight-chain oligomers or polymers, steroidal moieties, peptides, and the like In the lists above defining multivalent groups from which the or each linking group may be selected, each alkyl, alkenyl, alkynyl, aryl, carbocyclyl, heteroaryl, and heterocyclyl moiety may be optionally substituted. For avoidance of any doubt, where a given linking group contains two or more of such moieties (e.g. alkylaryl), each of such moieties may be optionally substituted with one, two, three or more optional substituents as herein defined.

In the lists above defining multivalent groups from which the or each linking group may be selected, where a given linking group contains two or more subgroups (e.g. [group A][group B]), the order of the subgroups is not intended to be limited to the order in which they are presented. Thus, a linking group with two subgroups defined as [group A][group B] (e.g. alkylaryl) is intended to also be a reference to a linking group with two subgroups defined as [group B][group A] (e.g. arylalkyl).

The or each linking group may be branched and/or optionally substituted. Where the or each linking group comprises an optionally substituted alkyl moiety, a preferred optional substituent includes where a —$CH_2$— group in the alkyl chain is replaced by a group selected from —O—, —S—, —C(O)— (i.e. carbonyl), —C(O)O— (i.e. ester), and —C(O)NR$^a$— (i.e. amide), where R$^a$ may be selected from hydrogen, alkyl, alkenyl, alkynyl, aryl, carbocyclyl, heteroaryl, heterocyclyl, arylalkyl, and acyl.

The anionic conjugates of the present invention preferably mimic the function of a GAG in the interaction between a GAG and a GAG receptor of, for example, a protein. Accordingly, the anionic conjugates may comprise at least one ligand domain which facilitates binding between the conjugate and a GAG receptor. In preferred embodiments the anionic conjugate comprises multiple ligand domains.

Linking groups preferably do not interact with the GAG receptor. Linking groups may affect the geometry, size, flexibility or rigidity, hydrophilicity and hydrophobicity of the anionic conjugate. Accordingly, linking groups are preferably chosen to maximize a given biological effect. In this regard, linking groups can be considered as a "framework" on which ligand domains are arranged in order to orient the ligand domains to produce a multibinding agent. The relative orientation within the conjugate of the ligand domains may depend on the particular point or points of attachment of the ligand domains to the linking group, and on the geometry of the framework. Knowledge of the structure-activity relationship between the GAG (or GAGs) wishing to be mimicked and/or congeners and/or structural information about ligand-receptor complexes (e.g., from X-ray crystallography, NMR) may influence the choice of linking group.

Different orientations of ligand domains within the conjugate can be achieved through choice of mono- or polycyclic linking groups, including aryl and heteroaryl groups, or structures incorporating one or more unsaturated carbon-carbon bonds (i.e., alkenes and alkynes). In some embodiments, the inclusion of cyclic groups (e.g., aryl, heteroaryl, cycloalkyl, heterocycles, etc.) imparts rigidity on the conjugate. In preferred embodiments, the cyclic group is a six- or ten-membered ring. The cyclic group may preferably be an aromatic group (for example phenyl or naphthyl).

The identification of an appropriate framework geometry for ligand domain presentation may be an important consideration in the construction of an anionic conjugate of the present invention. Systematic spatial searching strategies can be used to aid in the identification of preferred frameworks for GAG mimics. Accordingly, molecular design may aid in the design of the conjugates of the present invention.

Examples of linking groups are shown below (each M is the same or different and refer to glycosylated bacterial metabolites which may be ligand domains for binding to GAG receptors):
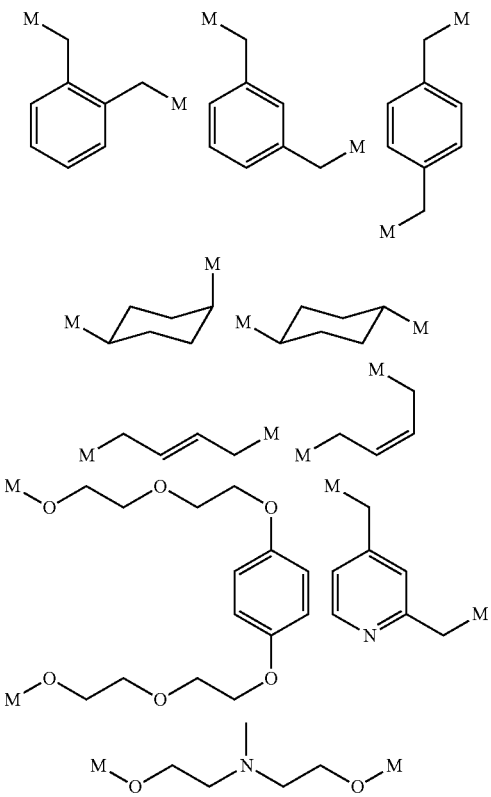

The linking groups shown above may further form part of a larger linking group, such that the spatial arrangement of the ligand domains is substantially determined by the substitution pattern of, for example, a phenyl group in the above linking groups.

The or each linking group may be independently selected from trivalent groups, for example:

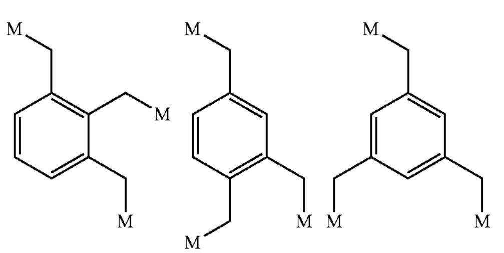

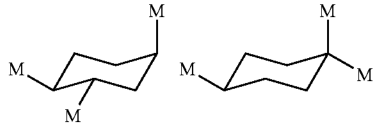

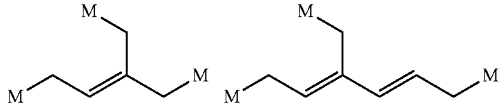

-continued

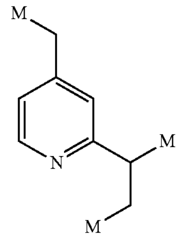

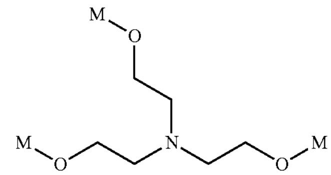

Cyanuric chloride based trivalent linking groups are preferred. Cyanuric chloride can be selectively functionalized by manipulation of pH and temperature. The ligand domains may be bound to the cyanuric core directly or via other groups.

Tetravalent and higher order linking groups may also be used. Tetravalent linking groups may be prepared by linking two trivalent linking groups by a bond or bridging group.

Linking groups may comprise one or more ancillary groups which may, for example, modulate the solubility of the multibinding agent (in water, fats, lipids, biological fluids, etc.), hydrophobicity, hydrophilicity, linker flexibility, antigenicity, molecular size, molecular weight, in vivo half-life, in vivo distribution, biocompatability, immunogenicity, stability, and the like.

Examples of groups that enhance the water solubility/hydrophilicity of the linking group are poly(ethylene glycol), alcohols, polyols (e.g., glycerin, glycerol propoxylate and saccharides such as mono-, oligo- and polysaccharides), carboxylates, polycarboxylates (e.g., polyglutamic acid, polyacrylic acid, etc.), amines, polyamines (e.g., polylysine, poly (ethyleneimine), etc). In preferred embodiments, the ancillary group used to improve water solubility/hydrophilicity will be a polyether. In particularly preferred embodiments, the ancillary group will be a poly(ethylene glycol).

Lipophilic ancillary groups may be incorporated into the linking group in order to enhance the lipophilicity and/or hydrophobicity of the anionic conjugates. Examples of such groups are optionally substituted alkyl, aryl and heteroaryl groups.

The flexibility of the linking group may be reduced by the inclusion of ancillary groups which are rigid and/or bulky. The presence of rigid or bulky groups may hinder free rotation about bonds in the linking group. Examples of rigid groups are those groups whose conformational flexibility is restrained by the presence of rings and/or multiple bonds, for example, aryl, heteroaryl, cycloalkyl and/or heterocyclic. Other groups which may impart rigidity include polymeric groups such as oligo- or polyproline chains. Rigidity may also be imparted by internal hydrogen bonding. Examples of bulky groups include large atoms and/or ions (e.g., iodine, sulfur, metal ions, etc.), polycyclic groups (including aromatic groups and non-aromatic groups) and groups comprising one or more alkenic and/or alkynic bonds. Bulky groups may also include oligomers and polymers which are branched- or straight-chain species. Species that are branched are expected to increase the rigidity of the structure more per unit molecular weight gain than are straight-chain species.

The antigenicity of the anionic conjugates may be eliminated or reduced as a result of the choice of linking group(s). In certain applications, the antigenicity of the anionic conjugate may be reduced or eliminated by the use of poly(ethylene glycol) linkers.

The preferred linker length will vary depending upon the distance between adjacent ligand recognition sites, and the geometry, flexibility and composition of the linker. The length of the linker will preferably be in the range of about 2-100 Å, more preferably about 2-50 Å.

The choice of functional groups on the linking group may be made with respect to the functionality present within the glycosylated bacterial metabolites (or modified bacterial metabolites) so as to facilitate conjugation. Such a choice of functional group on the linking group will be made routinely by those skilled in the art. The molecules to be conjugated may be covalently bonded to the linker or linkers using conventional chemical techniques, for example reaction between a carboxylic acid and an amine to form an amide, an amine and a sulfonyl halide to form a sulfonamide, an alcohol with an alkyl or aryl halide to form an ether, and so on. Glycosylated bacterial metabolites containing a saccharide moiety with a free reducing terminus (for example a hemiacetal or hemiaminal functionality) may be coupled through this group. The greater nucleophilicity of an amine group compared with an hydroxyl group, may obviate the need for protection and deprotection steps of, for example, the hydroxyl groups.

The glycosylated bacterial metabolites may be "optionally modified" prior to conjugation. Examples of such modifications are: chain shortening (such as oligosaccharide chain shortening); chain extension (such as oligosaccharide chain extension) oligosaccharide chain exchange (either in part or wholly, for example trans-glycosylation), N-acetylation and functional group interconversions (such as the conversion of a primary alcohol to an azide or the conversion of an alkenic moiety to an epoxide). Whilst some glycosylated bacterial metabolites may of themselves possess functionality which facilitates the conjugation of 2 or more such compounds, some glycosylated bacterial metabolites may be modified prior to conjugation to facilitate conjugation. Even those glycosylated metabolites that possess functionality which facilitates the conjugation of 2 or more such compounds may be modified to facilitate conjugation via a different type of linking group. Hydrolysis of one or more glycosidic linkages to expose the reducing terminus of a reducing sugar as a reactive handle is an example of a modification which may facilitate conjugation. It will be understood that the modification of a glycosylated bacterial metabolite prior to conjugation may produce one or more compounds which, of themselves, are no longer considered as glycosylated bacterial metabolites per se—such as the products formed from cleavage of the aglycone and glycone portions of a glycoside. Nonetheless, the one or more compounds produced from modification of a glycosylated bacterial metabolite prior to conjugation, are portions of a glycosylated bacterial metabolite and fall within the scope of the expression "glycosylated bacterial metabolite" as it is used herein.

There are many different coupling agents which may be used to couple two or more molecules together. Examples of such agents are (poly)ethyleneglycol, carbohydrates, alkyl groups, aryl groups, polyamino groups and heterocyclic groups. The length of the chemical moiety which couples the glycosylated products together may be varied. Examples of multi-functional groups suitable for coupling glycosylated products together include those based upon the alkyltriamines [such as $(H_2N(CH_2)_n)_2NH$ where n is an integer preferably from 2 to 6] and triazines such as cyanuric chloride. Modification of the free reducing terminus of a sugar moiety may facilitate conjugation through other linking groups. Shown below is the modification of the free reducing terminus of acarbose to produce an alkyl bromide, and subsequent conjugation of two of the derivatives via a thioether based linking group.

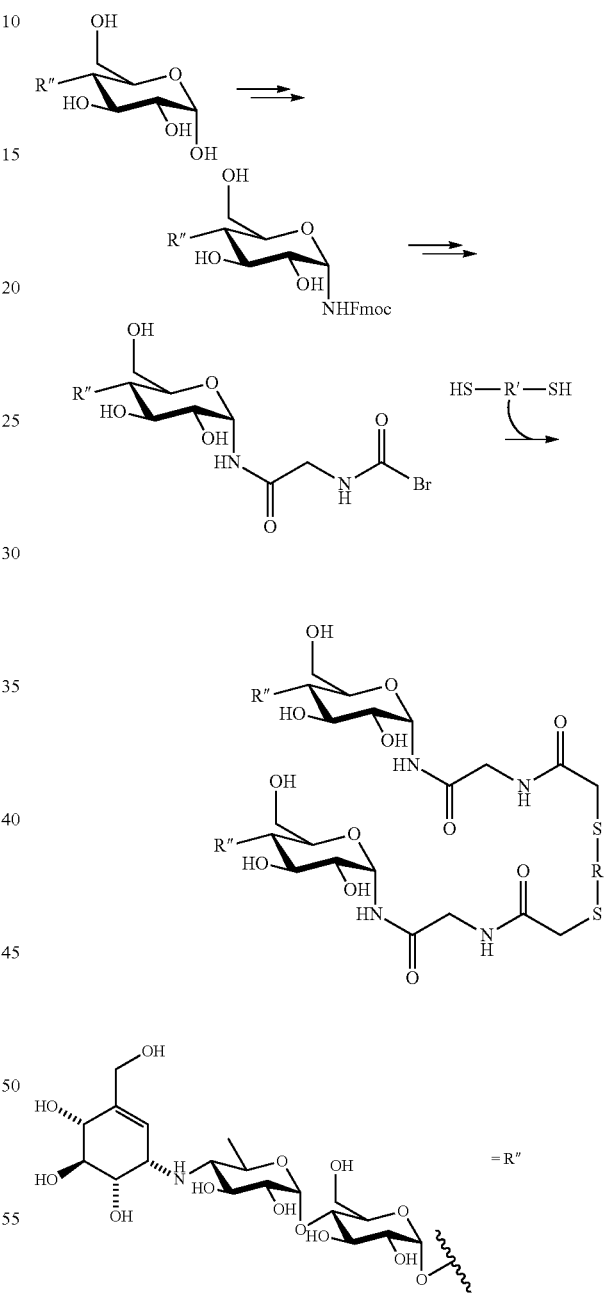

Metabolites possessing unsaturation (for example sisomicin and netilmicin) may be coupled through that moiety. An example of this mode of coupling is the UV catalysed addition of a dithiol agent across the unsaturation in the $C_7N$ cyclitol portion of members of the trestatin family of compounds (notably, the trestatins are non-reducing sugars and hence the aglycone is the preferred means to conjugate these types of molecules):

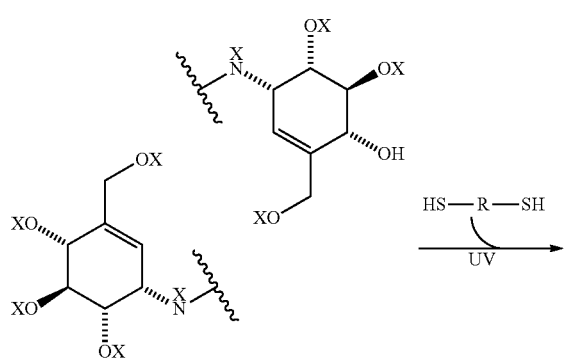

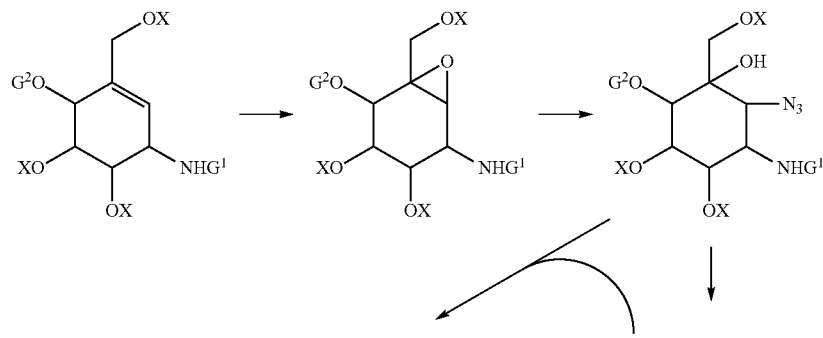

Some glycosylated bacterial metabolites possess epoxide functionality which provides a handle for further manipulation and/or conjugation. For example, ring-opening of epoxides can be accomplished with a variety of reagents and is even possible with thiols and amines using water as a co-solvent.

Alkenes and epoxides (and other strained 3-membered rings systems such as aziridines and episulfides) bear a close relationship because alkenes can be readily converted to these 3-membered ring systems. Shown below is a representative scheme for the conversion of an alkene into an azide which may be used to react with a similarly prepared acetylenic compound. These two compounds may undergo a 1,3-dipolar cycloaddition reaction to produce the conjugate shown. These, and other, concepts form the basis for the chemistry which has come to be known as "click" chemistry (see for example: Kolb, H. C., M. G. Finn, and K. B. Sharpless, *Click Chemistry: Diverse Chemical Function from a Few Good Reactions*. Angew Chem Int Ed Engl, 2001. 40(11): p. 2004-2021).

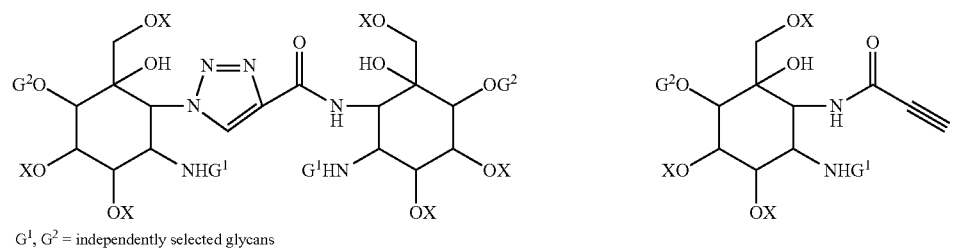

$G^1, G^2$ = independently selected glycans

-continued

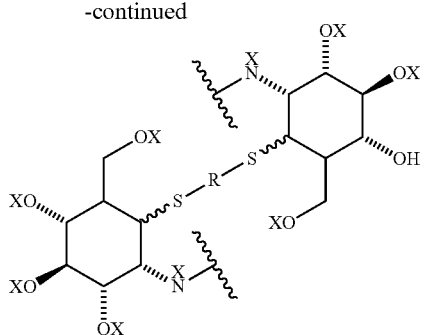

Another example of a glycosylated bacterial metabolite being modified to facilitate conjugation is the cleavage of the cyclitol residue from $C_7N$ cyclitol metabolites to generate a pseudo-oligosaccharide or oligosaccharide of lesser degree of polymerization comprising a primary amine terminus, and is shown below. The chain shortening may be accomplished by cleavage of a C—N bond using known methods such as: catalytic hydrogenation; oxidation with subsequent hydrolysis of the resultant imine; and enzymatic cleavage (with, for example, a C—N lyase).

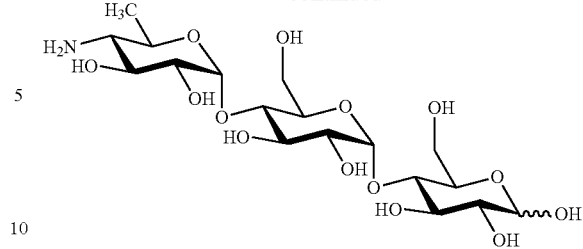

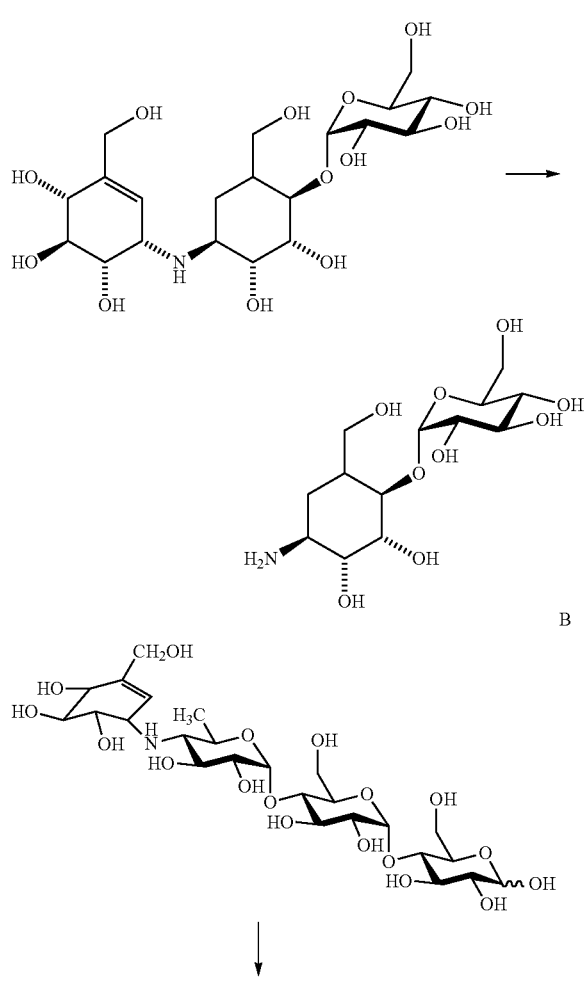

Chain shortening of validamycin, a pseudo-disaccharide with a 1-aminocyclitol, generates (A). Chain shortening of acarbose, a trisaccharide with a 4,6-dideoxy-4-aminoglucose residue at the non-reducing terminus, generates (B). Accordingly for acarbose, for example, this approach can be used to generate an oligosaccharide with a reactive handle at each end—being the reducing terminus, and a 4-deoxy-4-amino functionalised non-reducing terminus. These functional groups facilitate the head-to-tail construction of longer chain conjugates.

A similar modification strategy can be used to generate pseudo-oligosaccharides terminating with a cyclitol at the pseudo-reducing terminus. The choice of conditions to effect the cleavage, as well as the chosen isolation/purification conditions, will determine the substituents borne by the cylcitol residue. In the following two examples, an amine functionality or an α,β-unsaturated ketone may be formed. These are both useful functional groups that may facilitate subsequent conjugation.

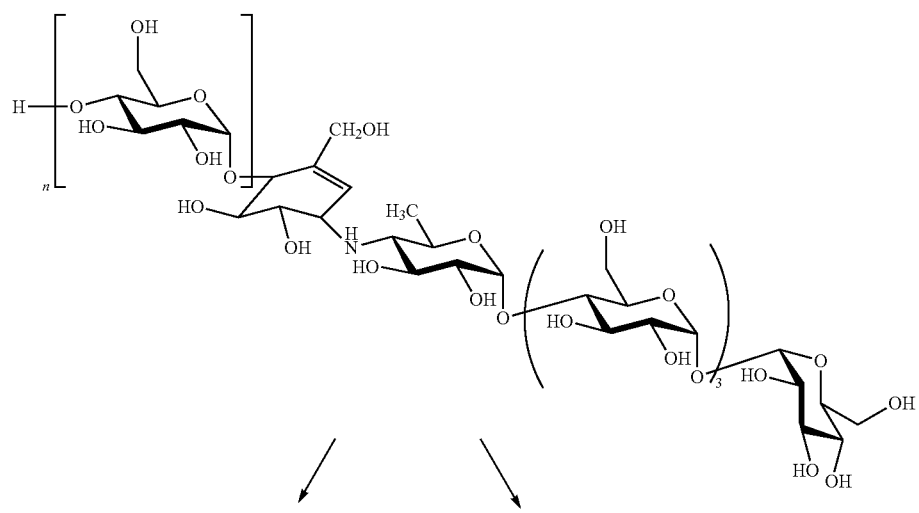

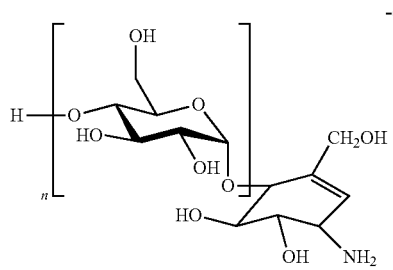
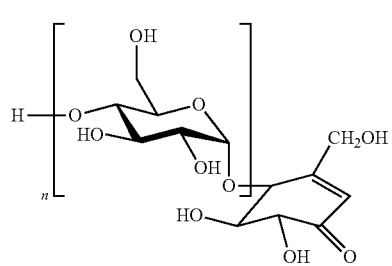
The ability to modify a glycosylated bacterial metabolite to produce a product comprising two attachment points enables the head-to-tail assembly of conjugates. In conjunction with an appropriate orthogonal protecting group strategy ($R_1$ and $R_2$), the trisaccharide derived from acarbose may be coupled in a head-to-tail fashion:
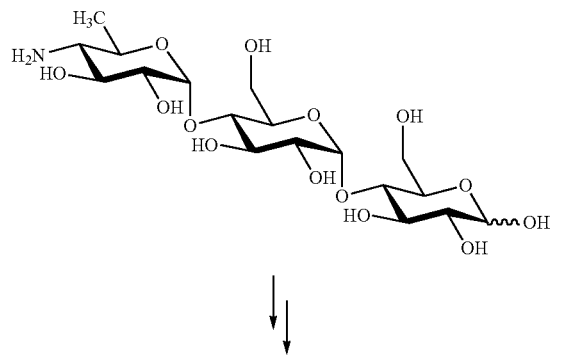
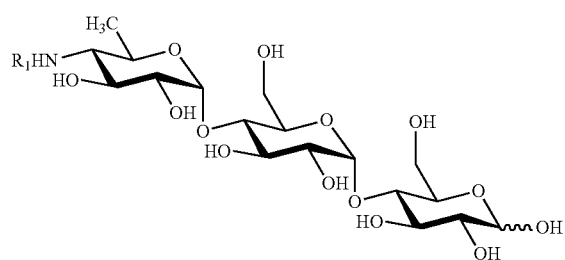
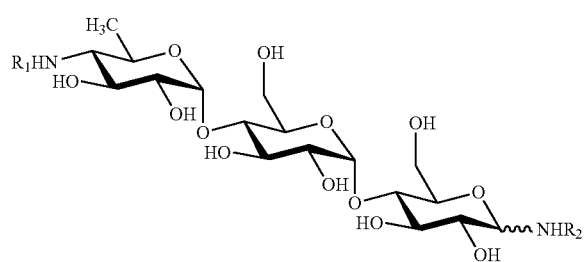

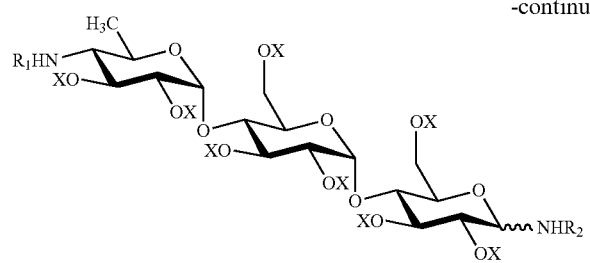

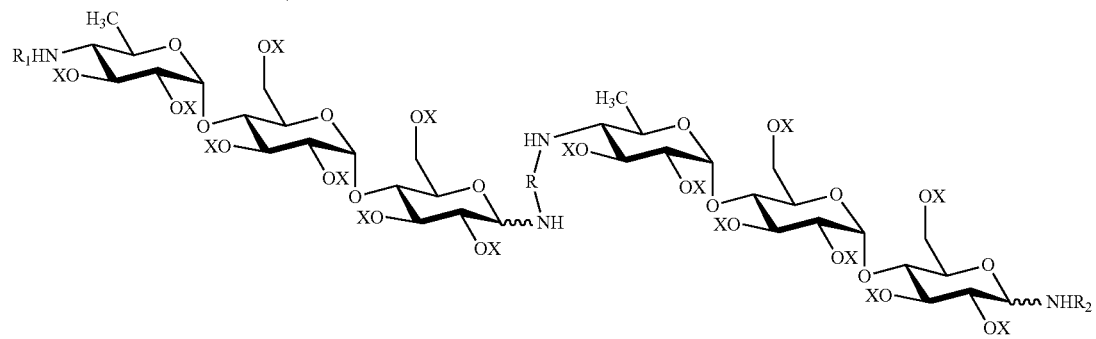

By extension of this procedure a 3 segment neo-nonasaccharide may be prepared:

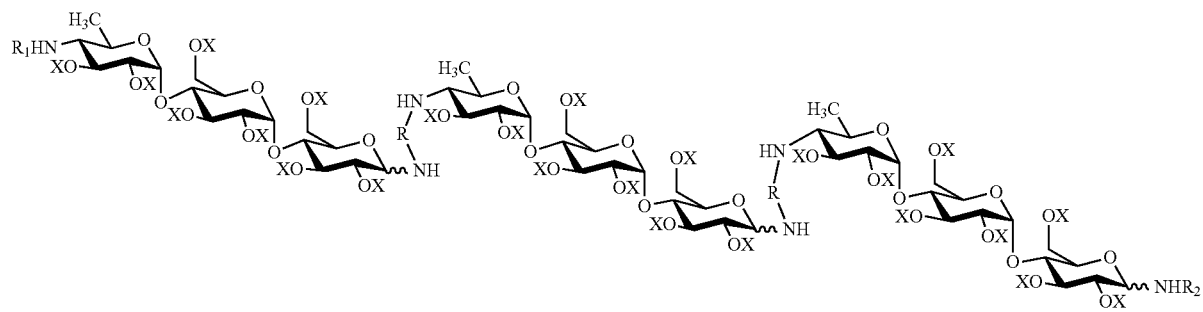

Furthermore, conjugation of 2 or more glycosylated bacterial metabolites may be achieved using such techniques as solid phase chemistry and fluorous tagging.

The structural characteristics of the moenomycins provide numerous options for conjugation. For example, ozonolysis of the aglycone of moenomycin A generates a modified glyscosylated bacterial metabolite comprising an aldehyde functional group which may be used to facilitate conjugation. Alternatively, hydrolysis or enzymatic cleavage of the phosphate group may be used to liberate the pentasaccharide portion of moenomycin. These two modifications are shown below:

33 34

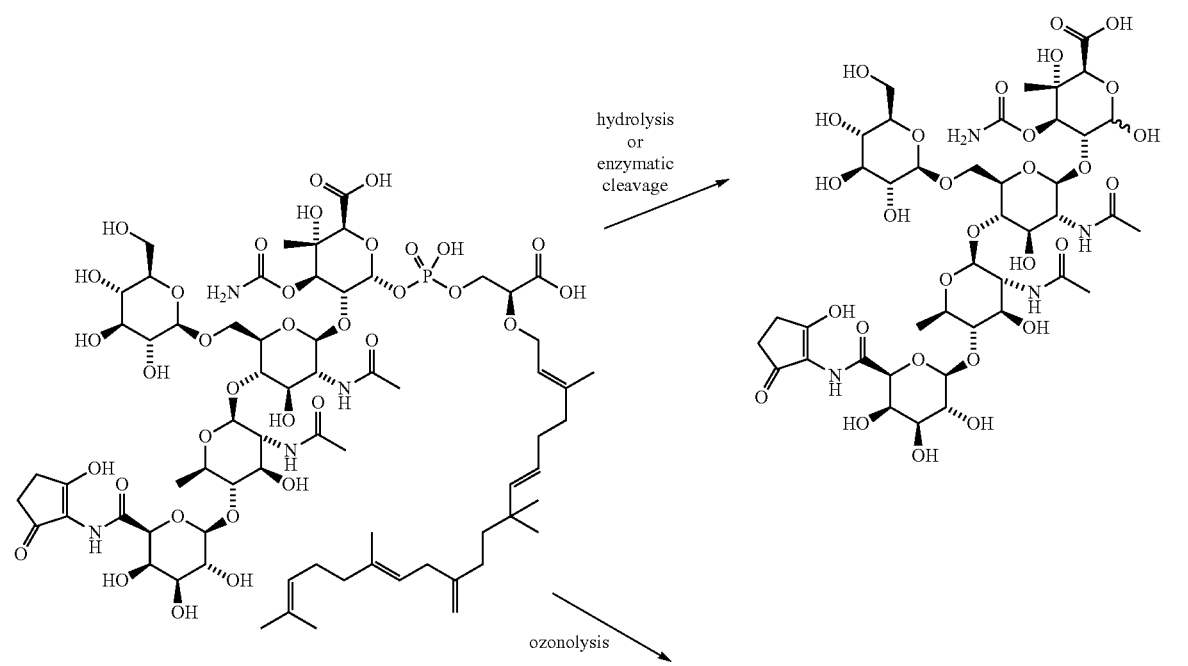

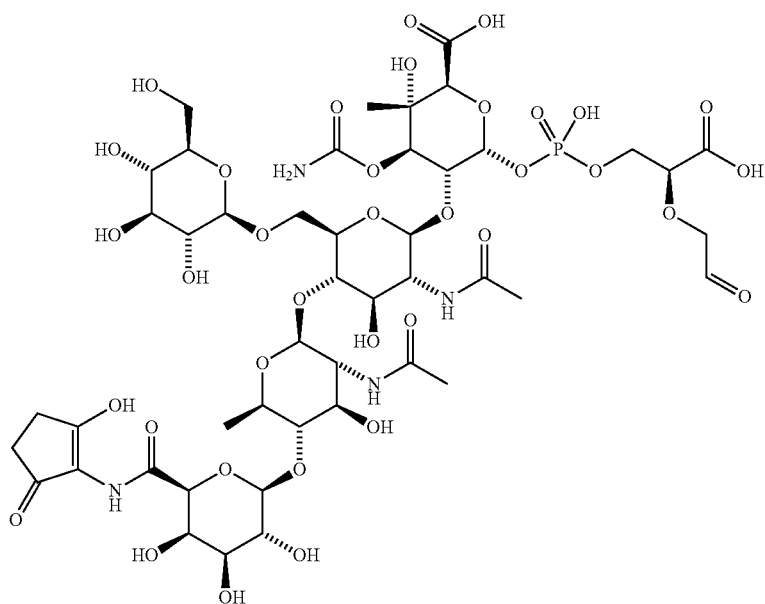

The cylopentanedione ring of moenomycin may also be used as a handle to facilitate conjugation. For example, reaction of a diazonium salt (which may form part of a linking group for example) with the cylopentanedione ring of moenomycin produces a triazole after rearrangement. In the following example the R substituent may comprise a glycosylated bacterial metabolite.

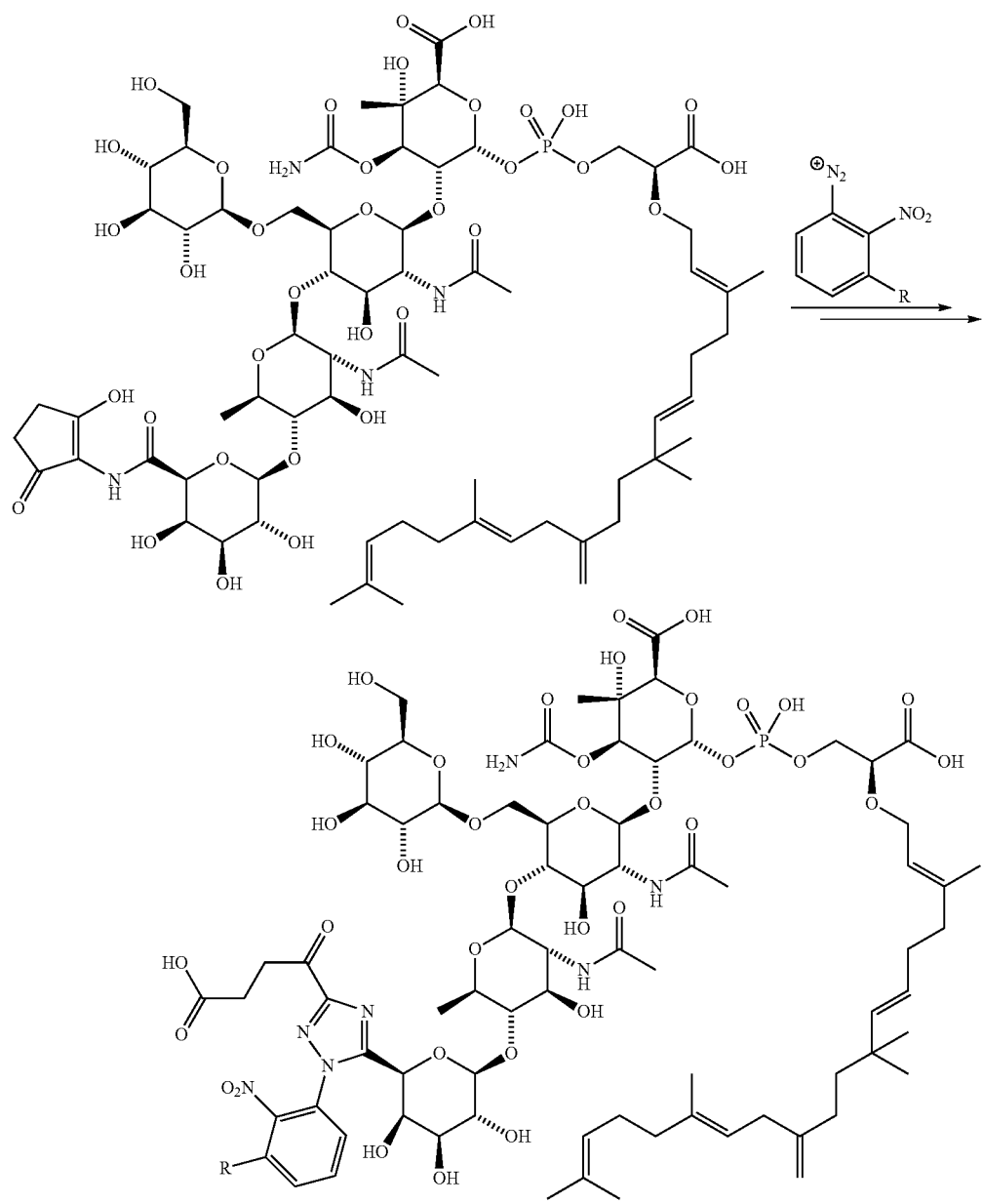
Conjugated glycosylated bacterial metabolites (Michael, K., H. Wang, and Y. Tor, *Enhanced RNA binding of dimerized aminoglycosides.* Bioorg Med Chem, 1999. 7(7): p. 1361-71) suitable for the formation of the anionic conjugates of the present invention are shown below:
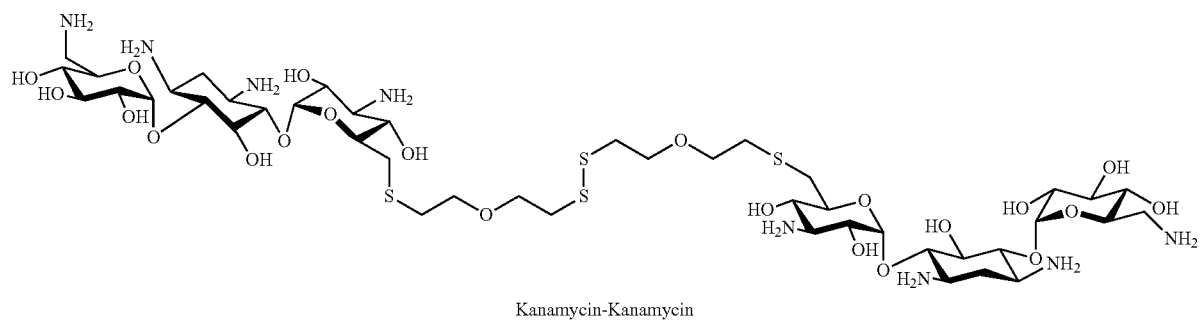
Kanamycin-Kanamycin -continued
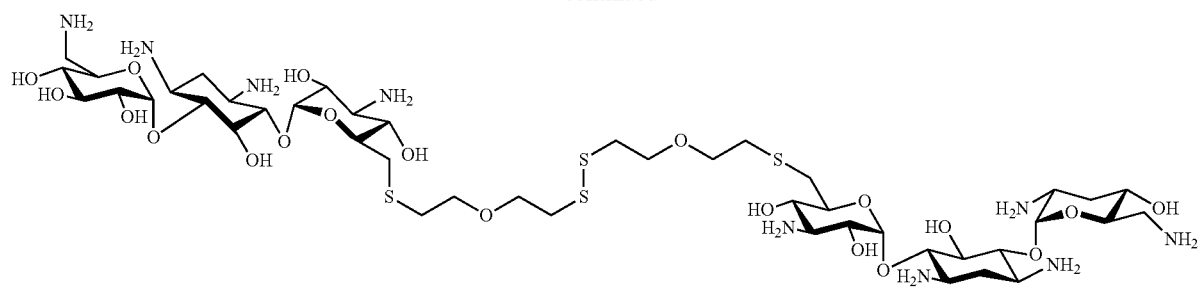
Kanamycin-Tobramycin
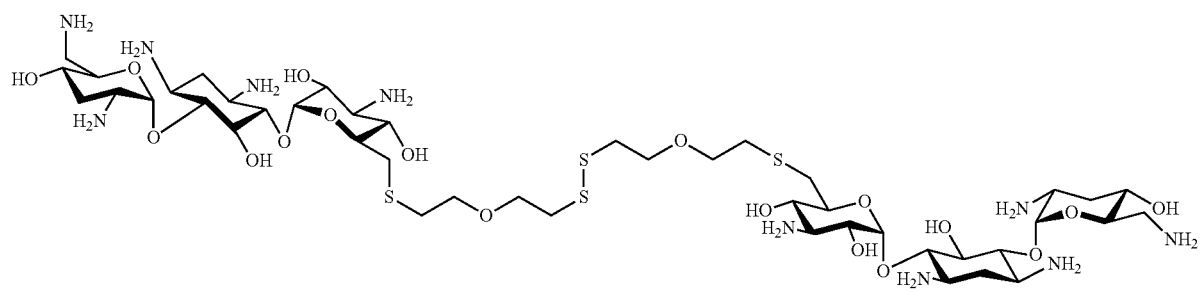
Tobramycin-Tobramycin
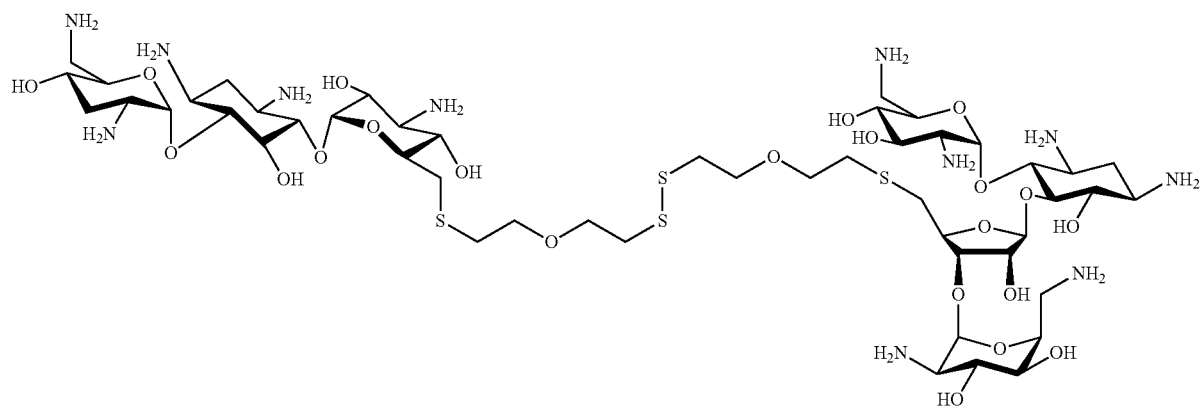
Tobramycin-Neomycin
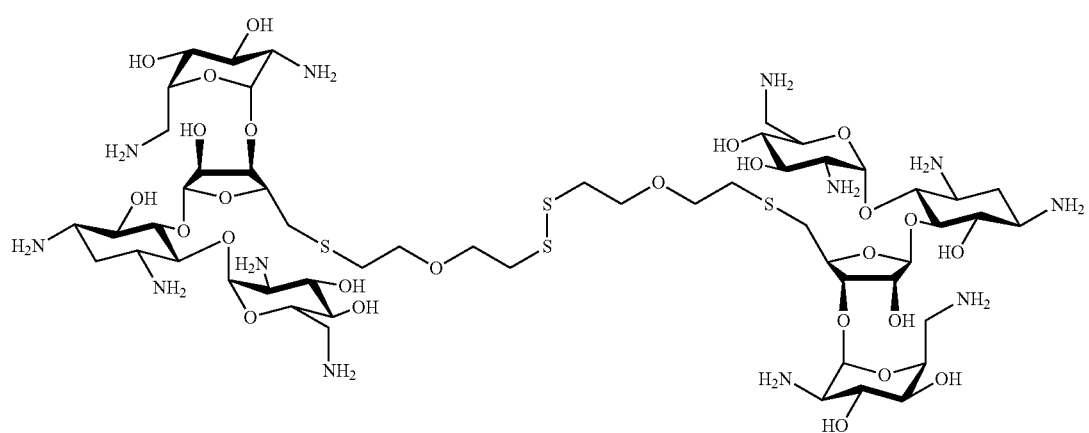
Neomycin-Neomycin A number of semi-synthetic antibiotics are known, including: amikacin (U.S. Pat. Nos. 4,902,790; 5,656,735; 5,763,587); dibekacin (U.S. Pat. No. 5,618,795); arbekacin; netilmicin (U.S. Pat. No. 4,831,123); and isepamicin (U.S. Pat. Nos. 4,230,847 and 5,442,047):

| antibiotic | derived from | derivatised moiety |
|---|---|---|
| amikacin | kanamycin A | $N^1$-aminohydroxybutanamide |
| dibekacin | kanamycin B | 3',4'-dihydroxy |
| arbekacin | dibekacin | $N^1$-aminohydroxybutanamide |
| netilmicin | sisomicin | $N^1$-ethyl |
| isepamicin | gentamicin B | $N^1$-aminohydroxypropanamide and $N^{3''}$-acetyl |

The present invention contemplates using the intermediates in the syntheses of these compounds as modified glycosylated bacterial metabolites in the preparation of anionic conjugates.

Another approach to preparing the conjugates of the present invention is to couple the glycosylated bacterial metabolites through a non-amino group, whilst concurrently using a selective amine group protection/deprotection strategy to modulate the degree of N-sulfation, for instance. In this respect, conjugates of neomycin may be prepared via Mitsunobu reaction of the fully N-protected derivative, wherein there is at least one unprotected hydroxyl group, thereby producing an epoxide intermediate on the ido ring. Subsequent azide opening affords the 3'''-azido functionalized derivative and access to "click" chemistry (R=protecting group):

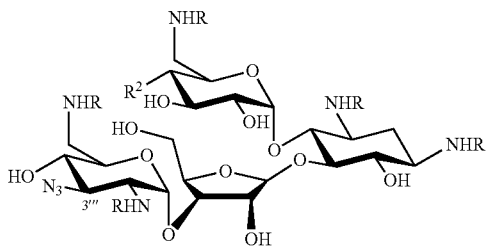

An alternative route is the selective reaction of the primary alcohol group of N-Boc protected derivative neomycin (for example) with triisopropylbenzenesulfonyl chloride, which upon azide displacement also yields a product which may be used in "click" chemistry (R=Boc):

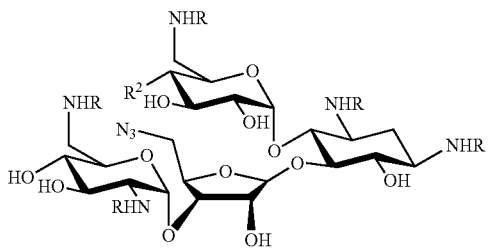

These two routes to monofunctionalized neomycin demonstrate how sulfate distribution can be explored in structure-function studies. Note how the lower structure can yield a single O-sulfated ribose ring and doubly sulfated ido ring, whereas the upper structure can yield a singly O-sulfated ido ring and doubly sulfated ribose. Further variations of the sulfation density and patterns can be made by the addition of N-sulfation at all or specific amine groups.

Linear assembly of the anionic conjugates of the present invention may utilise the orthogonal reactivity of two moieties. For example, this can be achieved using the two routes to monofunctionalization of neomycin which are shown above sequentially. In addition, a third route may involve performing the Mitsunobu reaction on the bisanhydro product (i.e. epoxide and aziridine derivative).

Selective manipulation of the acylation of neamine, which forms the core of neomycin B, can be achieved by using mixtures of transition metals (Haddad, J., M.-Z. Liu, and S. Mobashery, *Synthesis of Aminoglycoside Antibiotics*, in *Glycochemistry:Principles, Synthesis and Applications*, P. G. Wang, Bertozzi, C. R., Editor. 2001, Marcel Dekker: New York.) Accordingly, by extension to neomycin B a further array of N-protected derivatives can be generated which allows sulfation of the unprotected amines.

Glycosylated bacterial metabolites of the glycosyl nucleoside antibiotic family are preferably conjugated through the aglycone portion. For adenomycin this can be achieved by selective reaction at the adenine amine whilst the gulosamine amine is masked. The ribofuransoyl maleimide, showdomycin, can be incorporated into known maleimide polymerizations to yield polymeric derivatives. The tunicamycin type antibiotics may also be conjugated through the unsaturated lipid moiety.

Glycosylated bacterial metabolites of the glycopeptide antibiotic, glycosylated macrolide antibiotic and avermectin families may be transformed to introduce anionic groups in the non-cyclitol aglycone portion as well as the glycone portion. Linked (dimeric and higher order) forms of these anionic conjugates can also be prepared.

The anionic conjugates of the present invention may be represented by formula I:

wherein: n is a positive integer;
for a given n, there are n-1 successive values for i starting from 2 in the series 2, 3, . . . , n;
each M is independently a glycosylated bacterial metabolite or modified glycosylated bacterial metabolite;
the or each L is a linking group.

Examples of compounds which fit into the above formula are:
n=1: $M^1L^1$-$M^2$
n=2: $M^1L^1$-$M^2L^2$-$M^3$
n=3: $M^1L^1$-$M^2L^2$-$M^3L^3$-$M^4$
and so on.

Each linking group ($L^i$) may be the same or different and may further comprise one or more glycosylated bacterial metabolites. In this way complex molecular architectures may be prepared using linking groups of valencies greater than 2. An example of such a molecular architecture is a star shaped conjugate.

Derivatisation of amino and/or hydroxyl groups is a preferred method of preparing anionic conjugates of glycosylated bacterial metabolites, and in particular imparting a net negative charge on a material. Accordingly, polyaminated and polyhydroxylated glycosylated bacterial metabolites are preferred glycosylated bacterial metabolites for use in the present invention.

The conjugates of the present invention may comprise one or more of the following preferred functional groups: sulfur based groups such as —SO$_2$OH, —OSO$_2$OH, —OSO$_2$H, —SO$_2$H and —OSO$_2$—; and phosphorous based groups such as: —OPO$_2$OH, —OP(S)(OH)$_2$, —OP(O)(OR)$_2$, —OP(S)(OR)$_2$, —OP(O)OHR, —OP(S)OHR, —OP(O)OR$_1$R$_2$, —OP(S)OR$_1$R$_2$, —OP(S)(OH)(SH) and cyclic phosphate. It will be understood that a number of the functional groups above may be readily deprotonated and will become anionic in aqueous solution at, for example, a pH of 5. Other functional groups shown above are neutral (e.g. —OSO$_2$— and —OP(O)(OR)$_2$) and accordingly can be used in combination with anionic functional groups to control the degree of anionic character present within the conjugate.

Preferred anionic derivatives of hydroxyl groups include sulfate and phosphate groups. In particular, it will be understood that in aqueous solution at pH 5, sulfate and phosphate groups are anionic groups as defined herein.

It will be understood that the person skilled in the art will be familiar with many of the nitrogen analogs of the functional groups shown, which may be prepared from transformation of the corresponding amine. For example, the primary amine analog of the hydroxyl derived —OPO$_2$OH group is the —NHPO$_2$OH group.

Methods for the sulfation of hydroxyl and amino groups are known in the art, including methods for the selective sulfation of either primary hydroxyls or secondary hydroxyls or amino groups or combinations thereof.

It is understood that the person skilled in the art would be familiar with techniques which allow the selective modification of "sulfatable" groups within the glycosylated products of actinobacteria. For example, the molecules may undergo:
1) Complete sulfation of both amine and hydroxyl groups;
2) Specific sulfation at amine groups; or
3) Specific sulfation at hydroxyl groups can be achieved by prior blocking of amino groups or by specific de-N-sulfation after complete O- and N-sulfation.

Whilst the invention contemplates transforming the hydroxyl and/or amino groups of the glycosylated bacterial metabolites to anionic groups before and/or after preparing the conjugate, it is preferable to do so before formation of the conjugate. One reason for such a preference is to assist with controlling the homogeneity of the final product.

Without wishing to be bound by theory, it is believed that by coupling smaller anionic molecules together to form larger anionic molecules, greater control over the products and the degree of homogeneity is achieved. For example, the sulfation of small oligosaccharides (disaccharides to tetrasaccharides), containing 3 "sulfatable" groups per residue, proceeds to completion. On the other hand, sulfation of larger oligosaccharides is a more difficult process, and typically a heterogeneous mixture of undersulfated species is obtained. It is believed that in the larger systems, the extent of heterogeneity appears to be related to the number, or density, of sulfate groups—the more "sulfatable" groups that are present, the more heterogeneous the mixture. As an example, of the two pentasaccharides, Arixtra® and sulfomaltopentaose, the former contains 8 sulfate groups and is readily obtained in pure form, whereas the maltopentaose, which has 16 sulfatable groups, is obtained as a mixture. Furthermore, in the sulfation of the nonasaccharide Trestatin A, the average degree of sulfation obtained is 2.4 of a possible 3 per sub-unit (ignoring the reducing terminus), which equates to approximately 22 sulfate groups/molecule. Assuming sulfation is a stochastic event, and using the Poisson distribution to calculate the distribution of molecules with the designated number of sulfates, it would appear that the mixture contains molecules with between 14 and 27 sulfate groups. Moreover, except for the per-sulfated molecule, there are a very large number of possible isomers for each sulfated species—for example the number of isomers for the species containing 22 sulfate groups is 81,000. As can be seen, the sulfation of oligosaccharides of even modest length (nonasaccharide) can generate complex mixtures.

On the other hand sulfation of a trisaccharide, which may contain a total of 9 "sulfatable" groups, produces a mixture being 98% pure with respect to the persulfated trisaccharide. Coupling three such sulfated trisaccharides together produces a persulfated neo-nonasaccharide (27 sulfate groups) with a purity of 94%. Furthermore, the number of possible isomers for the undersulfated species is also reduced.

The present invention provides processes for preparing large numbers of structurally diverse anionic conjugates which may form the basis for libraries of GAG mimetics. The anionic conjugates may have applications in the treatment of diseases that involve interaction between GAG-like molecules and one or more ligands. Preferred diseases include: inflammatory or allergic diseases; metastatic cancers; and infection by a pathogenic agent. Particularly preferred diseases are: asthma; allergic respiratory disease; allergic rhinitis; subepithelial fibrosis in airway hyperresponsiveness; chronic sinusitis; perennial allergic rhinitis; allergic bronchopulmonary aspergillosis in cystic fibrosis patients; COPD; eosinophilic bronchitis; brochiectasis; bronchospasm; bronchial constriction; bronchial hyperreactivity; and bronchial hypertrophy.

Preferably, the ligand is a peptide, polypeptide or protein although the present invention extends to the ligand being a carbohydrate, lipid, glycoprotein or a molecule obtained from natural product screening or from a chemical library. Suitable protein targets include those that have been described as GAG (heparin, heparin sulphate, chondroitin and hyaluronan) binding proteins. Examples of protein ligands include, but are not limited to: a cytokine including an interleukin (e.g. IL-1, IL-2, IL-3, IL-4, IL-5, IL-6, IL-7, IL-8, IL-9, IL-10, IL-11, IL-12, IL-13, IL-14 or IL-15), interferon (e.g. α-interferon, β-interferon, γ-interferon) or a growth factor including but not limited to G-CSF, M-CSF, GM-CSF, BDNF, CNTF, EGF, EPO, FGF1, FGF2, FGF3, FGF4, FGF5, FGF6, FGF7, FGF8, FGF9, FGF10, FGF11, FGF12, FGF12, FGF13, FGF14, FGF15, FGF16, FGF17, FGF18, FGF19, FGF20, FGF21, FGF22, FGF23, LIF, MCP1, MCP2, MCP3, MCP4, MCP5, M-CSF, MIP1, MIP2, KC, NGF, NT 3, NT4, NT5, NT6, NT7, OSM, PBP, PBSF, PDGF, PECAM-1, PF4, RANTES, SCF, TGFα, TGFβ$_1$, TGFβ$_2$, TGFβ$_3$, TNFα, TNFβ, TPO, VEGF, GH, insulin and the like; an enzyme (e.g. superoxide dismutase, eosinophilic cationic protein, tryptases, elastases, phospholipase A2 or prostaglandin endoperoxide); chemokines such as eotaxin (eotaxin-1, -2 or -3); or a soluble or cell- or virus-bound receptor (e.g. inositol triphosphate receptor).

The interaction with a ligand may be by any convenient means such as gel retardation, filter retardation, affinity co-electrophoresis, bioluminescent resonance energy transfer (BRET) assays, fluoresence resonance energy transfer (FRET) assays, fluorescence polarisation (FP) assays, scintillation proximity assays or immobilization to biochips or other surfaces including those coupled with mass spectrometric detection.

The latter may be accomplished by first immobilizing the anionic conjugate to a chip and then adding the ligand. Alternatively, the ligand may be immobilized to a chip and used to screen for the ability of an anionic conjugate to bind thereto.

Yet another alternative is to immobilize a GAG, such as heparin, to a solid support and then screen for the ability of an anionic conjugate to inhibit binding of a ligand to the immobilized heparin.

Accordingly, a particularly useful assay is to admix the ligand and the anionic conjugate and screen for the ability of the anionic conjugate to inhibit binding of the ligand to a GAG (e.g. heparin or heparan sulfate) bound to a chip.

Another aspect of the present invention contemplates, therefore, a method for producing a GAG mimetic that interacts with a ligand such as a protein, said method comprising producing a library of anionic conjugates of glycosylated bacterial metabolites and then screening each member of said library for an ability to interact with said ligand or to inhibit the interaction between the ligand and Heparin-like GAGs (HLGAGs) known to interact with said ligand.

In a preferred embodiment, the anionic conjugate binds a secreted cellular product which may be a protein and, in so doing, inhibits the interaction between the ligand and a GAG such as heparin.

There are, of course, any number of other assays, which may be used to screen for interaction between an anionic conjugate and a ligand or used to screen for inhibition of interaction between a ligand and a GAG known to bind to the ligand. Another assay is a filter binding assay. In this assay, one of an anionic conjugate, or a ligand is labelled with a reporter molecule capable of providing an identifiable signal such as a fluorescent dye and both molecules are allowed to interact in solution. The resulting mixture is then passed through a filter capable of retarding one of the anionic conjugate or anionic conjugate composite molecule or the ligand or only an anionic conjugate-ligand complex or anionic conjugate composite molecule-ligand complex.

In one embodiment, for example, the filter is a nitrocellulose filter which retards proteins. In this case, if the anionic conjugate, labeled with a reporter molecule, fails to pass through the filter, then the presence of the reporter signal in the filter indicates binding of the anionic conjugate to the protein.

In another embodiment, heparin or heparan sulfate is labeled with the reporter molecule and reacted with the protein in the presence of different anionic conjugates. Passage of heparin or heparan sulfate through the filter is indicative of an anionic conjugate that has inhibited the interaction between the heparin/heparan sulfate and the protein.

Different anionic conjugates will interact with different ligands, or different ligands will interact with different anionic conjugates or both. Accordingly, another assay involves the use of affinity columns carrying immobilized ligands. The anionic conjugates are then passed through the column and the presence of retardation of the anionic conjugates determined. A salt gradient is conveniently used to elute bound anionic conjugates. Once a fraction that binds to a ligand on a column is identified, the fraction can be further analyzed to obtain an indication of the number of different structural entities therein. Such analysis may comprise, for example, anion exchange chromatography, mass spectrometry or electrophoresis.

The present invention is not limited to any particular order of the steps described herein.

Once anionic conjugates that bind to a particular ligand have been identified, this fraction itself may be useful as a therapeutic to inhibit interaction between a protein (or other ligand) and a cell surface GAG (e.g. heparin or heparan sulfate). The protein (or other ligand) may be cell free or associated with a cell or virus such as a cell surface or viral surface. The said anionic conjugate may also be useful as a therapeutic to modulate interaction between a secreted cellular product and extracellular matrix components or between a cell surface protein and extracellular matrix components, or between a protein and its ligand, both or either of which may be cell surface or cell associated. Alternatively, the anionic conjugate may be used as a target to identify natural products or products from a chemical library that mimic the anionic conjugate in terms of binding to a ligand or that inhibits or promotes the interaction between the GAG and the ligand. These molecules may be antagonists or agonist or chemical analogs of the GAG. Hence, an "analog" extends to and encompasses any structure which is functionally equivalent in that it binds and/or modulates a ligand in an analogous manner.

Reference herein to "modulate" or "modulation" extends to and encompasses inhibiting and/or promoting an interaction.

Accordingly, another aspect of the present invention is directed to a method for generating a medicament for treating a disease condition in a subject, said method comprising producing a range of anionic conjugates according to the process of the invention, and screening each anionic conjugate for an ability to interact with or modulate the ligand. The anionic conjugate that interacts with or modulates the ligand is identified and using same or an analog, agonist or antagonist thereof in the manufacture of said medicament.

In one preferred embodiment, the modulation is an inhibition.

Types of ligands contemplated herein include those listed above such as PECAM-1, Cyclophilin A, gp120 and cytokines such as interleukin (IL)-1,2,3,4, 5, 6, 7, 8, 10, 11, 12 and 13, G-CSF, GM-CSF, LIF, and M-CSF and chemokines such as eotaxin-1, eotaxin-2 and eotaxin-3. The diseases contemplated herein include allergic rhinitis, asthma, atopic dermatitis and other allergic diseases, HIV (human, canine, feline, equine, etc.), inflammatory diseases, deep vein thrombosis and melanoma and other cancers.

In one preferred embodiment the anionic conjugate which functions as a GAG mimetic is used as an anticoagulant and/or antithrombotic. Determination of such activity can be achieved using any of the standard analytical tests that distinguish the particular sites of activity of the various compounds in the clotting cascade and to distinguish between their overall anticoagulant effects and their antithrombotic activity. For example, the prothrombin time assay (PT) measures the extrinsic system of coagulation and is therefore used to detect deficiencies in factors II, V, VII, and X. The activated partial thromboplastin time assay (APTT) measures coagulation factors present in the intrinsic system of coagulation and is generally applicable for monitoring of heparin-like activity. In vitro screening of these activities can be done using plasma samples.

The subjects to be treated include humans, livestock animals (e.g. cattle, sheet, pigs, horses, donkeys), laboratory test animals (e.g. rabbits, guinea pigs, mice, rats) and companion animals (e.g. dogs, cats).

Yet another aspect of the present invention contemplates a method of prophylaxis and/or treatment of a disease condition in a subject, said disease condition resulting from interaction between a HLGAG on a surface of a cell in said host and a ligand, or a HLGAG in the extracellular matrix in said host and a ligand that may or may not be cell associated, or a protein-ligand interaction in said host that can be disrupted by a HLGAG where the protein may be cell associated and the ligand soluble or both protein and ligand may be cell associated, said method comprising administering to said subject a therapeutically effective amount of an anionic conjugate, produced and identified according to the invention, that interacts with said ligand.

Another aspect of the present invention provides a pharmaceutical composition comprising an anionic conjugate as defined herein and a pharmaceutically acceptable carrier and/or diluent.

The pharmaceutical forms suitable for injectable use include sterile aqueous solutions (where water soluble), sterile powders for the extemporaneous preparation of sterile injectable solutions and inhalable forms. Such forms are preferably stable under the conditions of manufacture and storage and are generally preserved against the contaminating action of microorganisms such as bacteria and fungi. The carrier can be a solvent or dilution medium comprising, for example, water, ethanol, polyol (for example, glycerol, propylene glycol and liquid polyethylene glycol, and the like), suitable mixtures thereof and vegetable oils. The proper fluidity can be maintained, for example, by the use of superfactants. The preventions of the action of microorganisms can be brought about by various anti-bacterial and anti-fungal agents, for example, parabens, chlorobutanol, phenol, sorbic acid, thirmerosal and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the anionic conjugate and carrier/diluent in the required amount in the appropriate solvent followed by sterilization or at least a process to reduce contaminating viruses, bacteria or other biological entities to acceptable levels for administration to a human or animal subject. In the case of sterile powders for the preparation of sterile injectable solutions, suitable methods of preparation include vacuum drying and the freeze-drying technique that yields a powder of active ingredient plus any additionally desired ingredient.

When the anionic conjugate is suitably protected, it may be orally administered, for example, with an inert diluent or with an assimilable edible carrier, or it may be enclosed in hard or soft shell gelatin capsule, or it may be compressed into tablets. For oral therapeutic administration, the active ingredient may be incorporated with excipients and used in the form of ingestible tablets, buccal tablets, troches, capsules, elixirs, suspensions, syrups, wafers and the like. Such compositions and preparations should preferably contain at least 1% by weight of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 0.1 µg and 200 mg of active compound. Alternative dosage amounts include from about 1 µg to about 1000 mg and from about 10 µg to about 500 mg. These dosages may be per individual or per kg body weight. Administration may be per second, minute, hour, day, week, month or year.

The tablets, troches, pills and capsules and the like may also contain the components as listed hereafter. A binder such as gum, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations.

Pharmaceutically acceptable carriers and/or diluents include any and all solvents, dispersion media, coatings, anti-bacterial and anti-fungal agents, isotonic and absorption delaying agents and the like. The use of such media and agents for pharmaceutical active substances is well known in the art and except insofar as any conventional media or agent is incompatible with the active ingredient, their use in the therapeutic compositions is contemplated. Supplementary active ingredients can also be incorporated into the compositions.

The composition may also be formulated for local or topical administration. Techniques formulation and administration may be found in "Remington's Pharmaceutical Sciences", Mack Publishing Co., Easton Pa., 16th edition, 1980, Ed. By Arthur Osol. Thus, for local or topical administration, the subject compositions may be formulated in any suitable manner, including, but not limited to, creams, gels, oils, ointments, solutions, suspensions, powders, mists or aerosols. For transmucosal administration, penetrants appropriate to the barrier to be permeated are used in the formulation. Such penetrants are generally known in the art and include, but are not restricted to, benzalkonium chloride, digitonin, dihydrocytochalasin B5 and capric acid.

The compositions of the subject invention in the form of lotions, creams or gels may contain acceptable diluents or carriers to impart the desired texture, consistency, viscosity and appearance. Acceptable diluents and carriers are familiar to those skilled in the art and include, but are not restricted to, ethoxylated and nonethoxylated surfactants, fatty alcohols, fatty acids, hydrocarbon oils (such as palm oil, coconut oil, and mineral oil), cocoa butter waxes, silicon oils, buffering agents, cellulose derivatives, emulsifying agents such as nonionic organic and inorganic bases, preserving agents, wax esters, steroid alcohols, triglyceride esters, phospholipids such as lecithin and cephalin, polyhydric alcohol esters, fatty alcohol esters, hydrophilic lanolin derivatives, and hydrophilic beeswax derivatives.

In one particularly preferred embodiment, the present invention contemplates an inhalant pharmaceutical composition.

The term "acyl" either alone or in compound words denotes a group containing the moiety C=O (and not being a carboxylic acid, ester or amide) Preferred acyl includes $C(O)—R^e$, wherein $R^e$ is hydrogen or an alkyl, alkenyl, alkynyl, aryl, heteroaryl, carbocyclyl, or heterocyclyl residue. Examples of acyl include formyl, straight chain or branched alkanoyl (e.g. $C_{1-20}$) such as acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl and icosanoyl; cycloalkylcarbonyl such as cyclopropylcarbonyl cyclobutylcarbonyl, cyclopentylcarbonyl and cyclohexylcarbonyl; aroyl such as benzoyl, toluoyl and naphthoyl; aralkanoyl such as phenylalkanoyl (e.g. phenylacetyl, phenylpropanoyl, phenylbutanoyl, phenylisobutylyl, phenylpentenoyl and phenylhexanoyl) and naphthylalkanoyl (e.g. naphthylacetyl, naphthylpropanoyl and naphthylbutanoyl]; aralkenoyl such as phenylalkenoyl (e.g. phenylpropenoyl, phenylbutenoyl, phenylmethacryloyl, phenylpentenoyl and phenylhexenoyl and naphthylalkenoyl (e.g. naphthylpropenoyl, naphthylbutenoyl and naphthylpentenoyl); aryloxyalkanoyl such as phenoxyacetyl and phenoxypropionyl; arylthiocarbamoyl such as phenylthiocarbamoyl; arylglyoxyloyl such as phenylglyoxyloyl and naphthylglyoxyloyl; arylsulfonyl such as phenylsulfonyl and napthylsulfonyl; heterocycliccarbonyl; heterocyclicalkanoyl such as thienylacetyl, thienylpropanoyl, thienylbutanoyl, thienylpentanoyl, thienylhexanoyl, thiazolylacetyl, thiadiazolylacetyl and tetrazolylacetyl; heterocyclicalkenoyl such as heterocyclicpropenoyl, heterocyclicbutenoyl, heterocyclicpentenoyl and heterocyclichexenoyl; and heterocyclicglyoxyloyl such as thiazolyglyoxyloyl and thienylglyoxyloyl. The $R^x$ residue may be optionally substituted as described herein.

As used herein, the term "acyloxy" refers to an "acyl" group wherein the "acyl" group is in turn attached through an oxygen atom. Examples of "acyloxy" include hexylcarbonyloxy(heptanoyloxy), cyclopentylcarbonyloxy, benzoyloxy, 4-chlorobenzoyloxy, decylcarbonyloxy(undecanoyloxy), propylcarbonyloxy(butanoyloxy), octylcarbonyloxy (nonanoyloxy), biphenylcarbonyloxy (e.g. 4-phenylbenzoyloxy), naphthylcarbonyloxy (e.g. 1-naphthoyloxy) and the like.

The term "alkaryl" or "aralkyl" refers to the groups-alkylene-aryl and -substituted alkylene-aryl in which alkylene and aryl are as defined herein. Such alkaryl groups are exemplified by benzyl, phenethyl and the like.

"Alkenyl" refers to a monovalent species of a branched or unbranched unsaturated hydrocarbon preferably comprising from 2 to 40 carbon atoms, preferably from 2 to 10 carbon atoms, more preferably from 2 to 6 carbon atoms, and preferably having from 1 to 6 double bonds. Examples of alkenyl groups which are contemplated by the present invention are vinyl, prop-2-enyl, pent-3-enyl, hex-5-enyl, 5-ethyldodec-3,6-dienyl, and the like.

The term "substituted alkenyl" refers to an alkenyl group wherein one or more hydrogen atoms have been independently substituted with a substituent selected from the group consisting of alkoxy, substituted alkoxy, acyl, acylamino, acyloxy, amino, aminoacyl, aminoacyloxy, oxyaminoacyl, azido, cyano, halogen, hydroxyl, keto, thioketo, carboxyl, carboxylalkyl, thiol, alkylthio, substituted alkylthio, aryl, heteroaryl, heterocyclic, aryloxy, thioaryloxy, heteroaryloxy, thioheteroaryloxy, heterocyclooxy, thioheterocyclooxy, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and —NR$_a$R$_b$ wherein R$_a$ and R$_b$ may be the same or different and are chosen from hydrogen, optionally substituted alkyl, cycloalkyl, alkenyl, cycloalkenyl, alkynyl, aryl, heteroaryl and heterocyclic. Preferably, substituted alkenyl groups contemplated by the present invention comprise from 1 to 5 substituents.

"Alkenylene" refers to a divalent unsaturated hydrocarbon species, preferably having from 2 to 40 carbon atoms, preferably from 2 to 10 carbon atoms, more preferably from 2 to 6 carbon atoms, and preferably having from 1 to 6 double bonds. Examples of alkenylene groups which are contemplated by the present invention are 1,2-ethenylene, 1,3-prop-2-enylene, 1,5-pent-3-enylene, 1,4-hex-5-enylene, 5-ethyl-1,12-dodec-3,6-dienylene, and the like.

The term "substituted alkenylene" refers to an alkenylene group wherein one or more hydrogen atoms have been independently substituted with a substituent selected from the group consisting of alkoxy, substituted alkoxy, acyl, acylamino, acyloxy, amino, aminoacyl, aminoacyloxy, oxyacylamino, azido, cyano, halogen, hydroxyl, keto, thioketo, carboxyl, carboxylalkyl, thiol, alkylthio, substituted alkylthio, aryl, aryloxy, thioaryloxy, heteroaryl, heteroaryloxy, thioheteroaryloxy, heterocyclic, heterocyclooxy, thioheterocyclooxy, nitro, and NR$_a$R$_b$ wherein R$_a$ and R$_b$ may be the same or different and are chosen from hydrogen, optionally substituted alkyl, cycloalkyl, alkenyl, cycloalkenyl, alkynyl, aryl, heteroaryl and heterocyclic. Additionally, such substituted alkenylene groups include those where 2 substituents on the alkenylene group are fused to form one or more cycloalkyl, substituted cycloalkyl, cycloalkenyl, substituted cycloalkenyl, aryl, heterocyclic or heteroaryl groups fused to the alkenylene group. Preferably, substituted alkenylene groups contemplated by the present invention comprise from 1 to 5 substituents.

The term "alkoxy" refers to the groups alkyl-O—, alkenyl-O—, cycloalkyl-O—, cycloalkenyl-O—, and alkynyl-O—, wherein alkyl, alkenyl, cycloalkyl, cycloalkenyl, and alkynyl are as defined herein. Preferred alkoxy groups are alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkoxyalkyl" refers to the groups alkoxyalkyl, (substituted)alkoxyalkyl, alkoxy(substituted)alkyl and (substituted)alkoxy(substituted)alkyl wherein alkyl, substituted alkyl, alkylene and substituted alkylene are as defined herein. Examples of such groups are methoxymethyl (CH$_3$OCH$_2$—), methoxyethyl (CH$_3$OCH$_2$CH$_2$—), iso-propoxypropyl ((CH$_3$)$_2$CHOCH$_2$CH$_2$CH$_2$—), t-butoxymethyl ((CH$_3$)$_3$COCH$_2$—) and the like.

As used herein, the term "alkyloxycarbonyl" refers to a "alkyloxy" group attached through a carbonyl group. Examples of "alkyloxycarbonyl" groups include butylformate, sec-butylformate, hexylformate, octylformate, decylformate, cyclopentylformate and the like.

As used herein, the term "alkyl" refers to a monovalent branched or unbranched saturated hydrocarbon chain, preferably comprising from 1 to 40 carbon atoms, preferably from 1 to 10 carbon atoms, more preferably from 1 to 6 carbon atoms. Examples of alkyl groups which are contemplated by the present invention are methyl, ethyl, n-propyl, isopropyl, n-butyl, sec-butyl, tert-butyl, n-hexyl, n-octyl, n-decyl, n-dodecyl, 2-ethyldodecyl, tetradecyl, and the like, unless otherwise indicated.

The term "substituted alkyl" refers to an alkyl group as defined above wherein one or more hydrogen atoms have been independently substituted with a substituent selected from alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, alkylthio, substituted alkylthio, aryl, aryloxy, heteroaryl, heteroaryloxy, heterocyclic, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$_a$R$_b$ wherein R$_a$ and R$_b$ may be the same or different and are chosen from hydrogen, optionally substituted alkyl, cycloalkyl, alkenyl, cycloalkenyl, alkynyl, aryl, heteroaryl and heterocyclic. Preferably, substituted alkyl groups contemplated by the present invention comprise from 1 to 5 substituents.

The term "alkylene" refers to a divalent branched or unbranched saturated hydrocarbon chain, preferably comprising from 1 to 40 carbon atoms, preferably from 1 to 10 carbon atoms, more preferably from 1 to 6 carbon atoms. Examples of alkylene groups which are contemplated by the present invention are methylene (—CH$_2$—), ethylene (—CH$_2$CH$_2$—), the propylene isomers (e.g. —CH$_2$CH$_2$CH$_2$— and —CH(CH$_3$)CH$_2$—) and the like.

The term "substituted alkylene" refers to an alkylene group as defined above wherein one or more hydrogen atoms have been independently substituted with a substituent selected from alkoxy, substituted alkoxy, cycloalkyl, substituted cycloalkyl, cycloalkenyl, substituted cycloalkenyl, acyl, acylamino (including, for example, N-glucosaminecarbonyl, benzoylamino, biphenylcarbonylamino, and the like), acyloxy, amino, aminoacyl, aminoacyloxy, oxyacylamino, azido, cyano, halogen, hydroxyl, keto, thioketo, carboxyl, carboxylalkyl, thiol, alkylthio, substituted alkylthio, aryl, aryloxy, thioaryloxy, heteroaryl, heteroaryloxy, thioheteroaryloxy, heterocyclic, heterocyclooxy, thioheterocyclooxy, nitro, and —NR$_a$R$_b$, wherein R$_a$ and R$_b$ may be the same or different and are chosen from hydrogen, optionally substituted alkyl, cycloalkyl, alkenyl, cycloalkenyl, alkynyl, aryl, heteroaryl and heterocyclic. Additionally, such substituted alkylene groups include those where 2 substituents on the alkylene group are fused to form one or more cycloalkyl, substituted cycloalkyl, cycloalkenyl, substituted cycloalkenyl, aryl, heterocyclic or heteroaryl groups fused to the alkylene group. The term "substituted alkylene" also refers to an alkylene group as defined above, wherein one or more carbon atoms within the alkylene portion of the group have been independently substituted with from 1 to 20 atoms or substituents independently selected from oxygen, sulfur and —NR$_a$—, wherein R$_a$ is chosen from hydrogen, optionally substituted alkyl, cycloalkyl, alkenyl, cycloalkenyl, alkynyl, aryl, heteroaryl and heterocyclic. The term "substituted alkylene" also refers to an alkylene group as defined above that has both from 1 to 5 substituents as defined above and wherein one or more carbon atoms within the alkylene portion of the group have been independently substituted with from 1 to 20 atoms or substituents independently selected from oxygen, sulfur and —NR$_a$—, wherein R$_a$ is chosen from hydrogen, optionally substituted alkyl, cycloalkyl, alkenyl, cycloalkenyl, alkynyl, aryl, heteroaryl and heterocyclic. Examples of substituted alkylenes which are contemplated by the present invention are chloromethylene (—CH(Cl)—), aminoethylene (—CH(NH$_2$)CH$_2$—), 1-(dodecahoylamino)propylene (—CH[NHC(O)(CH$_2$)$_{11}$CH$_3$]CH$_2$—), 1-(4-phenylbenzoylamino)pentylene (—CH[NHC(O)Ph](CH$_2$)$_4$—), 2-carboxypropylene isomers (—CH$_2$CH(CO$_2$H)CH$_2$—), ethoxyethyl (—CH$_2$CH$_2$OCH$_2$CH$_2$—), ethylmethylaminoethyl (—CH$_2$CH$_2$N(CH$_3$)CH$_2$CH$_2$—), 1-ethoxy-2-(2-ethoxy-ethoxy)ethane (—CH$_2$CH$_2$OCH$_2$CH$_2$OCH$_2$OCH$_2$CH$_2$—), and the like. Preferably, substituted alkyl groups contemplated by the present invention comprise from 1 to 5 substituents.

The term "alkylthioalkyl" refers to the groups alkylthioalkyl, alkylthio(substituted)alkyl, (substituted)alkylthioalkyl and (substituted)alkylthio(substituted)alkyl wherein alkyl, substituted alkyl, alkylene and substituted alkylene are as defined herein. Preferred alkylthioalkyl groups include, by way of example, methylthiomethyl (CH$_3$SCH$_2$—), methylthioethyl (CH$_3$SCH$_2$CH$_2$—), iso-propoxythiopropyl ((CH$_3$)$_2$CHSCH$_2$CH$_2$CH$_2$—), t-butylthiomethyl ((CH$_3$)$_3$CSCH$_2$—) and the like.

"Alkynyl" refers to a monovalent unsaturated hydrocarbon species, preferably having from 2 to 40 carbon atoms, preferably from 2 to 10 carbon atoms, more preferably from 2 to 6 carbon atoms, and preferably having from 1 to 6 triple bonds. Examples of alkynyl groups which are contemplated by the present invention are acetylenyl, prop-2-ynyl, pent-3-ynyl, hex-5-ynyl, 5-ethyldodec-3,6-diynyl, and the like.

The term "substituted alkynyl" refers to an alkynyl group wherein one or more hydrogen atoms have been independently substituted with a substituent selected from the group consisting of alkoxy, substituted alkoxy, acyl, acylamino, acyloxy, amino, aminoacyl, aminoacyloxy, oxyacylamino, azido, cyano, halogen, hydroxyl, keto, thioketo, carboxyl, carboxylalkyl, thiol, alkylthio, substituted alkylthio, aryl, aryloxy, thioaryloxy, heteroaryl, heteroaryloxy, thioheteroaryloxy, heterocyclic, heterocyclooxy, thioheterocyclooxy, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, —SO$_2$-heterocyclic, NR$_a$R$_b$ wherein R$_a$ and R$_b$ may be the same or different and are chosen from hydrogen, optionally substituted alkyl, cycloalkyl, alkenyl, cycloalkenyl, alkynyl, aryl, heteroaryl and heterocyclic.

"Alkynylene" refers to a divalent unsaturated hydrocarbon species, preferably having from 2 to 40 carbon atoms, preferably from 2 to 10 carbon atoms, more preferably from 2 to 6 carbon atoms, and preferably having from 1 to 6 triple bonds. Examples of alkynylene groups which are contemplated by the present invention are 1,3-prop-2-ynylene, 1,5-pent-3-ynylene, 1,4-hex-5-ynylene, 5-ethyl-1,12-dodec-3,6-diynylene, and the like.

The term, "amino" is used here in its broadest sense as understood in the art and includes groups of the formula NR$^a$R$^b$ wherein R$^a$ and R$^b$ may be any independently selected from hydrogen, alkyl, alkenyl, alkynyl, aryl, carbocyclyl, heteroaryl, heterocyclyl, arylalkyl, and acyl. R$^a$ and R$^b$, together with the nitrogen to which they are attached, may also form a monocyclic, or polycyclic ring system e.g. a 3-10 membered ring, particularly, 5-6 and 9-10 membered systems. Examples of "amino" include NH$_2$, NHalkyl (e.g. C$_{1-20}$alkyl), NHaryl (e.g. NHphenyl), NHaralkyl (e.g. NHbenzyl), NHacyl (e.g. NHC(O)C$_{1-20}$alkyl, NHC(O)phenyl), Nalkylalkyl (wherein each alkyl, for example C$_{1-20}$, may be the same or different) and 5 or 6 membered rings, optionally containing one or more same or different heteroatoms (e.g. O, N and S).

The term "alkylamino" refers to the group —NHR$_a$, where R$_a$ is alkyl. The term "dialkylamino" refers to the group —NR$_a$R$_b$ where R$_a$ and R$_b$ are each independently alkyl. The term "alkylaminoalkyl" refers to the group —R$_b$—NHR$_a$, where R$_a$ is alkyl, and R$_b$ is alkylene. Examples of alkylaminoalkyl groups which are contemplated by the present invention are n-decylaminoethyl, 3-(dimethylamino)propyl, and the like.

The term "aminoacyl" refers to the group —C(O)NR$_a$R$_b$ wherein R$_a$ and R$_b$ are each independently selected from hydrogen, alkyl, substituted alkyl, aryl, heteroaryl, heterocyclic or where both R groups are joined to form a heterocyclic group (e.g., morpholino) wherein alkyl, substituted alkyl, aryl, heteroaryl and heterocyclic are as defined herein.

The term "acylamino" refers to the group —NR$_a$C(O)R$_b$ wherein R$_a$ and R$_b$ are each independently selected from hydrogen, alkyl, substituted alkyl, aryl, heteroaryl, or heterocyclic wherein alkyl, substituted alkyl, aryl, heteroaryl and heterocyclic are as defined herein.

The term "alkoxyacylamino" refers to the group —$NR_a$C(O)$OR_b$ wherein $R_a$ and $R_b$ are each independently selected from hydrogen, alkyl, substituted alkyl, aryl, heteroaryl, or heterocyclic wherein alkyl, substituted alkyl, aryl, heteroaryl and heterocyclic are as defined herein.

The term "aminocarboxy" refers to the group —OC(O)$NR_aR_b$ wherein $R_a$ and $R_b$ may be the same or different and are chosen from hydrogen, alkyl, substituted alkyl, aryl, heteroaryl, or heterocyclic wherein alkyl, substituted alkyl, aryl, heteroaryl and heterocyclic are as defined herein.

The term "amido" is used here in its broadest sense as understood in the art and includes groups having the formula C(O)$NR^aR^b$, wherein $R^a$ and $R^b$ are as defined as above. Examples of amido include C(O)$NH_2$, C(O)NHalkyl (e.g. $C_{1-20}$alkyl), C(O)NHaryl (e.g. C(O)NHphenyl), C(O)NHaralkyl (e.g. C(O)NHbenzyl), C(O)NHacyl (e.g. C(O)NHC(O)$C_{1-20}$alkyl, C(O)NHC(O)phenyl), C(O)Nalkylalkyl (wherein each alkyl, for example $C_{1-20}$, may be the same or different) and 5 or 6 membered rings, optionally containing one or more same or different heteroatoms (e.g. O, N and S).

As used herein, the term "arylalkyl" refers to groups formed from straight or branched chain alkanes substituted with an aromatic ring. Examples of arylalkyl include phenylmethyl (benzyl) and phenylethyl and phenylpropyl.

As used herein, the term "alkylaryl" refers to groups formed from aryl groups substituted with a straight chain or branched alkane. Examples of alkylaryl include methylphenyl and propylphenyl.

The term "aryl" (or "carboaryl") denotes any of single, polynuclear, conjugated and fused residues of aromatic hydrocarbon ring systems. Examples of aryl include phenyl, biphenyl, terphenyl, quaterphenyl, naphthyl, tetrahydronaphthyl, anthracenyl, dihydroanthracenyl, benzanthracenyl, dibenzanthracenyl, phenanthrenyl, fluorenyl, pyrenyl, idenyl, azulenyl, chrysenyl. Preferred aryl include phenyl and naphthyl. An aryl group may or may not be optionally substituted by one or more optional substituents as herein defined. The term "arylene" is intended to denote the divalent form of aryl.

As used herein, the term "aryloxy" refers to an "aryl" group attached through an oxygen bridge. Examples of aryloxy substituents include phenoxy, biphenyloxy, naphthyloxy and the like.

The term "carbocyclyl" includes any of non-aromatic monocyclic, polycyclic, fused or conjugated hydrocarbon residues, preferably $C_{3-20}$ (e.g. $C_{3-10}$ or $C_m$). The rings may be saturated, e.g. cycloalkyl, or may possess one or more double bonds (cycloalkenyl) and/or one or more triple bonds (cycloalkynyl). Particularly preferred carbocyclyl moieties are 5-6-membered or 9-10 membered ring systems. Suitable examples include cyclopropyl, cyclobutyl, cyclopentyl, cyclohexyl, cycloheptyl, cyclooctyl, cyclononyl, cyclodecyl, cyclopentenyl, cyclohexenyl, cyclooctenyl, cyclopentadienyl, cyclohexadienyl, cyclooctatetraenyl, indanyl, decalinyl and indenyl. A carbocyclyl group may be optionally substituted by one or more optional substituents as herein defined. The term "carbocyclylene" is intended to denote the divalent form of carbocyclyl.

The term "carboxy ester" is used here in its broadest sense as understood in the art and includes groups having the formula —$CO_2R_g$, wherein $R_g$ may be selected from groups including alkyl, alkenyl, alkynyl, aryl, carbocyclyl, heteroaryl, heterocyclyl, aralkyl, and acyl. Examples of carboxy ester include —$CO_2C_{1-20}$alkyl, —$CO_2$aryl (e.g. —$CO_2$-phenyl), —$CO_2$aralkyl (e.g. —$CO_2$ benzyl).

The term "cycloalkenyl" refers to cyclic alkenyl groups of from 4 to 20 carbon atoms having a single cyclic ring or fused rings wherein at least one endocyclic bond is unsaturated. Examples of suitable cycloalkenyl groups include, for instance, cyclobut-2-enyl, cyclopent-3-enyl, cyclooct-3-enyl and the like.

The term "substituted cycloalkenyl" refers to cycloalkenyl groups wherein one or more hydrogen atoms have been independently substituted with a substituent selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, alkylthio, substituted alkylthio, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl, —$SO_2$-heteroaryl, and $NR_aR_b$ wherein $R_a$ and $R_b$ may be the same or different and are chosen from hydrogen, optionally substituted alkyl, cycloalkyl, alkenyl, cycloalkenyl, alkynyl, aryl, heteroaryl and heterocyclic.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups wherein one or more hydrogen atoms have been independently substituted with a substituent selected from the group consisting of alkoxy, substituted alkoxy, cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, alkylthio, substituted alkylthio, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl, —$SO_2$-heteroaryl, and $NR_aR_b$ wherein $R_a$ and $R_b$ may be the same or different and are chosen from hydrogen, optionally substituted alkyl, cycloalkyl, alkenyl, cycloalkenyl, alkynyl, aryl, heteroaryl and heterocyclic.

The term "halogen" ("halo") denotes fluorine, chlorine, bromine or iodine (fluoro, chloro, bromo or iodo).

"Haloalkyl" refers to alkyl as defined above substituted by from 1 to 4 halo groups as defined above, which may be the same or different. Example of haloalkyl groups contemplated by the present invention are: 3-fluorododecyl; 12,12,12-trifluorododecyl; 2-bromooctyl; 3-bromo-6-chloroheptyl; and the like.

The term "heteroatom" or "hetero" as used herein in its broadest sense refers to any atom other than a carbon atom which may be a member of a cyclic organic group. Particular examples of heteroatoms include nitrogen, oxygen, sulfur, phosphorous, boron, silicon, selenium and tellurium, more particularly nitrogen, oxygen and sulfur.

The term "heterocyclyl" when used alone or in compound words includes any of monocyclic, polycyclic, fused or conjugated hydrocarbon residues, preferably $C_{3-20}$ (e.g. $C_{3-10}$ or $C_{3-8}$) wherein one or more carbon atoms are replaced by a heteroatom so as to provide a non-aromatic residue. Suitable heteroatoms include O, N, S, P and Se, particularly O, N and S. Where two or more carbon atoms are replaced, this may be by two or more of the same heteroatom or by different heteroatoms. The heterocyclyl group may be saturated or partially unsaturated, i.e. possess one or more double bonds.

Particularly preferred heterocyclyl are 5-6 and 9-10 membered heterocyclyl. Suitable examples of heterocyclyl groups may include azridinyl, oxiranyl, thiiranyl, azetidinyl, oxetanyl, thietanyl, 2H-pyrrolyl, pyrrolidinyl, pyrrolinyl, piperidyl, piperazinyl, morpholinyl, indolinyl, imidazolidinyl, imidazolinyl, pyrazolidinyl, thiomorpholinyl, dioxanyl, tetrahydrofuranyl, tetrahydropyranyl, tetrahydropyrrolyl, tetrahydrothiophenyl, pyrazolinyl, dioxalanyl, thiazolidinyl, isoxazolidinyl, dihydropyranyl, oxazinyl, thiazinyl, thiomorpholinyl, oxathianyl, dithianyl, trioxanyl, thiadiazinyl, dithiazinyl, trithianyl, azepinyl, oxepinyl, thiepinyl, indenyl, indanyl, 3H-indolyl, isoindolinyl, 4H-quinolazinyl, chromenyl, chromanyl, isochromanyl, pyranyl and dihydropyranyl. A heterocyclyl group may be optionally substituted by one or more optional substituents as herein defined. The term "heterocyclylene" is intended to denote the divalent form of heterocyclyl.

The term "heteroaryl" includes any of monocyclic, polycyclic, fused or conjugated hydrocarbon residues, wherein one or more carbon atoms are replaced by a heteroatom so as to provide an aromatic residue. Preferred heteroaryl have 3-20 ring atoms, e.g. 3-10. Particularly preferred heteroaryl are 5-6 and 9-10 membered bicyclic ring systems. Suitable heteroatoms include, O, N, S, P and Se, particularly O, N and S. Where two or more carbon atoms are replaced, this may be by two or more of the same heteroatom or by different heteroatoms. Suitable examples of heteroaryl groups may include pyridyl, pyrrolyl, thienyl, imidazolyl, furanyl, benzothienyl, isobenzothienyl, benzofuranyl, isobenzofuranyl, indolyl, isoindolyl, pyrazolyl, pyrazinyl, pyrimidinyl, pyridazinyl, indolizinyl, quinolyl, isoquinolyl, phthalazinyl, 1,5-naphthyridinyl, quinozalinyl, quinazolinyl, quinolinyl, oxazolyl, thiazolyl, isothiazolyl, isoxazolyl, triazolyl, oxadialzolyl, oxatriazolyl, triazinyl, and furazanyl. A heteroaryl group may be optionally substituted by one or more optional substituents as herein defined. The term "heteroarylene" is intended to denote the divalent form of heteroaryl.

The term "heteroaryloxy" refers to the group heteroaryl-O—.

As used herein, the terms "inert organic solvent" or "inert solvent" mean a solvent inert under the conditions of the reaction being described in conjunction therewith an may refer to, for example, benzene, toluene, acetonitrile, tetrahydrofuran ("THF"), dimethylformamide ("DMF"), chloroform ("CHCl$_3$"), methylene chloride (or dichloromethane or "CH$_2$Cl$_2$"), diethyl ether, ethyl acetate, acetone, methylethyl ketone, methanol, ethanol, propanol, isopropanol, tert-butanol, dioxane, pyridine, and the like. Unless specified to the contrary, the solvents used in the reactions of the present invention are inert solvents.

As used herein, the expression "optionally substituted" is taken to mean that a group may or may not be substituted or fused (so as to form a condensed polycyclic group) with one, two, three or more of organic and inorganic groups, including those selected from: alkyl, alkenyl, alkynyl, carbocyclyl, aryl, heterocyclyl, heteroaryl, acyl, aralkyl, alkaryl, allcheterocyclyl, alkheteroaryl, alkcarbocyclyl, halo, haloalkyl, haloalkenyl, haloalkynyl, haloaryl, halocarbocyclyl, haloheterocyclyl, haloheteroaryl, haloacyl, haloaryalkyl, hydroxy, hydroxyalkyl, hydroxyalkenyl, hydroxyalkynyl, hydroxycarbocyclyl, hydroxyaryl, hydroxyheterocyclyl, hydroxyheteroaryl, hydroxyacyl, hydroxyaralkyl, alkoxyalkyl, alkoxyalkenyl, alkoxyalkynyl, alkoxycarbocyclyl, alkoxyaryl, alkoxyheterocyclyl, alkoxyheteroaryl, alkoxyaryl, alkoxyaralkyl, alkoxy, alkenyloxy, alkynyloxy, aryloxy, carbocyclyloxy, aralkyloxy, heteroaryloxy, heterocyclyloxy, acyloxy, haloalkoxy, haloalkenyloxy, haloalkynyloxy, haloaryloxy, halocarbocyclyloxy, haloaralkyloxy, haloheteroaryloxy, haloheterocyclyloxy, haloacyloxy, nitro, nitroalkyl, nitroalkenyl, nitroalkynyl, nitroaryl, nitroheterocyclyl, nitroheteroaryl, nitrocarbocyclyl, nitroacyl, nitroaralkyl, amino(NH$_2$), alkylamino, dialkylamino, alkenylamino, alkynylamino, arylamino, diarylamino, aralkylamino, diaralkylamino, acylamino, diacylamino, heterocyclamino, heteroarylamino, carboxy, carboxyester, amido, alkylsulphonyloxy, arylsulphenyloxy, alkylsulphenyl, arylsulphenyl, thio, alkylthio, alkenylthio, alkynylthio, arylthio, aralkylthio, carbocyclylthio, heterocyclylthio, heteroarylthio, acylthio, sulfoxide, sulfonyl, sulfonamide, aminoalkyl, aminoalkenyl, aminoalkynyl, aminocarbocyclyl, aminoaryl, aminoheterocyclyl, aminoheteroaryl, aminoacyl, amidoaralkyl, thioalkyl, thioalkenyl, thioalkynyl, thiocarbocyclyl, thioaryl, thioheterocyclyl, thioheteroaryl, thioacyl, thioaralkyl, carboxyalkyl, carboxyalkenyl, carboxyalkynyl, carboxycarbocyclyl, carboxyaryl, carboxyheterocyclyl, carboxyheteroaryl, carboxyacyl, carboxyaralkyl, carboxyesteralkyl, carboxyesteralkenyl, carboxyesteralkynyl, carboxyestercarbocyclyl, carboxyesteraryl, carboxyesterheterocyclyl, carboxyesterheteroaryl, carboxyesteracyl, carboxyesteraralkyl, amidoalkyl, amidoalkenyl, amidoalkynyl, amidocarbocyclyl, amidoaryl, amidoheterocyclyl, amidoheteroaryl, amidoacyl, amidoaralkyl, formylalkyl, formylalkenyl, formylalkynyl, formylcarbocyclyl, formylaryl, formylheterocyclyl, formylheteroaryl, formylacyl, formylaralkyl, acylalkyl, acylalkenyl, acylalkynyl, acylcarbocyclyl, acylaryl, acylheterocyclyl, acyiheteroaryl, acylacyl, acylaralkyl, sulfoxidealkyl, sulfoxidealkenyl, sulfoxidealkynyl, sulfoxidecarbocyclyl, sulfoxidearyl, sulfoxideheterocyclyl, sulfoxideheteroaryl, sulfoxideacyl, sulfoxidearalkyl, sulfonylalkyl, sulfonylalkenyl, sulfonylalkynyl, sulfonylcarbocyclyl, sulfonylaryl, sulfonylheterocyclyl, sulfonylheteroaryl, sulfonylacyl, sulfonylaralkyl, sulfonamidoalkyl, sulfonamidoalkenyl, sulfonamidoalkynyl, sulfonamidocarbocyclyl, sulfonamidoaryl, sulfonamidoheterocyclyl, sulfonamidoheteroaryl, sulfonamidoacyl, sulfonamidoaralkyl, nitroalkyl, nitroalkenyl, nitroalkynyl, nitrocarbocyclyl, nitroaryl, nitroheterocyclyl, nitroheteroaryl, nitroacyl, nitroaralkyl, cyano, sulfate and phosphate groups. Optional substitution may also be taken to refer to where a —CH$_2$— group in a chain or ring is replaced by a group selected from —O—, —S—, —C(O)— (i.e. carbonyl), —C(O)O— (i.e. ester), and —C(O)NR$^a$— (i.e. amide), where R$^a$ is as defined herein.

Preferred optional substituents include alkyl, (e.g. C$_{1-6}$ alkyl such as methyl, ethyl, propyl, butyl, cyclopropyl, cyclobutyl, cyclopentyl or cyclohexyl), hydroxyalkyl (e.g. hydroxymethyl, hydroxyethyl, hydroxypropyl), alkoxyalkyl (e.g. methoxymethyl, methoxyethyl, methoxypropyl, ethoxymethyl, ethoxyethyl, ethoxypropyl etc) alkoxy (e.g. C$_{1-6}$ alkoxy such as methoxy, ethoxy, propoxy, butoxy, cyclopropoxy, cyclobutoxy), halo, trifluoromethyl, trichloromethyl, tribromomethyl, hydroxy, phenyl (which itself may be further substituted e.g., by C$_{1-6}$ alkyl, halo, hydroxy, hydroxyC$_{1-6}$ alkyl, C$_{1-6}$ alkoxy, haloC$_{1-6}$alkyl, cyano, nitro OC(O)C$_{1-6}$ alkyl, and amino), benzyl (wherein benzyl itself may be further substituted e.g., by C$_{1-6}$ alkyl, halo, hydroxy, hydroxyC$_{1-6}$alkyl, C$_{1-6}$ alkoxy, haloC$_{1-6}$ alkyl, cyano, nitro OC(O)C$_{1-6}$ alkyl, and amino), phenoxy (wherein phenyl itself may be further substituted e.g., by C$_{1-6}$ alkyl, halo, hydroxy, hydroxyC$_{1-6}$ alkyl, C$_{1-6}$ alkoxy, haloC$_{1-6}$ alkyl, cyano, nitro OC(O)C$_{1-6}$ alkyl, and amino), benzyloxy (wherein benzyl itself may be further substituted e.g., by C$_{1-6}$ alkyl, halo, hydroxy, hydroxyC$_{1-6}$ alkyl, C$_{1-6}$ alkoxy, haloC$_{1-6}$ alkyl, cyano, nitro OC(O)C$_{1-6}$ alkyl, and amino), amino, alkylamino (e.g. C$_{1-6}$ alkyl, such as methylamino, ethylamino, propylamino etc), dialkylamino (e.g. $C_{1-6}$ alkyl, such as dimethylamino, diethylamino, dipropylamino), acylamino (e.g. NHC(O)CH$_3$), phenylamino (wherein phenyl itself may be further substituted e.g., by $C_{1-6}$ alkyl, halo, hydroxy, hydroxy$C_{1-6}$ alkyl, $C_{1-6}$ alkoxy, halo$C_{1-6}$ alkyl, cyano, nitro OC(O)$C_{1-6}$ alkyl, and amino), nitro, formyl, —C(O)-alkyl (e.g. $C_{1-6}$ alkyl, such as acetyl), O—C(O)-alkyl (e.g. $C_{1-6}$alkyl, such as acetyloxy), benzoyl (wherein the phenyl group itself may be further substituted e.g., by $C_{1-6}$ alkyl, halo, hydroxy hydroxy$C_{1-6}$ alkyl, $C_{1-6}$ alkoxy, halo$C_{1-6}$ alkyl, cyano, nitro OC(O)$C_{1-6}$alkyl, and amino), replacement of CH$_2$ with C=O, CO$_2$H, CO$_2$alkyl (e.g. $C_{1-6}$ alkyl such as methyl ester, ethyl ester, propyl ester, butyl ester), CO$_2$-phenyl (wherein phenyl itself may be further substituted e.g., by $C_{1-6}$ alkyl, halo, hydroxy, hydroxyl $C_{1-6}$ alkyl, $C_{1-6}$ alkoxy, halo $C_{1-6}$ alkyl, cyano, nitro OC(O)$C_{1-6}$ alkyl, and amino), CONH$_2$, CONHphenyl (wherein phenyl itself may be further substituted e.g., by $C_{1-6}$ alkyl, halo, hydroxy, hydroxyl $C_{1-6}$ alkyl, $C_{1-6}$ alkoxy, halo $C_{1-6}$ alkyl, cyano, nitro OC(O)$C_{1-6}$ alkyl, and amino), CONHbenzyl (wherein benzyl itself may be further substituted e.g., by $C_{1-6}$ alkyl, halo, hydroxy hydroxyl $C_{1-6}$ alkyl, $C_{1-6}$ alkoxy, halo $C_{1-6}$ alkyl, cyano, nitro OC(O) $C_{1-6}$ alkyl, and amino), CONHalkyl (e.g. $C_{1-6}$ alkyl such as methyl ester, ethyl ester, propyl ester, butyl amide) CONHdialkyl (e.g. $C_{1-6}$ alkyl)aminoalkyl (e.g., HN $C_{1-6}$ alkyl-, $C_{1-6}$alkylHN—$C_{1-6}$ alkyl- and ($C_{1-6}$ alkyl)$_2$N—$C_{1-6}$ alkyl-), thioalkyl (e.g., HS $C_{1-6}$ alkyl-), carboxyalkyl (e.g., HO$_2$C$C_{1-6}$ alkyl-), carboxyesteralkyl (e.g., $C_{1-6}$ alkylO$_2$C$C_{1-6}$ alkyl-), amidoalkyl (e.g., H$_2$N(O)C$C_{1-6}$ alkyl-, H($C_{1-6}$ alkyl)N(O) C$C_{1-6}$ alkyl-), formylalkyl (e.g. OHCC$_{1-6}$alkyl-), acylalkyl (e.g. $C_{1-6}$ alkyl(O)C$C_{1-6}$ alkyl-), nitroalkyl (e.g., O$_2$N $C_{1-6}$ alkyl-), sulfoxidealkyl (e.g., R(O)S$C_{1-6}$ alkyl, such as $C_{1-6}$ alkyl(O)S$C_{1-6}$ alkyl-), sulfonylalkyl (e.g., R(O)$_2$S$C_{1-6}$ alkyl- such as $C_{1-6}$ alkyl(O)$_2$S$C_{1-6}$ alkyl-), sulfonamidoalkyl (e.g., $_2$HRN(O)S$C_{1-6}$ alkyl, H($C_{1-6}$ alkyl)N(O)S$C_{1-6}$ alkyl-).

As used herein the expression "pharmaceutically acceptable salt" refers to the salt of a given compound, wherein the salt is suitable for administration as a pharmaceutical. For example, such salts may be formed by the reaction of an acid or a base with an amino or a carboxyl group respectively.

Pharmaceutically acceptable base addition salts may be prepared from inorganic and organic bases. Salts derived from inorganic bases include, but are not limited to, the sodium, potassium, lithium, ammonium, calcium, and magnesium salts. Salts derived from organic bases include, but are not limited to, salts of primary, secondary and tertiary amines, substituted amines including naturally-occurring substituted amines, and cyclic amines, including isopropylamine, trimethyl amine, diethylamine, triethylamine, tripropylamine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, and N-ethylpiperidine. It should also be understood that other carboxylic acid derivatives would be useful in the practice of this invention, for example carboxylic acid amides, including carboxamides, lower alkyl carboxamides, di(lower alkyl)carboxamides, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

The term "protecting group" or "blocking group" refers to any group which when bound to one or more hydroxyl, thiol, amino or carboxyl groups of the compounds prevents reactions from occurring at these groups and which protecting group can be removed by conventional chemical or enzymatic steps to re-establish the hydroxyl, thio, amino or carboxyl group. The particular removable blocking group employed is not critical and preferred removable hydroxyl blocking groups include conventional substituents such as allyl, benzyl, acetyl, chloroacetyl, thiobenzyl, benzylidine, phenacyl, t-butyl-diphenylsilyl and any other group that can be introduced chemically onto a hydroxyl functionality and later selectively removed either by chemical or enzymatic methods in mild conditions compatible with the nature of the product. Protecting groups are disclosed in more detail in T. W. Greene and P. G. M. Wuts, "Protective Groups in Organic Synthesis" 2.sup.nd Ed., 1991, John Wiley and Sons, N.Y.

Preferred removable amino blocking groups include conventional substituents such as t-butyoxycarbonyl (t-BOC), benzyloxycarbonyl (CBZ), fluorenylmethoxycarbonyl (FMOC), allyloxycarbonyl (ALOC) and the like, which can be removed by conventional conditions compatible with the nature of the product.

Preferred carboxyl protecting groups include esters such as methyl, ethyl, propyl, t-butyl etc. which can be removed by mild conditions compatible with the nature of the product.

"Selectivity" or "specificity" in general is a measure of the binding preferences of a ligand for different receptors and/or a measure of the binding preferences of different ligands for a receptor. The selectivity of a ligand with respect to its target receptor relative to another receptor is given by the ratio of the respective values of $K_d$ (i.e., the dissociation constants for each ligand-receptor complex), or in cases where a biological effect is observed below the $K_d$, selectivity is given by the ratio of the respective $EC_{50}$ values (i.e. the concentrations that produce 50% of the maximum response for the ligand interacting with the two distinct receptors).

The term "sulfonyl", either alone or in a compound word, refers to a group $S(O)_2$—$R_f$, wherein $R_f$ is selected from hydrogen, alkyl, alkenyl, alkynyl, aryl, heteroaryl, heterocyclyl, carbocyclyl and aralkyl. Examples of preferred $R_f$ include $C_{1-20}$alkyl, phenyl and benzyl.

The term "sulfonamide", either alone or in a compound word, refers to a group $S(O)NR_yR_f$ wherein each $R_f$ is independently selected from hydrogen, alkyl, alkenyl, alkynyl, aryl, heteroaryl, heterocyclyl, carbocyclyl, and aralkyl. Examples of preferred $R^y$ include $C_{1-20}$alkyl, phenyl and benzyl. In a preferred embodiment at least one $R_f$ is hydrogen. In another form, both $R_y$ are hydrogen.

The term "sulfoxide", either alone or in a compound word, refers to a group —$S(O)R_f$ wherein $R_f$ is selected from hydrogen, alkyl, alkenyl, alkynyl, aryl, heteroaryl, heterocyclyl, carbocyclyl, and aralkyl. Examples of preferred $R_f$ include $C_{1-20}$alkyl, phenyl and benzyl.

The term "thiol" refers to the group —SH. The term "alkylthio" refers to the group —S-alkyl. The term "substituted alkylthio" refers to the group —S-substituted alkyl. The term "arylthio" refers to the group aryl-S— wherein the aryl group is as defined above including optionally substituted aryl groups also defined above.

The term "therapeutically effective amount" refers to that amount which is sufficient to effect treatment, as defined above, when administered to an animal, preferably a mammal, more preferably a human in need of such treatment. The therapeutically effective amount will vary depending on the subject and disease state being treated, the severity of the affliction and the manner of administration, and may be determined routinely by one of ordinary skill in the art.

The term "treatment" as used herein covers any treatment of a condition or disease in an animal, preferably a mammal, more preferably a human, and includes: (i) preventing the disease or condition from occurring in a subject which may be predisposed to the disease but has not yet been diagnosed as having it; (ii) inhibiting the disease or condition, i.e. arresting its development; (iii) relieving the disease or condition, i.e. causing regression of the condition; or (iv) relieving the conditions caused by the disease, i.e. symptoms of the disease.

It is understood that the compounds of the present invention may exist in one or more stereoisomeric forms (e.g. enantiomers, diastereomers). The present invention includes within its scope all of these stereoisomeric forms either isolated (in for example enantiomeric isolation), or in combination (including racemic mixtures).

The invention will now be described with reference to the following non-limiting examples:

EXAMPLES

General Procedure 1: Sulfation

A. Glycosylated metabolite (1 mmol) is dissolved in DMF (20 mL), Py.SO$_3$ (3-fold molar excess over hydroxyl and amine groups) is added and the mixture stirred at 50° C. for 16 h. The reaction is quenched by addition of water (80 mL) and adjusted to pH 6 by addition of tributylamine. The sulfated product is extracted using preparative reverse-phase ion-pairing HPLC (RP-IP HPLC, see below).

B. For N- and O-sulfation, pyridine is used as solvent in place of DMF and the sample stirred at room temperature for 16 h, before heating at 50° C. for 24 h.

Either reaction is quenched by addition of water (80 mL) and adjusted to pH 6 by addition of tributylamine. In those instances when the products precipitates from the reaction mixture, the supernatant may be decanted and the remaining gum may be worked up similarly. The sulfated product is extracted using preparative reverse-phase ion-pairing HPLC (RP-IP HPLC, see below).

General Procedure 2: Acylation with Fmoc-glyOH

Fmoc-gly-OH (2 mmol), hydroxybenzotriazole (HOBT, 2 mmol), O-Benzotriazole-N,N,N',N''-tetramethyl-uronium-hexafluoro-phosphate (HBTU, 4 mmol) and DIPEA (2 mmol) is dissolved in a mixture of 20 mL DMSO:DMF (2:1). The resulting solution is added to the glycosylamine and the mixture stirred overnight. The reaction is quenched by addition of water (50 mL) and glacial acetic acid (0.5 mL) and allowed to cool to room temperature. The precipitate formed is removed and discarded. The liquor is washed with ethyl acetate (3×10 mL) and hexane (1×10 mL). Residual ethyl acetate and hexane in the aqueous layer is removed by concentrating in a rotary evaporator and the solution diluted to 60 mL by the addition of water.

The mixture is fractionated by preparative reverse-phase HPLC by repeated injection.

Example Conditions—
Column: Phenomenex Axia 100×21.2 mm Luna C18 (2) fitted with a security guard cartridge (or suitable substitute).
Eluent A: 0.1% formic acid.
Eluent B: 80% acetonitrile.
Flow: 20 ml/min.
Detector: UV @ 270 nm.

The desired fraction is collected and concentrated in a rotary evaporator and the resulting solution lyophilised to yield a white powder.

General Procedure 3: Aqueous Fmoc Removal

The Fmoc derivative is dissolved in water and adjusted to pH>13 with NaOH and incubated at room temperature for 15 minutes. The ppt/oil is extracted with pentane (2×10 mL) and discarded. Typically, the pH is lowered and the resulting aqueous solution is used for the subsequent acylation.

General Procedure 4: Bromoacetylation

The solution of amine (typically from Fmoc removal) is adjusted to pH 8.25. 3 aliquots of bromoacetyl bromide (3-fold molar excess) is added at 20 minute intervals to the solution with constant pH monitoring and addition of Na$_2$CO$_3$ to maintain pH 8-8.25. The progress of this reaction is monitored by analytical RP-IP HPLC (general procedure 6). The desired bromoacetylated derivative is precipitated by addition of 3 volumes of ethanol and the mixture cooled to 4° C. The precipitate is separated and redissolved in 0.4 M NaOAc pH 7, re-precipitated by addition of 3 volumes of ethanol and the mixture cooled to 4° C. The white precipitate of product is separated by centrifugation.

General Procedure 5: HPLC Purification of Sulfated Products
Column: Phenomenex Axia 100×21.2 mm Luna C18 (2) fitted with a security guard cartridge (or suitable substitute).
Eluent A: 8 mM tributylamine in 20% acetonitrile adjusted to pH 5.8 with acetic acid.
Eluent B: 80% acetonitrile.
Flow: 20 ml/min.
Detector: 1) Evaporative light scattering on 40:1 split ratio attained with a T-piece; 2) UV.

General Procedure 6: Analytical RP-IP HPLC of reactions with sulfated products.
Example Conditions—
Column: Phenomenex Luna 30×4.6 mm C18 (2) fitted with a security guard cartridge.
Eluent A: 8 mM tributylamine in 20% acetonitrile adjusted to pH 5.8 with acetic acid.
Eluent B: Acetonitrile.
Flow: 1 mL/min.
Detectors: UV and ELSD in series.

General Procedure 7: Coupling of Dithiols to Bromoacetylated Glycosides

To a solution containing the bromoacetyled glycoside (10 µmol) is added 0.2M EDTA (200 µL), 1M NaHCO$_3$ (2 mL) and adjusted to pH 8.75. Isopropanol is added to 33% v/v, dithiol is added (0.4 eq) and the mixture stirred at room temperature for 16 h. The reaction is monitored by RP-IP HPLC as described above and the products purified by general procedure 5.

General Procedure 8: Glycosylamine Formation

Oligosaccharide (0.2 M) and NH$_4$HCO$_3$ (0.2 M) is prepared in 25% ammonia, capped and incubated at 40° C. for 40 h. The ammonia is evaporated, the residue redissolved in a minimum of water and evaporated to dryness again. The residue is dissolved in a minimum of water and lyophilized to yield an off-white power.

General Procedure 9: Introduction of an Azide Group Via Diazo Transfer Reaction

Imidazole-1-sulfonyl azide hydrochloride (1.2 mmol) is added to a stirred suspension of the amine or its hydrochloride (1.0 mmol), potassium carbonate (2.0 mmol), and copper(II) sulfate pentahydrate (10 mmol, 1 mol %) in methanol (5 mL). Upon completion of the reaction, the mixture is concentrated and suspended in chloroform. After filtration through a Celite pad, the filtrate is concentrated and purified by flash chromatography.

General Procedure 10: Azido Reduction a) Staudinger reduction. Azide is dissolved in dry CH$_2$Cl$_2$ and PPh$_3$ (4 molar equiv) is added. The solution is stirred at room temperature for 24 h under argon, and then H$_2$O (~15 molar equiv) is added. This mixture is heated at reflux for 5 h, allowed to cool and the solvent evaporated in vacuo. The products are purified chromatographically.

b) Hydrogenation. Azide in ethanol is treated with Pd(C) (10% w/w, catalytic amount) and stirred under a hydrogen atmosphere overnight. At the completion of the reaction, the mixture is filtered through a celite cake and concentrated.

c) Zinc/Ammonium chloride. To the solution of azides (2 mmol) and ammonium chloride (10 mmol) in a mixture of ethanol (80 mL) and water (25 mL), zinc powder (60 mmol) is added, the mixture is stirred vigorously at room temperature for 3 h and filtered. The solvent is removed by evaporation and products are purified chromatographically.

d) Propane-1,3-dithiol. The azido compound is dissolved in methanol (or 50:50 methanol:water if necessary) and 4 equivalents of triethylamine and propane-1,3-dithiol is added. The mixture is incubated at room temperature until reduction is affected (typically 16 h).

e) 1-pot conversion to Boc-protected amine.

The method described in *J. Antibiotics* 1959, 12, 114-115 is followed. Briefly, all components are mixed together (azide, 1.1 equiv of PMe$_3$, and 1.1 equiv of Boc-ON) in toluene or THF at −20° C., and stirred at r.t. for 4-5 h. Aqueous workup and/or purification by preparative HPLC affords the products.

General Procedure 11: Thioacetylation

The solution of amine (typically from Fmoc removal) is adjusted to pH 8.25. 3 aliquots of N-hydroxysuccinimidyl-5-acetylthioacetate (3-fold molar excess each aliquot) is added at 20 minute intervals to the solution with constant pH monitoring and addition of Na$_2$CO$_3$ to maintain pH 8-8.25.

The progress of this reaction is monitored by analytical RP-IP HPLC (general procedure 6)

The products are purified by ethanol precipitation or chromatography.

General Procedure 12: De-S-acetylation

Hydroxylamine hydrochloride (1.2 eq), and EDTA is added to an aqueous solution of the S-acetyl derivative and the pH adjusted to 7.5. The solution is incubated at room temperature for 2 h and the free thiol purified by ethanol precipitation or chromatography.

General Procedure 13: Monothiol to Haloacetamide Coupling

To a solution containing the bromoacetyled glycoside (10 µmol) is added 0.2M EDTA (200 µL), 1M NaHCO$_3$ (2 mL) and adjusted to pH 8.75. Isopropanol is added to 33% v/v, thiol is added (3 eq) and the mixture stirred at room temperature for 16 h. The reaction is monitored by RP-IP HPLC as described above and the products purified by general procedure 5. Prior to purification, reducing agent (tris(2-carboxyethyl)phosphine or tributylphosphine) is added and incubated at room temperature for 1 hr.

General Procedure 14: Fmoc N-Protection of Sulfated Glycans

Fmoc-Cl (3 eq) is dissolved in acetone and added to an aqueous solution of the glycoside amine in 0.25 M NaHCO$_3$ pH 8.25 and sufficient methanol added to maintain solubility of the Fmoc. After 2 h the solution is concentrated to remove the acetone and methanol and the excess Fmoc is extracted with ethyl acetate:hexane (2:1). The Fmoc protected derivative is purified by HPLC.

General Procedure 15: Reductive Amination

The glycoside (1 mmol) is dissolved in 1M NH$_4$Cl and NaCNBH$_3$ added (5 mmol) and incubated at 60° C. overnight. For compounds with limited aqueous solubility, the compounds are dissolved in methanol, CH$_3$CO$_2$NH$_4$ (5 molar excess) and NaCNBH$_3$ (2 molar excess) added and the mixture incubated at 40° C. overnight. The products are purified chromatographically.

General Procedure 16: Sulfonylation of Primary Hydroxyls a) 2,4,6-triisopropylbenzenesulfonyl chloride. A solution of Boc-protected aminoglycoside (0.82 mmol) and excess 2,4,6-triisopropylbenzenesulfonyl chloride (7 g, 23 mmol) in dry pyridine (20 mL) is stirred at room temperature (18 h). Pyridine is removed in vacuo by co-evaporation with toluene. The crude residue is then dissolved in ethyl acetate (200 mL) and washed with water (2×100 mL). The aqueous layers are combined and extracted with ethyl acetate (2×100 mL). The combined organic layers are dried (Na$_2$SO$_4$), concentrated in vacuo, and subjected to flash chromatography affording the TPSO derivative as an amorphous white solid.

b) The Boc-protected aminoglycoside (10 mmol), carefully dried by coevaporation with pyridine, is reacted with 2,4,6-triisopropylbenzenesulfonychloride (5-fold molar excess) in anhydrous pyridine (120 mL) for 70 h at room temperature. The reaction mixture is poured into 5% aqueous NaHCO$_3$, (150 mL), stirred for 30 min and evaporated to dryness. Crude BOC-2 is extracted by treatment of the residue with CHCl$_3$ (2×75 mL) and purified by column chromatography.

General Procedure 17: Azide Displacement of Triisopropylbenzenesulfonyl Chlorides A solution of the TPSO derivative (0.3 mmol) and NaN$_3$ (150 mg, 2.3 mmol) in DMF (5 mL) is stirred at elevated temperature (100° C., 8 h). After cooling to room temperature the reaction mixture is diluted with ethyl acetate (100 mL) and washed with water (2×20 mL). The ethyl acetate layer is dried (Na$_2$SO$_4$) and evaporated, yielding the azido derivative as a white amorphous solid.

General Procedure 18: Click Coupling

A mixture of tert-butanol and water (1:1, 2 mL) is added to a mixture of the azidoglycan (0.04 mmol), prop-2-ynyl derivative (0.05 mmol), CuSO$_4$.5H$_2$O (1 mg), and copper powder (30 mg). The reaction mixture is stirred vigorously at room temperature (18 h) and then diluted with water (20 mL). Copper powder is removed by filtration and the filtrate is concentrated in vacuo. Purification by RP-IP HPLC (general procedure 5) and concentration of the fractions in vacuo yields the product.

General Procedure 19: Propynamide Formation

The solution of aminoglycan (5 mmol) is dissolved in ice-cold saturated NaHCO$_3$ (3 mL). 3 aliquots of propiolic acid NHS ester (15 mmol in 0.2 mL DMS, prepared as described in *Biokimiya* 1962, 27, 608) is added at 20 minute intervals to the solution. The progress of this reaction is monitored by analytical RP-IP HPLC (general procedure 6).

The desired propynamide derivative is isolated either by preparative RP-IP HPLC or by precipitation by addition of 3 volumes of ethanol and the mixture cooled to 4° C. The precipitate is separated and redissolved in 0.4 M NaOAc pH 7, re-precipitated by addition of 3 volumes of ethanol and the mixture cooled to 4° C. The white precipitate of product is separated by centrifugation.

General Procedure 20. Conversion of Amine to Azido

Imidazole-1-sulfonyl azide hydrochloride (0.05 g, 0.24 mmol) is added to the amine or ammonium salt substrate (0.2 mmol), K$_2$CO$_3$ (0.5 mmol) and CuSO$_4$.5H$_2$O (0.5 mg, 2 µmol) in MeOH (1 mL) and the mixture stirred at room temperature until completion indicated by monitoring with HPLC.

General Procedure 21: Epoxidation of Olefins a) mCPBA method. Unsaturated cyclitol (1 mmol) is dissolved in 1M NaH$_2$PO$_4$ (10 mL) and 1M Na$_2$HPO$_4$ (10 mL).

m-Chloroperbenzoic acid (1.5 mmol) dissolved in dichloroethane (20 mL) is added and the mixture stirred vigorously at 50° C. for 24 h. After separation of the layers the desired product is purified from the aqueous phase by cation exchange chromatography.

b) Metal catalyst.

General Procedure 22. Boc Removal

The Boc protecting group is removed in the conventional manner. Typically, 5-10 minutes of exposure to TFA at room temperature is required. TFA is removed in vacuo.

General procedure 23. N-Azidoacetylation a) Acylation with chloroacetyl chloride is achieved using general procedure 4. This intermediate is converted in situ to the azido derivative by stirring with 2 equivalents of $NaN_3$ at room temperature for 16 h.

b) Direct azidoacetylation is performed as described in general procedure 4, substituting azidoacetylchloride for bromoacetyl bromide.

General Procedure 24. N-Acetylation

A. Procedure 4 is followed, substituting acetic anhydride (or acetyl chloride) for bromoacetyl bromide.

B. The aminoglycoside (free base) is dissolved in methanol and 10% molar excess (relative to number of amino groups) of acetic anhydride is added and the reaction stirred at room temperature for up to 16 h. The reaction is monitored by RP HPLC (general procedure 25) and more acetic anhydride added if necessary.

General Procedure 25. RP HPLC Analysis of Aminoglycoside Reactions

Eluent A: 0.1% HFBA
Eluent B: Methanol
Column: Varian Pursuit C18, 5 μm, 100×4.6 mm.
Flow: 1 mL/min
Detector: 1) UV 2) ELSD
Gradient: Typically, 30% B initially, increased linearly to 70% over 15 minutes.

General Procedure 26. Size Exclusion Chromatography of Sulfated Products

Eluent: 50 mM $NH_4Cl$ containing 5% acetonitrile.
Column: 2 of BioSep 2000 (Phenomenex, Torrance, Calif.) 300×7.6 mm connected in series and fitted with a GFC2000 guard cartridge (Phenomenex, Torrance, Calif.).
Flow: 0.5 mL/min
Column Temperature: 35° C.
Detector: Refractive index
Injection: 25 μL.

Clexane is used to establish the relationship between size and elution. Sulfated β-cyclodextrin sulfate (Sigma, St Louis Mo.) is used as a quantitive standard.

Reagents—

Set 1. Tri(bromoacetamidyl)reagents.

N,N',N''-tri(bromoacetamidyl)ethylenetriamine (R1) and N,N',N''-tri(bromoacetamidyl) hexamethylenetriamine (R2) is prepared using the procedure described in U.S. Pat. No. 2,909,566 for the corresponding trichloroacetamides.

Set 2. Diacetylenic pegs (n=1-5):

a) Diol-terminated oligoethyleneglycol is treated with NaH (12 mg, 0.5 mmol) in THF (35 mL). A solution of propargyl bromide, dissolved as an 80% weight solution in xylene (0.56 mL, 5 mmol, 50 equiv., Aldrich), and a catalytic amount of KI is then added to the solution and the resulting mixture is heated to reflux for 2 h. Water (1 mL) is then added and the solvent is removed under vacuum. To the residue is added $CH_2Cl_2$ (25 mL) and the organic layer is separated, dried over anhydrous $Na_2SO_4$, and the volume is reduced to approximately 2 mL. This $CH_2Cl_2$ solution is added to diethyl ether (150 mL) drop-wise. The resulting precipitate is collected, washed with several portions of cold diethyl ether, and dried to afford propargyl-O-PEG.

b) Oligoethyleneglycol diol ([—OH]=10 mmol) was dissolved in dry toluene, refluxed, and dried in a vacuum to remove water. Phosgene solution (15 mL, 20% in toluene) was then added into the dried PEG with stirring. The reaction was allowed to proceed overnight in a fume hood. The excess phosgene was removed in vacuum. DCM (20 mL) was used to dissolve the viscous residue. Propargyl amine (1.65 g, 30 mmol) was then added into the solution. The reaction was allowed to proceed for 7-8 h at room temperature. The product was precipitated into diethyl ether three times and purified by a LH-20 column. Yield: 83.3%. $^1H$ NMR ($D_2O$) δ (ppm): 4.23 (t, PEG, —$CH_2$—), 3.89 (s, propargyl amide, —$CH_2$—), 3.68 (m, PEG, —$CH_2$—). $^{13}C$ NMR ($CDCl_3$) δ(ppm): 155.80, 79.74, 71.24, 70.32, 69.22, 64.01, 30.44. To confirm the 100% derivatization of PEG diol into acetylene-terminated PEG, the product was also analyzed by $^1H$ NMR ($CDCl_3$). No —OH signal (δ=2.63 ppm) was detected.

Set 3. Azido PEGS

O-Propargyl-tetra(ethylene glycol) tosylate (3). p-Toluenesulfonyl chloride (1 g, 5.4 mmol) and DMAP (25 mg, 0.2 mmol) was added to a solution of 2 (1.044 g, 4.5 mmol) in 1:1 pyridine-dichloromethane (10 mL). After 5 h, the solution was poured into ice-water (20 mL), and the aqueous phase was extracted with dichloromethane (3×20 mL). The combined organic phases were washed with $NH_4Cl$ (20 mL) and brine (20 mL), dried over anhydrous $Na_2SO_4$, and concentrated. The yellow oil was chromatographed on silica gel (EtOAc:hexane 3:1) to yield 3 (1.404 g, 81%) as a clear oil. $^1H$ NMR ($CDCl_3$) δ: 7.75 (d, 2H, J=8.4 Hz, Ph), 7.26 ((d, 2 H, J=8.4 Hz, Ph), 4.19 (d, 2 H, J=2.4 Hz, $OCH_2C$—CH), 4.16 (t, 2 H, J=7.8 Hz, $OCH_2CH_2OTs$), 3.70-3.55 (m, 14 H, ($OCH_2CH_2$)O), 2.54 (s, 3 H, Ph-$CH_3$), 2.52 (t, 1 H, J=2.4 Hz, $OCH_2C$≡CH).

Set 3. Diazido PEGS.

Diazide terminated monodisperse PEGs are prepared as described in *Tetrahedron Letters* 2001, 42(23), 3819-3822.

Set 4. Tetrameric Acetylenes in a Dimer of Dimer Arrangement.

RI1

↓

-continued

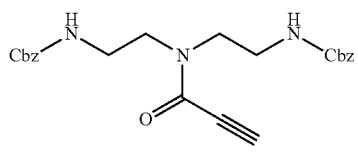

RI2

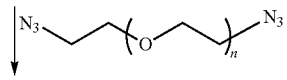

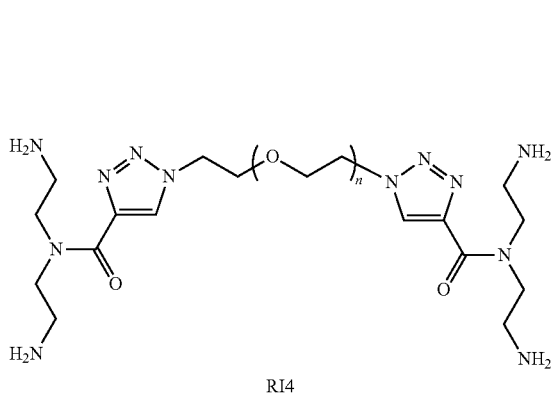

RI3

↓

RI4

Di-Cbz protected diethylenetriamine (RI1) is propynylated and the resulting acetylene (RI2) reacted with the diazido PEG (n=0) using standard click chemistry conditions. The product (RI3) is deprotected to generate the core unit RI4.

Likewise, reagents wherein n=1, 2, 4, 8 and 12 may be prepared.

a) Propynylation.

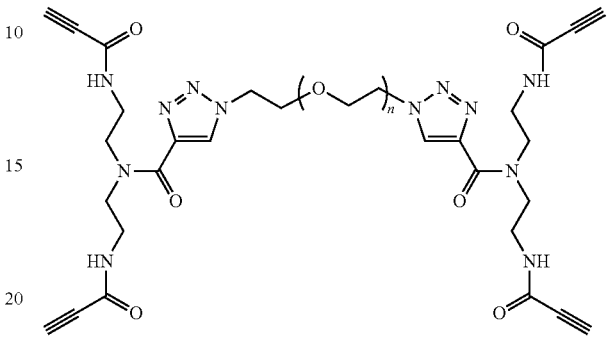

RI4 is transformed to the tetrakispropynamide derivative using the mixed anhydride reagent (Reagent 6b, below) to afford Reagent T4-1.

coupled to 0.4 equivalents of PEG dithiol in methanol/TEA.

Likewise reagents wherein n=1, 2, 4, 8 and 12 may also be prepared.

b) Tetraazido.

T4-101

RI4 is transformed to the tetraazido derivative (T4-101) using general procedure 9.

Likewise, reagents wherein n=1, 2, 4, 8 and 12 may be prepared.

c) Pendant PEG Alkyne.

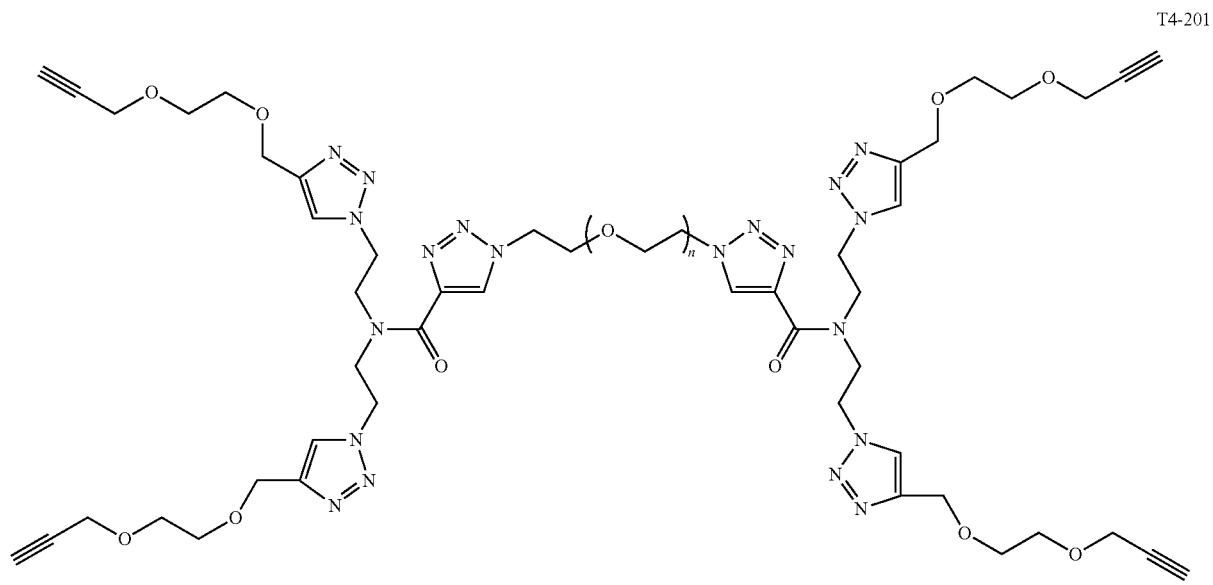

T4-201

101 is transformed to the tetrakis(PEG) derivative T4-201 using general procedure 18 and a 20-fold excess of di(O-propargyl)ethylene glycol.

Likewise, reagents wherein n=1, 2, 4, 8 and 12 may be prepared.

Reagent 5.a) 2,4,6-Tris(prop-2-ynyloxy)-1,3,5-triazine. Propargyl alcohol (10 mL) is added slowly to a suspension of cyanuric chloride (2.2 g, 12.1 mmol) in 15 ml THF at room temperature followed by $K_2CO_3$ (5.2 g, 36.3 mmol) and the mixture heated to 60° C. overnight. The reaction mixture is filtered. After evaporation of solvent, the residue is dissolved in 80 ml $CH_2Cl_2$, and washed with dilute citric acid (10%), saturated brine. Dried over $MgSO_4$, evaporated to give 23 as white solid in 90% yield. $^1$H NMR (600 MHz, [D6]Acetone): δ=3.13 (t, J=2.2 Hz, C≡CH, 3H), 5.10 (d, J=2.2 Hz, CH2C≡CH, 6H). 13C NMR (150 MHz, [D6]Acetone): δ=53.4 (s, CH2C≡CH, 3C), 77.3 (s, CH2C≡CH, 3C), 78.4 (s, C≡CH, 3C), 173.5 (s, Ar—C, 3C). m.p. 69-70° C.

b) N,N',N''-tri(propiolyl)ethylenetriamine (R1) and N,N',N''-tri(propiolyl)hexamethylenetriamine (R2) was prepared using a procedure analogous to that described for the tri(bromoacetamido) derivatives.

Reagent 6. Propynylation reagents.

The NHS ester (Reagent 6a) and mixed anhydride (Reagent 6b) of propynoic acid is prepared as described *Synth. Comm.* 1993, 23(14), 2003-2010.

Reagent 7. N-Hydroxy-5-norbornene-2,3-dicarboximide (NBD-Boc).

endo-N-Hydroxy-5-norbornene-2,3-dicarboximide (NBD) (3.59 g, 20 mmol) is dissolved in absolute ethanol (100 mL), and is then evaporated to dryness in vacuo to remove the residual moisture from the reagent. The residue is redissolved in freshly prepared absolute ethanol (60 mL), and thallous ethoxide (1.42 mL, 20 mmol) is added dropwise with vigorous stirring. The solution is stirred for 3 h at room temperature and then overnight at 4° C. The white precipitate which forms in the course of the reaction is collected by filtration, washed with cold ethanol, and dried under high vacuum. The solid material is suspended in methylene chloride (100 mL), and di-tert-butyl dicarbonate (4.37 g, 20 mmol) is added dropwise. The solution is stirred overnight at room temperature and is then washed with water (2×10 mL). The organic layer is dried over anhydrous $MgSO_4$, filtered, and evaporated to dryness to give the crude product as a white solid. The solid is suspended, with vigorous stirring, in anhydrous ether (60 mL) for 2 h, followed by filtration, to give 3.0 g of the pure product. Upon storage of the filtrate at −20° C. overnight, additional pure product precipitates giving a total of 3.63 g of the title compound in two crops in an overall yield of 65%.

Reagent 8. Azidoacetyl Chloride.

According to the procedure of *J. Am. Chem. Soc.* 2002, 124(23), 6626-6635, sodium azide (2.0 g, 30.8 mmol) was dissolved in 15 mL distilled $H_2O$ and cooled to 0° C. Bromoacetic acid (2.14 g, 15.4 mmol) was then added over 10 min and the reaction mixture was allowed to slowly warm to room temperature overnight. The reaction mixture was acidified to a pH of 1 and extracted three times with 20 mL diethyl ether. The organics were combined, dried over $MgSO_4$ and concentrated. The crude mixture was then dissolved in 50 mL of $CH_2Cl_2$ with two drops of DMF and cooled to 0° C. Oxalyl chloride (2.44 g, 19.3 mmol) was slowly added by syringe over 15 min. The reaction was allowed to warm overnight to room temperature and then the solvent was removed under reduced pressure. The crude oil was distilled under high vacuum at room temperature into a receiving flask at −78° C. to yield pure azidoacetyl chloride as a colorless oil (1.56 g, 85%). NBD and Phthalimide esters of azidoacetic acid. The NBD and Phthalimide esters were prepared by adopting the procedures described in *Bioorg. & Med. Chem.* 2007, 15(8), 2944-2951. N-benzyloxycarbonyloxy-5-norbornene-endo-2,3 dicarboximide was prepared as described in US20080227213.

Reagent 9. Oligoethyleneglycol dithiols.

The dithiols of tetraethyleneglycol and pentaethyleneglycol were prepared by adopting the procedures described in *Organic Syntheses, Coll. Vol.* 4, p. 401; *Vol.* 30, p. 35 and *Organic Syntheses, Coll. Vol.* 5, p. 249; *Vol.* 48, p. 51.

PEG Dithiols

Example 1

Glycosylamine Formation

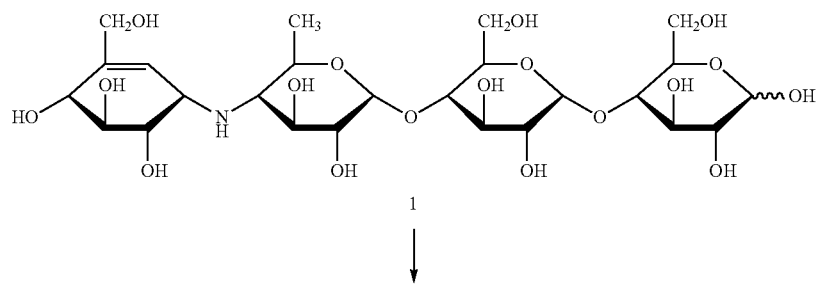

1

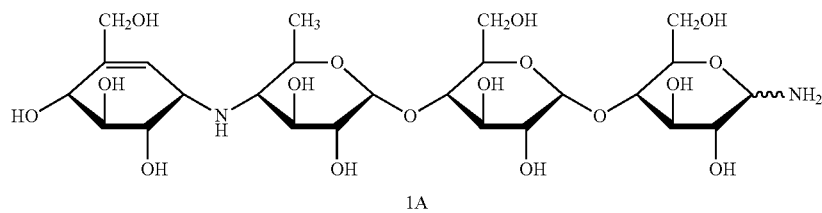

1A

Acarbose (1) is converted to glycosylamine (1A) using general procedure 8 and the crude material is used for further reactions.

Likewise the following starting materials are converted to their corresponding glycosylamines: Acarbose component A (Acarviosyl-1,4Glc1,4-Fm); Acarbose component D (Acarviosyl-1,4Glc1,4-Man); A carbose component 4b (Acarviosyl-1,4Glc-1,4-Glc-1,4-Fru); Acarbose component 4a (Acarviosyl-1,4Glc-1,4-Glc-1,1-Glc); Pseudo-acarbose (Acarviosyl-1-4-(6-desoxy)Glc-1-4-Glc); amylostatin XG; amylostatin XGGG; amylostatin GXG; amylostatin GXGG; amylostatin GXGGG; adiposin-1; adiposin-2; Oligostatin C; Oligostatin D; and Oligostatin E.

Example 2

Protection of the Glycosylamine

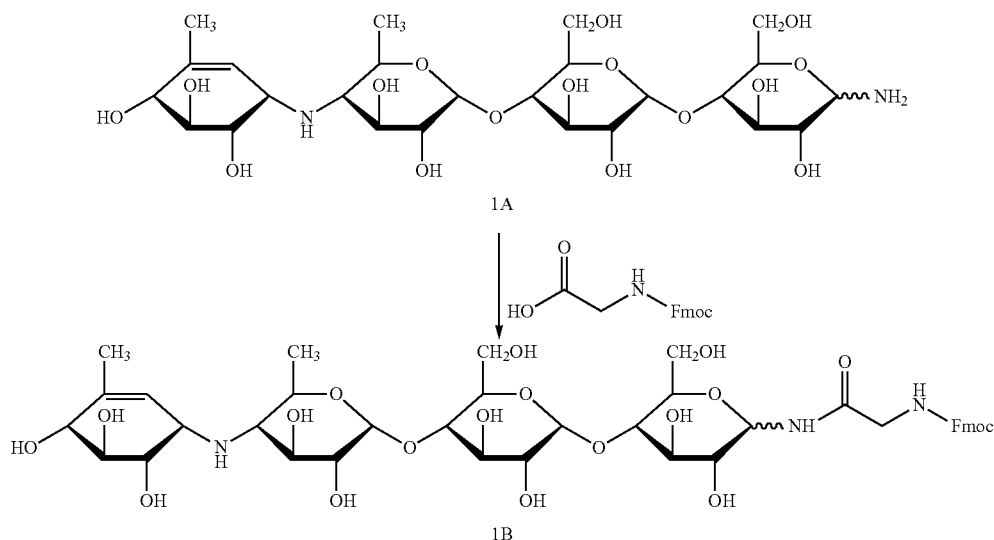

Crude acarbose glycosylamine (1A) is protected as the Fmoc-glycine derivative (1B) using general procedure 2b.

Likewise the other glycosylamines of Example 1 are converted into their corresponding Fmoc-glycine derivatives.

Example 3

Sulfation of Fmoc-Derivatives

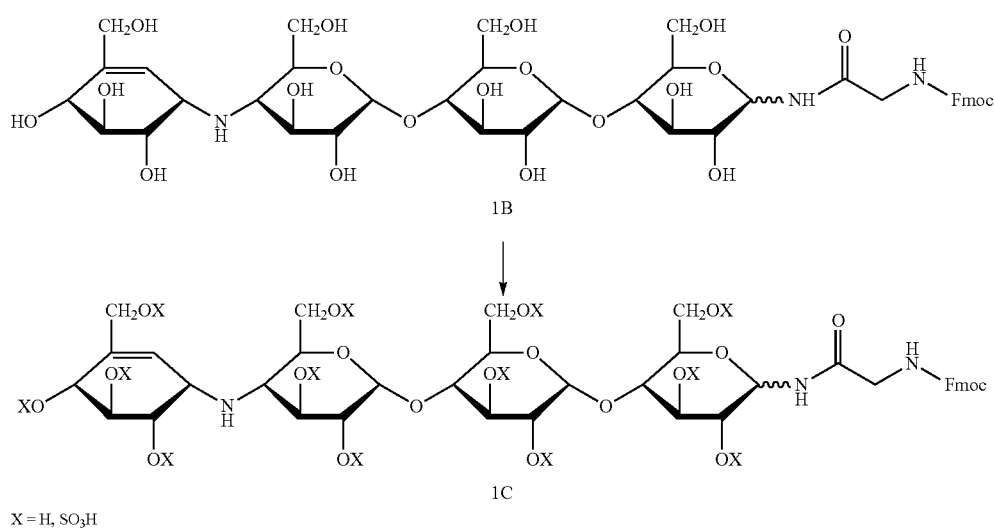

X = H, SO₃H

The Fmoc-acarbose derivative (1B) is sulfated using general procedure 1 to generate the sulfated Fmoc-acarbose (1C).

Likewise the other Fmoc-glycine derivatives of Example 2 are sulfated.

Example 4

Fmoc Deprotection and Bromoacetylation of Sulfated Derivatives

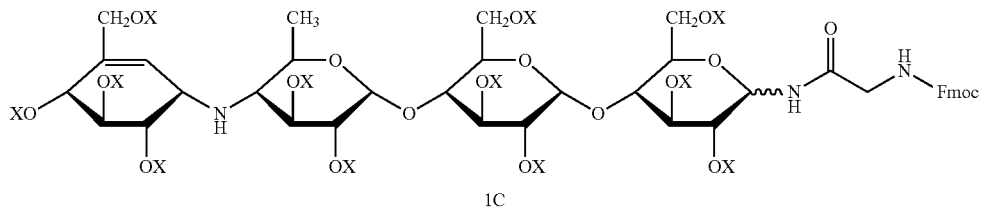

1C

1. NaOH
2. BrAcOBr

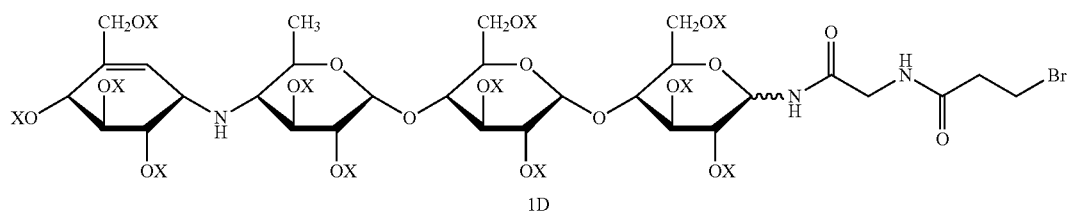

1D

X = H, SO₃H

The sulfated acarbose-Fmoc derivative (1C) is deprotected using general procedure 3 and in the same pot this intermediate is bromoacetylated using general procedure 4.

Likewise the other Fmoc-glycine derivatives of Example 3 are converted into the corresponding alkyl bromides.

Example 5

Formation of Homodimers Via Coupling with 2,2'-Oxydiethanethiol

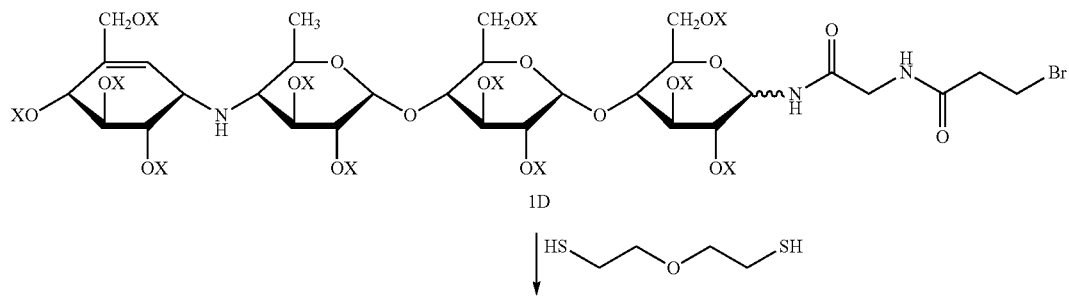

1D

-continued

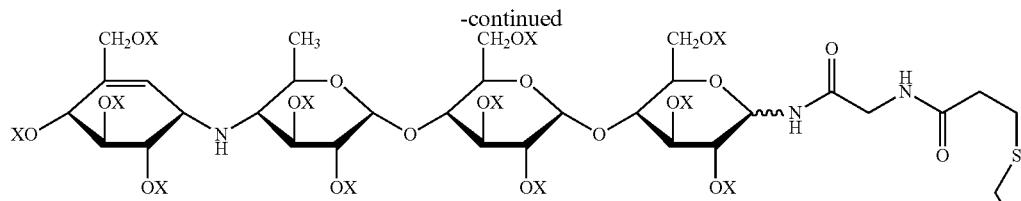

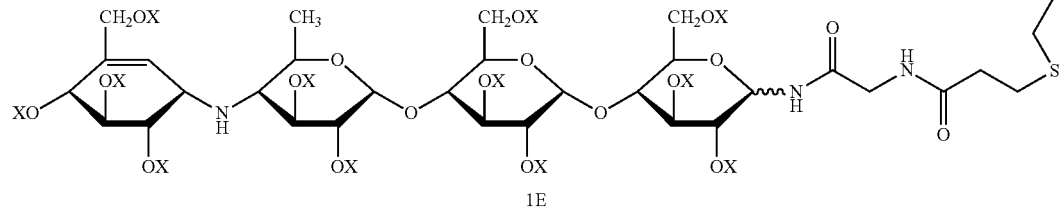

1E

X = H, SO₃H

Bromoacetylacarbose derivative (1D) is coupled to 2,2'-oxydiethanethiol using general procedure 7.

Likewise the other bromoacetamide derivatives of Example 4 are coupled.

Example 6A

Coupling of Sulfated Acarboseglycosylamine to PEG Linkers of Different Lengths

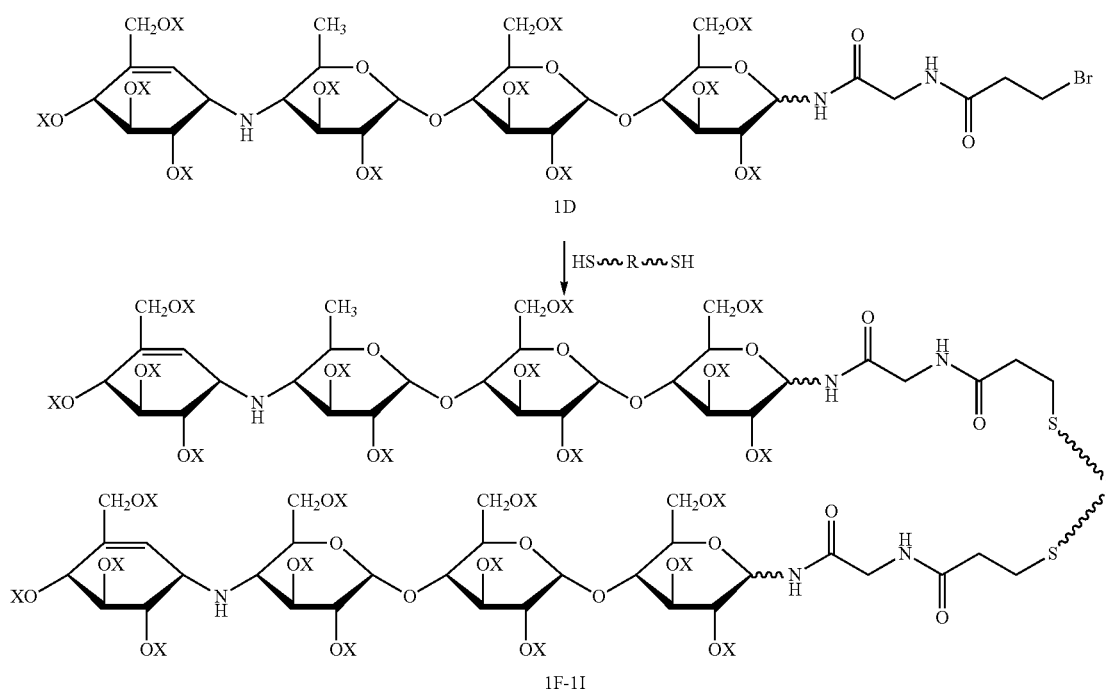

1F-1I

X = H, SO₃H

Bromoacetylacarbose derivative (1D) is coupled to dithiol terminated oligoethleneglycols and ethanedithiol using general procedure 7.

|  | Linker | | | | |
|---|---|---|---|---|---|
|  | $HS(CH_2)_2SH$ | $HS[(CH_2)_2O]_2(CH_2)_2SH$ | $HS[(CH_2)_2O]_3(CH_2)_2SH$ | $HS[(CH_2)_2O]_4(CH_2)_2SH$ | $Na_2S$ |
| Product | 1F | 1G | 1H | 1I | 1F0 |

Likewise the other alkyl bromide derivatives of Example 4 are coupled using linking groups of varying lengths.

Example 6B

Sulfation of Dimers Formed from Acarbose

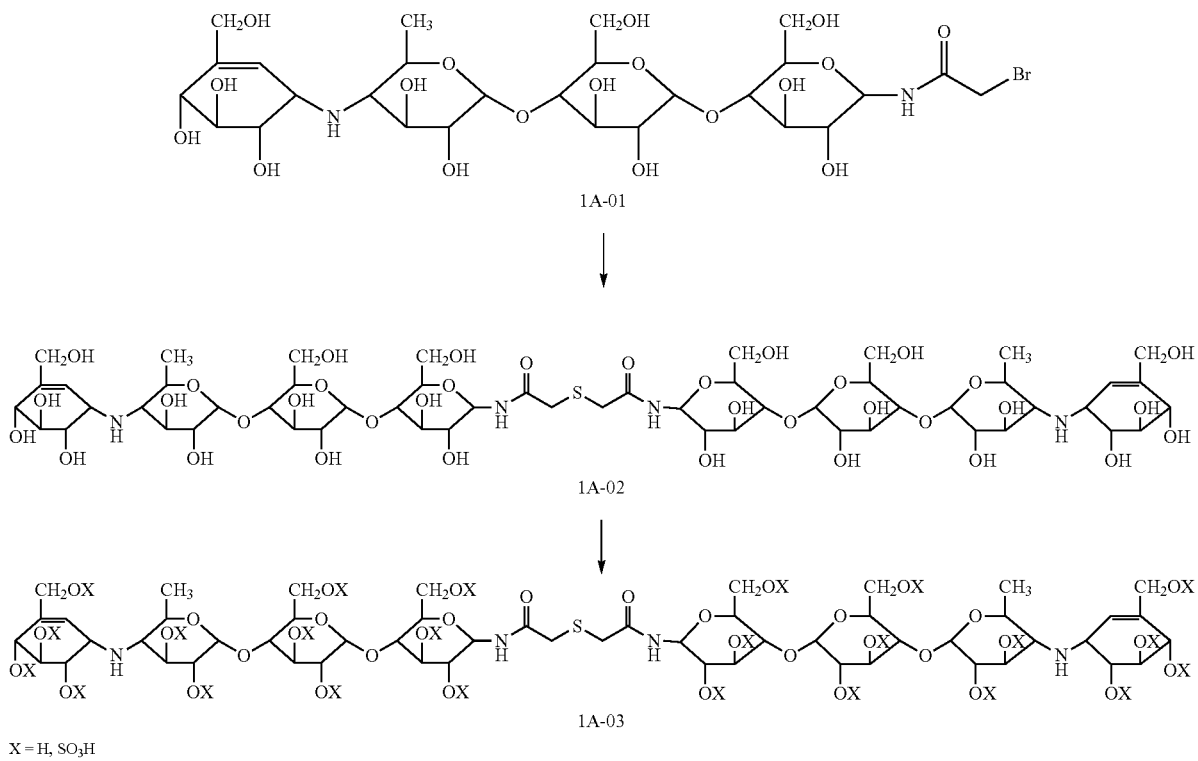

X = H, SO₃H

Analogs of the products in examples 5 and 6A can be prepared by variation of the sequence of steps, i.e. coupling of the acarbose sub-units prior to sulfation. Thus, 1A was bromoacetylated (general procedure 4) and the product purified by chromatography on a column of Hypercarb (Grace Davison, Deerfield Ill.) using a water-ethanol gradient. ESI/MS 765.23, 767.23 (Calc [M+H]⁺ 765.19 (100%) 767.18 (97.3%)).

The bromoacetamide 1A-01 was dissolved in saturated sodium bicarbonate and solid sodium sulphide added. The dimer 1A-02 forms instantaneously and was purified on the Hypercarb column. 7. ESI/MS 702.45 (m/z=2); 1404.46 (100%), 1403.46 (94%) (Calc [M+2]⁺² 702.75; [M+H]⁺ 1403.5 (100%) 1404.5 (63%). 1A-02 is sulfated using general procedure 1 and the product 1A-03 purified by RP IP HPLC.

In a cognate manner, the linkers in the following table are reacted with the bromoacetamide using general procedure 7.

|  | Linker | | | | |
|---|---|---|---|---|---|
|  | $HS(CH_2)_2SH$ | $HS[(CH_2)_2O(CH_2)_2SH$ | $HS[(CH_2)_2O]_2(CH_2)_2SH$ | $HS[(CH_2)_2O]_3(CH_2)_2SH$ | $HS[(CH_2)_2O]_4(CH_2)_2SH$ |
| Product | 1A-04 | 1A-05 | 1A-06 | 1A-07 | 1A-08 |

Example 6C

The Procedure in Example 6B is Modified

Compound 1B is deprotected and then treated in the same manner as the preceeding example. Thus, the following products are generated.

| | | | Linker | | | |
|---|---|---|---|---|---|---|
| | $Na_2S$ | $HS(CH_2)_2$ $SH$ | $HS(CH_2)_2O$ $(CH_2)_2SH$ | $HS[(CH_2)_2O]_2$ $(CH_2)_2SH$ | $HS[(CH_2)_2O]_3$ $(CH_2)_2SH$ | $HS[(CH_2)_2O]_4$ $(CH_2)_2SH$ |
| Product | 1B-04 | 1B-05 | 1B-06 | 1B-07 | 1B-08 | 1B-09 |

Example 7

Sulfation of $C_7N$ Cyclitol Metabolites

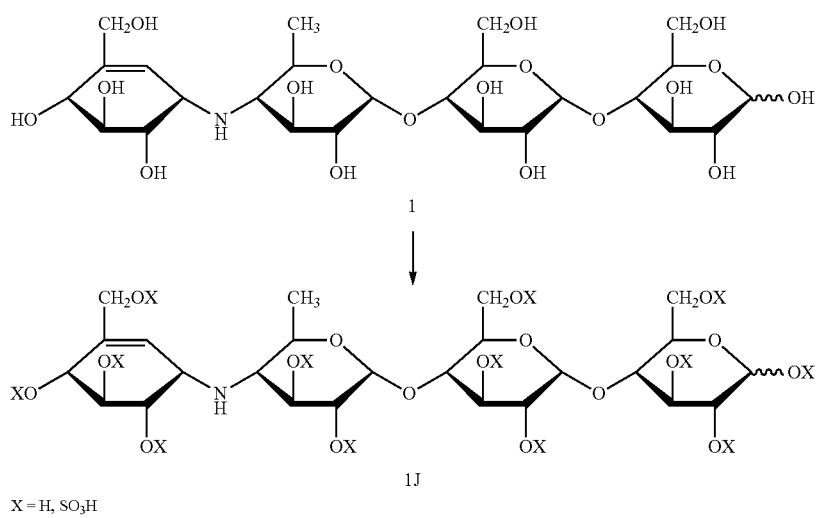

X = H, $SO_3H$

Acarbose (1) is sulfated using general procedure 1 to generate the sulfated acarbose (1J).

Likewise the following starting materials are sulfated: Acarbose component A (Acarviosyl-1,4Glc-1,4-Fru); Acarbose component B (Acarviosyl-1,4Glc-1,4-(1-epi-valeinol)); Acarbose component C (Acarviosyl-1,4Glc1,1-Glc); Acarbose component D (Acarviosyl-1,4Glc-1,4-Man); Acarbose component 4b (Acarviosyl-1,4Glc1,4-Glc1,4-Fru); Acarbose component 4a (Acarviosyl-1,4Glc-1,4-Glc-1,1-Glc); Acarbose component 4c (Acarviosyl-1,4Glc-1,4-Glc1,1-Glc); Pseudo-acarbose (Acarviosyl-1-4-(6-desoxy)Glc-1-4-Glc); amylostatin XG; amylostatin XGGG; amylostatin GXG; amylostatin GXGG; amylostatin GXGGG; CK-4416; CKD-711; CKD 711A; adiposin-1; adiposin-2; NS-1; NS-2; NS-3; NS-4; NS-5; NS-6; NS-7; NS-8; NS-9; NS-10; NS-11; NS-12; NS-13; NS-14; NS-15; NS-16; NS-17; Oligostatin C; Oligostatin D; Oligostatin E; Validoxylamine A; Validoxylamine B; Validoxylamine C; Validamycin A; Validamycin B; Validamycin C; Validamycin D; Validamycin E; Validamycin F; Validamycin G; Validamycin H; amylostatin L; amylostatin M; amylostatin N; amylostatin A; amylostatin B; amylostatin C; amylostatin D; amylostatin E; amylostatin F; Trestatin A; Trestatin B; Trestatin C; Ro 09-766; Ro 09-0767; Ro 09-0768; W46A; W46B; W46C; W46H; W46P; and Salbostatin.

Example 8

Homodimeric Conjugates of $C_7N$ Cyclitol Metabolites Linked by Coupling 2,2'-oxydiethanethiol to the Unsaturation

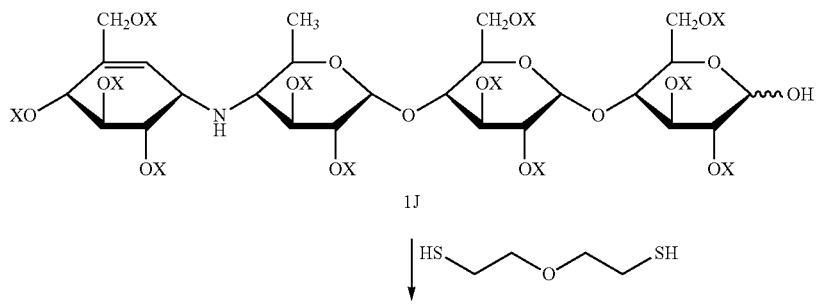

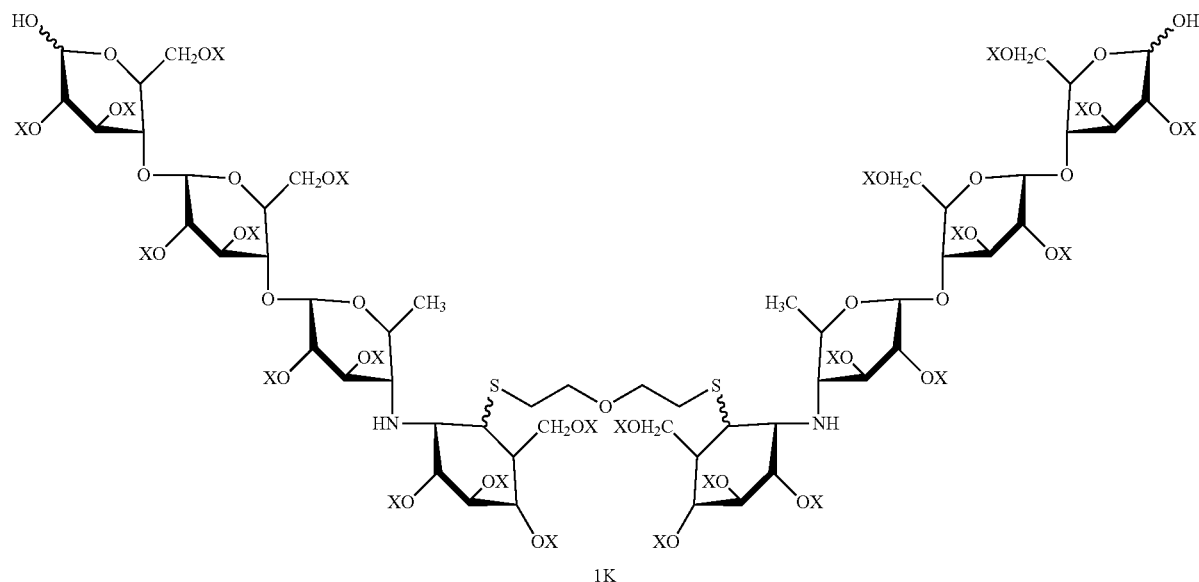

1K

X = H, SO₃H

An excess of acarbose polysulfate (1J) is reacted with 2,2'-oxydiethanethiol in a mixture of water and methanol and exposed to UV irradiation. The reaction is monitored by RP-IP HPLC with ELSD detection and the products may be purified by RP-IP HPLC to afford the linked conjugate (1J).

Likewise, the other sulfated compounds of Example 7 that comprise a single unsaturated cyclitol are coupled.

Example 9

Conjugates of C₇N Cyclitol Metabolites Linked by Coupling PEG Dithiols to the Unsaturation

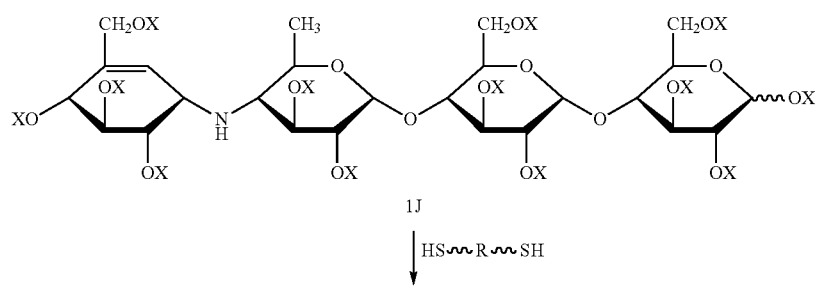

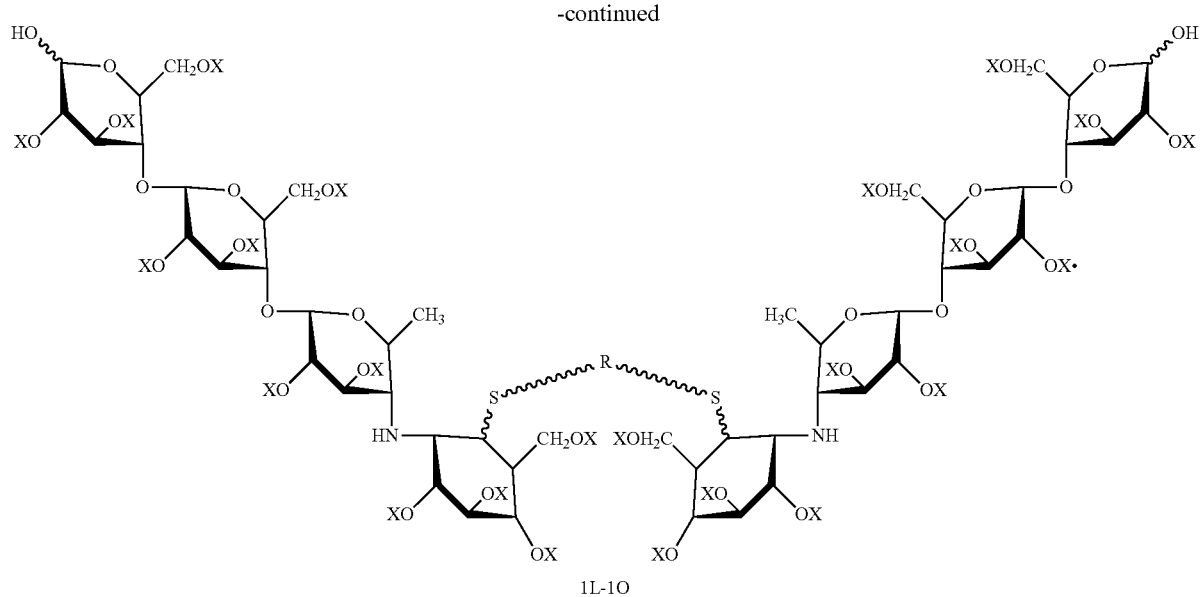

1L-1O

X = H, SO₃H

An excess of acarbose polysulfate (1J) is reacted with dithiol terminated oligoethyleneglycols or ethanedithiol in a mixture of water and methanol and exposed to UV irradiation. The reaction is monitored by RP-IP HPLC with ELSD detection and the products may be purified by RP-IP HPLC to afford the linked conjugates (1L-1O).

| | Linker | | | |
|---|---|---|---|---|
| | HS(CH₂)₂SH | HS[(CH₂)₂O]₂(CH₂)₂SH | HS[(CH₂)₂O]₃(CH₂)₂SH | HS[(CH₂)₂O]₄(CH₂)₂SH |
| Product | 1L | 1M | 1N | 1O |

Likewise, the other sulfated compounds of Example 7 that comprise a single unsaturated cyclitol are coupled using linking groups of varying lengths.

Example 10

Coupling of Oxirane Oligosaccharides to 2,2'-Oxydiethanethiol

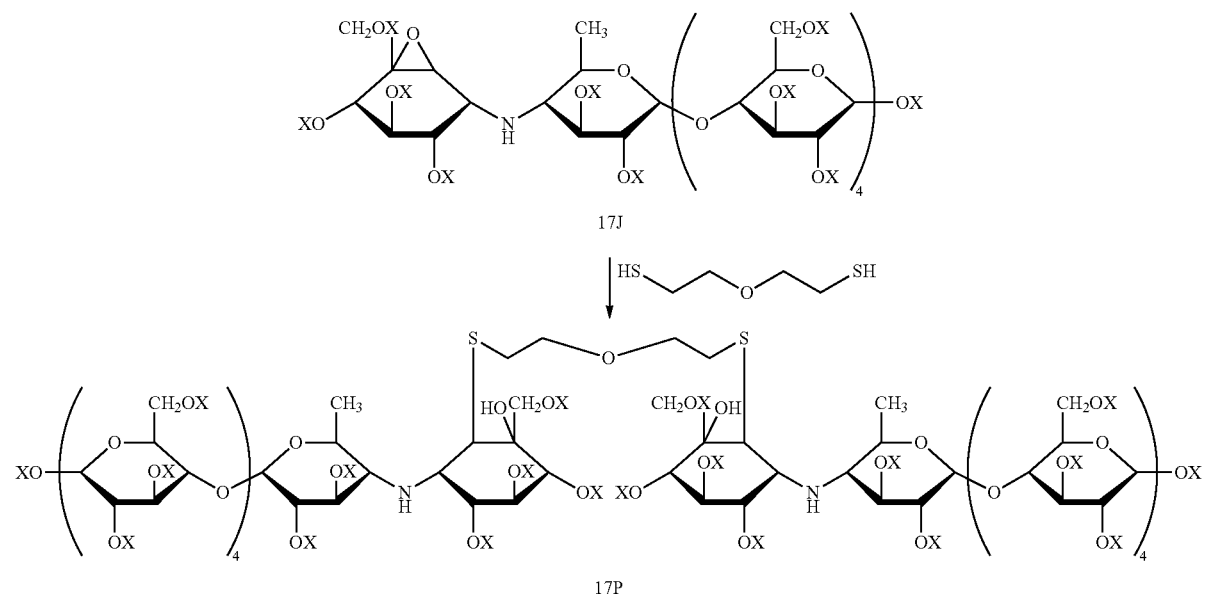

17P

X = H, SO₃H

The sulfated epoxide CKD711a (17J), either DABCO or Et$_3$N (1 mol %) in water, 2,2'-oxydiethanethiol (0.4 mmol) and 2-propanol (not exceeding 35% v/v) is stirred at room temperature. The reaction mixture is stirred at room temperature and monitored by RP-IP HPLC with ELSD detection and the products may be purified by RP-IP HPLC to afford the linked conjugates (1L-10).

Likewise, the other sulfated compounds of Example 7 that possess epoxide functionality are coupled.

Example 10a

Acarbose is epoxidised using 3-chloroperbenzoic acid (mCPA) and the epoxy derivative 1001J isolated using cation exchange and carbon chromatography. The epoxy derivative is coupled as for Example 10.

Likewise, the glycosylated bacterial metabolites comprising a single unsaturated cyclitol may be epoxidised and coupled.

Example 11

Azide Addition to Oxirane Oligosaccharides

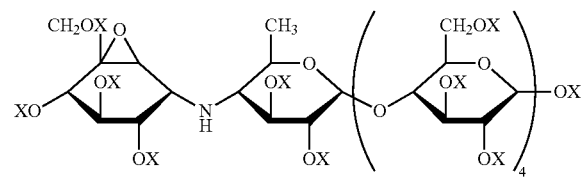

17J

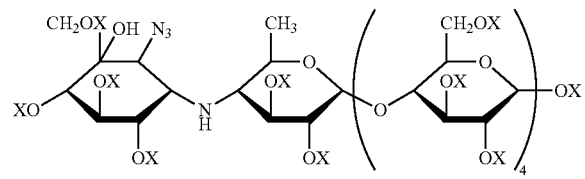

17Q

X = H, SO$_3$H

To a solution of the epoxide 17J in a 3:1 methanol-water mixture is added portionwise NaN$_3$ (10 equivalents) and NH$_4$Cl (60 equivalents). After stirring at 80° C. for 24 h, the reaction mixture is cooled and the azido product (17Q) purified by RP-IP HPLC.

Likewise the epoxidised compounds of Example 7 are reacted with sodium azide.

Example 11a

Likewise the epoxides formed as intermediates in Example 10a are converted to their corresponding azides Example 12

Reduction of Cyclitol Azides

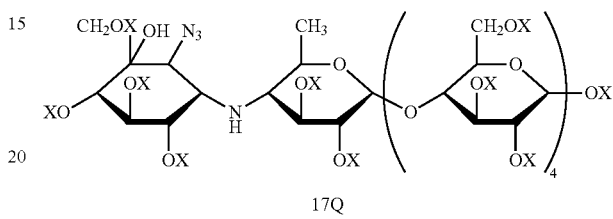

17Q

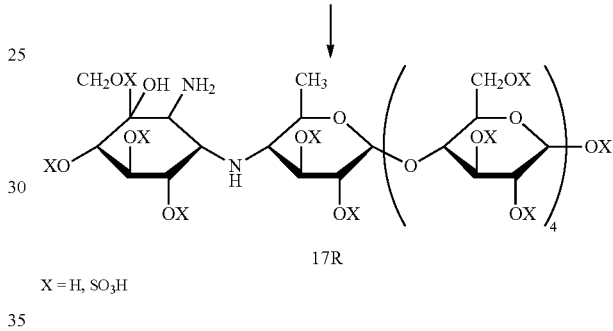

17R

X = H, SO$_3$H

The azidoglycan 17Q is reduced using general procedure 10c. The mixture is filtered and the product (17R) may be purified by RP-IP HPLC.

Likewise reduction of the other azides of Example 11 may be performed.

Example 12a

Likewise the azides of Example 11a are reduced to their corresponding amines

Example 13

Propynylation of Aminated Glycans

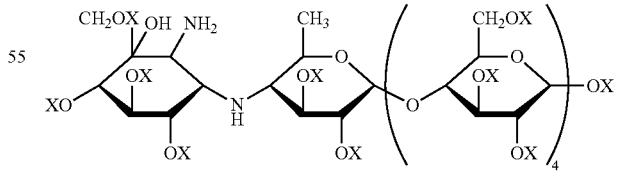

17R

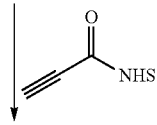

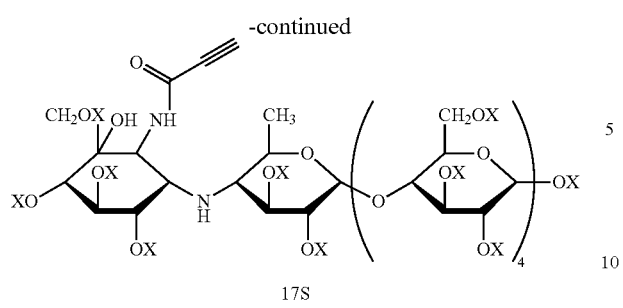

17S

X = H, SO₃H

Aminoglycan 17R is propynylated using general procedure 19. The product, 17S, is purified by RP-IP HPLC.

Likewise the other amines of Example 12 are propynylated.

Example 13a

Likewise the amines of Example 12a are propynylated

Example 14

Click Coupling of Oxirane Oligosaccharides to Form Homodimers

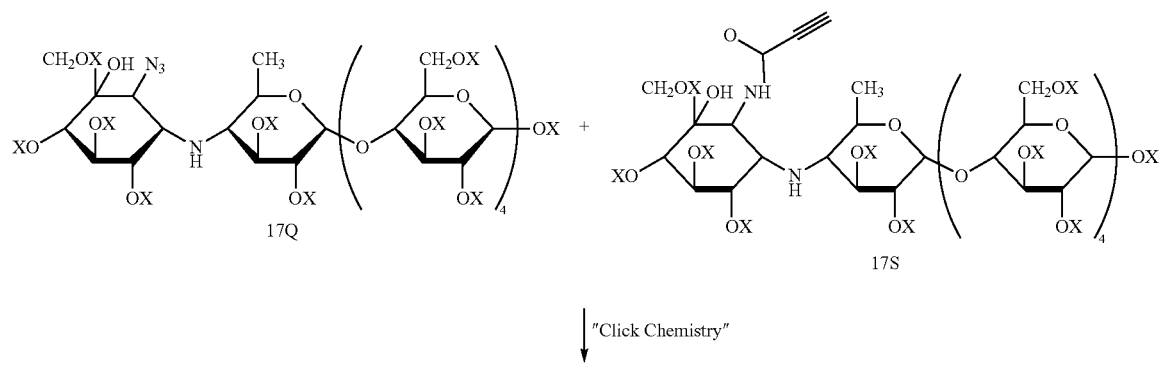

"Click Chemistry"

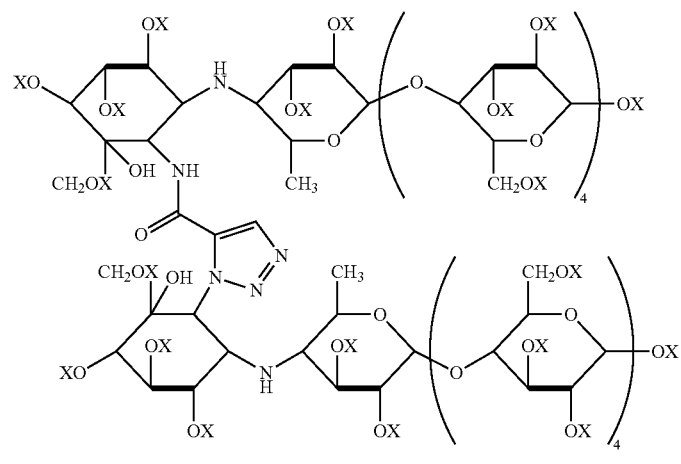

17T

X = H, SO₃H

Azido derivative 17Q is conjugated to the acetylene 17Q using general procedure 18 and the dimeric product 17T is purified by RP-IP HPLC.

Likewise the other propynylated species of Example 13 undergo conjugation with the azide compounds of Example 11.

Example 14a

Likewise the propynylated species of Example 13a undergo conjugation with the azide compounds of Example 11a

Example 15

Addition of a Single Acarbose to 2,2'-Oxydiethanethiol

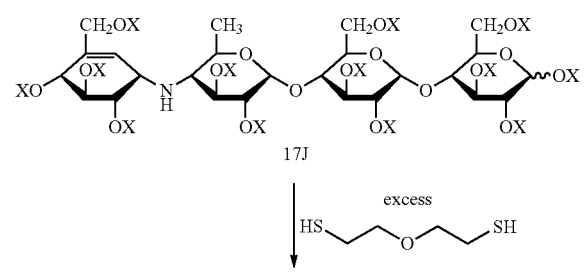

Sulfated acarbose (1J) is mixed with a 20-fold excess of 2,2'-oxydiethanethiol in a 1:1 mixture of water and methanol and exposed to UV irradiation with monitoring of the reaction by RP-IP HPLC with ELSD detection. The product (1U) is purified by RP-IP HPLC.

Likewise 2,2'-oxydiethanethiol may undergo an addition reaction with the compounds of Example 7 that comprise a single unsaturated cyclitol.

Example 16

Monomeric Conjugates of Acarbose with Thiol Linkers of Different Lengths

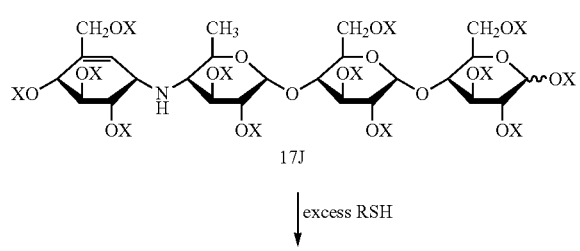

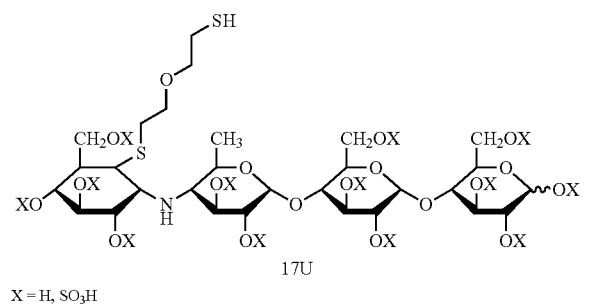

Sulfated acarbose (1J) is mixed with a 20-fold excess of thiol (RSH) and reacted as described in the previous example.

| | Thiol | | | | |
|---|---|---|---|---|---|
| | $HS(CH_2)_2SH$ | $HS[(CH_2)_2O]_2$ $(CH_2)_2SH$ | $HS[(CH_2)_2O]_3$ $(CH_2)_2SH$ | $HS[(CH_2)_2O]_4$ $(CH_2)_2SH$ | $HS(CH_2)_2NH_2$ |
| Product | 1V | 1W | 1X | 1Y | 1Z |

Likewise the thiols of varying lengths that are tabulated above undergo addition reactions with: the compounds of Example 7 that comprise a single unsaturated cyclitol; and the sulfate compounds of Example 3.

Example 17
Trimer Formation by Coupling Cyclitol Thiol Derivatives to Tris-Bromoacetamides
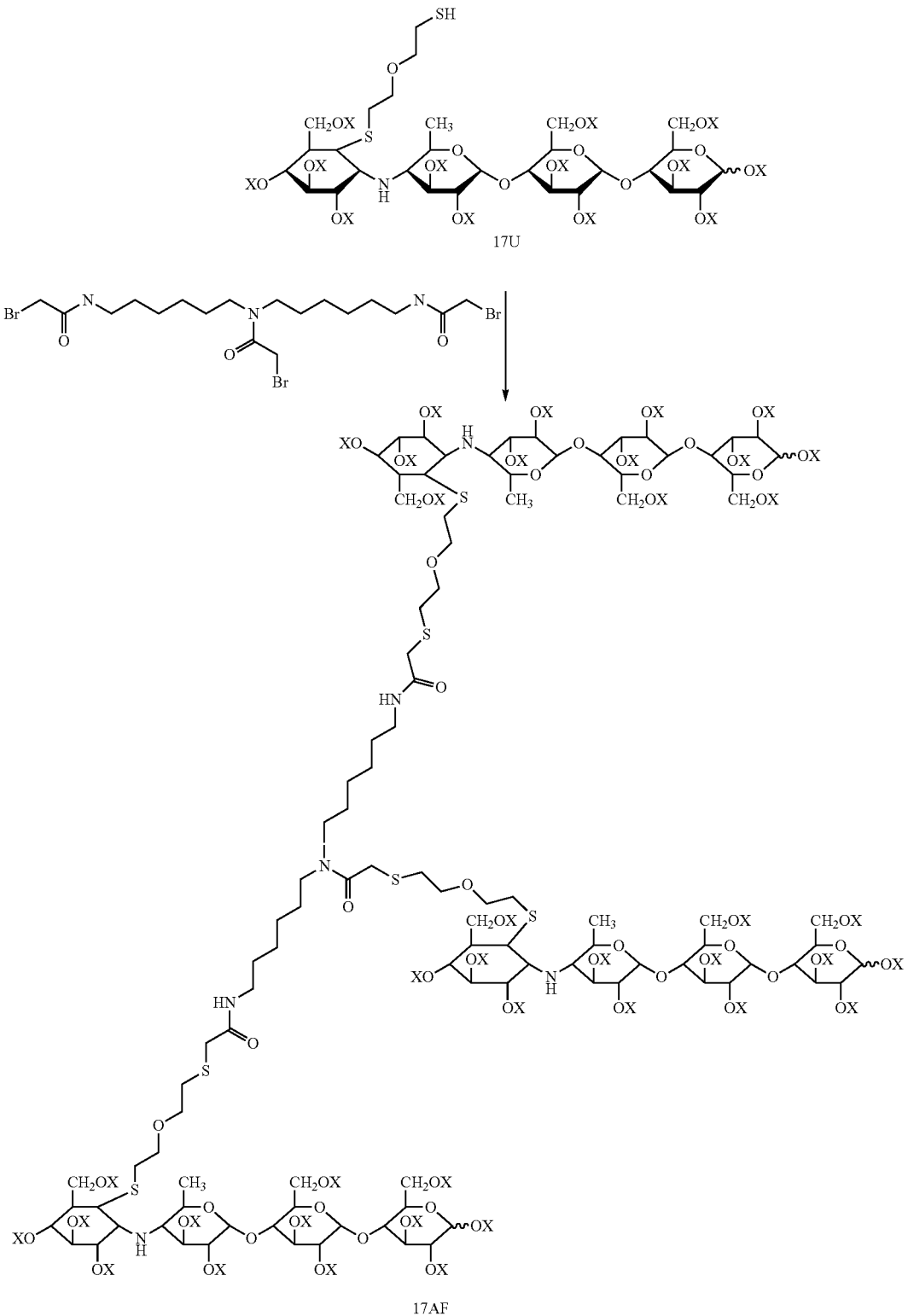
X = H, SO₃H Acarbose thiol derivative 17U is reacted with N,N',N"tri(bromoacetamidyl)-bis(hexamethylene)triamine (Reagent 1) using general procedure 13. The reaction is monitored by RP-IP HPLC and the trimeric product 17AF is purified by preparative RP-IP HPLC.

Likewise the thiol additions products of Example 15 and those thiol addition products of Example 16 which are derived from the compounds of Example 15 undergo coupling with tris-bromoacetamides.

Example 17B

Coupling to Tris-Bromoacetamides Via the Reducing Terminus

Bromoacetamide 1D is reacted with a 20-fold excess of $HS(CH_2)_2$—O—$(CH_2)_2SH$ using general procedure 13 and the product 1DA isolated.

Likewise, the following dithiols are also reacted.

| | Linker | | | |
|---|---|---|---|---|
| | $HS(CH_2)_2SH$ | $HS[(CH_2)_2O]_2$ $(CH_2)_2SH$ | $HS[(CH_2)_2O]_3$ $(CH_2)_2SH$ | $HS[(CH_2)_2O]_4$ $(CH_2)_2SH$ |
| Product | 1DB | 1 DC | 1DD | 1DE |

1DA is reacted with N,N',N"tri(bromoacetamidyl)-bis(ethylene)triamine (Reagent 1) using general procedure 13. The reaction is monitored by RP-IP HPLC and the trimeric product 1DF is purified by preparative RP-IP HPLC.

1DB, 1DC, 1DD and 1DE are treated in a similar manner to generate 1DG, 1DH, 1DI, 1DJ.

Example 17C

Coupling of Monothiols to Dimeric Cores

One equivalent of thiol 1DA is reacted with 0.45 equivalents of 1,3-bis(bromomethyl)benzene following general procedure 7 to isolate 1DK. 1DB, 1DC, 1DD and 1DE are treated in a similar manner to generate 1DL, 1DM, 1DN, 1DO.

Example 17D

Dimers Prepared by Disulfide Formation

DMSO is added to a solution of thiol 1DA upto 10% and the mixture incubated at room temperature for 2 days. The disulfide 1DAAD is purified by RP IP HPLC. Likewise, the thiols 1DB-1DE are treated similarly to generate 1 DBBD, 1DCCD, 1DDD and 1DEED.

Example 18

Azido Formation from Cyclitols with a Single Primary Amine

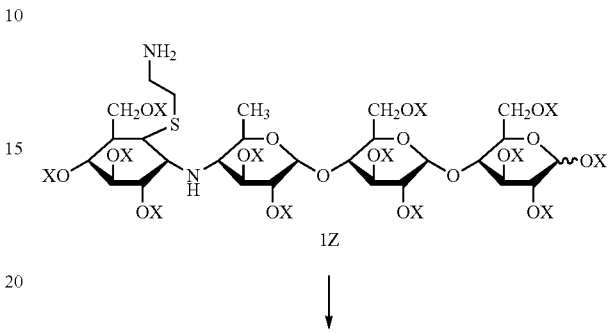

The conjugate of cystamine with acarbose (1Z) is transformed to the azido derivative using general procedure 20. The product 1AJ is purified by RP-IP HPLC.

Likewise, the cystamine derived products of Example 16 are converted into the corresponding azide derivatives.

Example 19

Azide Formation from Protected Glycosylamine Derivatives

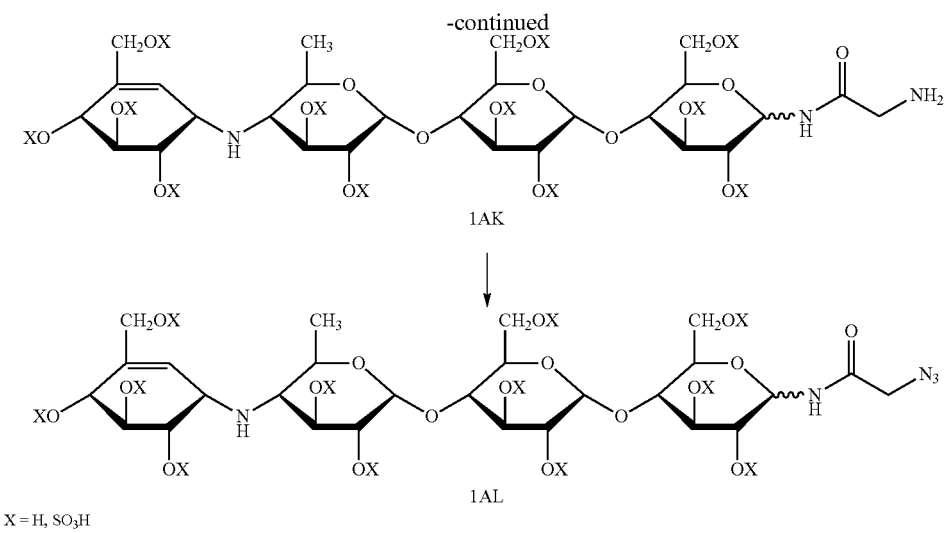

X = H, SO₃H

The Fmoc protected glycosylamine (1C) is deprotected as described in example 4 and the intermediate amine purified by RP-IP HPLC and used directly for the next step. The amine intermediate (1AK) is transformed to the azido product (1AL) using general procedure 20, and is purified by RP-IP HPLC.

Likewise, the other compounds of Example 3 may be transformed into the amines and subsequently the azides.

Example 20

Dimerization of Azido Cyclitols to Diacetylene Terminated Ethyleneglycol

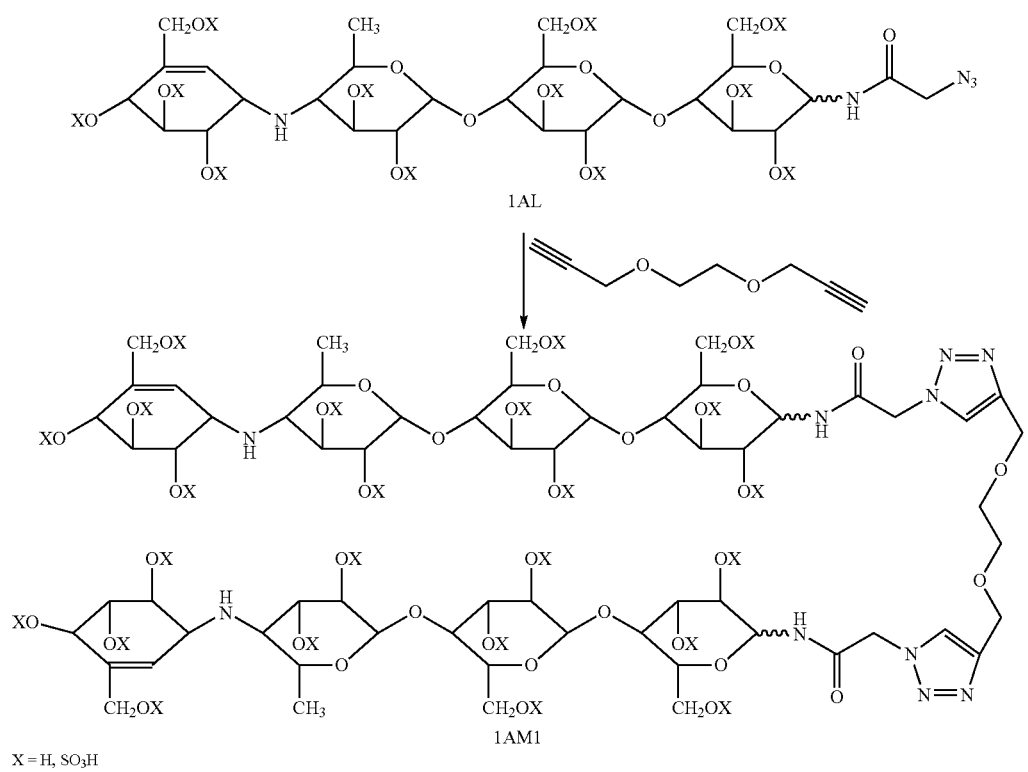

X = H, SO₃H

Azido cyclitol 1AL is conjugated to the diacetylene terminated ethyleneglycol (reagent 2) using general procedure 18. The dimeric product is purified by RP-IP HPLC.

Likewise, the other azido compounds of Example 19 may be coupled.

Example 21

Preparation of Homodimeric Conjugates from Acarbose Azides by Coupling to Acetylene Terminated Linkers of Different Lengths

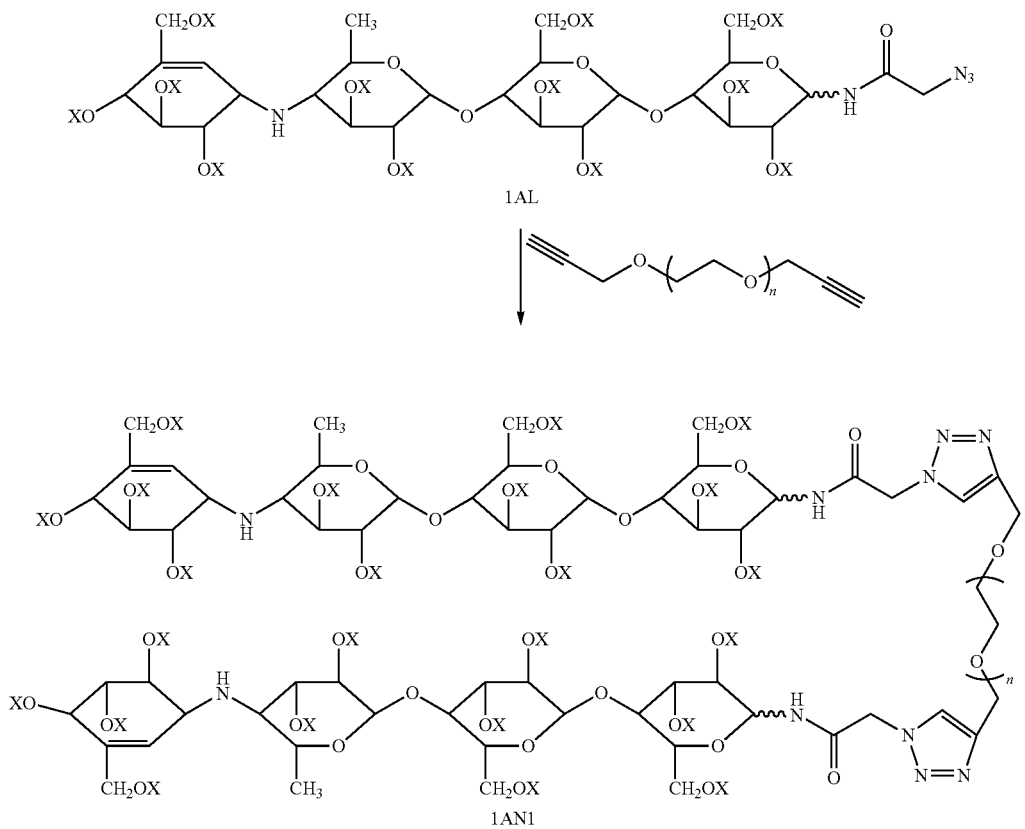

X = H, SO₃H

Azido cyclitol 1AL is conjugated to the diacetylene terminated ethyleneglycol linkers in the table below using general procedure 18. The dimeric products is purified by RP-IP HPLC.

| | Product formed with linker Propargyl-O—(CH$_2$CH$_2$O)$_n$-Propargyl | | | |
|---|---|---|---|---|
| | n = 2 | n = 3 | n = 4 | n = 5 |
| product | 1AN1 | 1AO1 | 1AP1 | 1AQ1 |

Likewise, the other azido compounds of Examples 11, 18 and 19 are coupled through the linking groups of varying lengths (n=2, 3, 4 and 5) that are tabulated above.

Example 22
Tetrameric Products Formed from Acarbose Azide
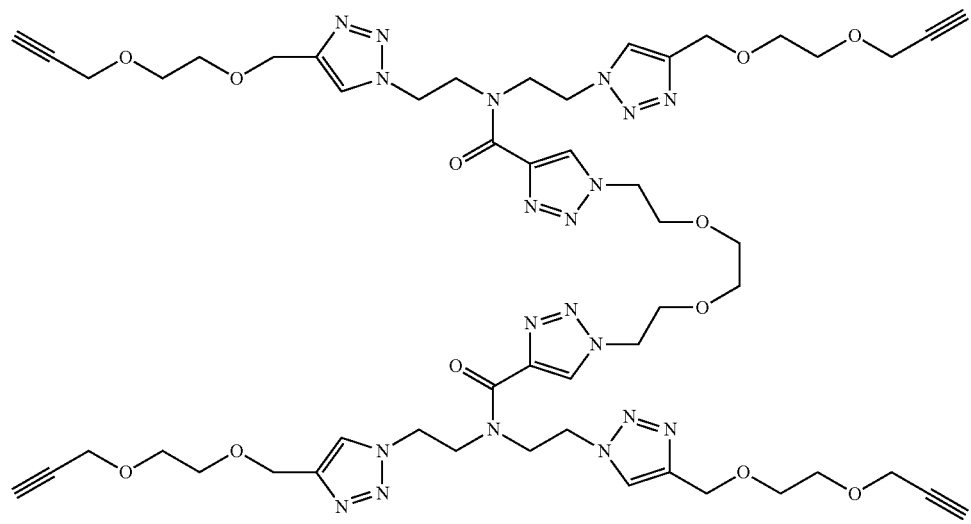
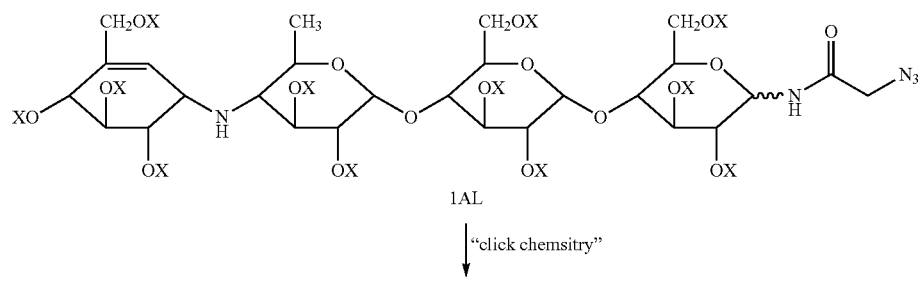
1AL
"click chemsitry"
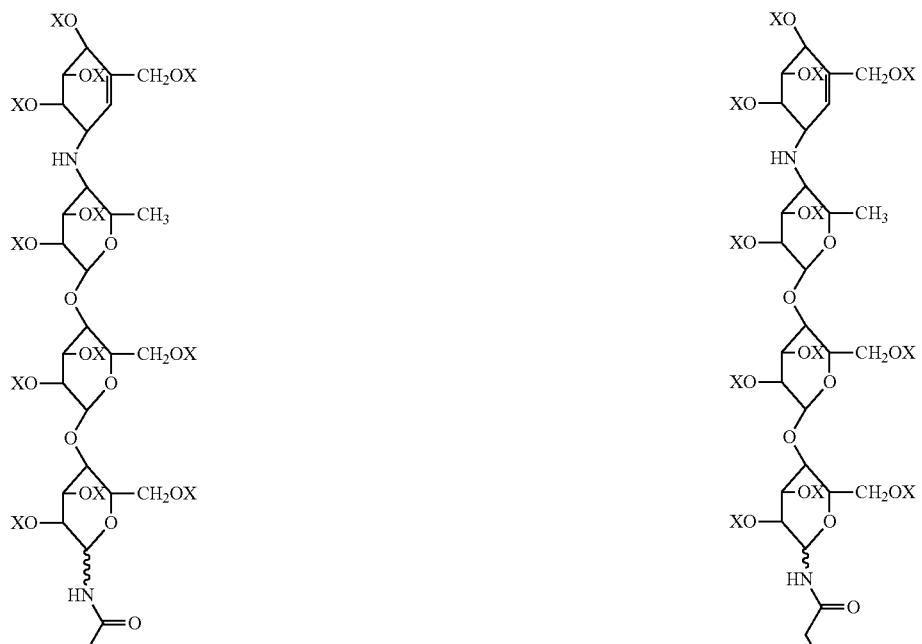

-continued
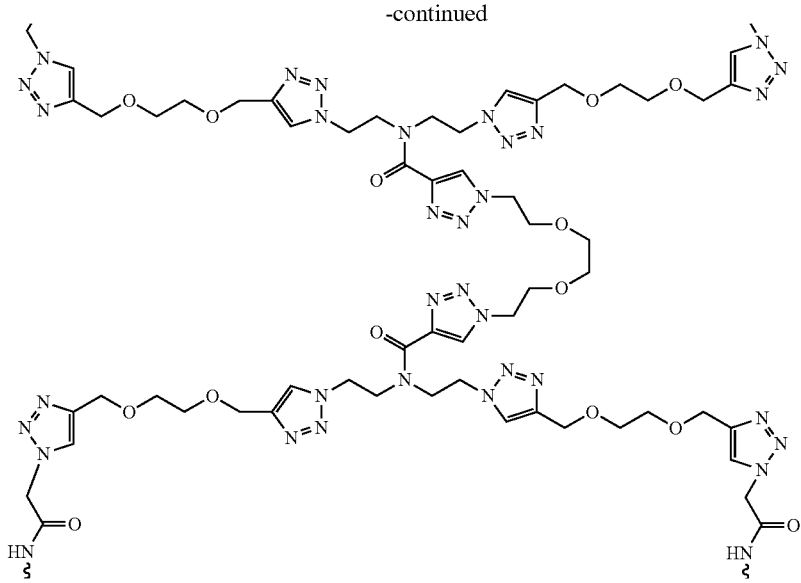
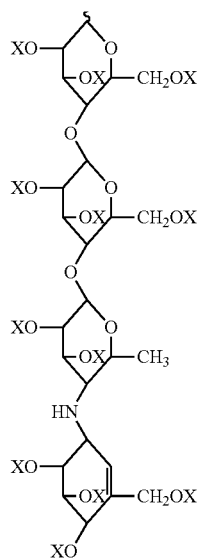
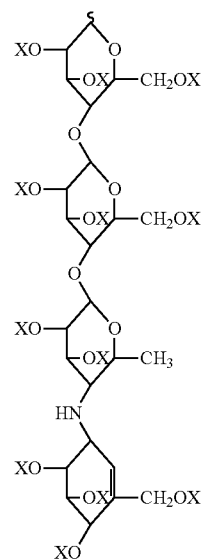
1AR
X = H, SO₃H
Azido acarbose derivative (1AL) is coupled to reagent T4-203 using general procedure 18. The tetrameric product is purified by RP-IP HPLC.
Likewise the other azido compounds of Examples 11, 18 and 19 may be coupled.

Example 23

Formation of Tetrameric Products with Different Length Oligoethyleneglycol Spacers May Also Occur

Example 24

Trimeric Conjugates with Cyanuric Acid at the Core

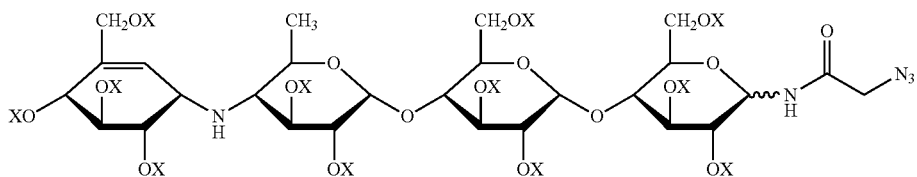

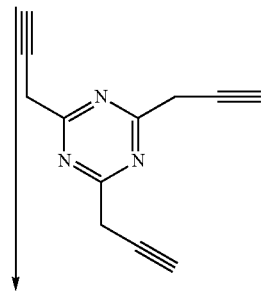

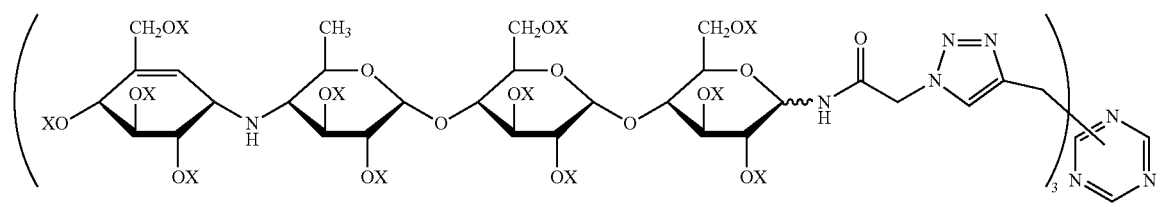

X = H, SO₃H

The azido acarbose derivative 1AL is coupled to 2,4,6-Tris(prop-2-ynyloxy)-1,3,5-triazine using general procedure 18. The product, 1AW is purified by RP-IP HPLC.

Likewise the other azides of Examples 11, 18 and 19 may be similarly coupled.

Example 24B

To a solution containing the bromoacetylated glycoside 1D (example 4, 10 µmol) was added 1 M NaHCO₃ (2 mL) and adjusted to pH 8.5-9.5. 1,3,5-Triazine-2,4,6-trithiol trisodium salt solution (15% in water) was added (0.3 eq) into the reaction mixture. The mixture stirred at room temperature for 1 h. The trimer product (1AW2) was purified by HPLC.

Example 25
Direct Conjugation to Cyanuric Chloride
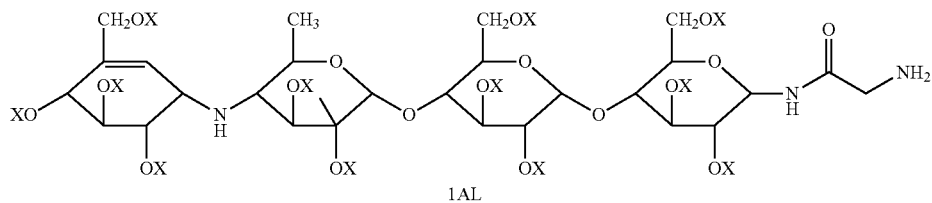
1AL
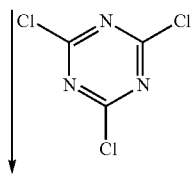
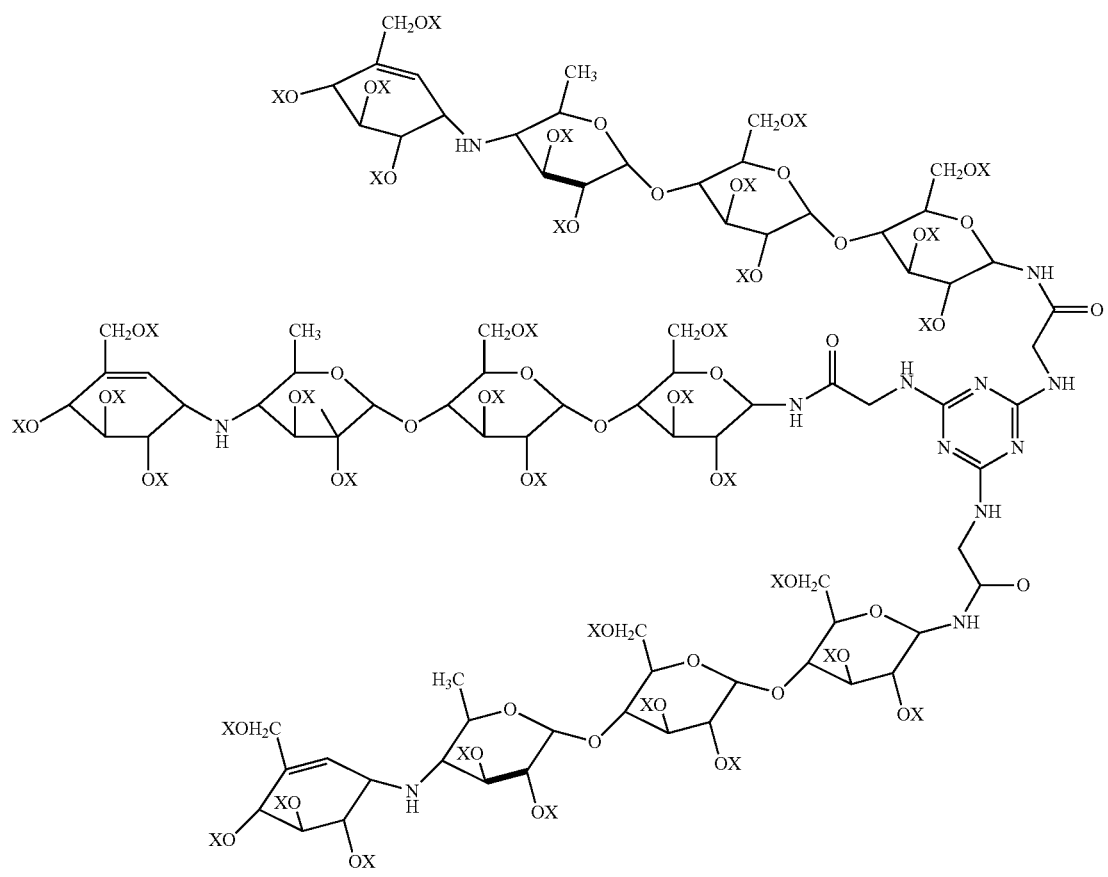
1AU
X = H, SO₃H
Intermediate 1AK (example 19) is reacted with cyanuric chloride using the procedures described in *J Biol Chem* 2005, 280(10), 8842-9. The product, 1AU, is purified by RP-IP HPLC.

Likewise the amine intermediates of Example 19 and the cystamine derivatives of Example 16 derived from the sulfates of Example 7.

Example 26

Chain Shortening of Acarbose Derivatives to Generate Amine Terminated Glycans

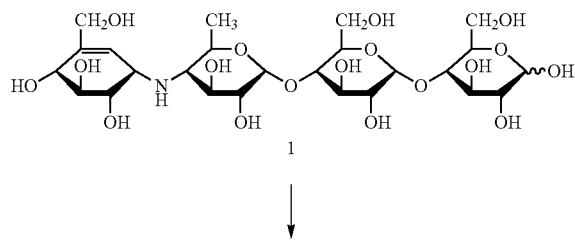

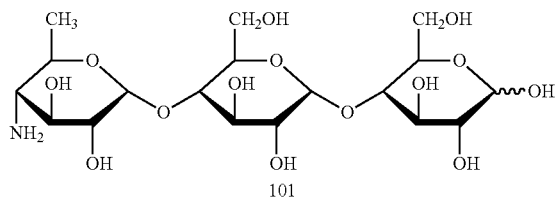

4a. Hydrogenolysis.

Acarbose (1) was subjected to hydrogenolysis as described in Truscheit, E. and B. J. Werner Frommer, Lutz Muller, Delf D. Schmidt, and Winfried Wingender, *Chemistry and Biochemistry of Microbial a-Glucosidase Inhibitors*. Angew. Chem. Int. Ed. Engl., 1981. 20: p. 744-761 and Bock, K., M. Meldal, and S. Refn, *Controlled reduction of acarbose: conformational analysis of acarbose and the resulting saturated products*. Carbohydrate Research, 1991. 221: p. 1-16 and the desired product (101) purified by cation exchange chromatography and carbon chromatography or RP HPLC. ESI/MS 488.12 (calc [M+H]$^+$ 488.19).

4b). N-bromosuccinimide and Similar.

Acarbose (1) is treated with an oxidizing agent as described in U.S. Pat. No. 6,150,568 or N-bromosuccinimide (Ogawa, S., Nakajima, A. and Miyamoto, Y., *Cleavage of Validoxylamine A derivatives with N-Bromosuccinimide: Preparation of blocked synthons useful for the construction of carba-oligosaccharides composed of imino linkages*. J. Chem. Soc. Perkin Trans. 1, 1991: p. 3287-3290) and worked up as described for example 4a.

Likewise the glycosylated bacterial metabolites of Examples 1 bearing a single unsaturated cyclitol and the derivatives of Example 2 bearing a single unsaturated cyclitol may undergo chain shortening.

Example 27

Fmoc Protection of 4-Deoxyamino Oligosaccharides

4-Deoxyamino trisaccharide (101) is N-protected with Fmoc chloride in the standard manner and the product (101B) isolated by reverse phase chromatography. Likewise, validamycin was reduced following the procedure described in the previous example and then protected with Fmoc. ESI/MS 562.02 (calc [M+H]$^+$ 562.22). Likewise the other chain-shortened compounds of Example 26 may be subjected to N-protection with either Fmoc chloride or Fmoc-GlyOH (general procedure 2). ESI/MS of Fmoc-gly derivatives: 4-Deoxyamino trisaccharide 767.0 ([M+H]$^+$ calc 767.28); and 4-Deoxyamino pentasaccharide (161B2, from trestatin B) 1091.1 ([M+H]$^+$ calc 1091.4).

Example 28A

Sulfation of Fmoc Protected 4-Deoxyamino Oligosaccharides

The Fmoc derivative 101B is sulfated using general procedure 1 and isolated by RP-IP HPLC.

Likewise the N-protected chain-shortened compounds of Example 27 are sulfated.

Example 28B

Homodimeric Coupling of Sulfated 4-Deoxyamino Oligosaccharides

The sulfated Fmoc derivative of 101B from the previous example is treated to the deprotection, bromoacetylation and coupling steps described in examples 4-6. Likewise the other N-protected chain-shortened compounds from example 28 maybe treated similarly. In a cognate manner, 161B2 is transformed to 161C2, 161D2 and coupled with bis-thiol linkers to generate the compounds in the following table.

|  | Linker | | | | | |
| --- | --- | --- | --- | --- | --- | --- |
|  | Na$_2$S | HS(CH$_2$)$_2$SH | HS(CH$_2$)$_2$O (CH$_2$)$_2$SH | HS[(CH$_2$)$_2$O]$_2$ (CH$_2$)$_2$SH | HS[(CH$_2$)$_2$O]$_3$ (CH$_2$)$_2$SH | HS[(CH$_2$)$_2$O]$_4$ (CH$_2$)$_2$SH |
| Product | 161E | 161F | 161G | 161H | 161I | 161J |

Example 29

Homodimeric Conjugates Formed Using Squaric Acid Coupling of 4-Deoxyamino Sugars

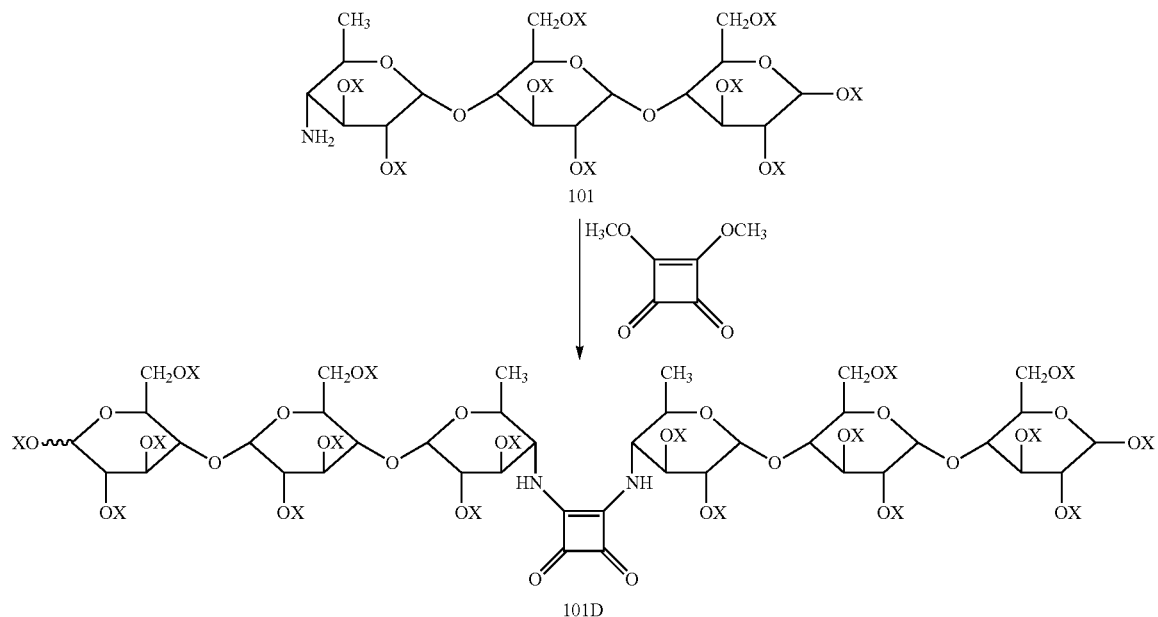

X = SO$_3$H or H.

The sulfated trisaccharide 101B is de-protected using general procedure 3 and used directly for the next step without purification. The pH is adjusted to 8.5, sodium bicarbonate (0.5 eq), methanol (40%) and 0.4 equivalents of squaric acid diethylester added. The reaction is stirred at room temperature until the amine is consumed (monitoring by HPLC) and the product (101D) purified by RP-IP HPLC.

Likewise the sulfated compounds of Example 28 are coupled.

Example 30

Propynylation of Sulfated 4-Deoxyamino Oligosaccharides

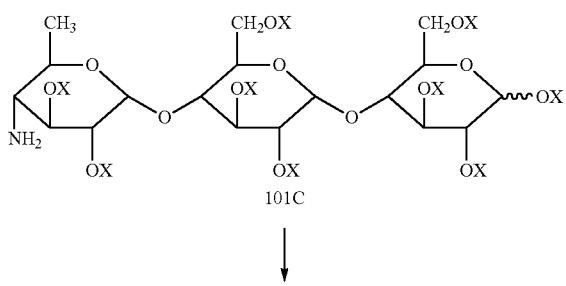

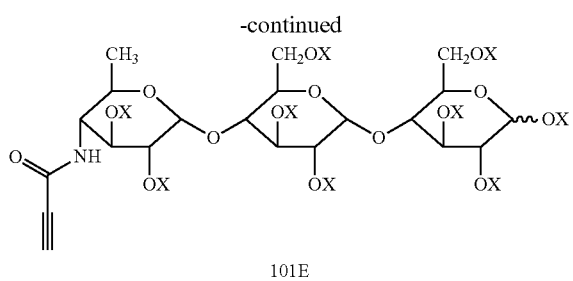

X = SO$_3$H or H.

Sulfated trisaccharide 101B is deprotected as described in the previous example and propynylated using general procedure 19. The product 101D is purified by RP-IP HPLC. Likewise the sulfated compounds of Example 28 undergo propynylation.

Example 31

Coupling of 4-deoxyamino Oligosaccharides to Diazidoethane

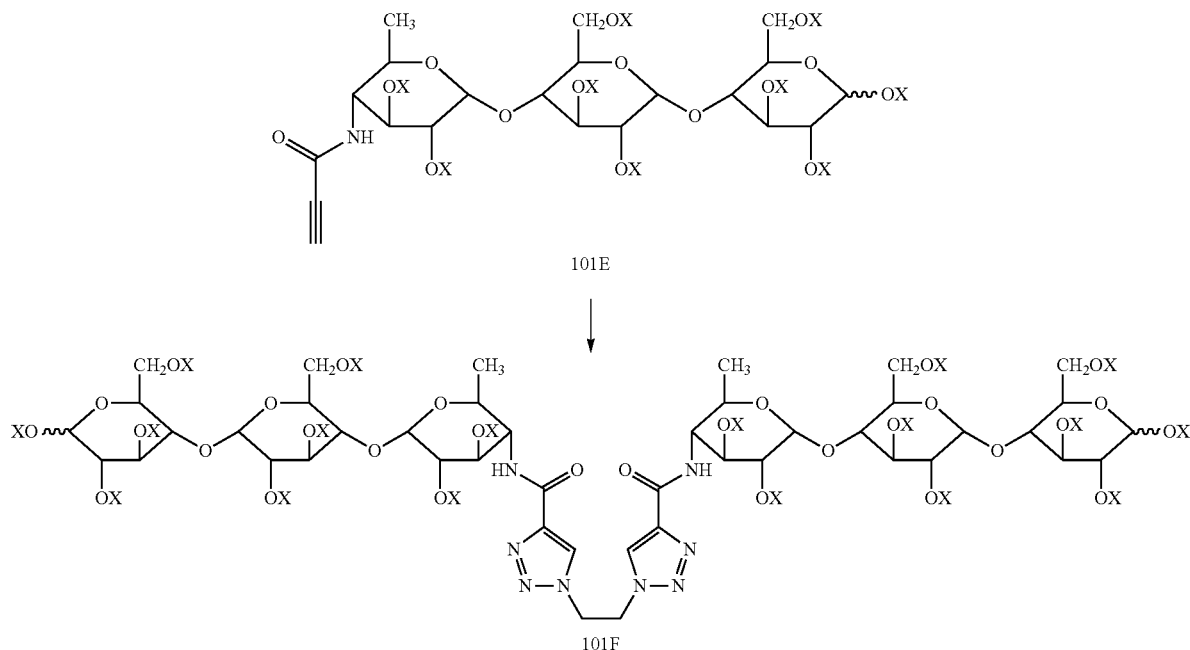

X = SO₃H or H.

Propynamide (101E) is reacted with diazidoethane using general procedure 18 and may be purified by RP-IP HPLC to give the products.

Likewise the propynylated compounds of Example 30 are coupled.

Example 32

Coupling of 4-deoxyamino Oligosaccharides to Diazido PEGs

Propynamide (101E) is reacted with diazidoPEGs (shown in the table below) using general procedure 18 and may be purified by RP-IP HPLC to give the following products.

| | $N_3(CH_2)_2[O(CH_2)_2]_nN_3$ | | | |
|---|---|---|---|---|
| | n = | | | |
| | 1 | 2 | 3 | 4 |
| Product | 101G | 101H | 101I | 101J |

Likewise the propynylated compounds of Example 30 undergo coupling.

Example 33

Formation of 4-deoxy-4-azido Oligosaccharides

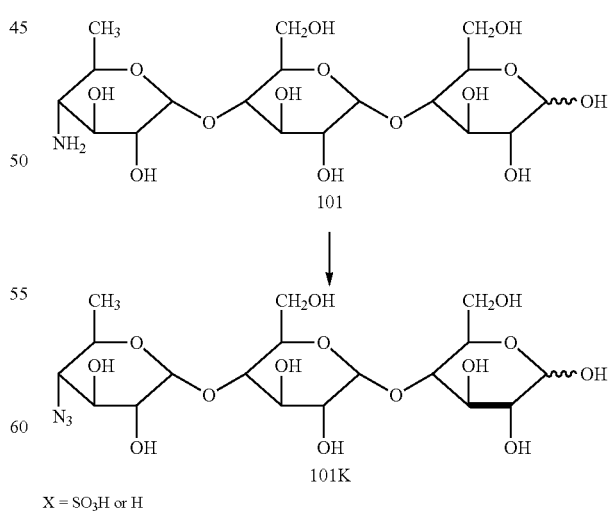

X = SO₃H or H

4-Deoxyaminb trisaccharide (101) is transformed into the azido derivative (101K) using general procedure 20.

Likewise, the azido derivatives of the chain shortened compounds of Example 26 are prepared.

Example 4

Sulfation of 4-deoxy-4-azido Oligosaccharides

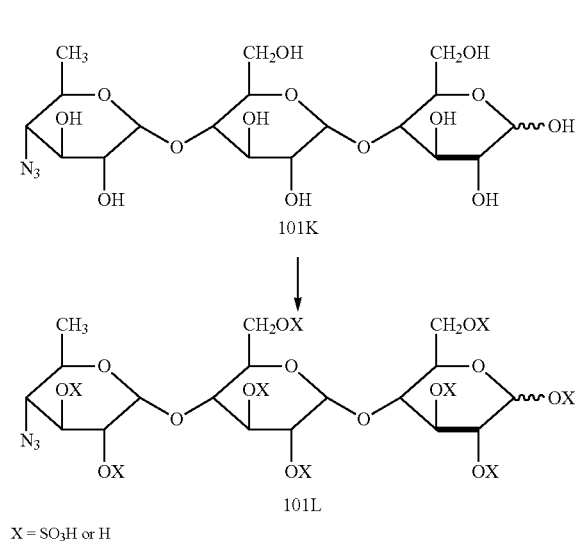

X = SO₃H or H

The sulfated azido trisaccharide 101L is prepared from 101K in the same manner as described in example 27.

Likewise the azido compounds of Example 33 undergo sulfation.

Example 35

Formation of Head-to-Tail Neo-Oligosaccharides Using Thiol Chemistry

The trisaccharide 1B01L (see example 33) has orthogonally protected functionalities at the head and tail of the chain that enable the head of one molecule to be coupled to the tail of another in a controlled fashion. Deprotection of the resulting dimeric construct enables the cycle to be repeated. The following sequence demonstrates how this is accomplished.

a) Formation of Sulfated 4-Deoxyamino Oligosaccharides with a Fmoc Protected Reducing Terminus.

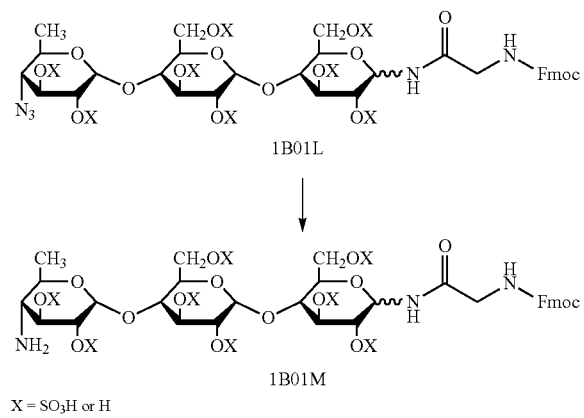

X = SO₃H or H

The azidoglycan 1B01L is reduced using general procedure 10c. The mixture is filtered and the product (1B01M) may be purified by RP-IP HPLC.

b) S-Acetylthioacetate Derivatives (SATA) of Sulfated 4-Deoxyamino Oligosaccharides.

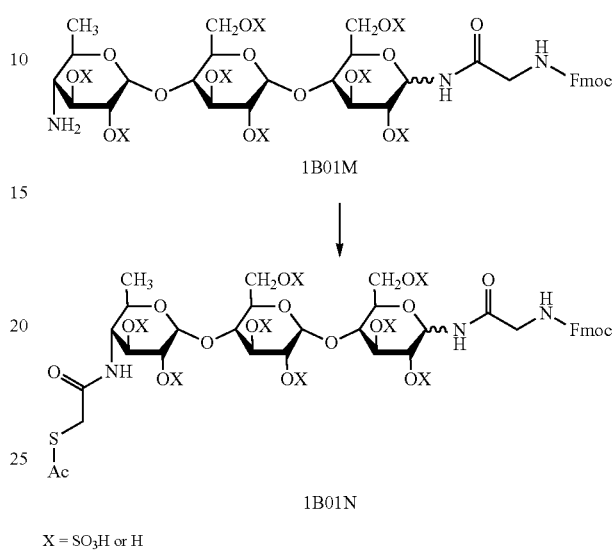

X = SO₃H or H 4-deoxyamino trisaccharide, 101M, is S-acetylthioacetylated using general procedure 11.

c) Fmoc Deprotection and Bromoacetylation of SATA Derivatives

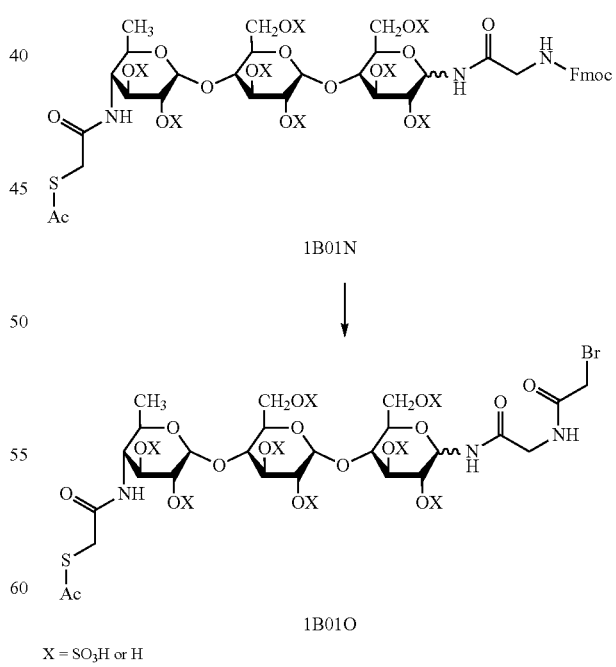

X = SO₃H or H

SATA derivative 101N is subjected to the sequence of Fmoc removal and bromoacetylation as described in example 4. The product, 101O, displays satisfactory LC-MS data. This product is considered as a chain extension building block.
d) De-S-Acetylation of SATA Derivative
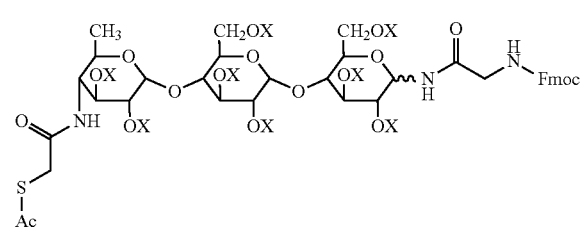
1B01N
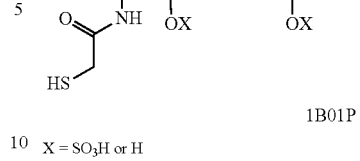
1B01P
X = SO₃H or H
SATA derivative 101N is de-S-acetylated using general procedure 12. The product, 101P, is the foundation block for starting the chain.
e) Formation of Dimeric Conjugate.
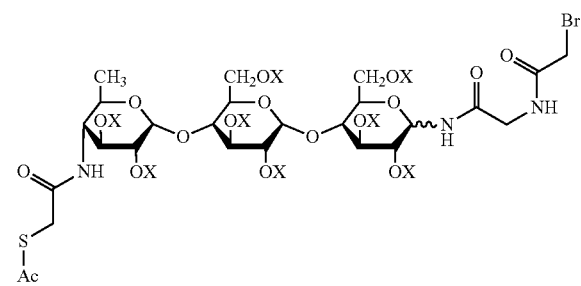
1B01O
+
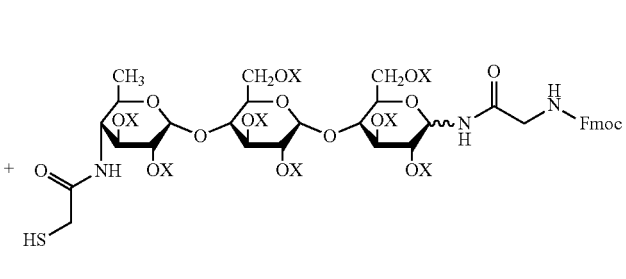
1B01P
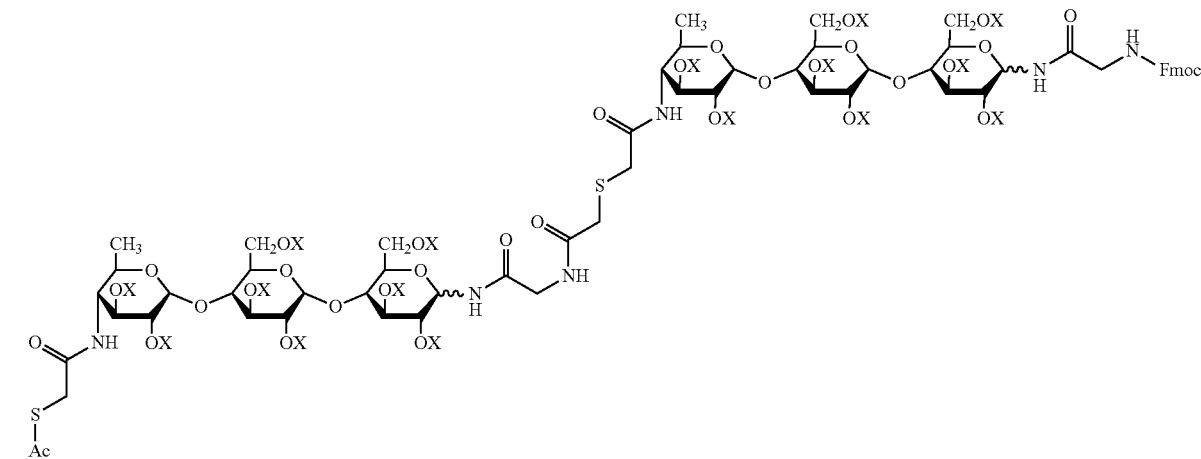
1B01Q
X = SO₃H or H Foundation block 101P is reacted with chain extension building block 101O using general procedure 13 and the product. The product, 101Q, may be purified by RP-IP HPLC.

f) De-S-Acetylation of Dimeric Conjugate.

The dimeric conjugate from the preceding step, 101Q, is de-S-acetylated using general procedure 12 and the product, 101R, may be purified by RP-IP HPLC.

g) Formation of Trimeric Conjugate.

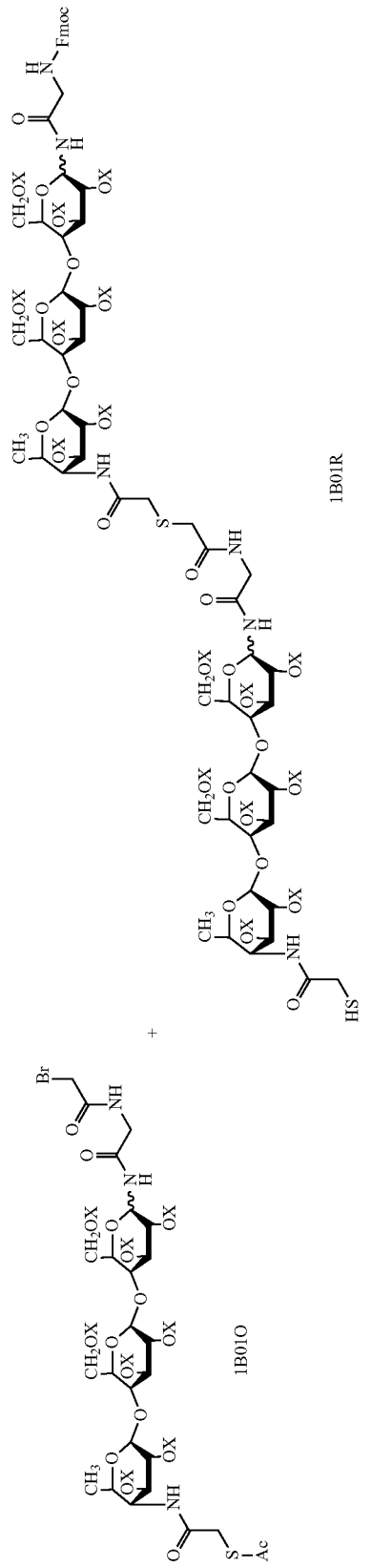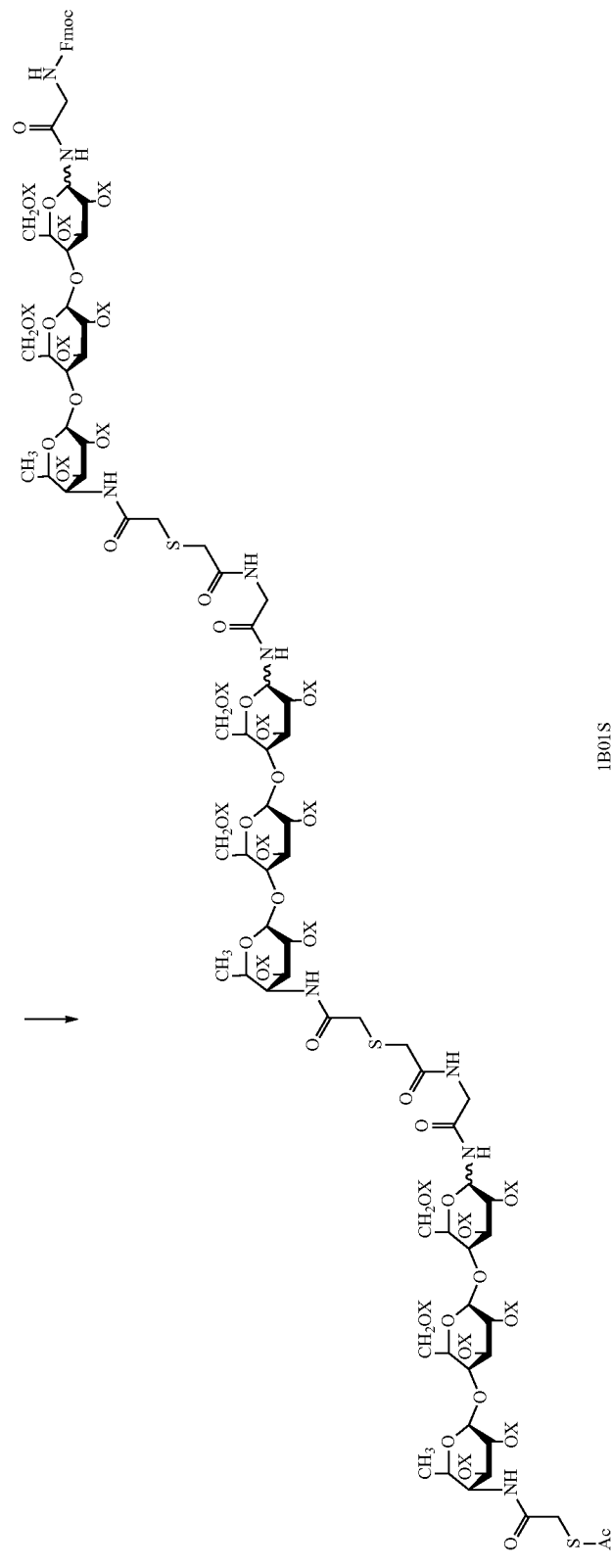

The free thiol dimeric conjugate from the preceding step, 101R, is reacted with chain extension building block 101O using general procedure 13 and the product, 101S may be purified by RP-IP HPLC.

h) De-Fmoc and Chain Capping.

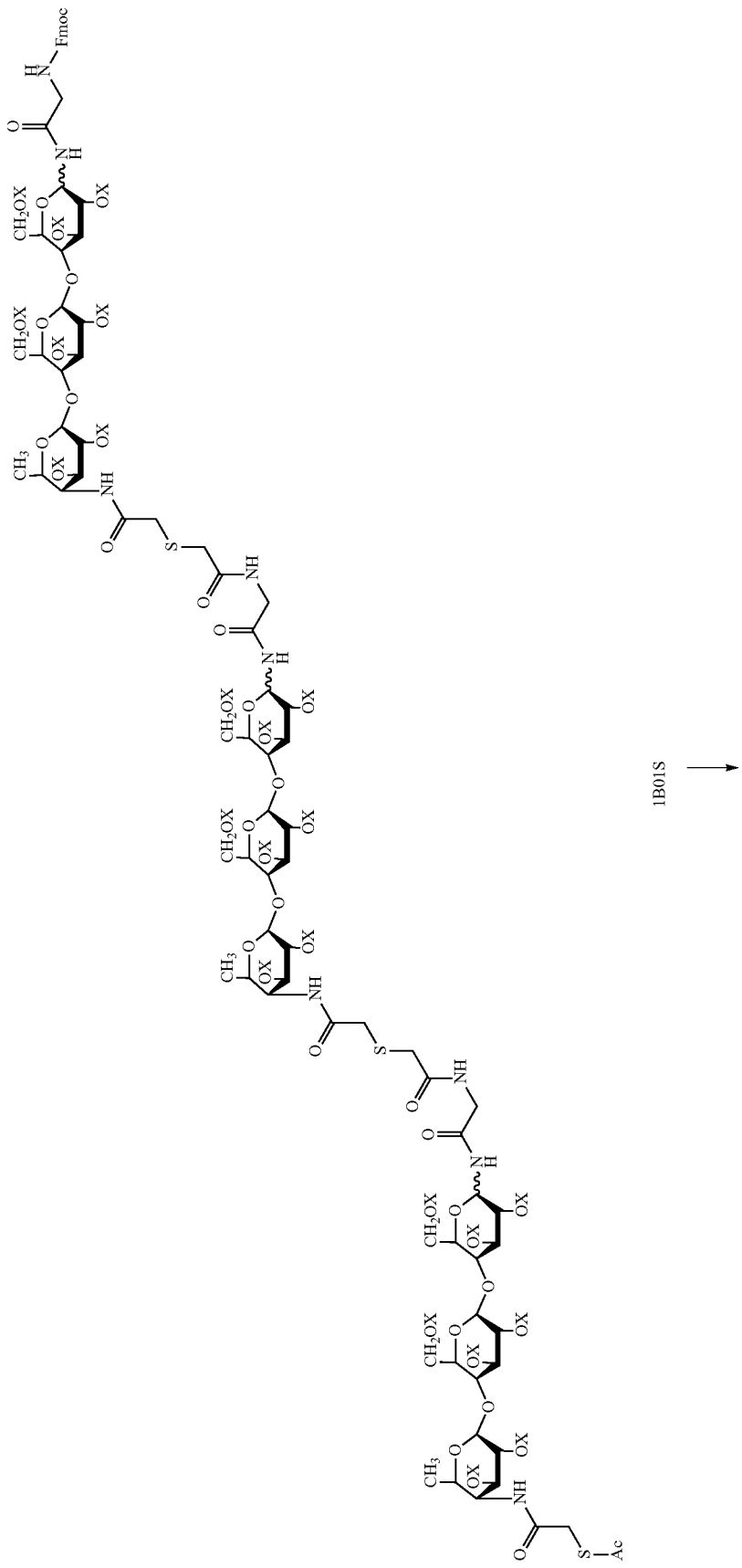

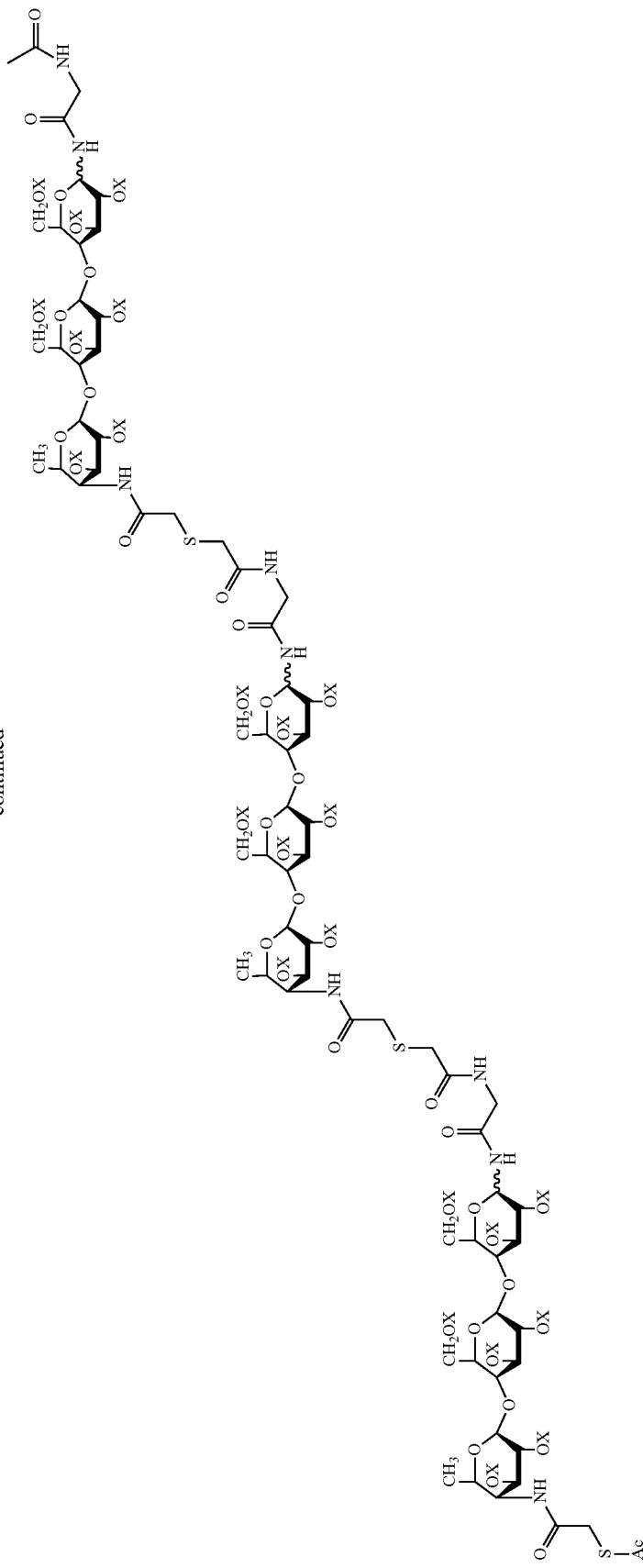

Fmoc removal and subsequent N-acetylation of 101S is achieved using a modification of general procedure 4 in which acetic anhydride is substituted for bromoacetylbromide. The product 101T is purified by RP-IP HPLC.

Example 36

Formation of Trimeric Conjugates with Other Oligosaccharides

The sequence of reactions described for Example 35 is applied to the other difunctional oligosaccharides, such as the other sulfated compounds of Example 33 that are derived from Example 2.

Example 37

Formation of a Head-to-Tail Neo-Nonasaccharide Using Click Chemistry

In this variation to example 34, azide and Fmoc are used as the orthogonal protecting groups at the head and tail of the molecule. The conjugate is constructed from addition to the head of the molecule and the chain extension unit is 1B01L.

The sequence of reactions is as follows:

a) N-Acetylation of the 4-Deoxyamino Oligosaccharide

The aminoglycan 1B01M is N-acetylated using a modification of general procedure 4 where acetic anhydride is substituted for bromoacetyl bromide.

b) De-Fmoc and N-Propynylation

Trisaccharide 1B01U is N-deprotected as described in first step of general procedure 4 and the amine N-propynylated in the same pot. The product 1B01V is purified by RP-IP HPLC.

c) Formation of Dimeric Conjugate

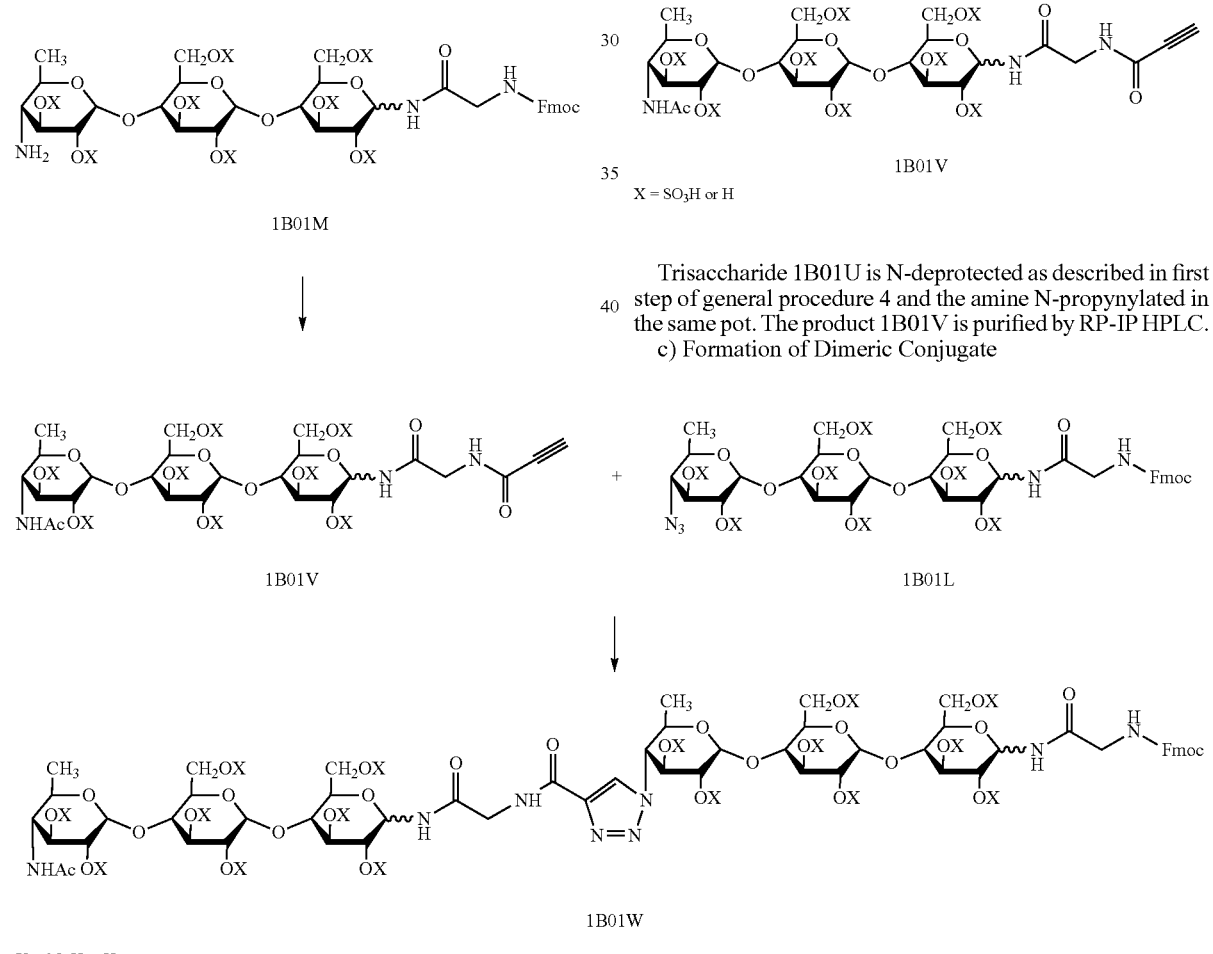

X = SO₃H or H

1B01V is conjugated to the chain extension unit 1B01L using general procedure 20. The product 1B01W is purified by RP-IP HPLC.
d) De-Fmoc and N-Propynylation of the Dimeric Conjugate.
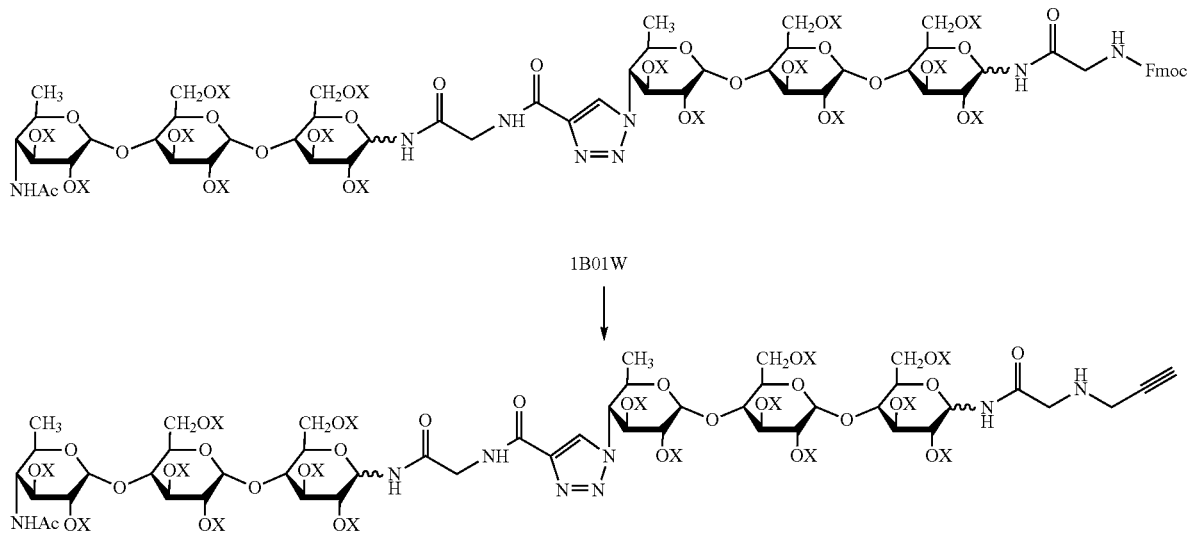
X = SO₃H or H
The procedure described for step b is repeated to generate the product 1B01X
e) Formation of Trimeric Conjugate

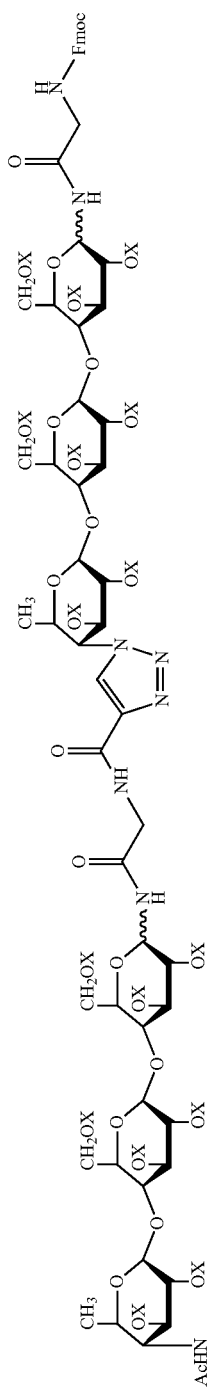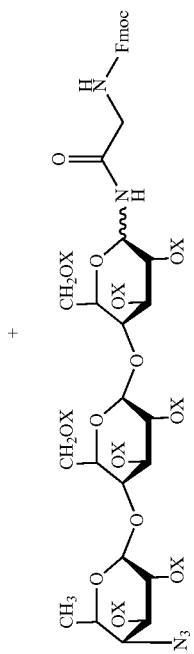

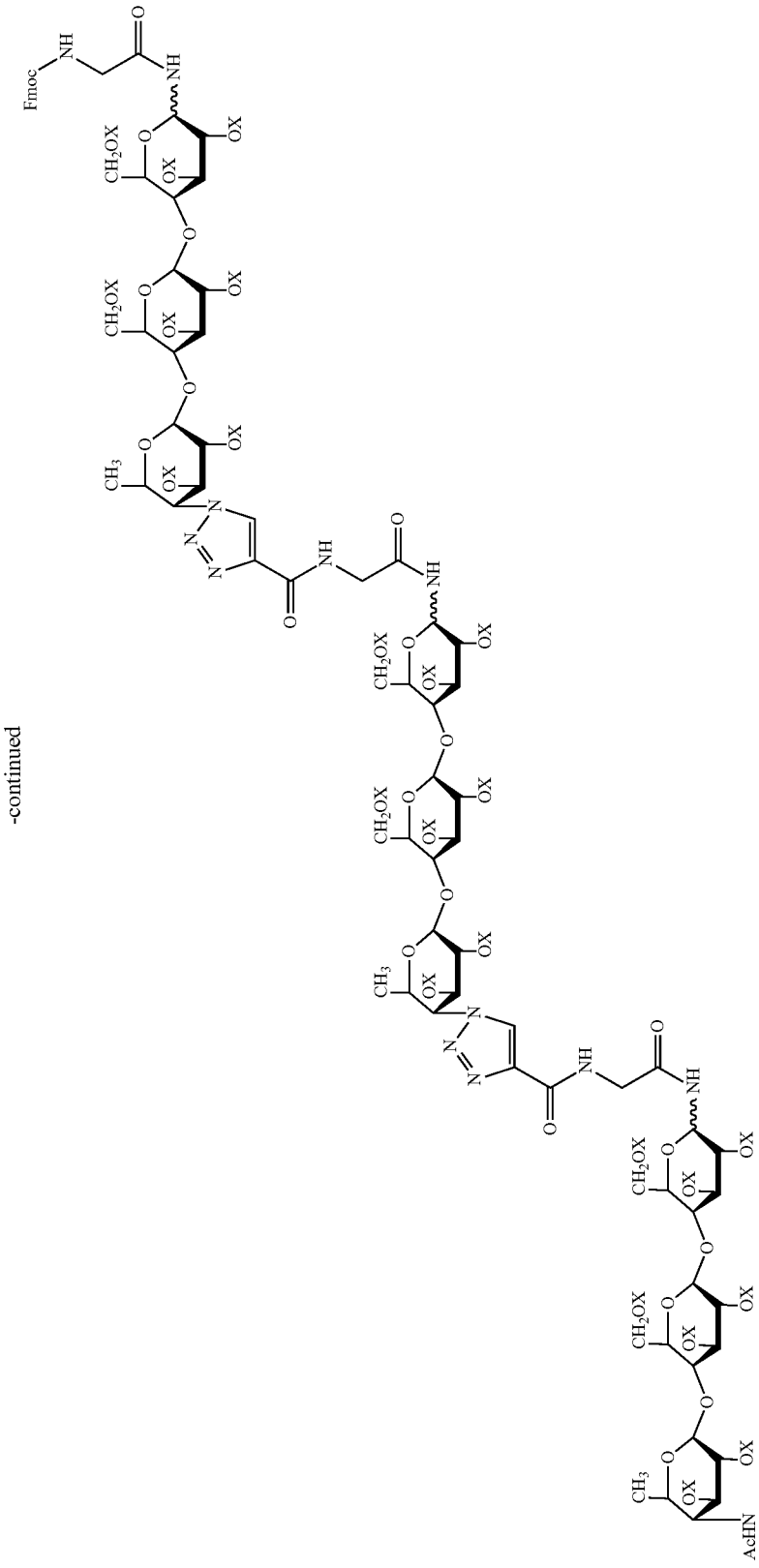
1B01Y
X = SO$_3$H or H

1B01X is conjugated to the chain extension unit 1B01L using general procedure 20. The product 1B01Y is purified by RP-IP HPLC.

f) Termination and Capping.

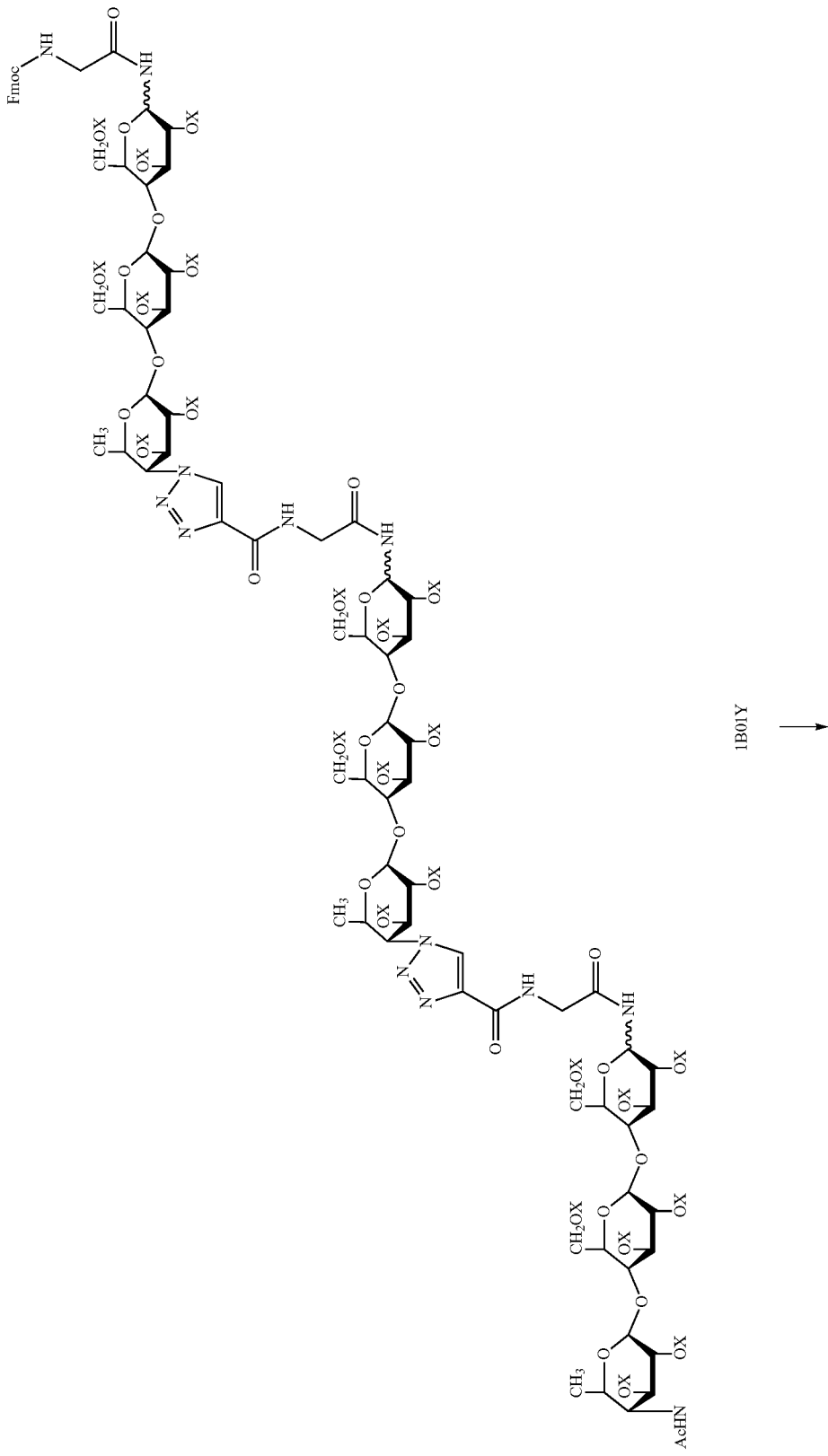

-continued
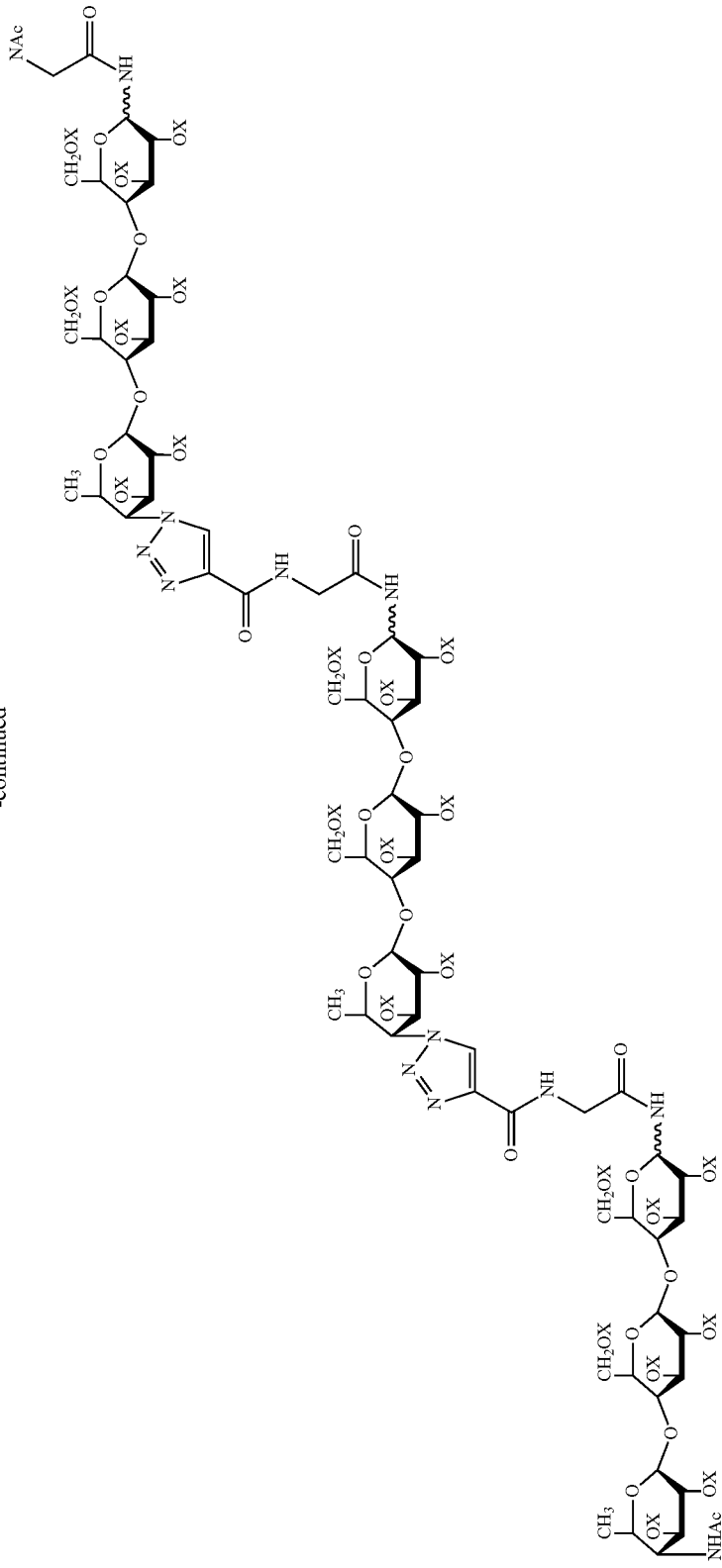
1B01Z

Fmoc removal and subsequent N-acetylation of 1B01Y is achieved using a modification of general procedure 4 in which acetic anhydride is substituted for bromoacetylbromide. The product 1B01Z is purified by RP-IP HPLC.

Example 38

Formation of Head-to-Tail Neo-Oligosaccharides Using Click Chemistry

The sequence of reactions described for example 37 is applied to the other difunctional oligosaccharides of Example 34.

Example 39

Formation of Neo-Dodecasaccharide Using a Mixture of Head-to-Tail and Head-to-Head Coupling In this example 1B01U and 1B01M are again the chain extension unit and initiation unit respectively. A homodifuntional linker is used for coupling.

a) Deprotection and Addition of Squarate to the Free Amine.

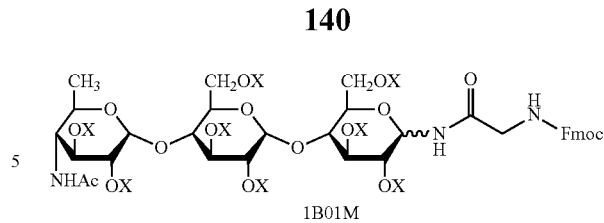

1B01M

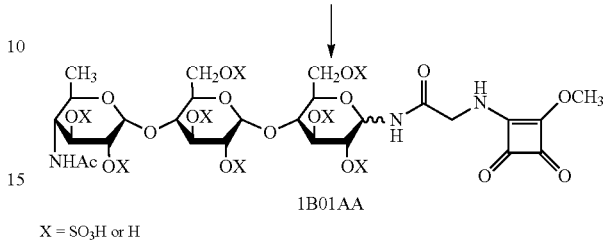

1B01AA

X = SO$_3$H or H

1B01M is N-deprotected and coupled with a squaric acid by using a modification of the procedure described in example 28 in which a 20-fold molar excess of squaric acid is used at pH 7-7.5 to ensure only a single amine adds to the squarate. The product, 1B01AA is purified by RP-IP HPLC.

b) Chain Extension

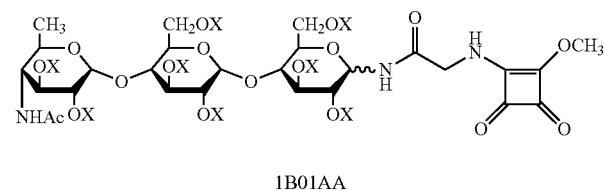

1B01AA

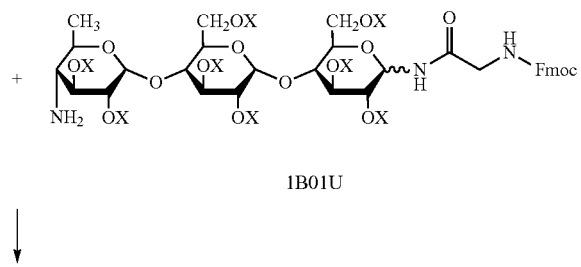

1B01U

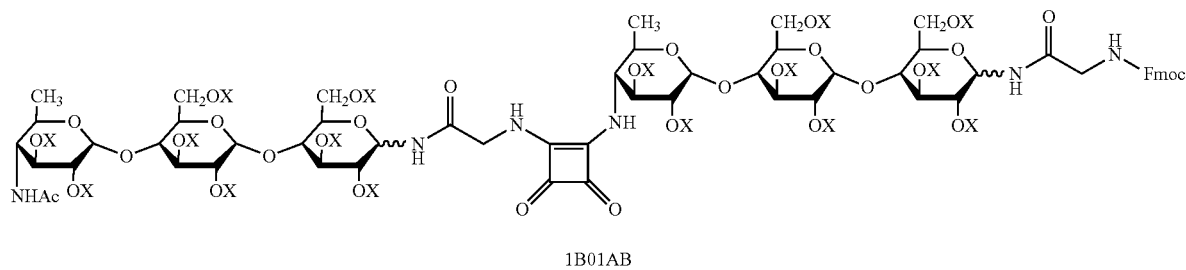

1B01AB

X = SO$_3$H or H

1B01AA is mixed with 1.2 equivalents of 1B01U as described in example 28 (i.e. at pH >8). The product, 1B01AB is purified by RP-IP HPLC.

c) Coupling of Two Dimeric Conjugates.
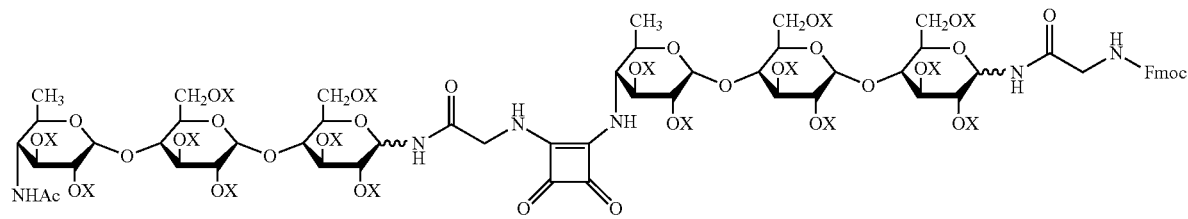
1B01AB
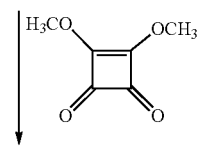
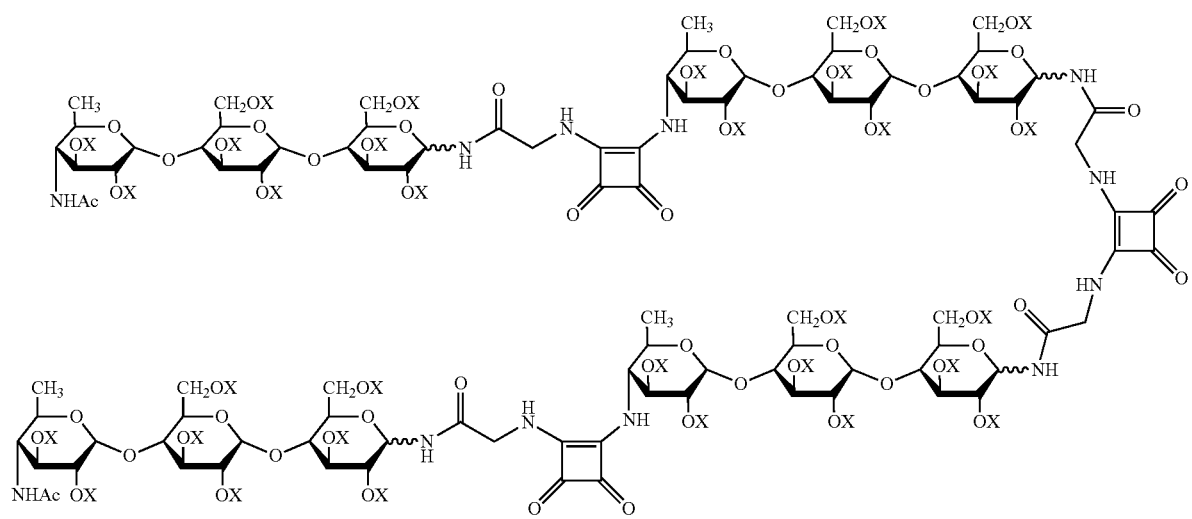
1B01AC
X = SO₃H or H
The dimer 1B01AB is N-deprotected and coupled to both reactive sites of squaric acid using the procedure described in example 28. The product, 1B01AC is purified by RP-IP HPLC.

Example 40

2"-Azido Streptomycin Derivatives

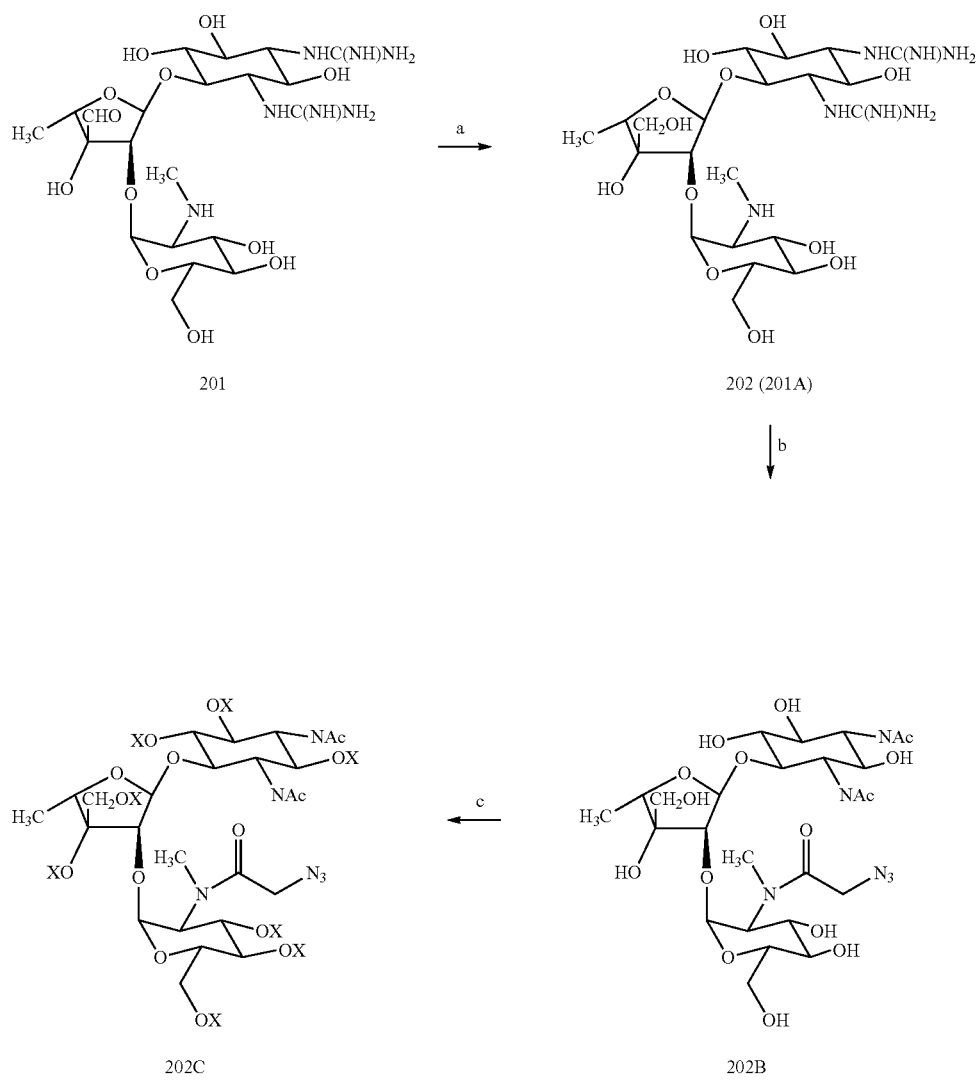

X = SO₃H or H a) Streptomycin (201) is reduced using the procedure described in U.S. Pat. No. 3,397,197 to produce dihydroxystreptomycin 202.

b) 202B is deguanidinylated using the procedure described in *J. Org. Chem.* 1962, 1923.

At the completion of this reaction, the pH of the reaction mixture is adjusted and the amino groups N-acetylated. The product, 202B, is purified chromatographically.

c) 202B is sulfated using general procedure 1. The product may be purified using RPIP-HPLC 202C.

The corresponding azide derivatives of the following glycosylated bacterial metabolites may also be prepared: Dihydrostreptomycin; 5'-Hydroxystreptomicin; N-Demethyl-streptomicin; Bluensomycin; Mannosido-Hydroxystreptomicin; Dimannosidostreptomicin; and Ashimycin A.

Example 41

3'-Azido Streptomycin Derivatives

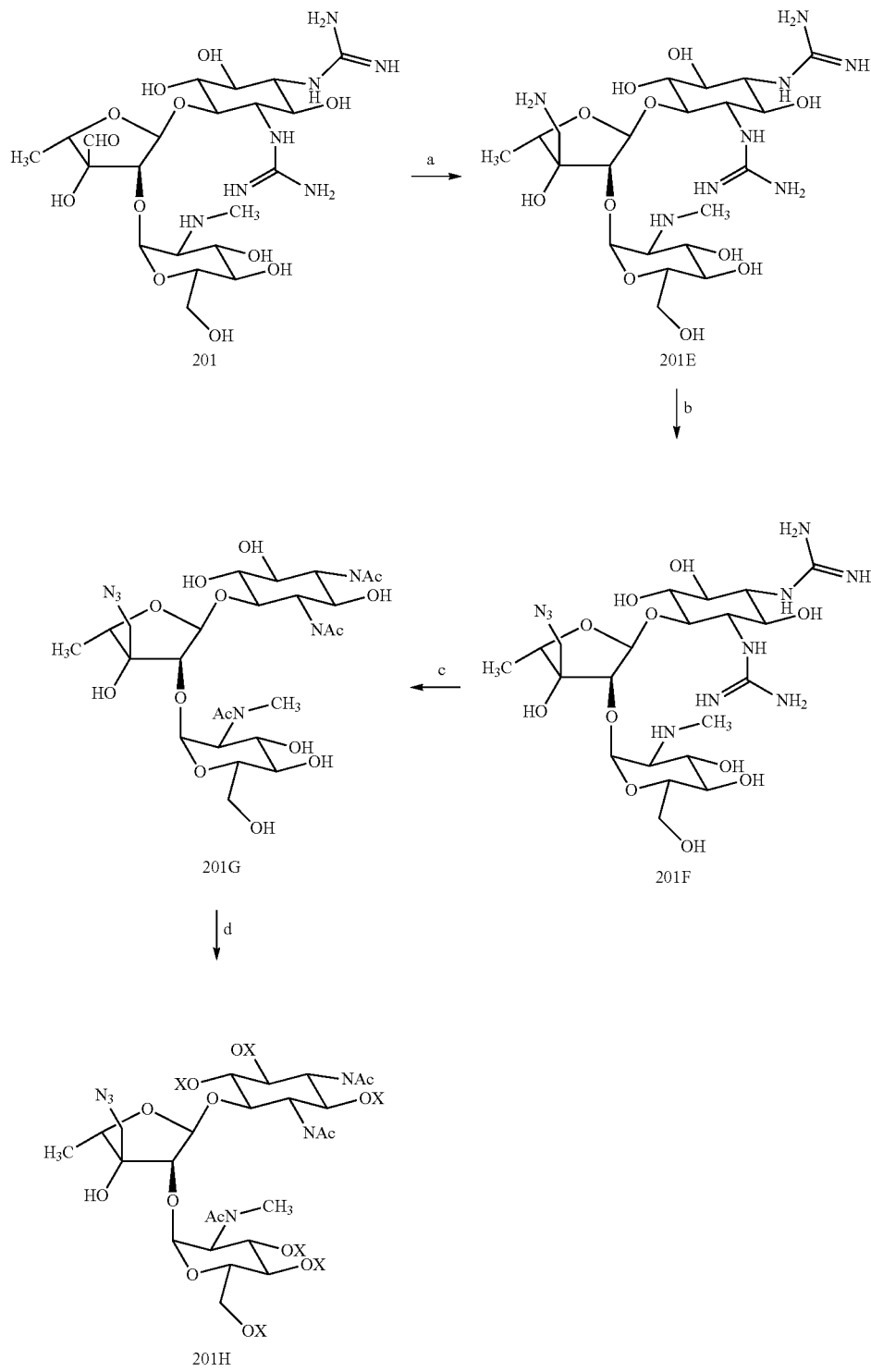

b) Diazotransfer. Amine-209A is converted to azide 209B using general procedure 20.

c) The azide 209B is deguanidinylated and N-acetylated as described in example 40.

a) Reductive amination. Streptomycin is reductively aminated using general procedure 15 to generate 209A.

d) 209C is sulfated using general procedure 1. The product 209D is purified by RPIP-HPLC.

The corresponding azide derivatives of the following glycosylated bacterial metabolites may also be prepared: 5'-Hydroxystreptomicin; N-Demethylstreptomicin; Bluensomycin; Mannosido-Hydroxystreptomicin; Dimannosidostreptomicin; Ashimycin A; and Ashimycin B.

Example 42

Neomycin B Ido Ring Azido Derivative

Neomycin B is transformed to the ido ring azido derivative using the procedure described in *J. Org. Chem.* 2007, 72(6), 1962-79.

bonate (5 g, 22 mmol) is then added, and the resultant reaction mixture is stirred at elevated temperature (55° C., 16 h). Methanol is removed by evaporation and the residue is partitioned between ethyl acetate (200 mL) and water (100 mL). The aqueous layer is extracted with fresh ethyl acetate (2×50 mL) and the combined organic layers were dried (Na$_2$SO$_4$) and concentrated in vacuo. Purification by flash chromatography on silica (DCM/acetone 3:2) affords 1,3,2',6',2''',6'''-hexa-N-(tert-butoxycarbonyl)-neomycin B (210B) as an amorphous white solid (2.42 g, 90%).

b) Epoxidation. DIAD (170 μL, 0.82 mmol) is added slowly to a stirred ice-cold solution of 210B (500 mg, 0.41 mmol) and TPP (215 mg, 0.82 mmol) in dry toluene (3 mL)

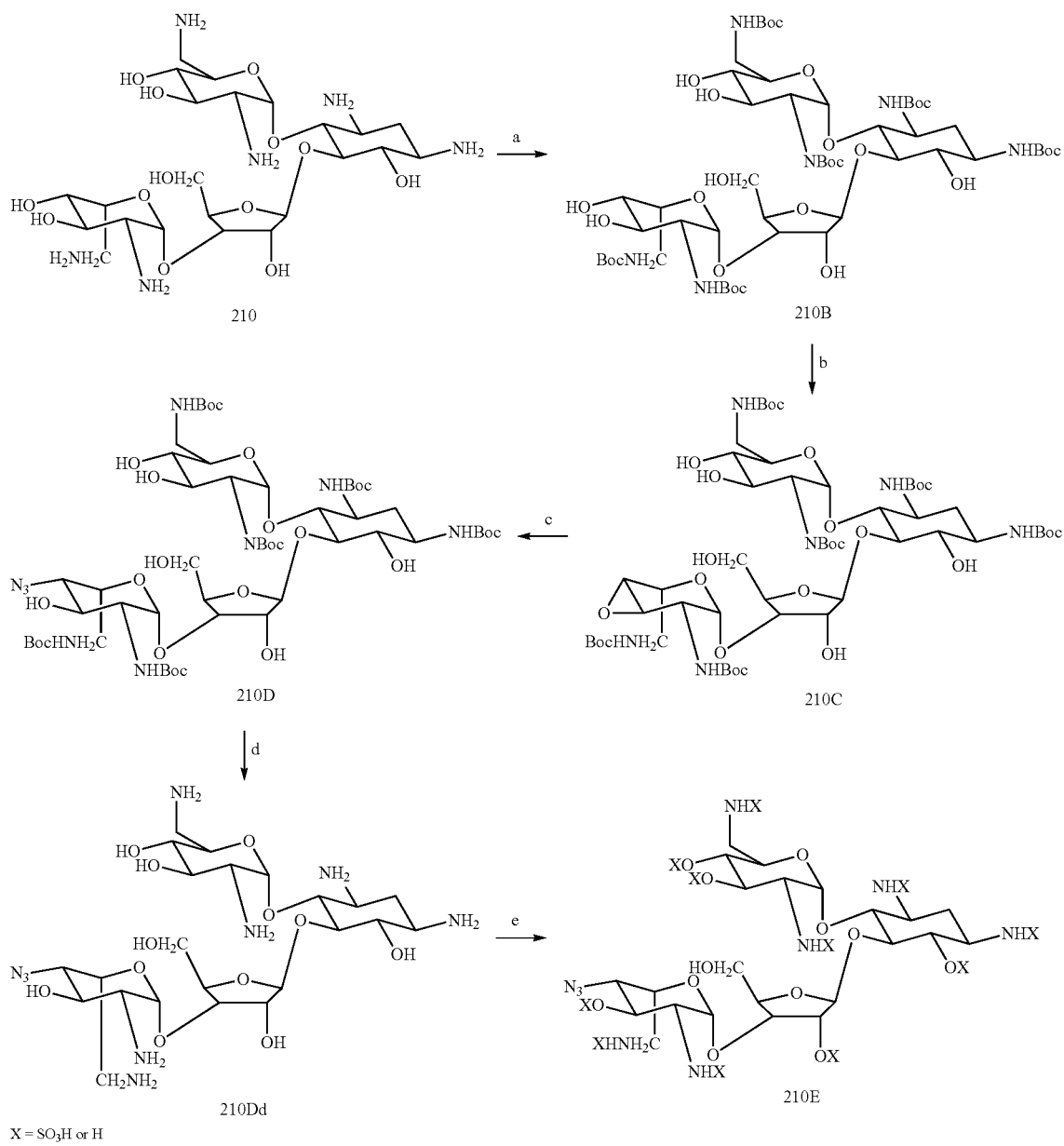

a) Boc protection. Triethylamine (TEA) (7 mL) and methanol (10 mL) are added to a stirred solution of neomycin B sulfate (2 g, 2.2 mmol) in water (10 mL). Di-tert-butyl dicarand the resultant reaction mixture is stirred at room temperature under a dry N$_2$ atmosphere (12 h). A second aliquot of a toluene solution of TPP (215 mg, 0.82 mmol, 2 mL) is then added, followed by the addition of a second portion of DIAD (170 μL, 0.82 mmol) and the reaction is stirred for a further 12 h prior to removal of the solvent in vacuo. Column chromatography of the residue on silica (DCM/MeOH 97:3 to 95:5) affords 210C as an amorphous white solid (305 mg, 62%).

c) NaN₃ (130 mg, 2 mmol) is added to a solution of 210B (400 mg, 0.33 mmol) in DMF (10 mL) and the mixture is stirred at room temperature (2 d). The reaction mixture is then diluted with ethyl acetate (200 mL) and washed with water (2×100 mL). The ethyl acetate layer is dried (Na₂SO₄), concentrated in vacuo, and purified by flash chromatography (DCM/MeOH 97:3) yields 210D as a white amorphous solid (352 mg, 85%).

d) Boc deprotection. The Boc groups are removed using general procedure 21 to yield 210Dd.

e) Sulfation. 210Dd is sulfated using general procedure 1, and subsequently may be purified.

The corresponding sulfate derivatives of the following glycosylated bacterial metabolites may also be prepared: Neomycin C; Paromomycin I; Paromomycin II; Lividomycin B.

Example 43

Neomycin Furanose Ring Azide Derivative

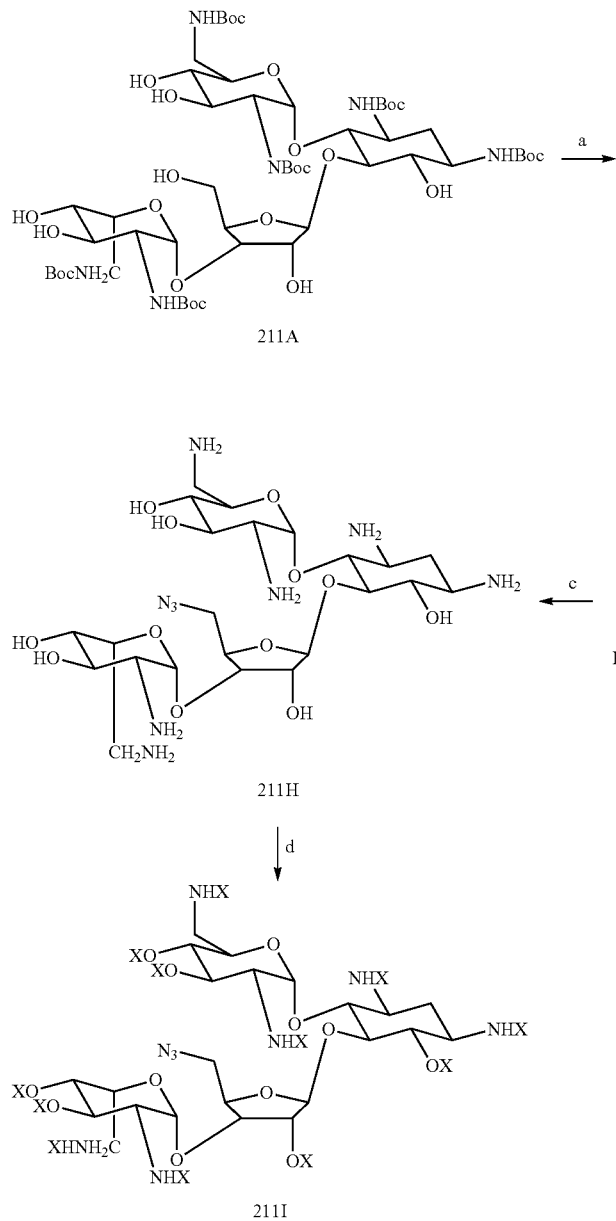
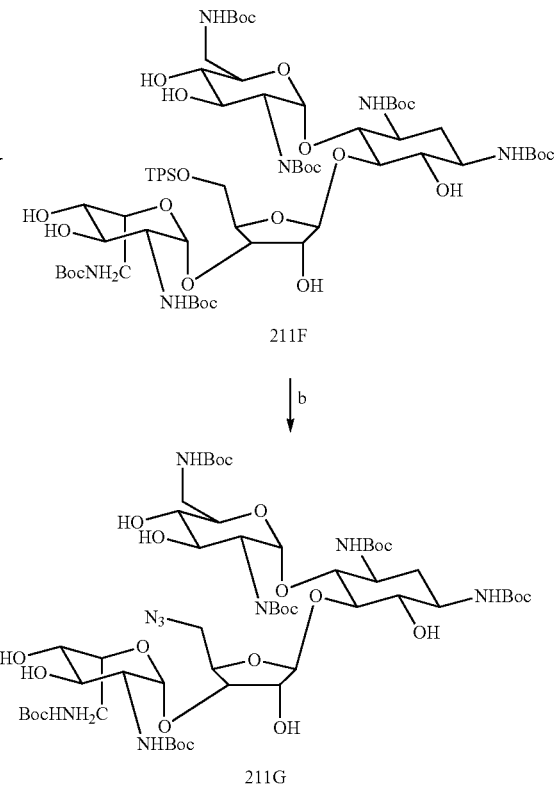

a) A solution of 211A (1 g, 0.82 mmol) and excess 2,4,6-triisopropylbenzenesulfonyl chloride (7 g, 23 mmol) in dry pyridine (20 mL) is stirred at room temperature (18 h). Pyridine is removed in vacuo by coevaporation with toluene. The crude residue is then dissolved in ethyl acetate (200 mL) and washed with water (2×100 mL). The aqueous layers were combined and extracted with ethyl acetate (2×100 mL). The combined organic layers were dried (Na₂SO₄), concentrated in vacuo, and subjected to flash chromatography. Unreacted 2,4,6-triisopropylbenzenesulfonyl chloride (6 g, nip identical with that of authentic sample) is recovered using DCM as eluent. The residue (1.2 g) is eluted from the silica column (DCM/MeOH 5:1) and then rechromatographed (DCM/MeOH 98:2 to 95:5) affording 211F as an amorphous white solid (0.75 g, 61%). $^1$H NMR (400 MHz, methanol-d4, 298 K): δ 7.33 (s, 2H), 5.52 (br s, 1H), 5.22 (br s, 1H), 4.99 (br s, 1H), 4.39 (m, 1H), 4.30 (m, 2H), 4.19 (m, 4H), 3.91 (m, 1H), 3.82 (m, 1H), 3.77 (m, 2H), 3.62 (m, 1H), 3.54 (m, 4H), 3.47-3.36 (m, 4H), 3.24 (m, 2H), 2.96 (m, 2H), 1.96 (m, 1H), 1.51-1.40 (m, 54H), 1.31 (m, 18H).

b) A solution of 211F (500 mg, 0.3 mmol) and NaN$_3$ (150 mg, 2.3 mmol) in DMF (5 mL) is stirred at elevated temperature (100° C., 8 h). After cooling to room temperature the reaction mixture is diluted with ethyl acetate (100 mL) and washed with water (2×20 mL). The ethyl acetate layer is dried (Na$_2$SO$_4$) and evaporated, to yield 211G (365 mg, 98%) as a white amorphous solid. The crude product is of sufficient purity to use in the next step without need for further purification. IR (KBr disk) 2106.3 cm$^{-1}$ (N$_3$). HRMS (ESI): calculated for (M+Na$^+$) C$_{53}$H$_{93}$N$_9$O$_{24}$ 1262.62311. found 1262.62835.

c) 211G is deprotected in the standard manner to yield 211G.

d) Sulfation. 211H is sulfated using general procedure 1, and subsequently may be purified.

Likewise, other 2,4,6-triisopropylbenzenesulfonyl protected primary alcohols of Neomycin C; Paromomycin I; Paromomycin II; Lividomycin B; Butirosin A; Butirson B; Butirsoin E1; Butirsoin E2; Butirsoin C1; Butirsoin C2; Ribostamycin; Xylostain; and LL-Bm 408αare transformed into the corresponding azides.

Example 44

Lividomycin B 6' Azido Derivative

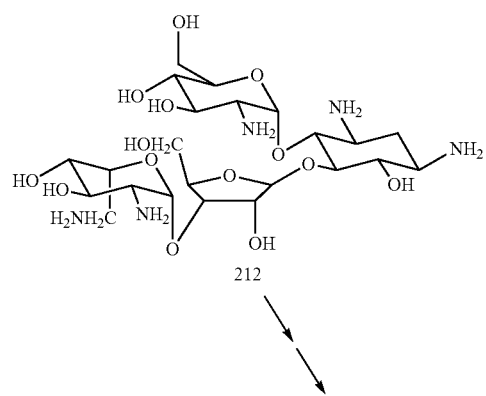
212

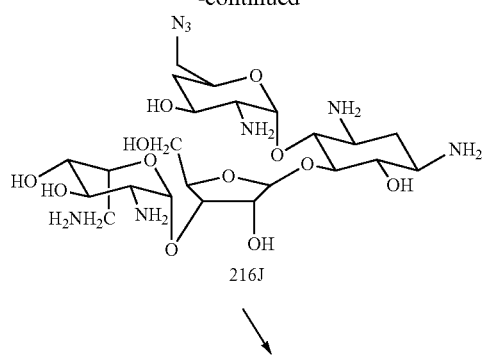
216J

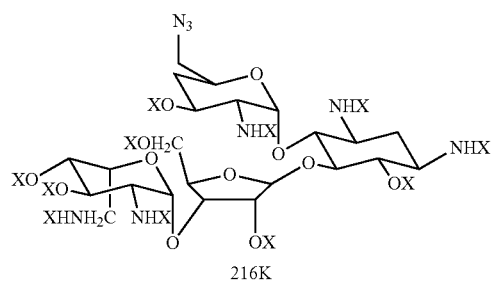
216K

Starting with paromomycin I, the procedure of U.S. Pat. No. 4,247,687 is followed to generate the azido derivative 216J. Note that this process leads to loss of the 4' hydroxyl group, thus generating the lividomycin B structure. 216J is sulfated using general procedure 1 to yield 216K, which displayed satisfactory LC-MS analysis.

Likewise the corresponding derivatives of paramomycin II are prepared.

Example 45

Paromomycin I 6' Azido Derivative II

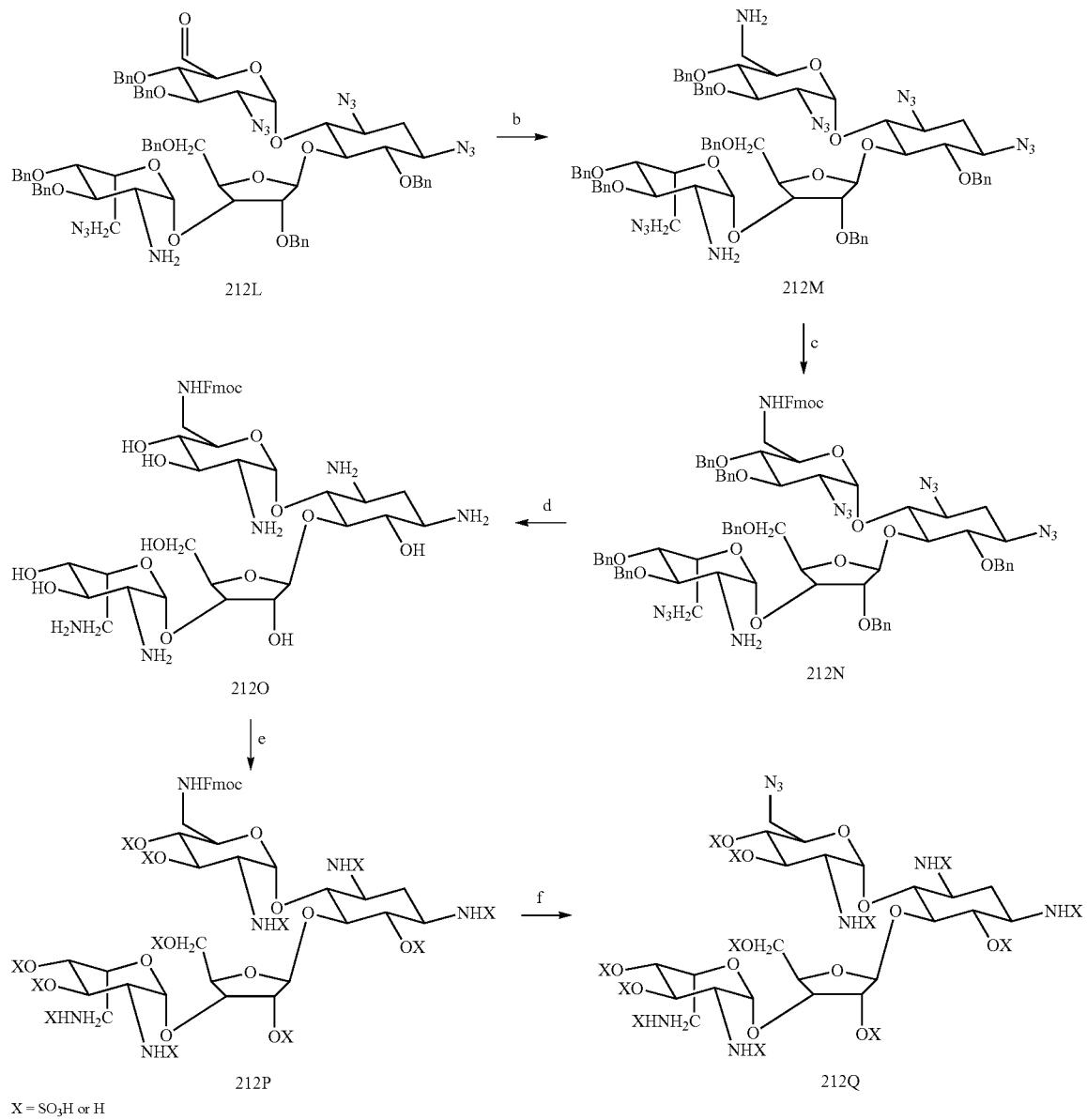

X = SO₃H or H a) Starting with paromomycin I, the procedure described in WO2007/064954 is followed to generate the aldehyde 212L.

b) Reductive amination is performed using general procedure 15 to generate the amine 212M.

c) Fmoc protection of the amine is performed in the standard manner with Fmoc-Cl to generate 212N.

d) 212N is deprotected as described in WO2007/064954 to generate 212O.

e) 212O is sulfated using general procedure 1 to yield 212P.

f) The sulfated paramomycin 212P is deprotected and converted to the azide as described in example 19 to generate 212Q.

Likewise Paramomycin II is derivatised.

Example 46

Lividomycin a Azido Derivative

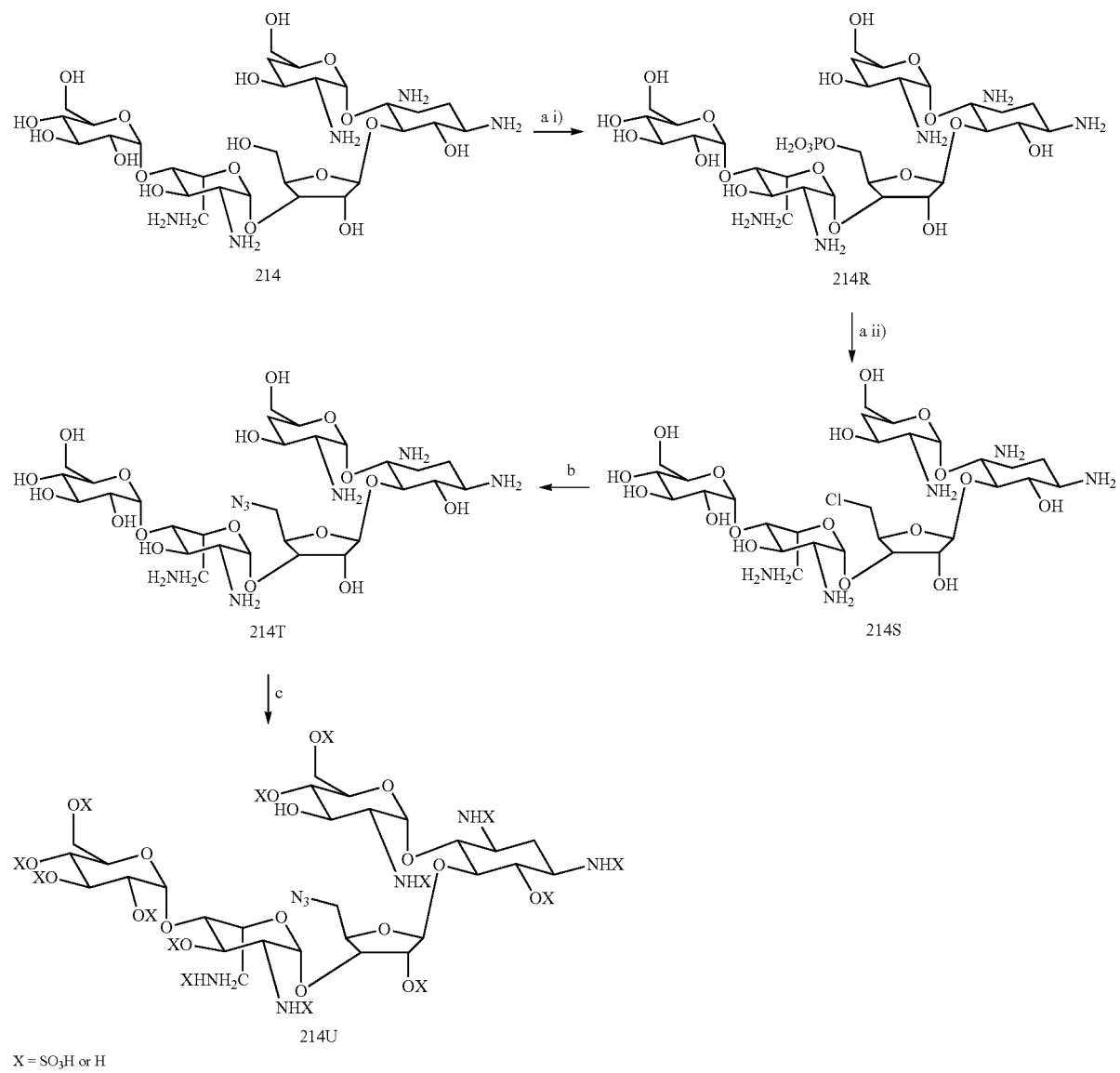

X = SO₃H or H a) Lividomycin is enzymatically phosphorylated and converted to the chloro derivative 214S as described in U.S. Pat. No. 4,029,833.

b) The chloro derivative 214S is mixed with NaN$_3$ in HMPA and heated at 55° C. for 6 hrs. The mixture is cooled to 0° C., ice water is added, and the precipitate is filtered and washed with water. Chromatography on silica gel using chloroform-ethyl-acetate and methanol (20:5:2) as eluent eliminated trace amounts of impurities and affords the desired compound, as a chromatographically homogeneous amorphous solid.

c) The azide 214T is sulfated using general procedure 1 to generate 214U.

Example 47A

Kanamycin 6'-Azido Derivative

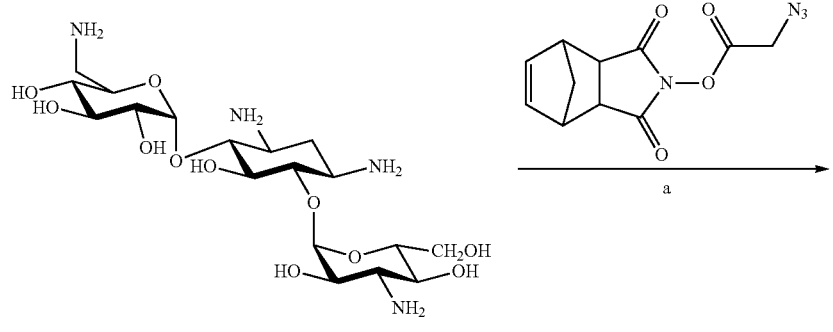

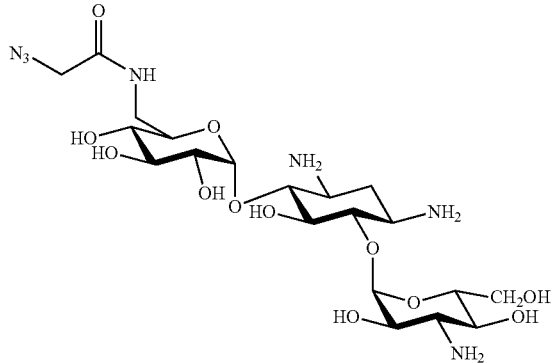

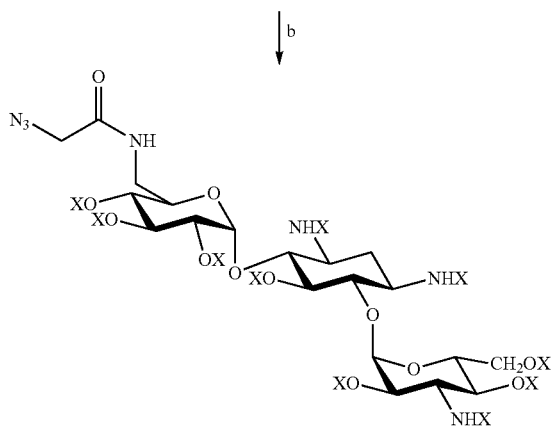

X = SO₃H or H

Kanamycin is selectively acylated at the unhindered 6'-amine using NBD-azidoacetate as described in *Bioorg. Med. Chem.* 2007, 15(8), 2944-2951 to generate 226AA. The azide 226A is sulfated using general procedure 1 to generate 226AB.

The following starting materials are likewise transformed: Kanamycin B; NK-1001; NK. 1012.1; Tobramycin; Nebramycin 4; and Nebramycin 5.

Example 47B

NBD-Azidoacetate Reactions with Paromomycin

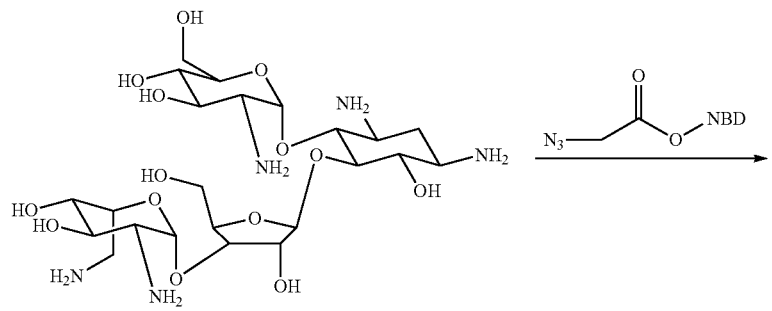

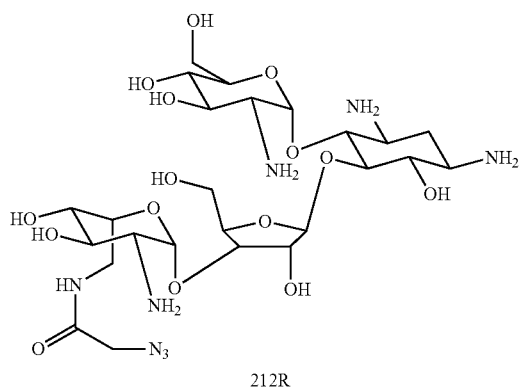

212R

In a similar manner, paromomycin was reacted with NBD-azidoacetate to yield (predominantly) the 6'''-azidoacetamide derivative, 212R, which was purified by RP HPLC (0.1% HFBA gradients) and sulfated using general procedure 1 to generate 212S.

Example 47C

226AB is deprotected using standard hydrogenation conditions (general procedure 10b) to from 226AC. In a cognate trimmer to examples 4 and 5, 226AC is bromoacetylated and coupled with the $HS(CH_2)_2$—O—$(CH_2)_2SH$, thus generating 226AD and 226AD1, respectively.

The other derivatives prepared in example 47A may be treated similarly.

Example 47D

Likewise, 226AD can be coupled with the linkers in the following table to generate the corresponding products.

|  | | Linker | | |
| --- | --- | --- | --- | --- |
| $Na_2S$ | $HS(CH_2)_2SH$ | $HS[(CH_2)_2O]_2$ $(CH_2)_2SH$ | $HS[(CH_2)_2O]_3$ $(CH_2)_2SH$ | $HS[(CH_2)_2O]_4$ $(CH_2)_2SH$ |
| Product 226AD2 | 226AD3 | 226AD4 | 226AD5 | 226AD6 |

Example 47E

The paromomycin derivative 212S from example 47B can be treated as described in example 47C, thus generating 212T and 212T1, respectively.

Example 47F

Likewise, 212T may be reacted with other linkers according to the table below.

| | | Linker | | |
|---|---|---|---|---|
| Na₂S | HS(CH₂)₂SH | HS[(CH₂)₂O]₂(CH₂)₂SH | HS[(CH₂)₂O]₃(CH₂)₂SH | HS[(CH₂)₂O]₄(CH₂)₂SH |
| Product 212T2 | 212T3 | 212T4 | 212T5 | 212T6 |

Example 47G

Derivatizations with Cbz-NBD Esters

For the reaction with paromomycin, N-benzyloxycarbonyloxy-5-norbornene-endo-2,3 dicarboximide was used in place of NBD-azidoacetate in the procedure in example 47B. The resulting mixture, which contains predominantly the 3'''-Cbz-paromomycin derivative (212U) is sulfated using general procedure 1 and the major component purified by RPIP-HPLC (212V). This is treated to the bromoacetylation and thiol coupling procedures described in examples 4 and 5, thus generating 212W and 212W1, respectively.

In a similar manner, 212W is reacted with the linkers shown in the following table.

| | | Linker | | |
|---|---|---|---|---|
| Na₂S | HS(CH₂)₂SH | HS[(CH₂)₂O]₂(CH₂)₂SH | HS[(CH₂)₂O]₃(CH₂)₂SH | HS[(CH₂)₂O]₄(CH₂)₂SH |
| Product 226W2 | 226W3 | 226W4 | 226W5 | 226W6 |

Example 48

Kanamycin 6''-Azido Derivatives

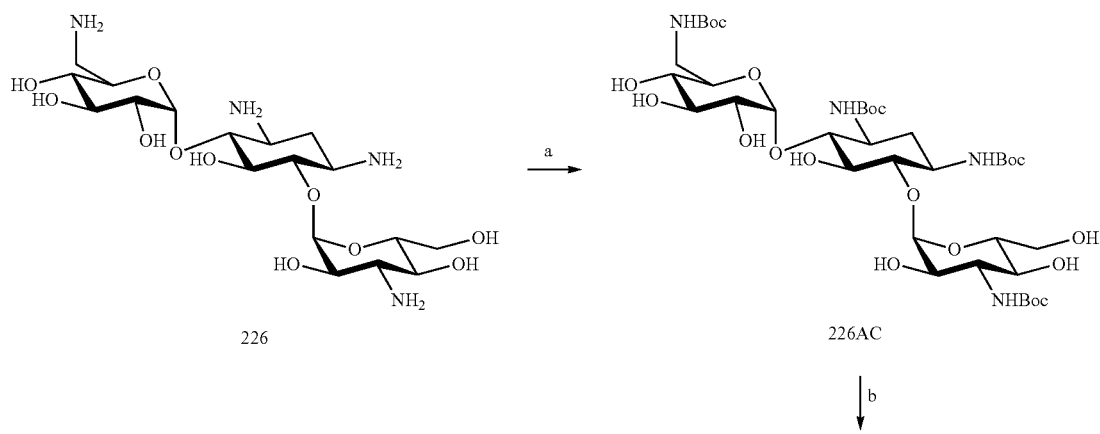

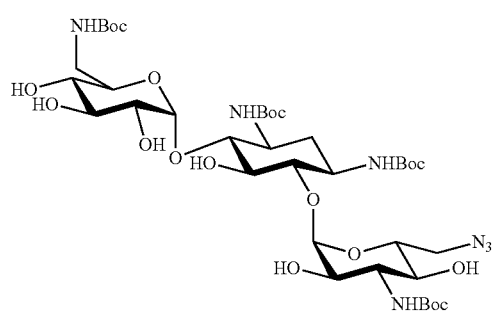

226AE

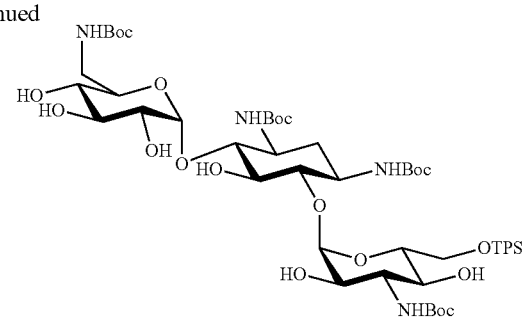

226AD

-continued

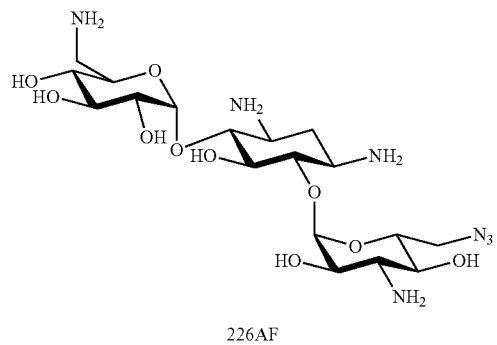

226AF

X = SO₃H or H

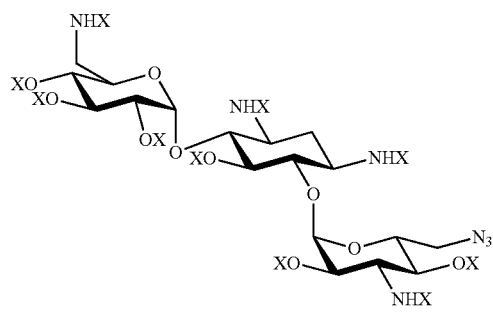

226AG

Kanamycin A is converted to the 6"-azido derivative using the TPS activation of the primary hydroxyl route adopted in example 43, which has been described for Kanamycin A previously in *Bioorg. Med. Chem.* 1999, 7(7), 1361-71. Briefly, this involves the steps of Boc protection of amines (a, 226AC), TPS-Cl derivatisation (b, 226AD), azide displacement (c, 226AE) and De-N-protection (d, 226AF). In the final step, e, 222AF is sulfated using general procedure 1 to yield 226AG.

The following starting materials are likewise transformed: Kanamycin B; NK-1001; NK-1012.1; and Tobramycin.

Example 49A

Metal Ion Temporary Protection of Kanamycins

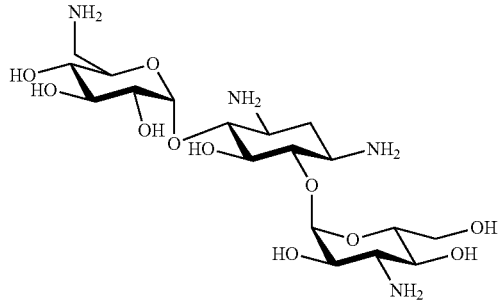

226

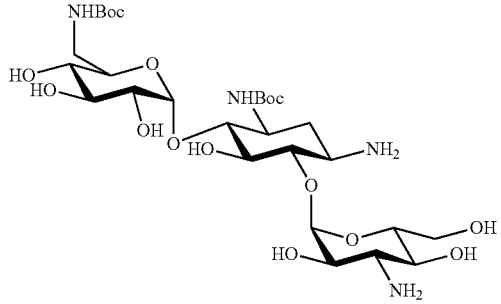

226AH

-continued

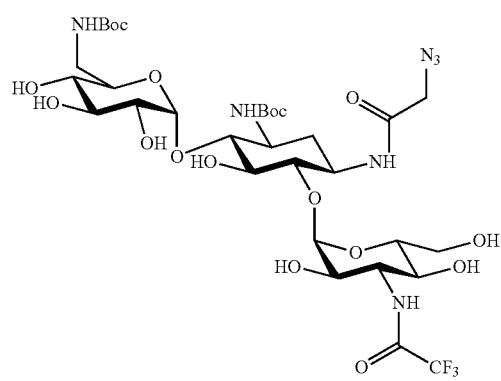

226AJ

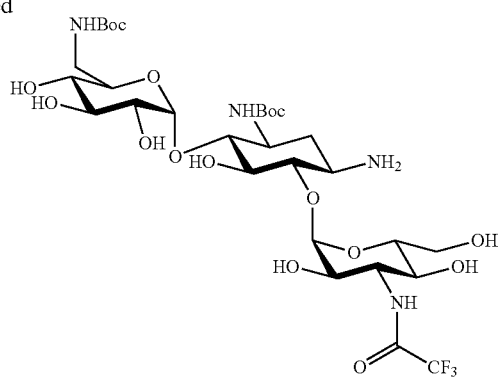

226AI

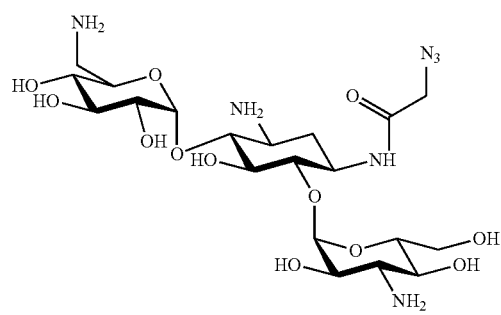

226AK

X = SO₃H or H

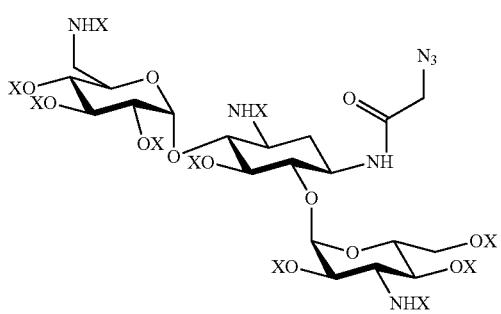

226AL a) The procedure for the preparation of amikacin, which is described in U.S. Pat. No. 4,297,485, is followed to generate the tri-protected intermediate 226AI. This is azidoacetylated using general procedure 22 (step c), deprotected as described in U.S. Pat. No. 4,297,485 to yield 226AK (step d) and this is sulfated (step e) using general procedure 1. The same product is also prepared without the need of preparing the trifluoroacetamide intermediate, i.e. 226A1 direct to 226AK by following the directions given in example 72 of U.S. Pat. No. 4,297,485.

The following starting materials are likewise transformed into their azide derivatives: Kanamycin B; Kanamycin C; NK-1001; NK-1012.1; Tobramycin; Nebramycin 4; and Nebramycin 5.

Example 49B 3,6'-diN-benzyloxycarbonylkanamycin A

The title compound (226BA) is prepared as described in U.S. Pat. No. 4,297,485.

Example 49C

6'-N-Cbz Kanamycin Derivatives

The title compound (226CA) is prepared as described in U.S. Pat. No. 4,297,485 is used.

Example 49D

1-Pot Preparation of 6'-N-benzyloxycarbonyl-3-N-acetylkanamycin

Kanamycin A was reacted with Cbz-Osu as described in the procedure for the preparation of 6'-N-benzyloxycarbonylkanamycin A described in U.S. Pat. No. 4,297,485 and at the completion of the first reaction, 1.25 equivalents of acetic anhydride was added and the mixture stirred at room temperature for a further 4 h before workup as described in U.S. Pat. No. 4,297,485. The crude 6'-N-benzyloxycarbonyl-3-N-acetylkanamycin (226CB) contained a few percent of each of 3,6' diacetyl kanamycin and 3,6'-di-Cbz kanamycin. A portion was purified by RP HPLC (0.1% HFBA gradients) for characterization. ESI/MS 661.25 (calc [M+H]⁺ 661.29). MS/MS of 661.3 (500.17, 3"-N-unprotected ring) 366.17 (loss of 6-N-Z protected ring).

Example 49E

6'-N-benzyloxycarbonyl-3''-N-fluorenylmethoxycarbonyl-1,3-diN-acetylkanamycin

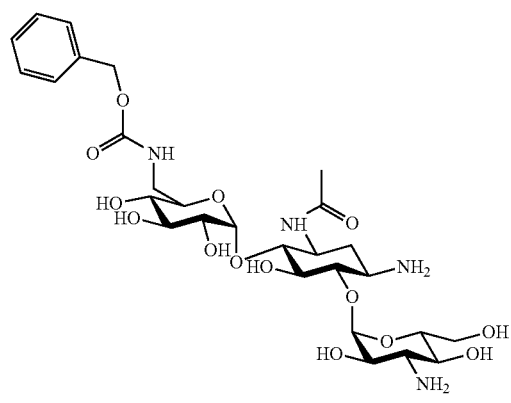

226CB

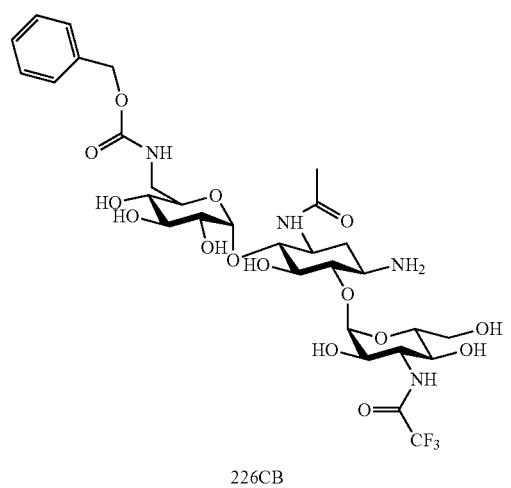

226CB

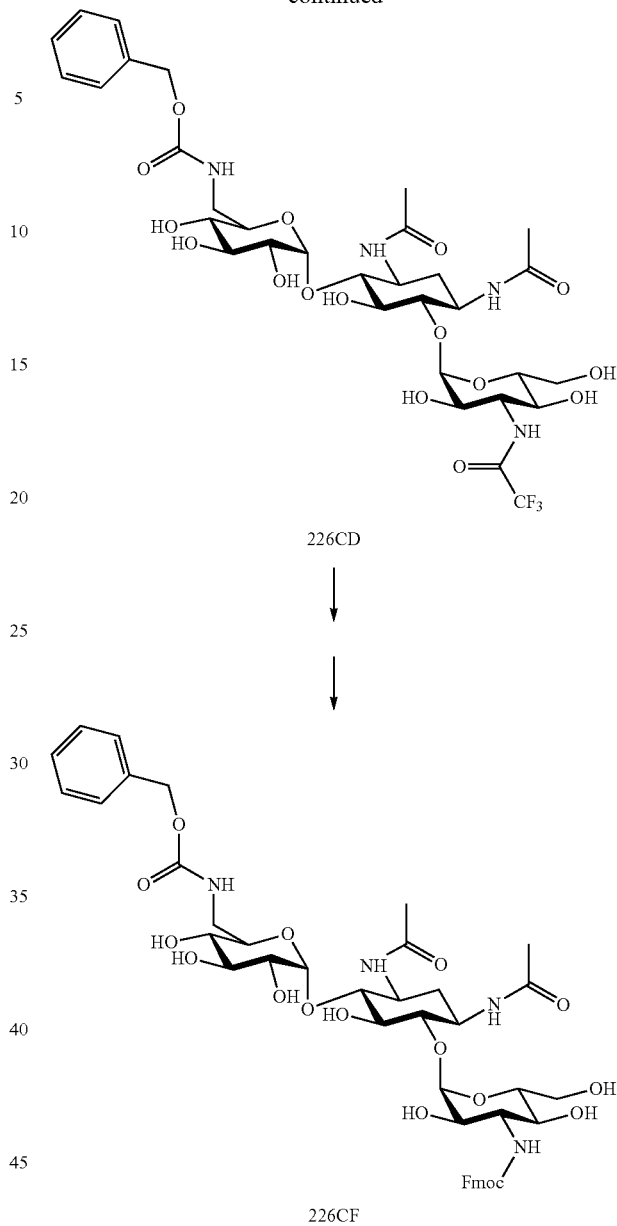

Crude 226CB (0.4 g) from above was dissolved in pyridine (3 ml) and ethyltrifluoroacetate (1.2 eq) added and stirred at room temperature for 4 h, the formation of 226CC being monitored by RP HPLC. ESI/MS 757.25 (calc [M+H]+ 757.27). 757 MS/MS 462.22 (loss of 6'-Z-ring), 500.27 (loss of 3''-TFA-ring). The solution was diluted with methanol (10 ml) and acetic anhydride (50 eq) added and stirred at room temperature for 16 h upon which 226CD was formed. The TFA group was deprotected in situ by addition of 25% aqueous ammonia (3 ml) and the reaction stirred overnight. The solution was evaporated to dryness and reconstituted in 50:50 water:methanol and sodium bicarbonate and Fmoc-Cl (10 eq) added. The reaction was stirred at room temperature overnight, diluted with water and the precipitate collected. The crude material (contaminated with the hydrolysed Fmoc-Cl) was dried at reduced pressure. A small portion was purified for characterization of 226CF. ESI/MS 925.0 (calc [M+H]+ 925.26).

Example 49F

Sulfated 6'-N-Linked Kanamycin Dimers

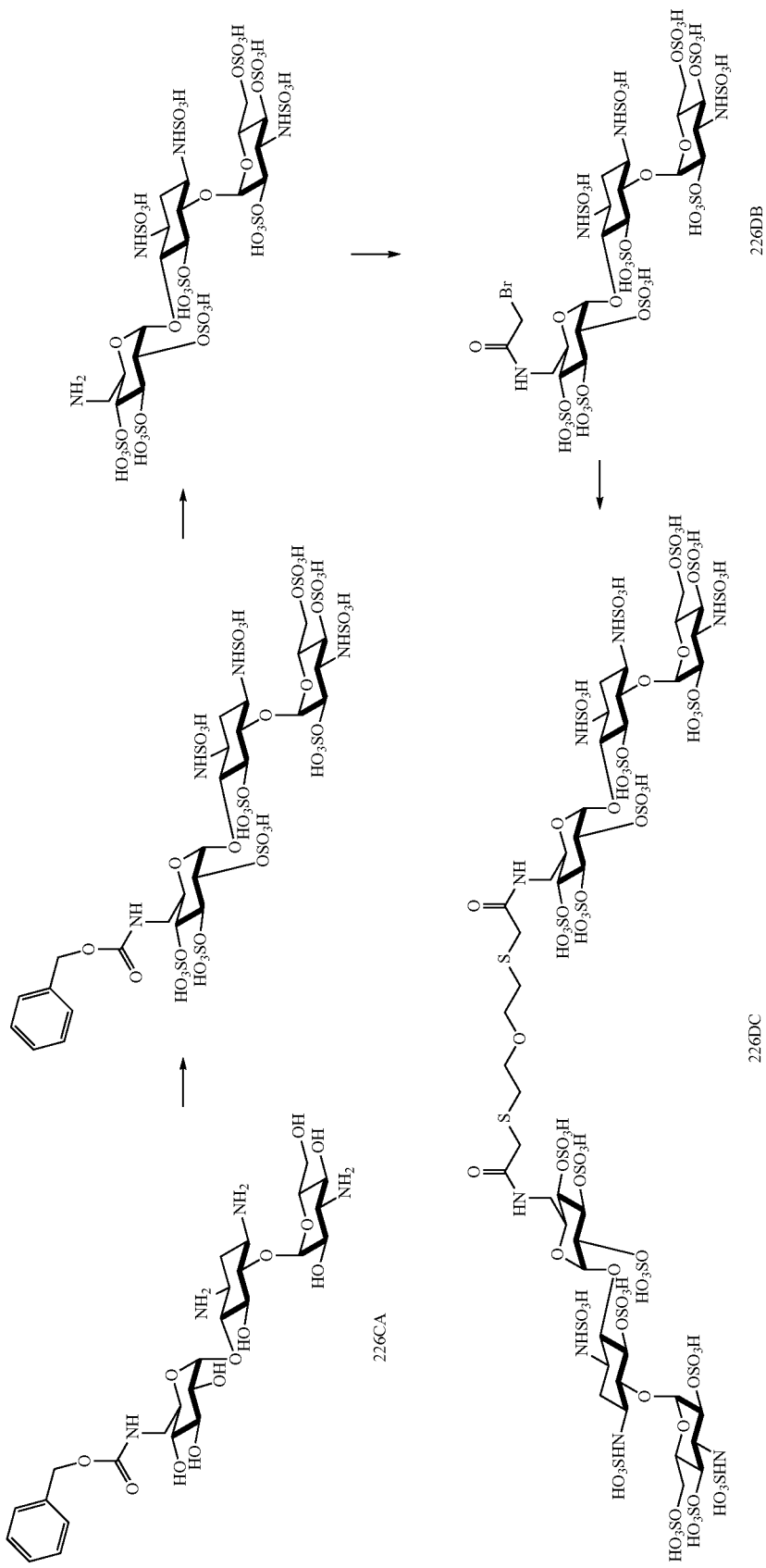

226CA is sulfated (general procedure 1) and the supernatant decanted to recover the precipitant. The product isolated by RP-IP HPLC (general procedure 5). This is reduced (general procedure 10b) and bromoacetylated (general procedure 4) to afford 226 DB, which is purified by RP-IP HPLC (general procedure 5). 226 DB was coupled with the dithiol as described in example 4 to afford 226DC.

In a similar manner the reaction of 226 DB with the following linkers generates the products shown in the following table.

| | | Linker | | |
|---|---|---|---|---|
| Na$_2$S | HS(CH$_2$)$_2$SH | HS[(CH$_2$)$_2$O]$_2$ (CH$_2$)$_2$SH | HS[(CH$_2$)$_2$O]$_3$ (CH$_2$)$_2$SH | HS[(CH$_2$)$_2$O]$_4$ (CH$_2$)$_2$SH |
| Product 226DD | 226DE | 226DF | 226DG | 226DH |

Example 50

Kanamycin 3"-Azido Derivative a) The 1-amino group in 226AI (from the previous example) is protected as the Boc derivative in the standard manner to yield 226AM.

b) 226AM is dissolved in 2 N aqueous ammonia-tetrahydrofuran (5:3 by volume) and the solution is allowed to stand overnight at ambient temperature to effect the removal of the 3"-N-trifluoroacetyl group to generate 226AN.

c) 226AN is transformed to the azido derivative 226AO using general procedure 9.

d) 226AO is N-deprotected in the usual manner to generate 226AP e) 226AO is sulfated using general procedure 1 to generate 226AQ.

The trifluoroacetamide intermediates of each of: Kanamycin B; NK-1001; NK•1012•1; Tobramycin; Nebramycin 4; and Nebramycin 5 produced in Example 49 are likewise transformed.

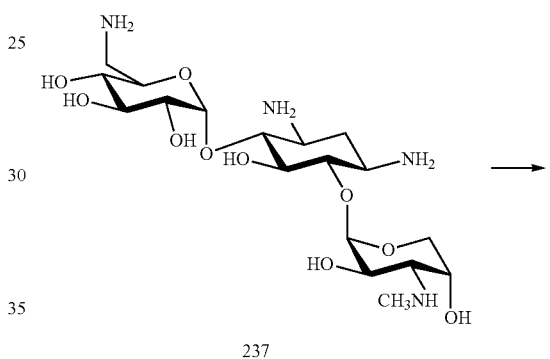

237

Example 51

6'-Azido Derivative of Gentamicin A$_3$

Metal ions are used to selectively mask some amino groups of an aminoglycoside whilst allowing others to react and many selectively protected derivatives are described in: U.S. Pat. Nos. 4,136,254; 4,297,485; 4,831,123; 4,230,847; and 4,337,335. The use of these techniques has already been illustrated in the preceding 2 examples. Further illustration of how these techniques are used is provided in this and subsequent examples.

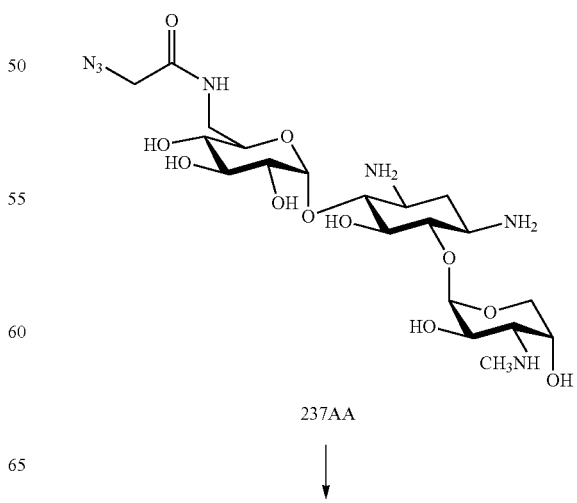

237AA

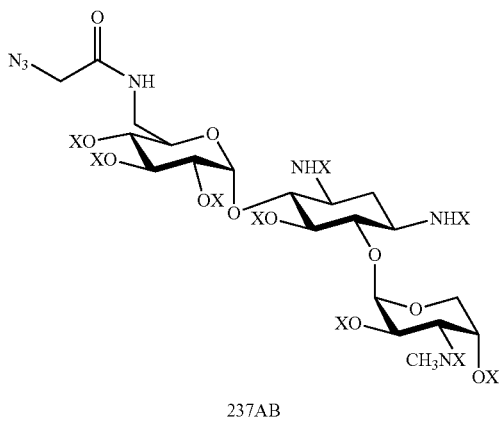

237AB

X = SO₃H or H

Selective 6'-azidoacyl protection of gentamicin A₃ to generate 237AA is achieved using $Cu^{2+}$ complexation and the phthalimide ester of azidoacetic acid, in the manner described in U.S. Pat. No. 4,136,254. 237AA is sulfated using general procedure 1 to generate 237AB, which affords satisfactory LC-MS analysis.

Similar products are prepared using the following starting materials: Gentamicin B; JI•20A; JI•20B; Gentamicin $C_1$; Gentamicin $C_{2\text{-}III}$; Sagamicin; Sisomicin; 66-40B; and 66-40D.

Example 52

Metal Complexation for the Preparation of N-3" Derivatives of Gentamicin $C_{1a}$ This procedure is analogous to example 50, except the triprotected derivative is used for the trifluoroacetylation step.

a) Gentamicin $C_{1a}$ is converted to the 3,2',6'-tri-N Boc protected derivative (245AS) using the procedures described in U.S. Pat. Nos. 4,297,485 and 4,337,335.

b) Trifluoroacetylation is performed as described in U.S. Pat. No. 4,297,485 to generate 245AM.

c) The 1-N-Boc derivative is prepared in the standard manner to generate 245AN.

d) The trifluoroacetyl group is removed as described in U.S. Pat. No. 4,297,485 to generate 245AO.

e) The 3" amine is azidoacetylated as described in example 50 to generate 245AP.

f) The Boc groups are removed in the standard manner to generate 245AQ g) The deprotected derivative is sulfated using general procedure 1 to generate 245AR.

Likewise the same methodology is applied to: Gentamicin C2; Gentamicin C2a; Gentamicin C2-111a; Sagamicin; Sisomicin; Verdamicin; G.S2; 66-40B; and 66-40D.

Example 53

6'-Azido of Gentamicin a

The 6'-primary hydroxyl groups of gentamicin A are converted to the azido derivatives using the TPS activation of the primary hydroxyl route adopted in example 43. Thus, the following intermediates and product are produced in this process.

| Starting material | | Product formed at each step | | | | |
|---|---|---|---|---|---|---|
| Name | Ref | a | b | c | d | e |
| Gentamicin A | 234 | 234AC | 234AD | 234AE | 234AF | 234AG |

Likewise the same methodology is applied to: Gentamicin A; Gentamicin A₂; Gentamicin A₄; Gentamicin B₁; Gentamicin X₂; Seldomycin 1; Apramycin; Oxyapramycin; Saccharocin (KA-5685); and Seldomycin 3.

Example 54

1-N-Azido Derivative of Seldomycin 5

The 1-N-azido derivative of seldomycin 5 is prepared in a procedure analogous to example 52 and adopted from U.S. Pat. No. 4,214,077. Thus, the following intermediates and product are produced in this process.

| | Product formed at each step | | | | | | |
|---|---|---|---|---|---|---|---|
| Starting material | a | b | c | d | e | f | g |
| Seldomycin 5 | 258AS | 258AM | 258AN | 258AO | 258AP | 258AQ | 258AR |

A similar methodology is applied to seldomycin 3 to produce its 1-N-azido derivative.

Example 55A

Controlled Variation of the Degree of Sulfation by O-Sulfation Only

In examples 42-44 and 46-54 it is evident that in the penultimate step, the aminoglycoside intermediate has free amino groups and these become sulfated during the final step. In example 45, this occurs at the step prior to the penultimate step. Thus, the compounds which are prepared in examples 42-54 are transformed into analogues with a precisely controlled lower degree of sulfation by N-acetylating these intermediates using general procedure 23. Thus, the analogues of the fully sulfated compounds are prepared. It is clear to those skilled in the art that further variation is possible by applying the selective N-masking techniques described in many of the preceding examples.

Example 55B

Sulfated Di-N-Benzyloxycarbonyl Kanamycin A Dimers

The sequence described in U.S. Pat. No. 4,297,485 for the preparation of 3,6'-di-N-benzyloxycarbonyl-3"-N-trifluoroacetyl kanamycin A was followed. The product was bromoacetylated (general procedure 4) to generate 226BC, which was purified by RP HPLC. ESI/MS 970.94 (100%)

968.9 (90%); (Calcd [M+H]+ 970.2, 968.2). The bromoacetamide was coupled with $HS(CH_2)_2$—O—$(CH_2)_2SH$ (general procedure 7) and the product, 226BD, purified by RP HPLC. ESI/MS 958.28 (m/z+2) (calc ([M+2H]$^{+2}$ 958.3. This intermediate was sulfated (general procedure 1) and the product 226BE purified by RPIP HPLC (general procedure 5).

In a similar manner the bromoacetamide 226BC is reacted with the linkers in the following table and then sulfated to generate the corresponding products shown

| | | Linker | | | |
|---|---|---|---|---|---|
| | $Na_2S$ | $HS(CH_2)_2SH$ | $HS[(CH_2)_2O]_2$ $(CH_2)_2SH$ | $HS[(CH_2)_2O]_3$ $(CH_2)_2SH$ | $HS[(CH_2)_2O]_4$ $(CH_2)_2SH$ |
| Product | 226BF | 226B G | 226BH | 226B1 | 226BJ |

Example 55C

Sulfated Tetra-N-Acetylparomomycin Dimers

Paromomycin derivative 212R was dissolved in methanol and acetic anhydride (10 eq) added and the reaction stirred at room temperature for 16 hours. The reaction was diluted with water and the tetra-acetyl derivative 212B1 purified by RP HPLC as described in general procedure 2. The azide was reduced to 212B2 using general procedure 10b, bromoacetylated using general procedure 4 and 212B3 purified by RP HPLC. The bromoacetamide was coupled with of $HS(CH_2)_2O(CH_2)_2SH$ (general procedure 7) and the product, 212B4, purified by RP HPLC. ESI/MS 950.45 (calc ([M+2H]$^{+2}$ 950.35). This intermediate was sulfated (general procedure 1) and the product 212B5 purified by RPIP HPLC (general procedure 5).

In a similar manner the bromoacetamide is reacted with the linkers in the following table and then sulfated.

| | | Linker | | | |
|---|---|---|---|---|---|
| | $Na_2S$ | $HS(CH_2)_2SH$ | $HS[(CH_2)_2O]_2$ $(CH_2)_2SH$ | $HS[(CH_2)_2O]_3$ $(CH_2)_2SH$ | $HS[(CH_2)_2O]_4$ $(CH_2)_2SH$ |
| Product | 212B6 | 212B7 | 212B8 | 212B9 | 212B10 |

Example 55D

Sulfated Tri-N-Acetylkanamycin A Dimers

Compound 226AA is N-acetylated using general procedure 24b and the product, 226AH, purified by RP HPLC. 226AH was subjected to the steps of reduction, bromoacetylation and coupling with $HS(CH_2)_2O(CH_2)_2SH$, as described in the preceeding example. ESI/MS 777.46 (m/z+ 2) calc ([M+2H]$^{+2}$ 799.30). This intermediate was sulfated (general procedure 1) and the product 226AI purified by RPIP HPLC (general procedure 5). In a similar manner the bromoacetamide is reacted with the linkers in the following table and then sulfated.

| | | Linker | | | |
|---|---|---|---|---|---|
| | $Na_2S$ | $HS(CH_2)_2SH$ | $HS[(CH_2)_2O]_2$ $(CH_2)_2SH$ | $HS[(CH_2)_2O]_3$ $(CH_2)_2SH$ | $HS[(CH_2)_2O]_4$ $(CH_2)_2SH$ |
| Product | 226AJ | 226AK | 226AL | 226AM | 226AN |

Example 55E

Sulfated Terephthalamide Linked Kanamycin A

The di-NBD ester of terepthalic acid was prepared according to Chengxun L and Qiang L, Polymer Communications, 42-47, 1985. This reagent was reacted with kanamycin A in the same manner as used for other NBD esters to generate the dimer 226TA. The crude material was N-acetylated using general procedure 24b and the product, 226TB, purified by RP HPLC (0.1% acetic acid gradients). ESI/MS 676.31 (m/z+2) (calc $[M+2H]^{+2}$ 676.15) This intermediate was sulfated (general procedure 1) and the product 226TC purified by RPIP HPLC (general procedure 5).

Additionally, 226TA was converted to the per-azido compound 226TD using general procedure 9 and purified by RP HPLC (0.1% acetic acid gradients). ESI/MS 1255.02 (calc [M+H]+ 1255.4). This was sulfated as described above to yield 226TE.

226TA is purified by RP HPLC using 0.1% TFA as ion-pairing agent in place of 0.1% acetic acid (general procedure 2). 226TA is subject to N,O-sulfation (general procedure 1) to yield 226TF.

Example 55F

Sulfated Terephthalamide Linked Paromomycin

In a similar manner to example 55E, paromomycin is converted to the three sulfated derivatives, 212TC, 212TE and 212TF.

Example 56

N-Sulfated Streptomycin Derivatives

In the penultimate step of examples 40 and 41, the streptomycin type aminoglycoside is deguanidinylated and N-acetylated. Omitting the N-acetylation step enables both N- and O-sulfation (general procedure 1) to be incorporated. Thus, the N-sulfated analogues of the preceding N-acetylated streptomycin type compounds of Examples 40 and 41 are prepared.

Example 57

Moenomycin Monofunctionalization

Moenomycin is dephosphorylated enzymatically as described Tetrahedron 1992, 48, 8401 to generate the reducing terminus glycan (399), converted to the glycosylamine 399A (general procedure 8) and protected by Fmoc-gly (general procedure 2) to yield 399B. This is sulfated (general procedure 1, 399C), deprotected (general procedure 3, 399D) and transformed to the azido derivative (general procedure 20).

Example 58

Click Coupling of Monoazido Aminoglycosides to Diacetylenic PEGs

Azido derivative 202D is coupled to diacetylene terminated ethyleneglycol in the manner of example 20. The product 202D-1 is purified chromatographically.

Likewise, all of the sulfated mono-azido derivatives produced in examples 40-54 are coupled to diacetylene terminated ethyleneglycol.

Example 59

Coupling of Azido Aminoglycosides to Acetylene Terminated Linkers of Other Lengths In the manner described in example 21 all of the sulfated mono-azido derivatives produced in examples 40-54 are coupled with diacetylene terminated linkers of varying length.

Example 60

Trimeric Streptomycin Derivatives by Coupling to 2,4,6-tris(prop-2-ynyloxy)-1,3,5-triazine Likewise all of the sulfated mono-azido derivatives produced in examples 40-54 are coupled to 2,4,6-tris(prop-2-ynyloxy)-1,3,5-triazine.

Example 61

Trimeric Streptomycin Derivatives by Coupling to N,N',N"-Tris(prop-2-ynyloxy)-ethylenetriamine and hexamethylentriamine In the manner of the preceding example, all of the sulfated mono-azido derivatives produced in examples 40-54 are coupled to the trimeric acetylene linkers based upon ethylenetriamine and hexamethylentriamine.

Example 62

Tetrameric Aminoglycoside Derivatives

In the manner of example 22, all of the sulfated mono-azido derivatives produced in examples 40-54 are coupled to the tetrameric acetylene linkers.

Example 63

Difunctional Aminoglycosides: Streptomycins

To demonstrate the concepts behind the preparation of difunctionalized aminoglycoside building blocks, derivatives bearing azido and Fmoc protected amines will be described. This is also the strategy exemplified in example 36. Clearly there are many other suitable combinations of appropriately protected and or functionalized building blocks.

Difunctionalized streptomycin is prepared by combining the steps in examples 40 and 41 thus. 201F is prepared as described in example 41 and the secondary amine protected as the Boc derivative (201F-A). 201F-A is deguanidinylated and N-acetylated as described in example 40 (201F-B). The Boc group is removed (201F-C) and the amine acylated with Fmoc-glycine (general procedure 2, 201F-D), which is then sulfated to generate 201F-E. In the language of example 36, 201F-E is a chain extension unit.

The other azides of Example 41 undergo a similar transformation.

Example 64

Difunctionalized Neomycin 210D (example 42) is reduced to the amine (general procedure 10, 210D-A) and protected as the Fmoc derivative (210D-B). This is then subjected to the 4 steps in example 43 to generate, 210D-C, 210D-D, 210D-E and 210D-F. 210D-F is a chain extension unit.

The other azides of Example 42 are similarly transformed.

Example 65

6', 6"-Difunctional Kanamycin Building Blocks

226AF (example 48) is subjected to the 2 steps in example 47 with the modification that NBD-(N-Fmoc)glycine ester is used in place of NBD-azidoacetate. Thus, 226AF-A and 226AF-B are generated. 226AF-B is a chain extension unit.

The other primary amines of Example 48 are similarly transformed.

Example 66

Moenomycin Difunctionalization

Moenomycin derivative 399B is coupled with the diazonium salt bearing the azido protected side chain as described in *Tetrahedron* 1997, 53(52), 17669-17690 to generate 399B-1. This is sulfated (general procedure 1) to yield 399-B2.

Example 67

1, 3"-Difunctional Kanamycin Building Blocks

The trifluoroacetyl group of 226AJ (example 49) is removed as described in example 50, acylated with Fmoc-gly (general procedure 2, 226AJ-A) and sulfated (general procedure 1) to yield 226AJ-B.

The other trifluoroacetamides of Example 49 are similarly transformed.

Example 68

6',3"-difunctional Gentamicin Building Blocks

237AA (example 51) is subjected to steps a-d of example 52 (generating compounds 237AA-A, 237AA-B, 237AA-C and 237AA-D). 237AA-D is protected as the 3"-Fmoc derivative (237AA-E) and sulfated using general procedure 1 to yield 237AA-F. The other azides of Example 51 (excluding Gentamicin B and JI 20A) are similarly transformed.

Example 69A

Chains of Aminoglycoside Neo-Oligosaccharides

The sequence is similar to that described in example 36 and represented schematically as follows:

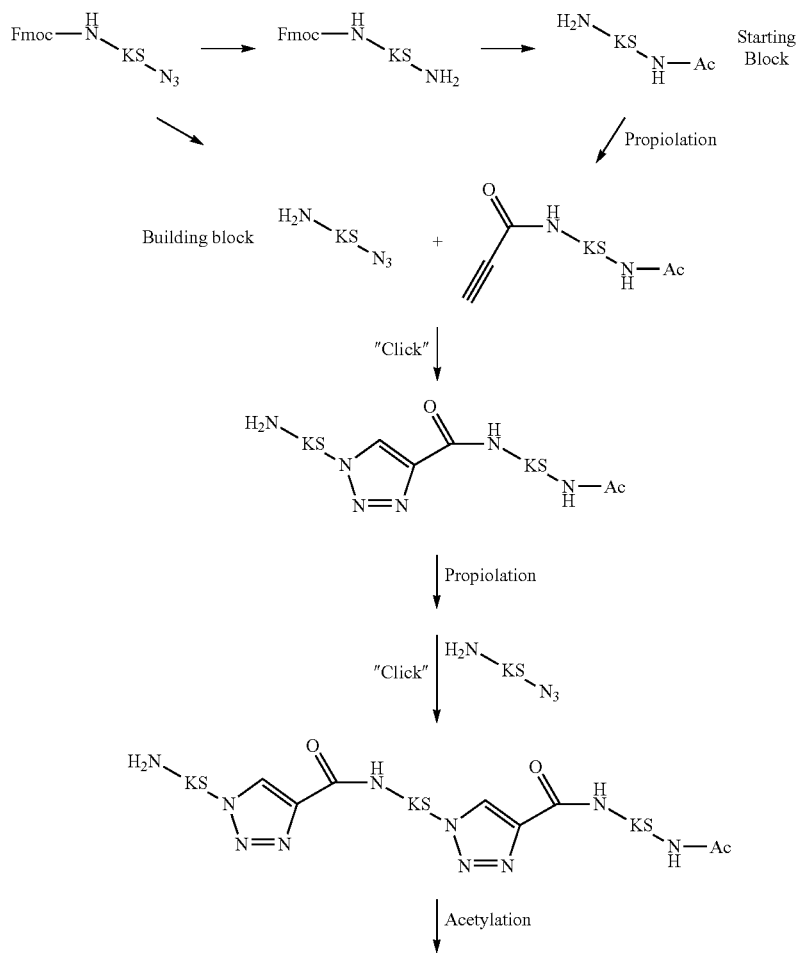

-continued

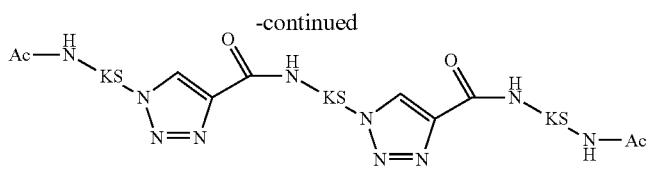

Schematic for the formation of a linear, head-to-tail neo-oligosaccharide from kanamycin. KS denotes the sulfated kanamycin backbone with the Boc at 6' and the azido group at 6".

a) 226AF-B is reduced to the free amine (general procedure 20) to generate 226AF-B1 which is N-acetylated (general procedure 23, 226AF-B2). The starting block 226AF-B3 is made by removal of the Fmoc group and propiolation in the 1-pot using general procedures 3 and 19.

b) The chain extension unit, 226AF-B4, is made by removal of the Fmoc group.

c) 226AF-B4 is coupled to 226AF-B3 using general procedure 18 to generate 226AF-B5.

c) The trimer is made by propiolation of 226AF-B5 (general procedure 19, 226AF-B6) and coupling with a further unit of 226AF-B4 (general procedure 18).

d) The process is terminated by N-acetylation (general procedure 23) to yield the trimeric product 226AF-B7.

The chain extended units of Examples 63, 64, 65, 66 and 68 are similarly transformed.

Example 69B

Kanamycin Trimers Linked at the 3- and 6"-N Positions

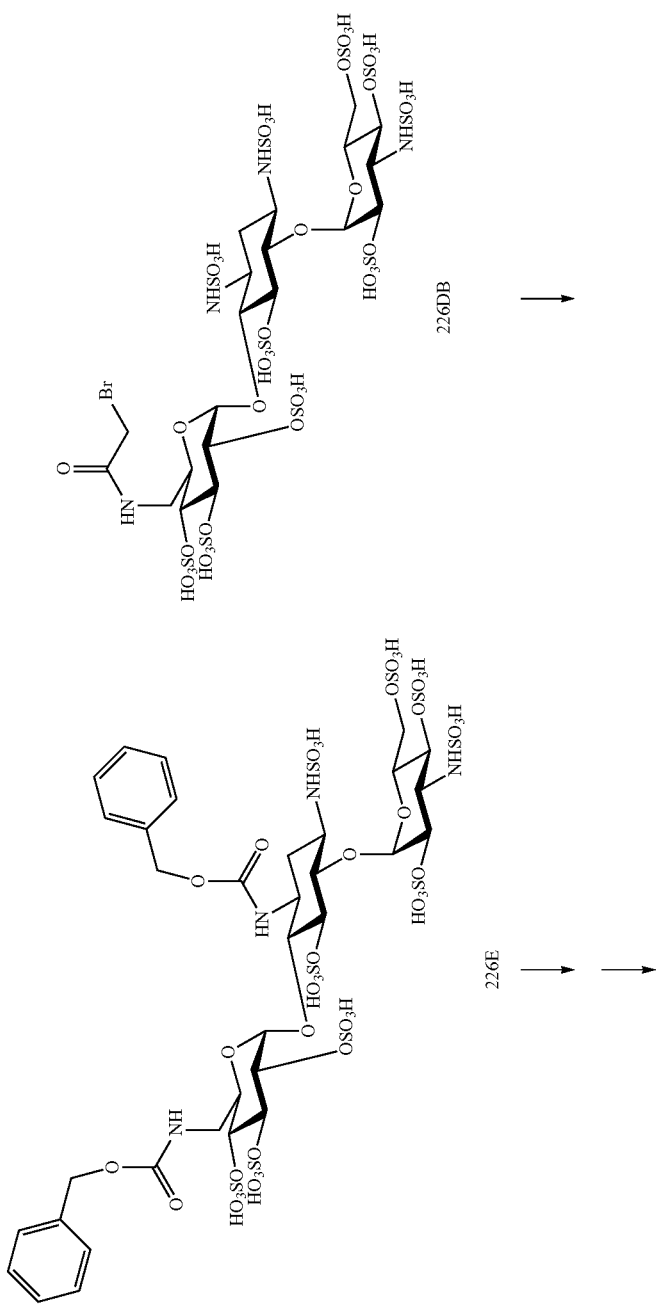

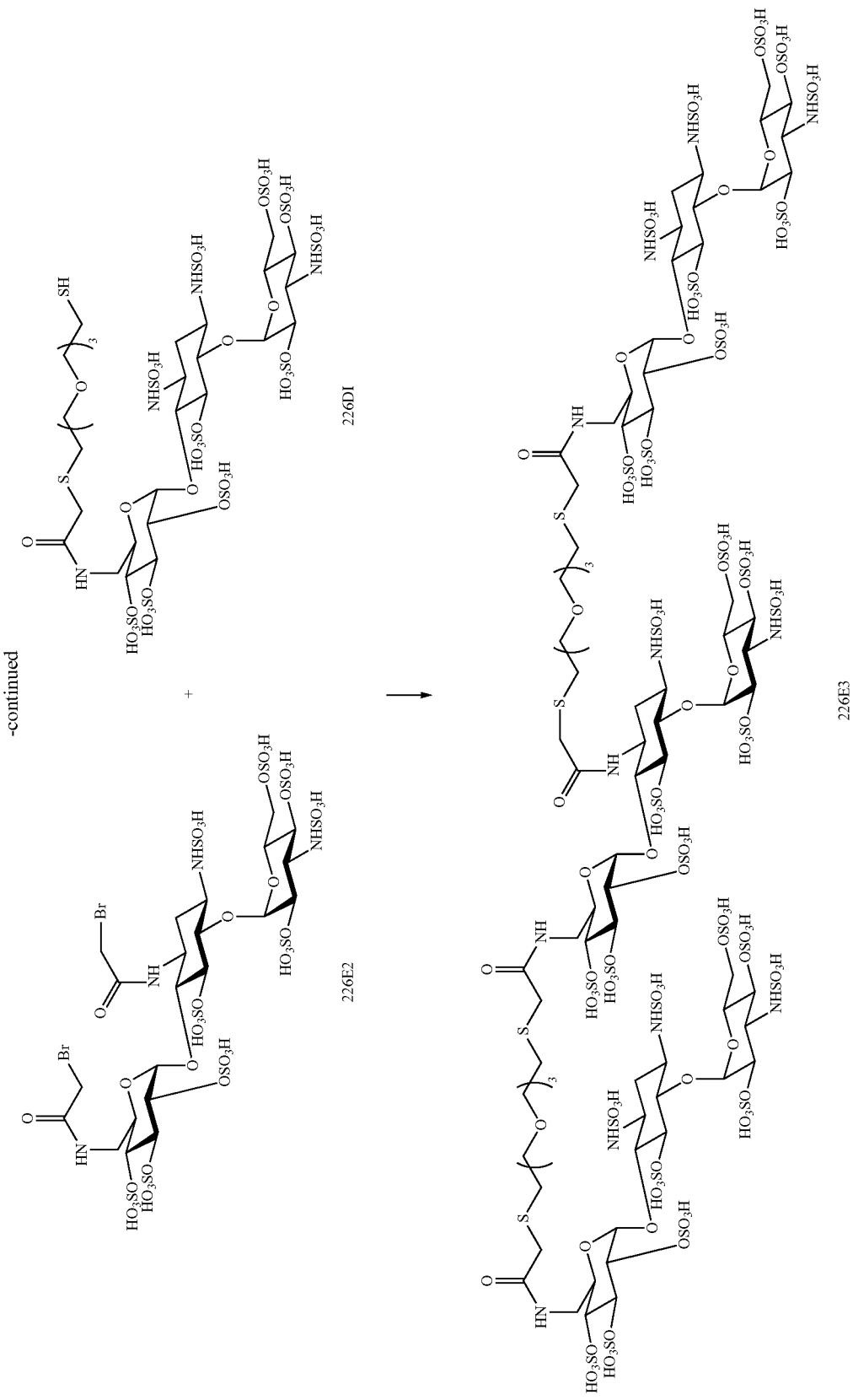

226BA (example 49B) is subjected to N- and O-sulfation (general procedure 1) to generate 226E. 226E is deprotected (general procedure 10b) and dibromoacetylated to afford 226E2, which is purified by RPIP HPLC. Separately, 226 DB is reacted with a 20-fold excess of $HSCH_2(CH_2OCH_2)_3CH_2SH$ to form the thiolated derivative 226DI by adapting general procedure 7. The excess dithiol is removed by exhaustive extraction with ethylacetate before 226E2 is added and the reaction monitored by RPIP HPLC. The trimeric product, 226 E3 is purified by preparative RPIP HPLC.

Example 69C

Kanamycin Tetramer

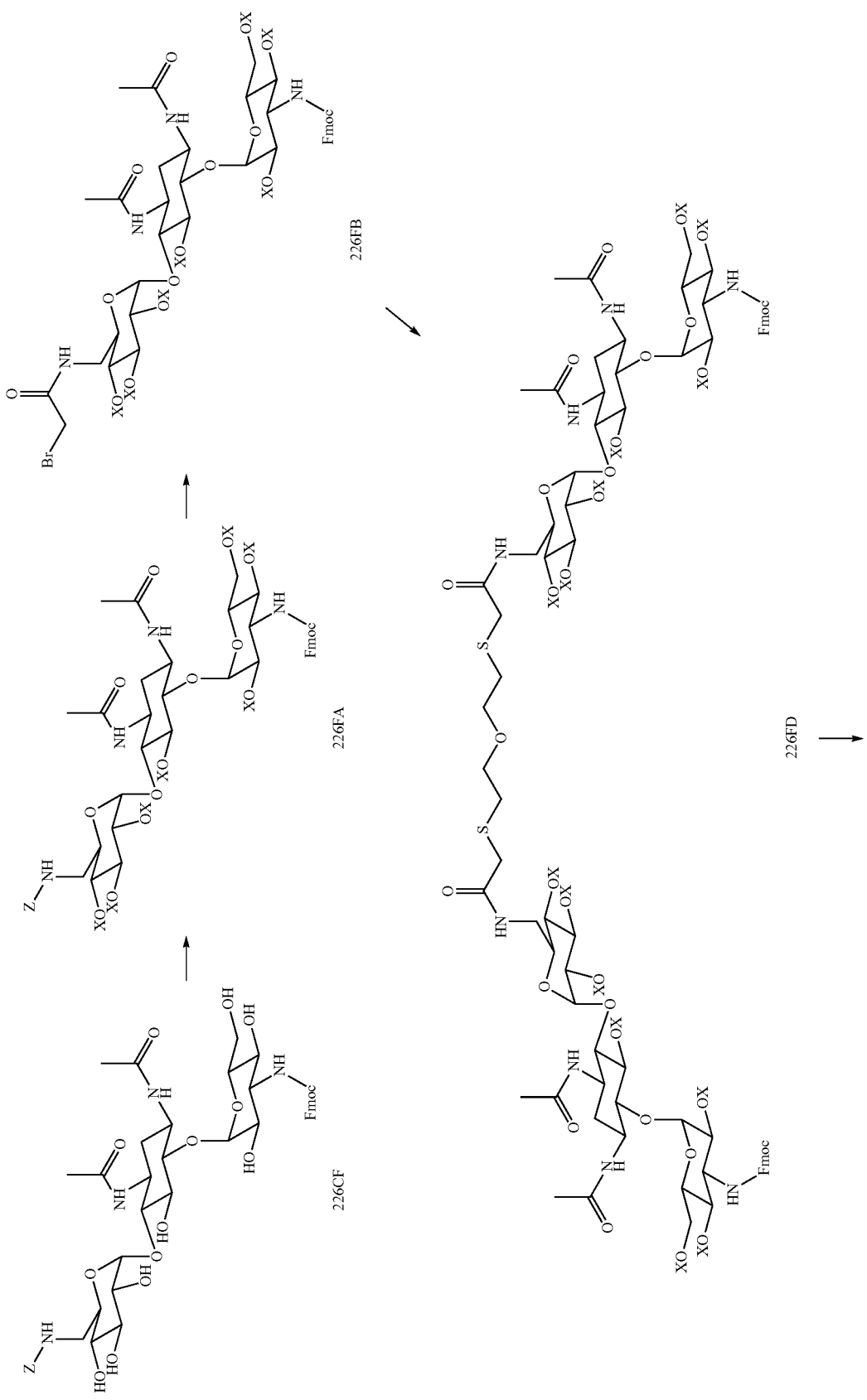

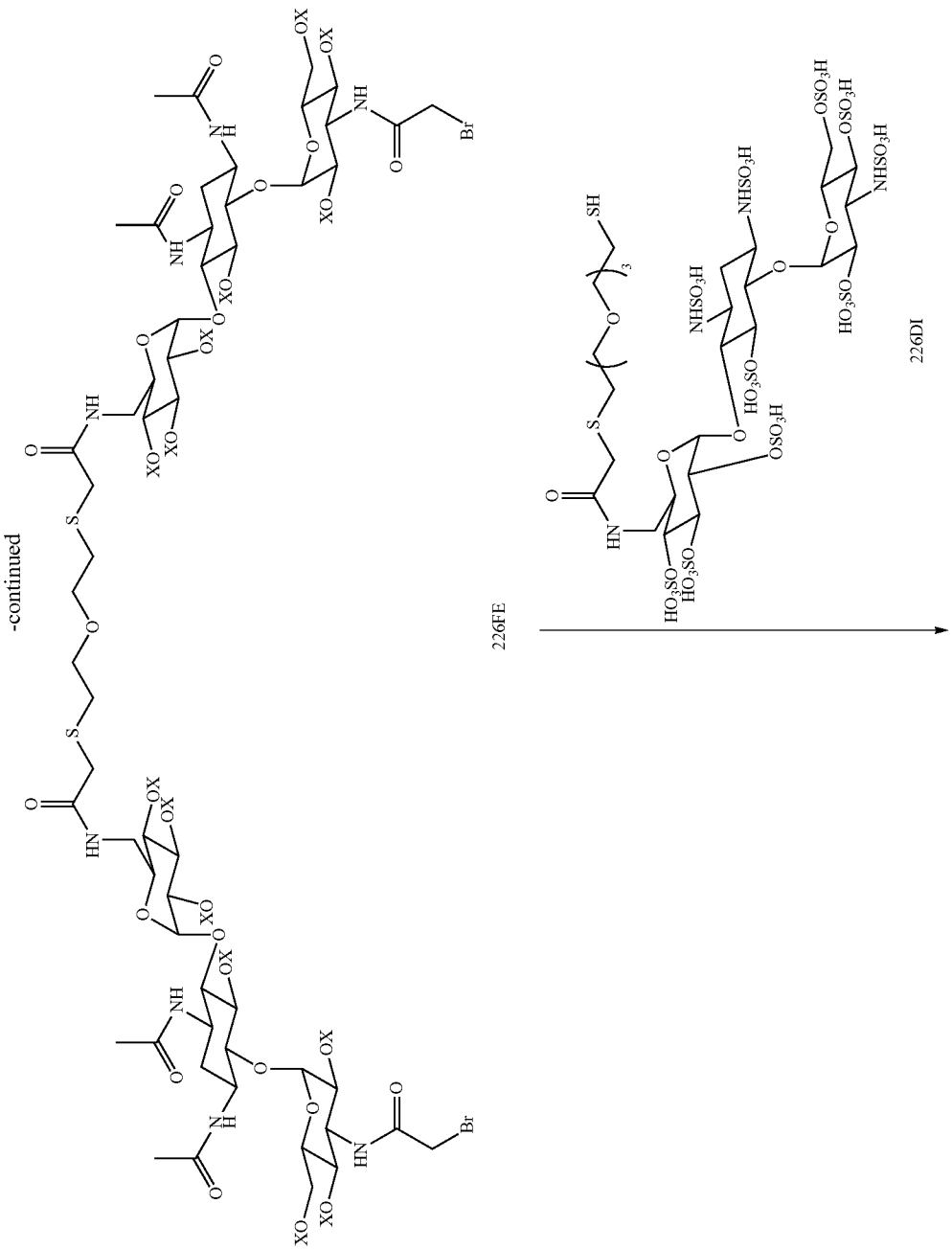

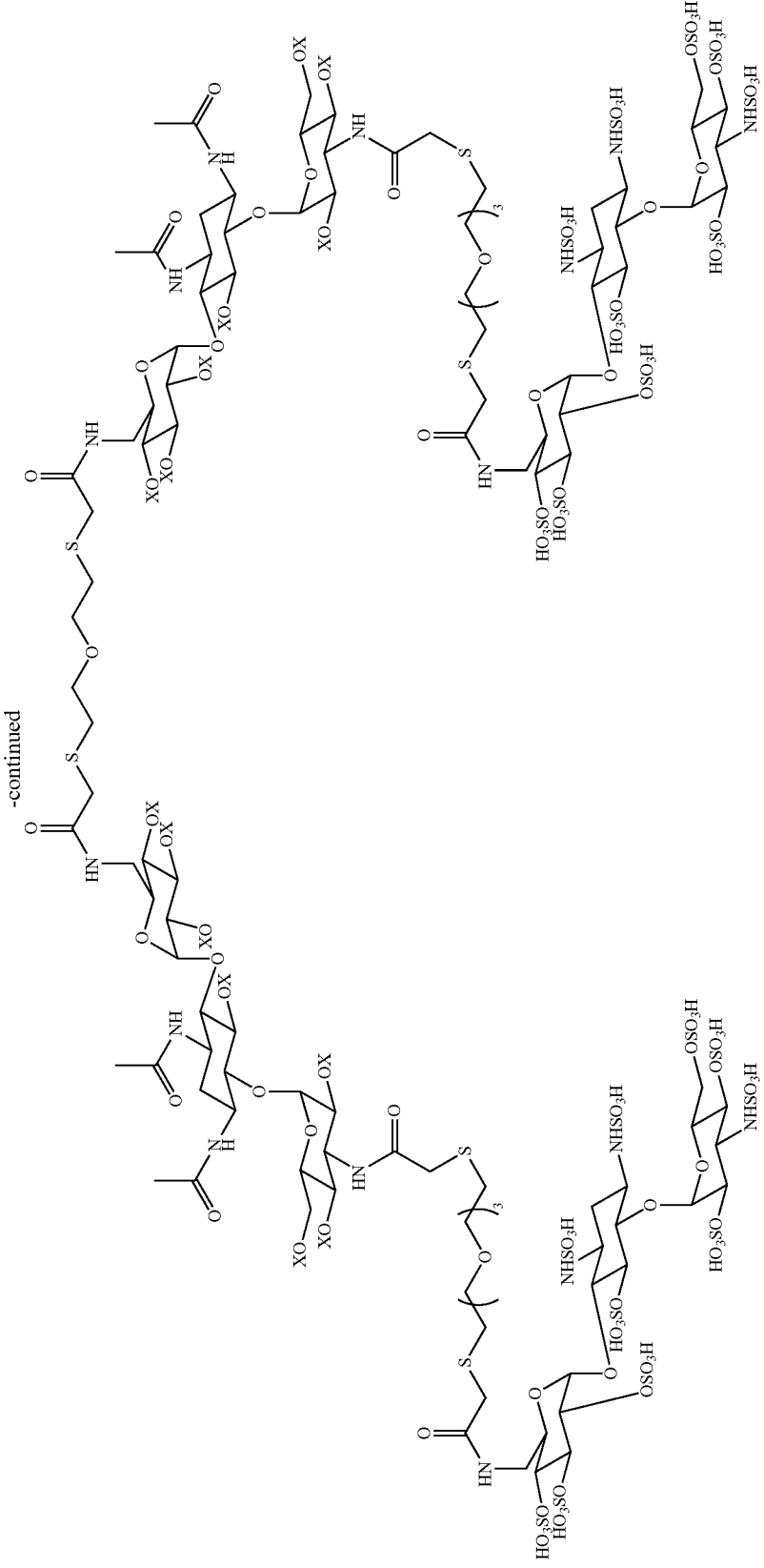

226CF (example 49F) was sulfated (general procedure 1) and the product 226CG, which precipitated as a gum, was collected and purified by RPIP HPLC. 226CG was hydrogenated (general procedure 10b) and bromoacetylated (general procedure 4). 226CH was purified by RPIP HPLC. Reaction with the dithiol as described in example 4 afforded 226CI which was purified by RP-IP HPLC (general procedure 5). The Fmoc groups were removed using DABCO in acetonitrile. Upon completion the reaction mixture was diluted with water and extracted with ethyl acetate and the aqueous layer lyophilized. The dried amine was dissolved in methanol with 1.25 equivalents each of TEA and nitrophenyl bromoacetate and incubated at room temperature for 16 h with monitoring by RPIP HPLC. The bromoacetamide 226CJ was purified by RP-IP HPLC (general procedure 5) and coupled with thiol 226DI. The reaction was monitored by RPIP HPLC and SEC (general procedure 26). The product was purified by preparative RPIP HPLC.

Likewise, thiols prepared in the other examples may also be incorporated into this final coupling.

Example 70

BIAcore Assay

This technology uses the optical phenomenon of surface plasmon resonance to monitor physical interactions between molecules. Passing a protein solution over a sensor surface to which the ligand is coupled monitors the real-time binding of proteins to an immobilized ligand. Detection is achieved by measuring refractive index changes very close to the sensor surface. When the refractive index is altered, the angle at which plasmon resonance occurs changes and this change directly correlates with the amount of protein interacting with the surface. A BIAcore 2000 is conveniently used. It is very sensitive and its microfluidics ensures that only small amounts of material are required.

The anionic conjugates of the present invention may be immobilized on a biosensor chip. Intact anionic conjugates are biotinylated via amino groups, or reducing termini modified with ammonia by reductive amination, using sulfo-NHS-biotin. Biotinylated anionic conjugates are immobilized on streptavidin-coupled sensor chips. Solutions containing proteins of interest are injected over the sensor chip surface, and the binding is measured in real time (Fernig, In: Proteoglycan protocols, Ed. R. V. Iozzo, Humana Press, Totowa, N.J., USA, 2001). The inventors have demonstrated that baculovirus and *E. coli* expressed human IL-4 (rhIL-4) and baculovirus expressed human IL-5 (rhIL-5) readily bind to heparin immobilized by this method.

Example 71

Screening of the Library

Preparations of anionic conjugates of the present invention were tested for their ability to inhibit binding of the target proteins to heparin or heparan sulfate, respectively, using the BIAcore. A mixture of an anionic conjugate and the target protein was equilibrated before analysis using the BIAcore. The binding observed in this instance is expressed relative to the binding observed in the absence of the anionic conjugate and the $IC_{50}$ determined as being that concentration of inhibitor which caused a decrease in binding of 50%. A selection of results is shown below, with particular compounds showing potent activity against 1 or more cytokines. Thus, importantly, the compounds display selectivity of binding.

TABLE 1

$IC_{50}$ values for the inhibition of binding of IL-5, IL-4 and IL-13 to heparin by selected compounds.

| Compound | $IC_{50}$ (nM) | | |
|---|---|---|---|
| | IL-5 | IL-4 | IL-13 |
| 1F | >650 | >100 | >400 |
| 1E | 2000 | 200 | >250 |
| 1G | 750 | 150 | 85 |
| 1H | >650 | >200 | >400 |
| 1I | >650 | >200 | >500 |
| 1AW2 | 200 | 5 | 5 |
| Sulfated Trestatin A | >400 | <100 | <150 |
| Sulfated Trestatin B | >1000 | <300 | |
| 161G | 450 | 30 | 290 |
| 161I | 225 | 18 | 250 |
| 1DK (example 17C) | 45 | 25 | <200 |
| 1DM | >150 | <100 | <200 |
| 1DN | >150 | <100 | <200 |
| 1DO | <150 | <100 | <200 |
| 1DI | 100 | 7 | <200 |
| 1DJ | 160 | 14 | <200 |

Example 71B

L-Selectin Screening

Chronic obstructive pulmonary disease (COPD) and asthma are inflammatory diseases of the lung involving excessive leukocyte infiltration which leads to reduced airflow and damage to the tissues. Cell adhesion molecules (e.g. Selectins) play a key role in directing leukocyte infiltration from the blood vessels and into the tissues. L-selectin is constitutively expressed on the surface of leukocytes. Leukocyte infiltration into inflamed tissues is considered to involve sequential steps of rolling over the endothelium, adhesion, and transmigration. In this model, the leukocyte adhesion molecule L-selectin and its ligands expressed on inflamed endothelial cells are involved in leukocyte rolling. L-selectin is considered to be an important therapeutic target as numerous animal studies have indicated an essential role for L-selectin in lung inflammation. The naturally occurring L-selectin ligands are the sialyl 6-sulfo Lewis X structure and heparan sulfates (Uchimura and Rosen. 2006. Trend Immunol. 27(12):559-565; Celie et al., 2007. Am. J. Pathol. 170(6): 1865-1878).

L-selectin was expressed as an IgG-Fc fusion protein in COS-7 cells and purified by protein A chromatography. A full-length cDNA clone of human L-selectin was obtained from ImaGenes GmBH, Berlin, Germany. The expression vector used was pcDNA3.1 (Invitrogen, USA) containing the DNA for the Fc portion of human IgG, which is spliced onto the carboxy terminus of any protein cloned. PCR primers were designed to introduce restriction enzyme sites for cloning at the 5' end and at the transmembrane domain of the L-selectin cDNA. In addition, a splice donor site was appended to the 3' end to allow fusion with the human Fc DNA.

Primer sequences were:

```
Forward- SEQ ID NO 1:
5' ccaagctttcaatgggctgcagaagaactagag 3'  (HinDIII)

Reverse- SEQ ID NO 2:
5' acggatccacttacctgtataatcaccctccttaat cattgag 3'
(BamH1)
```

(Splice)

PCR conditions included 2 mM MgCli$_2$, 160 µM dNTP's. -5 ng template, 1 µM each primer.

Cycles: denature 94° C. 1 min. anneal 58° C. 1 min, extend 72° C. 2 min, total 30 cycles, followed by a 5 min extension at 72° C. The -1 kilobase product was ligated into pCR3.1 T-cloning vector (Invitrogen, USA) and transformed into E. coli JM109 bacteria. Colonies were selected, analysed by restriction digest and an apparently correct clone was confirmed as such by sequencing. The correct L-selectin cDNA was digested from pCR.3.1 and ligated into the pcDNA3.1-IgG-Fc expression vector. Clones were analysed by restriction digest and a correct clone was selected for testing in COS 7 cells. Western blotting, using the DREG56 mouse anti-human L selectin antibody; (Immunotech, France) confirmed expression of a protein of -210 kDa, which corresponds to an L-selectin dimer. L-selectin protein was produced by bulk transfections of COS 7 cells, growth in immunoglobulin depleted media, and subsequent purification on a protein A affinity column.

The purified protein was used in the BIAcore assay design described above with the modification that the buffer was 10 mM BisTris pH 6.5 with 0.15 M NaCl. The test compound (2 µM final concentration) was incubated with the L-selectin-Fc fusion protein and the residual binding of the L-selectin-Fc fusion protein to heparin on the BIAcore chip was measured. Selected results are shown below, with good efficacy being achieved for particular compounds.

| Compound | Residual binding at 2 µM |
|---|---|
| Heparin | 10% |
| 212B5 | >100% |
| 212B9 | >100% |
| 226BE | 41% |
| 226BI | 70% |
| 212TC | 2% |
| 212TE | 23% |
| 212W2 | 40% |

Example 72

Anticoagulant Tests

Anticoagulant and antithrombotic activities (e.g. APTT, PT, anti-Factor Xa and anti-factor IIa) were screened using standard automated haematological analyzers fitted with appropriate reagent kits. The values obtained were compared with those obtained using reference standards of heparin and/or low-molecular weight heparin.

Coagulation tests were performed on a STA-R coagulation analyser (Diagnostica Stago). INR (and dilute prothrombin time) used the Neoplastin reagent kit (Stago) and aPTT employed the Platelin LS (bioMerieux) reagent kit using standard clotting tests. Anti FXa activity was a chromogenic assay using a STAGO reagent kit. All tests used a pooled standard plasma.

All of the tested compounds showed anti-Factor Xa activity less than 2% of LMWH. In the aPTT assay the concentration of additive which caused a doubling in the clotting time of pooled plasma is determined ($ED_{200}$). In the following table the $ED_{200}$ for the test compounds was expressed relative to the $ED_{200}$ observed for heparin.

TABLE 2

The $ED_{200}$ of test compound relative to the $ED_{200}$ for heparin in aPTT assays.

| Compound | $ED_{200}$ [test compound]/$ED_{200}$ [heparin] |
|---|---|
| 1G | 3.2 |
| 1H | 1.5 |
| 161Q | 15 |
| 161I | 15 |
| 212B6 | 11 |
| 212B5 | 11 |
| 212B9 | 2.6 |
| 226AJ | 42 |
| 226AI | 12 |
| 226BF | 18 |
| 226BE | 3.2 |
| 226BI | 1.5 |
| 212TF | 6.4 |
| 226TF | 11 |
| 212TE | 24 |
| 226TE | 12 |
| 212TC | 22 |
| 226TC | 80 |
| 226DD | 9 |
| 226DC | 14 |
| 212W2 | 24.0 |
| 212W1 | 17 |

Thus, unlike heparin which shows both dual aPTT and FXa activity several compounds show a greater specificity of action as they possess negligible FXa activity but are able to prolong aPTT.

The reference in this specification to any prior publication (or information derived from it), or to any matter which is known, is not, and should not be taken as an acknowledgement or admission or any form of suggestion that that prior publication (or information derived from it) or known matter forms part of the common general knowledge in the field of endeavour to which this specification relates.

Throughout this specification and the claims which follow, unless the context requires otherwise, the word 'comprise', and variations such as 'comprises' and 'comprising', will be understood to imply the inclusion of a stated integer or step or group of integers or steps but not the exclusion of any other integer or step or group of integers or steps.

The invention claimed is:

1. An anionic conjugate of 2 or more gyclosylated bacterial metabolites selected from the group consisting of paromomycin, streptomycin, butirosin A, G418 and neamine, wherein prior to conjugation one or more of the gyclosylated bacterial metabolites is modified to facilitate conjugation.

2. The conjugate according to claim 1 wherein at least one of the gyclosylated bacterial metabolites is polyhydroxylated.

3. The conjugate according to claim 2 wherein at least one of the hydroxyl groups is transformed into an anionic group.

4. The conjugate according to claim 3 wherein the anionic group is a sulfate or phosphate group.

5. The conjugate according to claim 1 wherein the gyclosylated bacterial metabolites are conjugated by a linking group.

6. The conjugate according to claim 1 which is represented by formula I:

$$M^1L^1 - (M^iL^i)_{n-1} - M^{n+1} \quad (I)$$

wherein: n is a positive integer;

for a given n, there are n-1 successive values for i starting from 2 in the series 2,3, ..., n;

each M is the gyclosylated bacterial metabolite; and each L is a linking group.

7. A pharmaceutical composition comprising a therapeutically effective amount of the anionic conjugate according to claim 1 and a pharmaceutically acceptable carrier and/or diluent.

* * * * *